US009110074B2

(12) United States Patent
Jamieson Jr.

(10) Patent No.: US 9,110,074 B2
(45) Date of Patent: *Aug. 18, 2015

(54) **MASS SPECTROMETRY ASSAY FOR *EIF4E* AND *EIF4E* REGULON ACTIVITY**

(75) Inventor: Gordon A. Jamieson Jr., Alrington, MA (US)

(73) Assignee: Translational Therapeutics, Inc., Arlington, MA (US)

( * ) Notice: Subject to any disclaimer, the term of this patent is extended or adjusted under 35 U.S.C. 154(b) by 880 days.

This patent is subject to a terminal disclaimer.

(21) Appl. No.: 13/102,669

(22) Filed: May 6, 2011

(65) Prior Publication Data

US 2011/0319295 A1 Dec. 29, 2011

Related U.S. Application Data

(63) Continuation-in-part of application No. 12/775,013, filed on May 6, 2010, now Pat. No. 8,604,692, which is a continuation-in-part of application No. PCT/US2008/082611, filed on Nov. 6, 2008.

(60) Provisional application No. 60/985,787, filed on Nov. 6, 2007.

(51) Int. Cl.
*C12Q 1/00* (2006.01)
*G01N 33/68* (2006.01)

(52) U.S. Cl.
CPC ........ *G01N 33/6842* (2013.01); *G01N 33/6848* (2013.01); *G01N 33/6851* (2013.01); *G01N 2440/14* (2013.01)

(58) Field of Classification Search
CPC .................................................. G01N 33/6848
USPC ............................................. 313/564; 435/4
See application file for complete search history.

(56) References Cited

U.S. PATENT DOCUMENTS

| | | | |
|---|---|---|---|
| 6,586,190 | B2 | 7/2003 | Bernasconi et al. |
| 6,951,757 | B2 | 10/2005 | Sabatini |
| 7,258,974 | B2 | 8/2007 | Chou |
| 2002/0049307 | A1 | 4/2002 | Aebersold et al. |
| 2002/0137888 | A1 | 9/2002 | Bernasconi et al. |
| 2003/0228694 | A1 | 12/2003 | Sabatini |
| 2005/0176085 | A1 | 8/2005 | Betancourt Nunez et al. |
| 2008/0171394 | A1 | 7/2008 | Eriksson et al. |

FOREIGN PATENT DOCUMENTS

| | | |
|---|---|---|
| JP | 2003-107066 A | 4/2003 |
| JP | 2005-189232 A | 7/2005 |
| JP | 2007-525639 A | 9/2007 |
| WO | WO-00/11208 A1 | 3/2000 |
| WO | WO-2004/070352 A2 | 8/2004 |
| WO | WO-2008/060369 A2 | 5/2008 |
| WO | WO-2009-061904 A2 | 5/2009 |
| WO | WO-2009147650 A2 | 12/2009 |

OTHER PUBLICATIONS

Extended European Search Report from corresponding European regional application EP 11778429.8 dated Feb. 6, 2014.
International Search Report for PCT/US2011/035559 dated Feb. 8, 2012.
Japanese Office Action for Application No. 2010-532339 mailed Aug. 26, 2013.
Rychlik, et al. "Phosphorylation Site of Eurkaryotic Initiation Factor 4E*" The Journal of Biological Chemistry, 262 (22): 10434-37 (1987).
Cui, Li, et al. "Comparative proteome analysis of human lung squamous carcinoma tissue," The Chinese-German Journal of Clinical Oncology, 5(4):232-239 (Aug. 1, 2006).
Cutillas, Pedro R, et al. "Quantification of gel-separated proteins and their phosphorylation sites by LC-MS using unlabeled internal standards: analysis of phosphoprotein dynamics in a B cell lymphoma cell line," Molecular & Cellular Proteomics, 4(8):1038-1051 (Aug. 2005).
Gingras, Anne-Claude, et al. "Regulation of 4E-BP1 phosphorylation: A novel two-step mechanism," Genes and Development, 13(11): 1422-1437 (Jun. 1, 1999).
Gygi, S.P., et al. "Protein analysis by mass spectrometry and sequence database searching: tools for cancer research in the post-genomic era," Electrophoresis, 20(2):310-319 (Feb. 1999).
Hale, J.E., et al. "A simplified procedure for the reduction and alkylation of cysteine residues in proteins prior to proteolytic digestion and mass spectral analysis," 333(1):174-181 (Oct. 1, 2004).
Mayya, Viveka, et al. "Absolute quantification of multisite phosphorylation by selective reaction monitoring mass spectrometry: determination of inhibitory phosphorylation status of cyclin-dependent kinases," 5(6):1146-1157 (Jun. 2006).
Whalen, S.G., et al. "Phosphorylation of eIF-4E on serine 209 by protein kinase C is inhibited by the translational repressors, 4E-binding proteins," The Journal of Biological Chemistry, 271(20):11831-11837 (May 17, 1996).
International Search Report for PCT/US2008/082611 mailed Jun. 29, 2009.
Supplementary European Search Report for EP 08 84 6730 mailed Feb. 24, 2011.

*Primary Examiner* — Bin Shen
(74) *Attorney, Agent, or Firm* — Foley Hoag LLP

(57) ABSTRACT

Provided is a highly sensitive high throughput mass spectrometry-based quantitative assay for 4E/4E regulon pathway proteins has been developed which provides for single sample multiplexed analysis, as well as the analysis of protein phosphorylation states. It may be adapted for use as the first single sample analytical method of the 4E/4E regulon biological pathway.

7 Claims, 92 Drawing Sheets

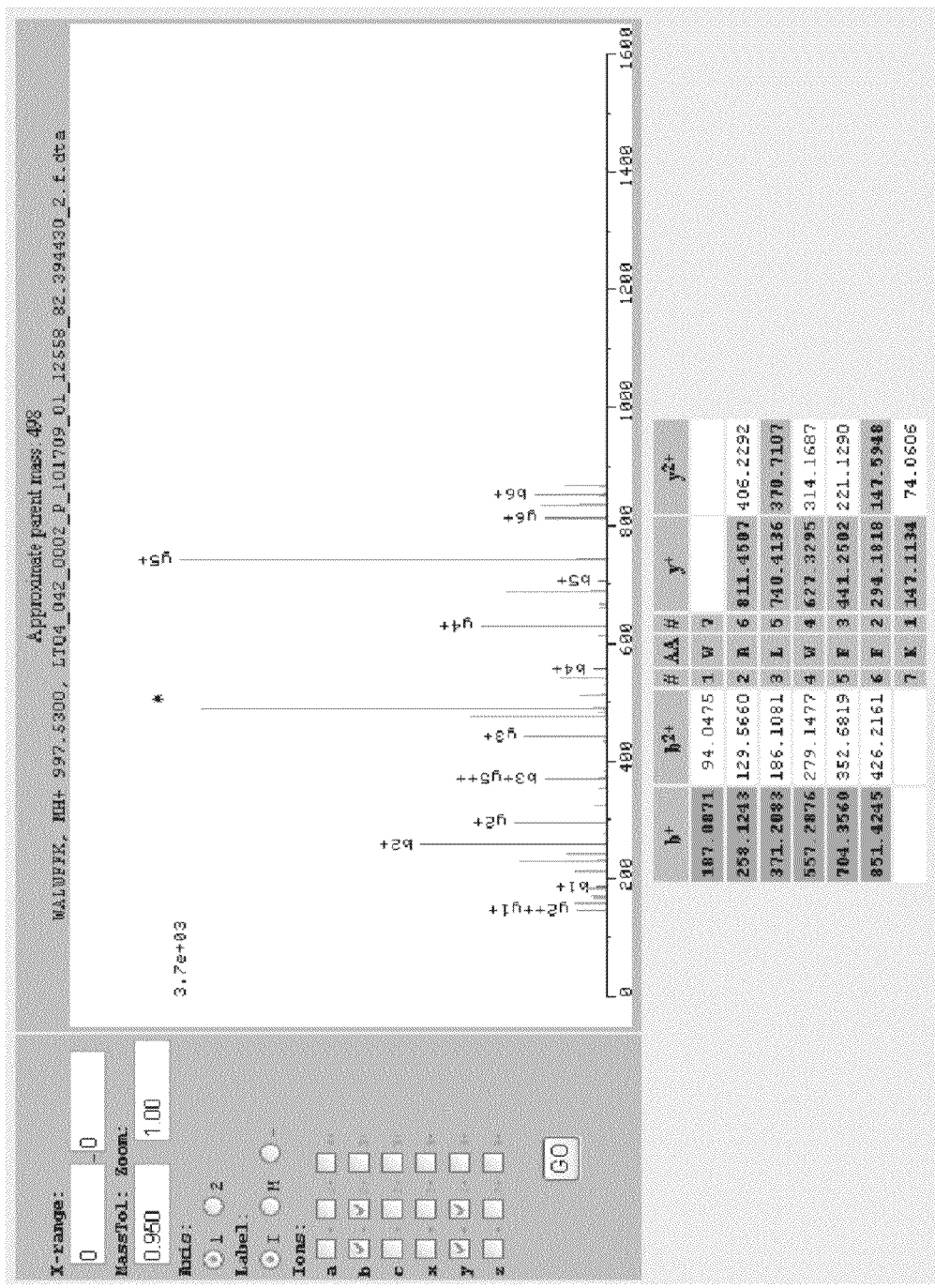
FIG. 1C cont. -- gi|IPI00027485.3|sp|P06730|rs|NP_001959|NP_001959.1 Eukaryotic translation initiation factor 4E|gs|EIF4E LY400723

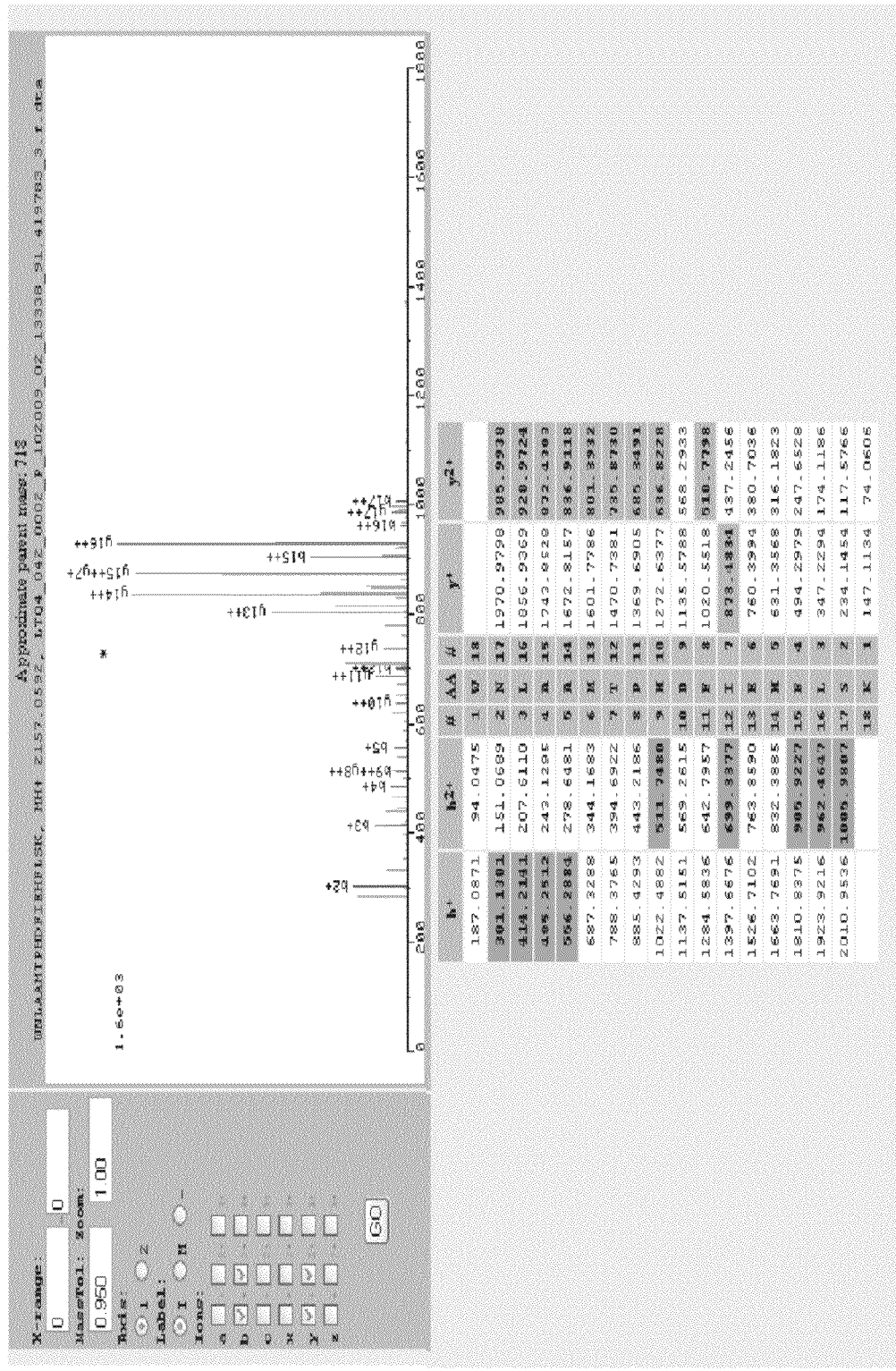
FIG. 1D cont. -- gi|IPI00028098.1|sp|P24385|rs|NP_444284| NP_444284.1 G1/S-specific cyclin-D1|gs |CCND1 LY403284

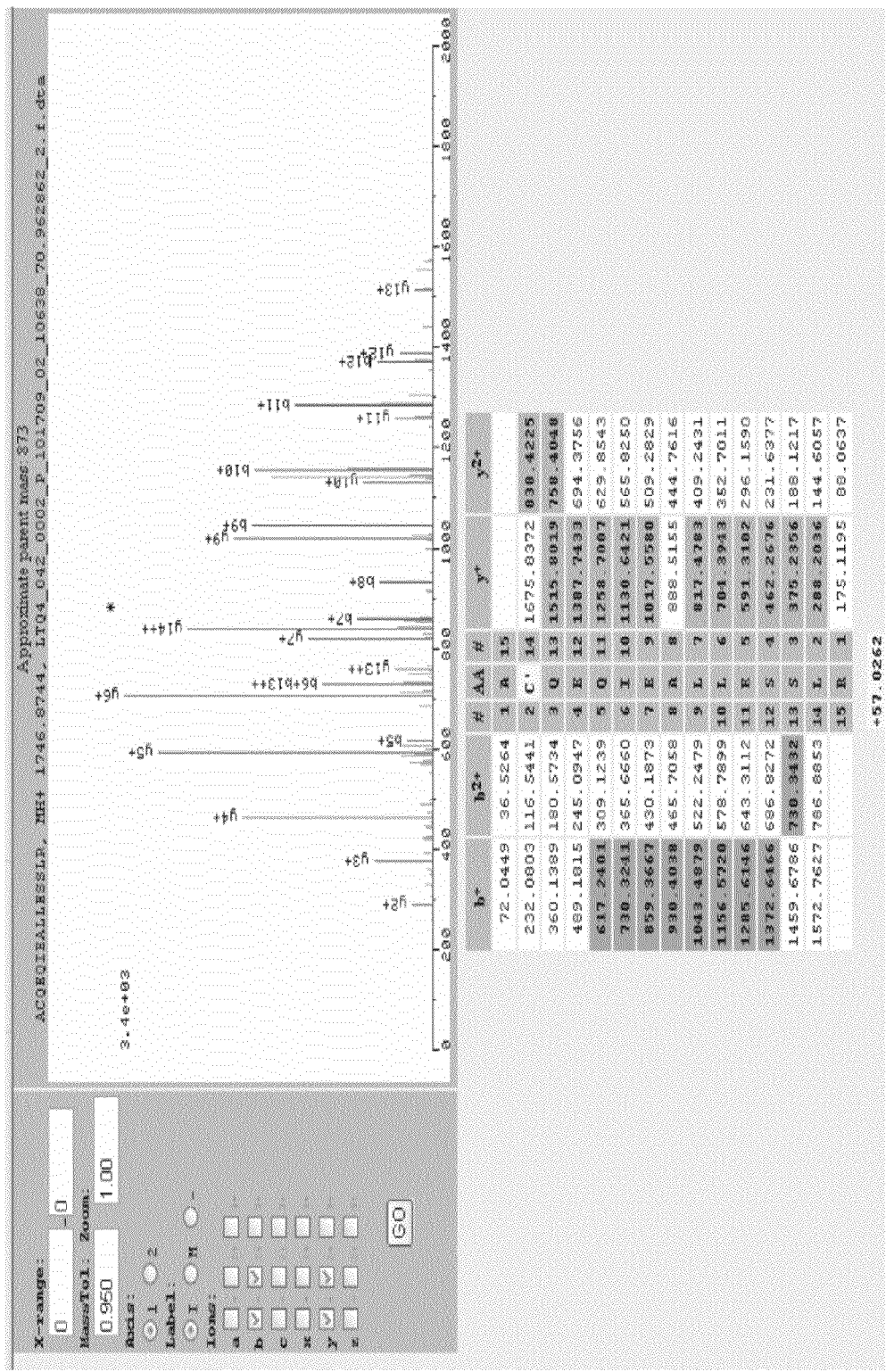
FIG. 1E cont. -- gi|IPI00028098.1|sp|P24385|rs|NP_444284| NP_444284.1 G1/S-specific cyclin-D1|gs|CCND1 LY403284

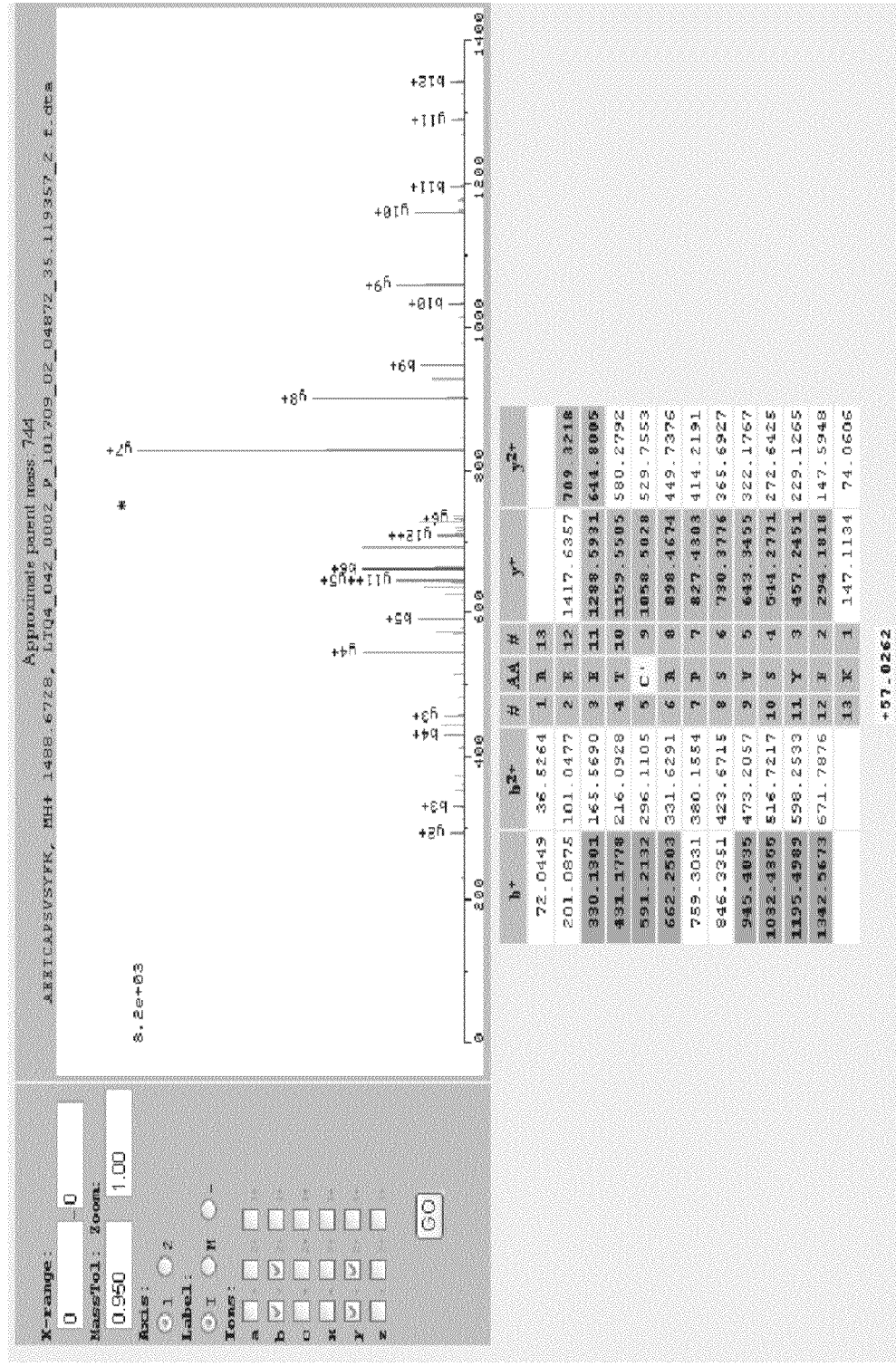
FIG. 1F cont. -- gi||IPI00028098.1|sp|P24385|rs|NP_444284| NP_444284.1 G1/S-specific cyclin-D1|gs|CCND1 LY403284

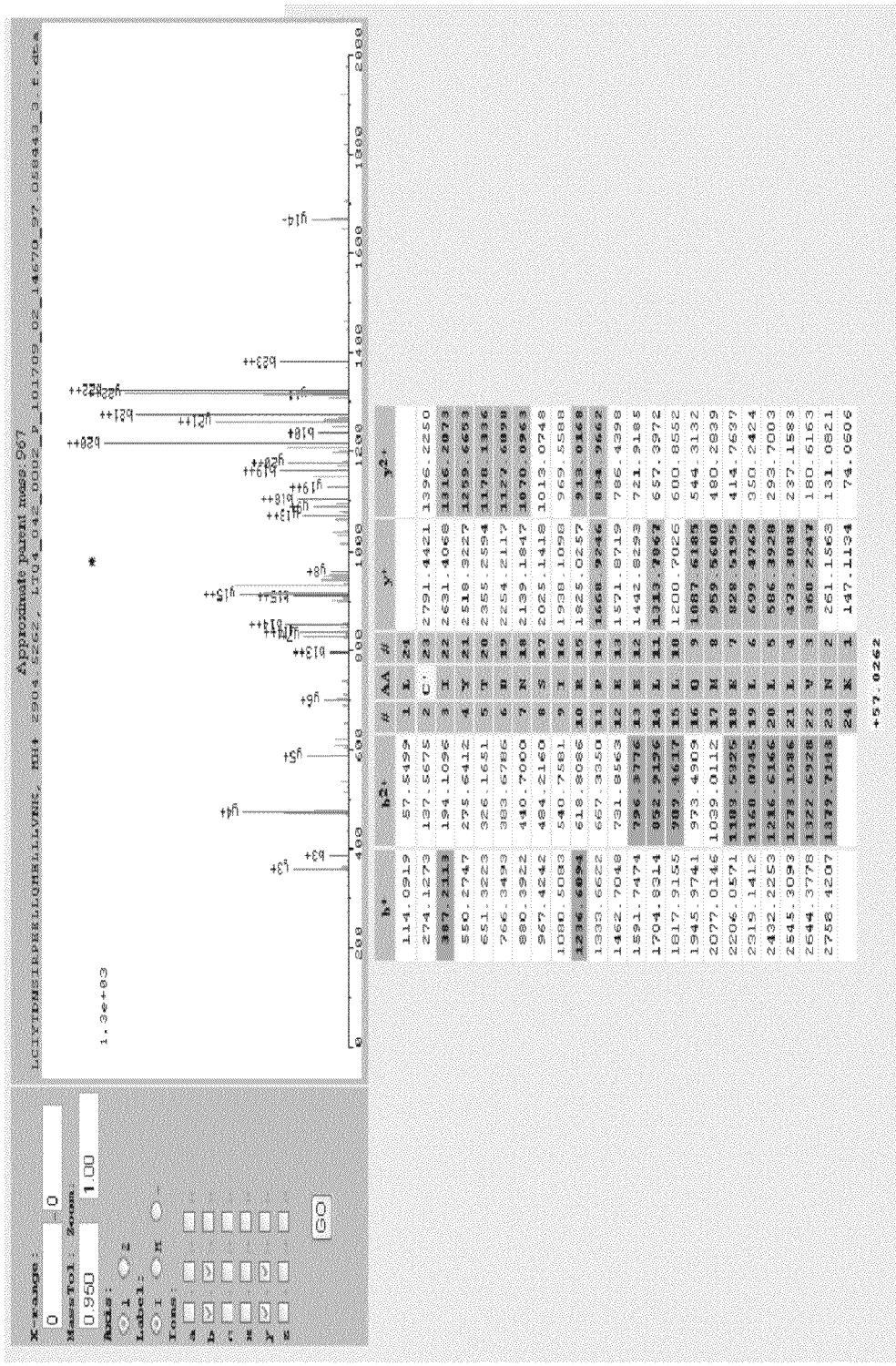
FIG. 1G cont. -- gi|IPI00028098.1|sp|P24385|rs|NP_444284| NP_444284.1 G1/S-specific cyclin-D1|gs|CCND1
LY403284

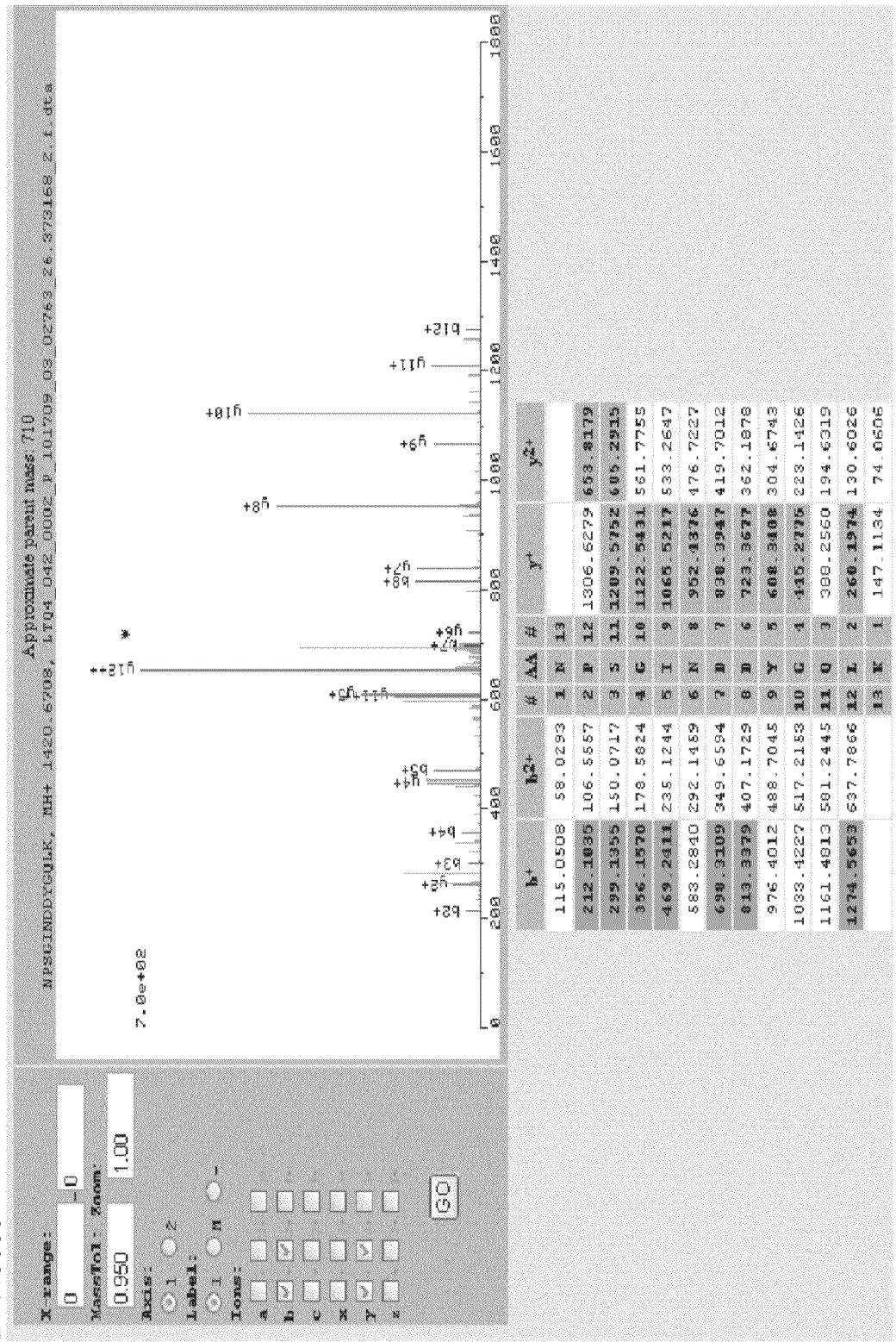
FIG. 1H cont. -- gi|IPI00299463.1|sp|O60934|rs|NP_002476|NP_002476.2 Nibrin|gs|NBN
LY419300

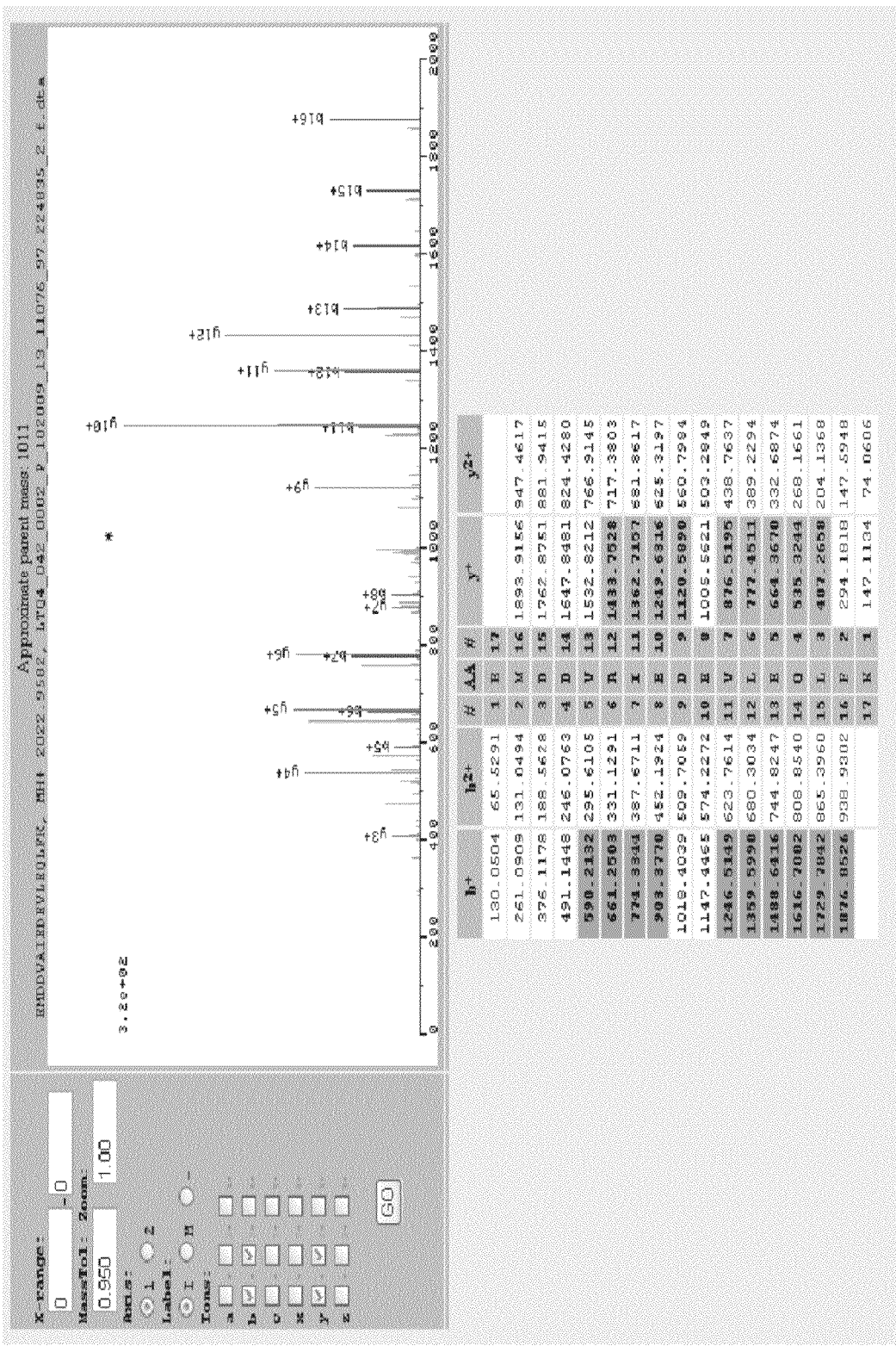
FIG. 1I cont. – gi|IPI00299463.1 |sp|O60934|rs|NP_002476| NP_002476.2 Nibrin|gs|NBN LY419300

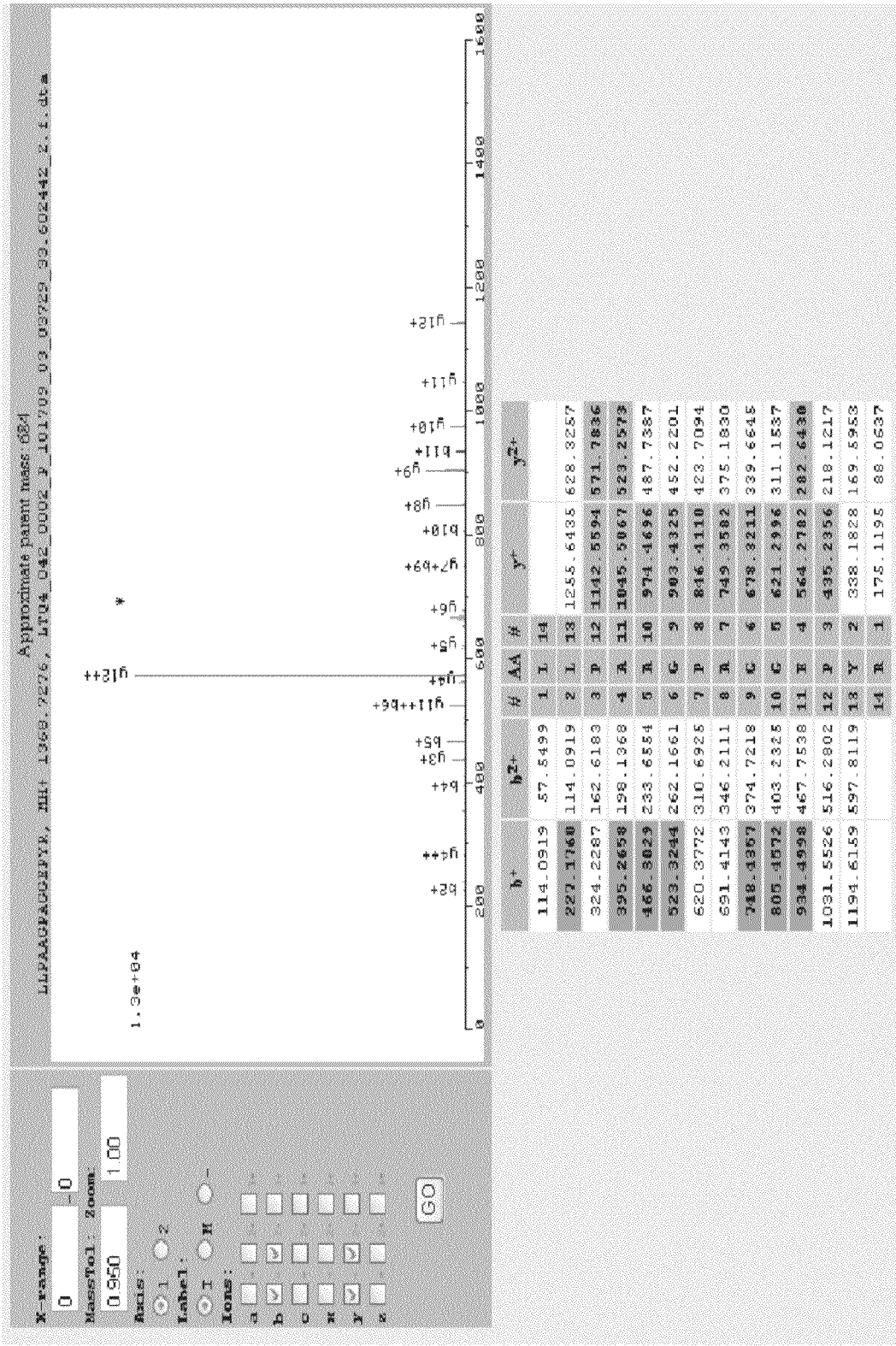
FIG. 1J cont. -- gi|IPI00299463.1|sp|O60934|rs|NP_002476|NP_002476.2 Nibrin|gs|NBN LY419300

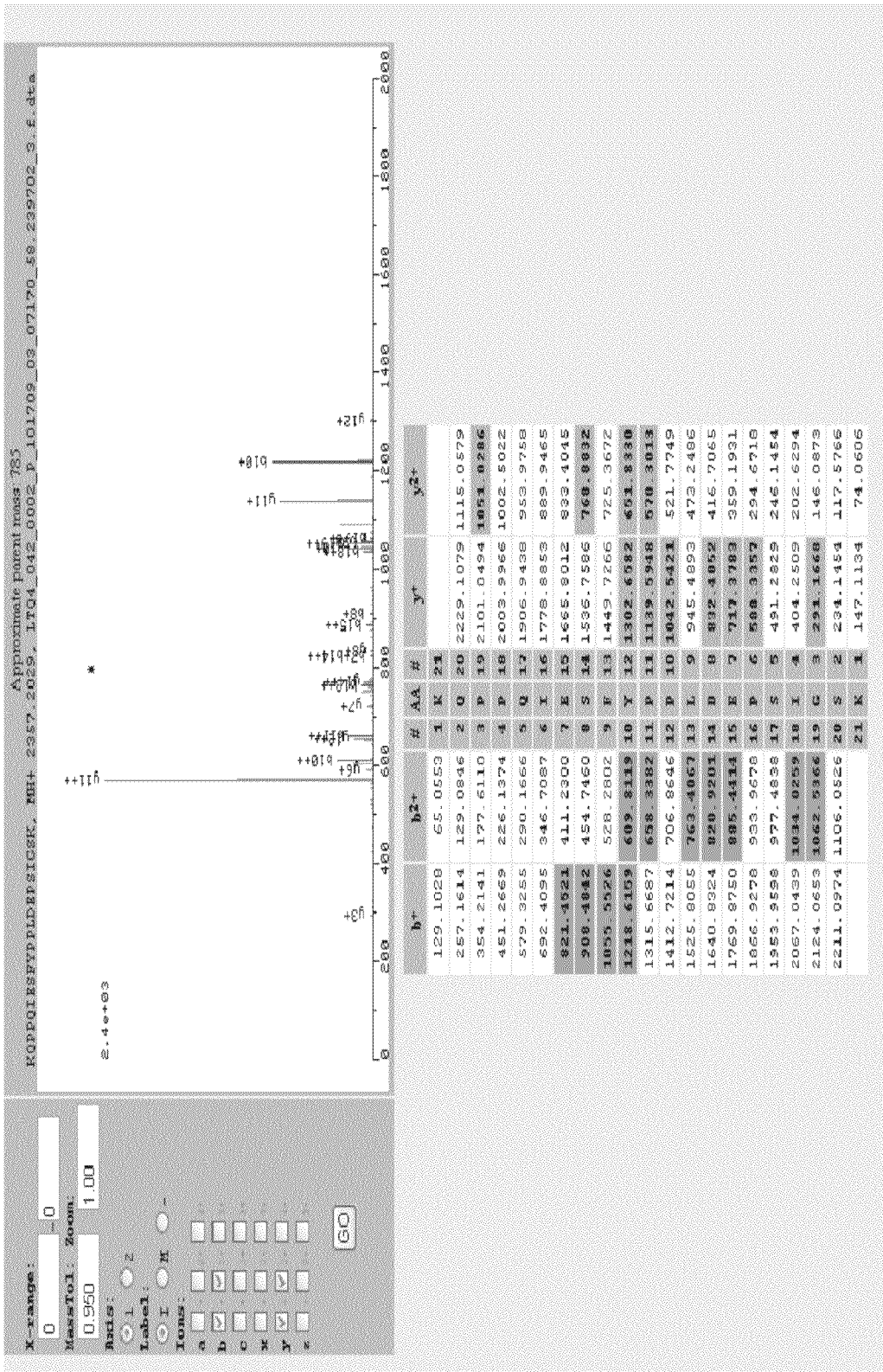
FIG. 1K cont. -- gi|IPI00299463.1|sp|O60934|rs|NP_002476| NP_002476.2 Nibrin|gs|NBN
LY419300

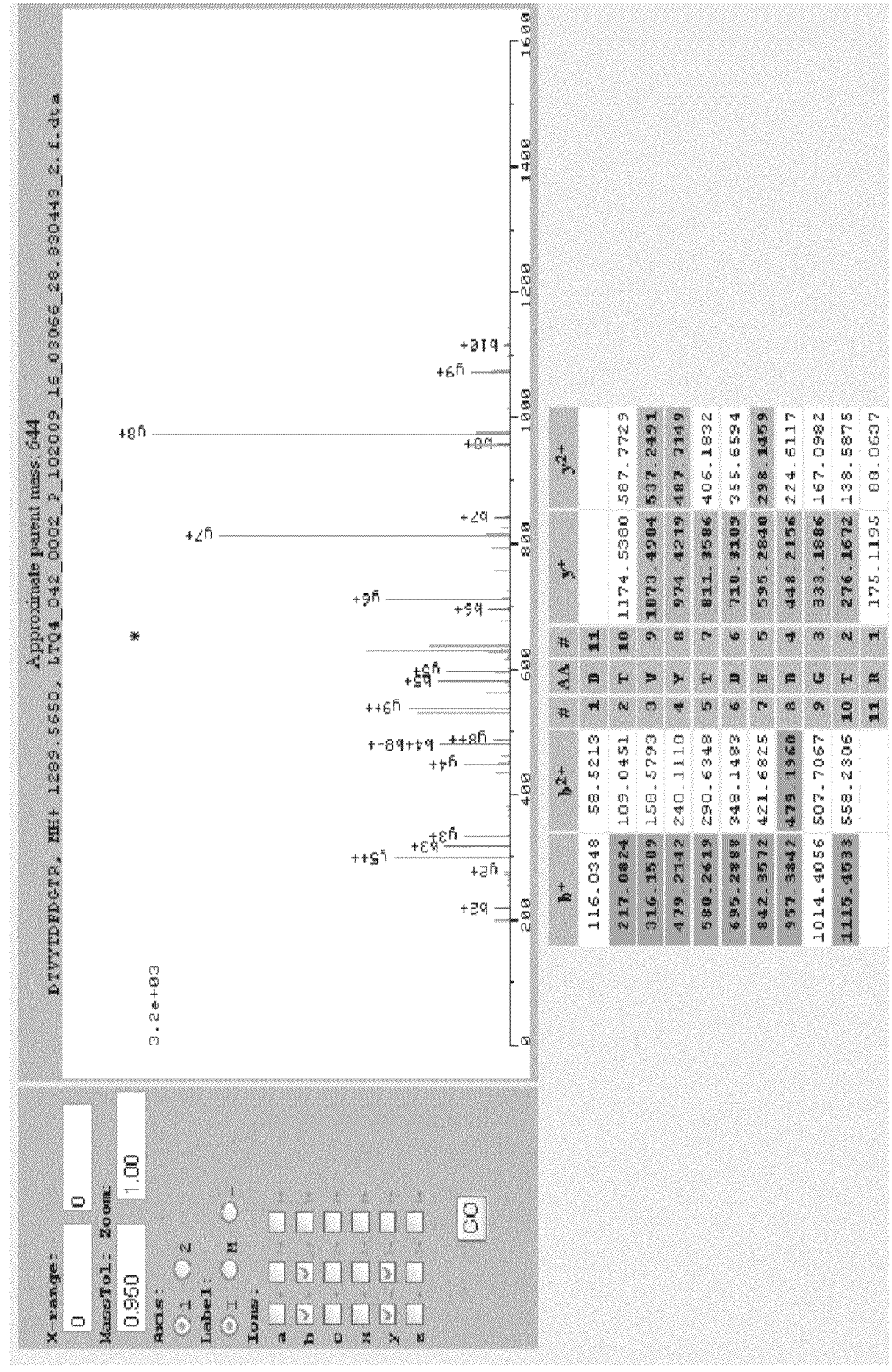
FIG. 1M cont. -- gi||PI00005014.2|sp|P11309-1|rs|| Isoform 1 of Protooncogene serine/threonine-protein kinase Pim-1|gs|PIM1 LY419183 NP_002639, NP_002639.1

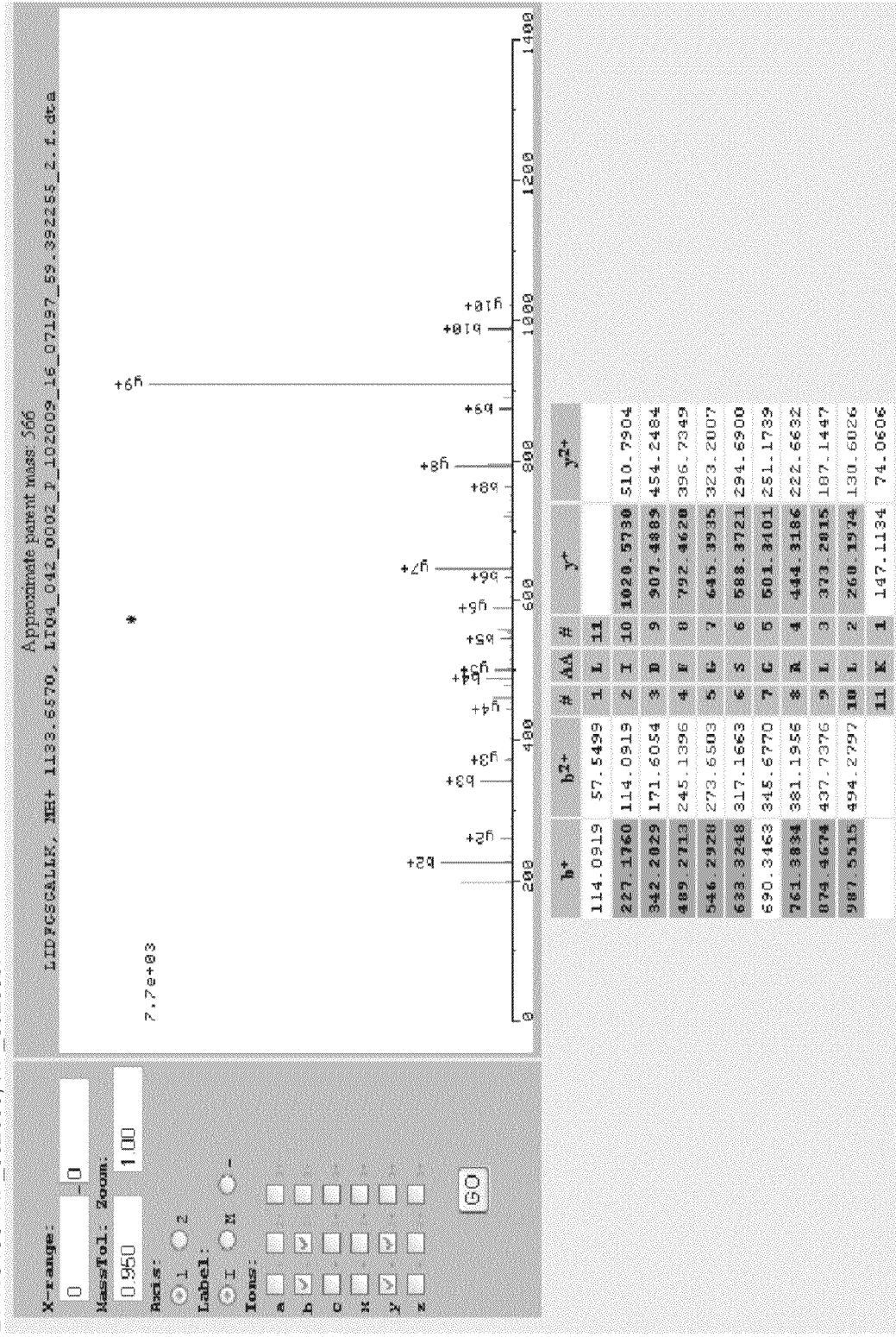
FIG. 1N cont. -- gi|IPI00005014.2|sp|P11309-1|rs|| Isoform 1 of Protooncogene serine/threonine-protein kinase Pim-1|gs|PIM1 LY419183 NP_002639, NP_002639.1

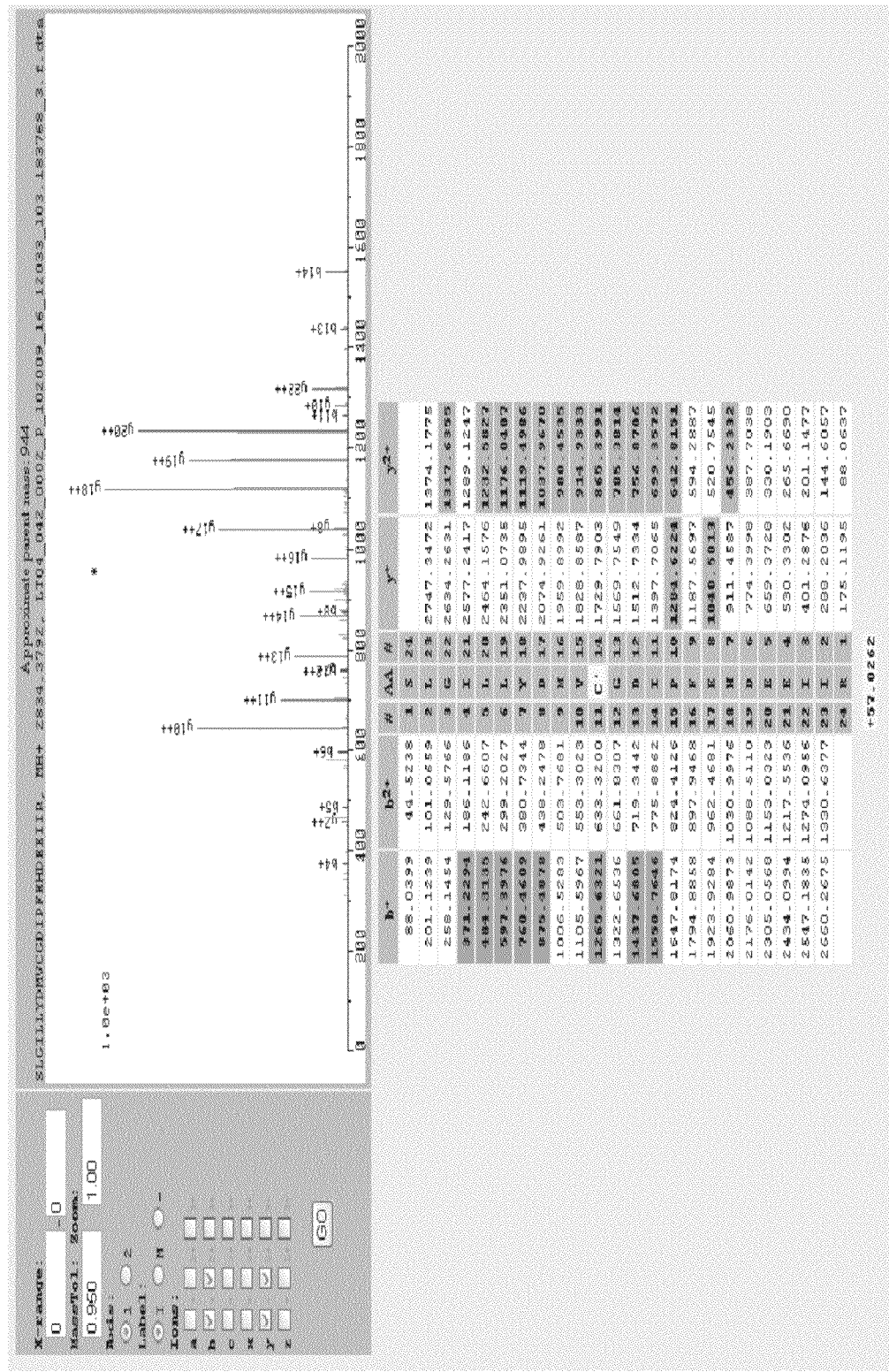
FIG. 1O cont. -- gi|IPI00005014.2|sp|P11309-1|rs|| Isoform 1 of Protooncogene serine/threonine-protein kinase Pim-1|gs|PIM1 LY419183_NP_002639, NP_002639.1

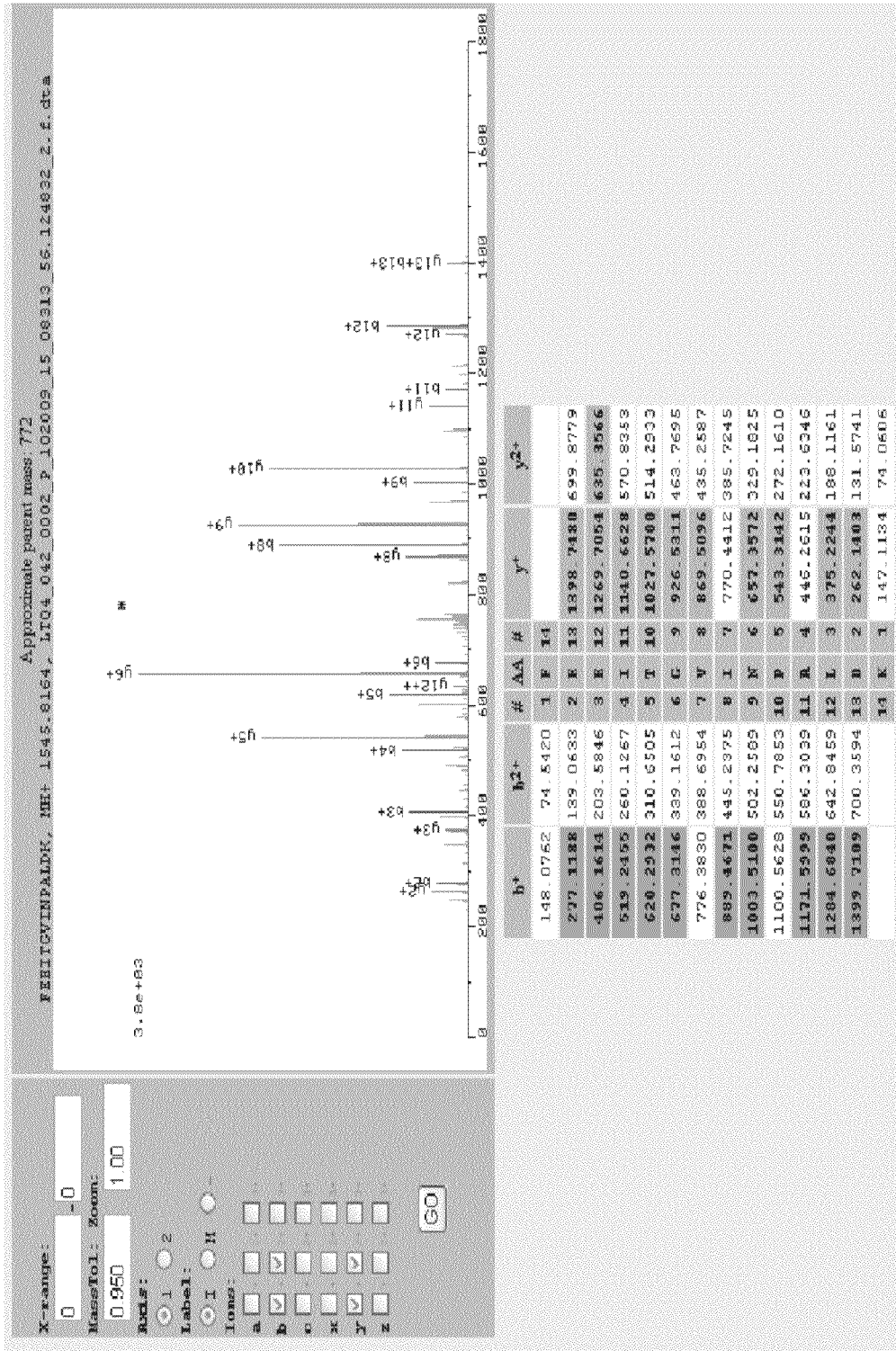
FIG. 1P cont. -- gi|IPI00008497.1|sp|P11926|rs|NP_002530|NP_002530.1 Ornithine decarboxylase|gs|ODC1 LY400909

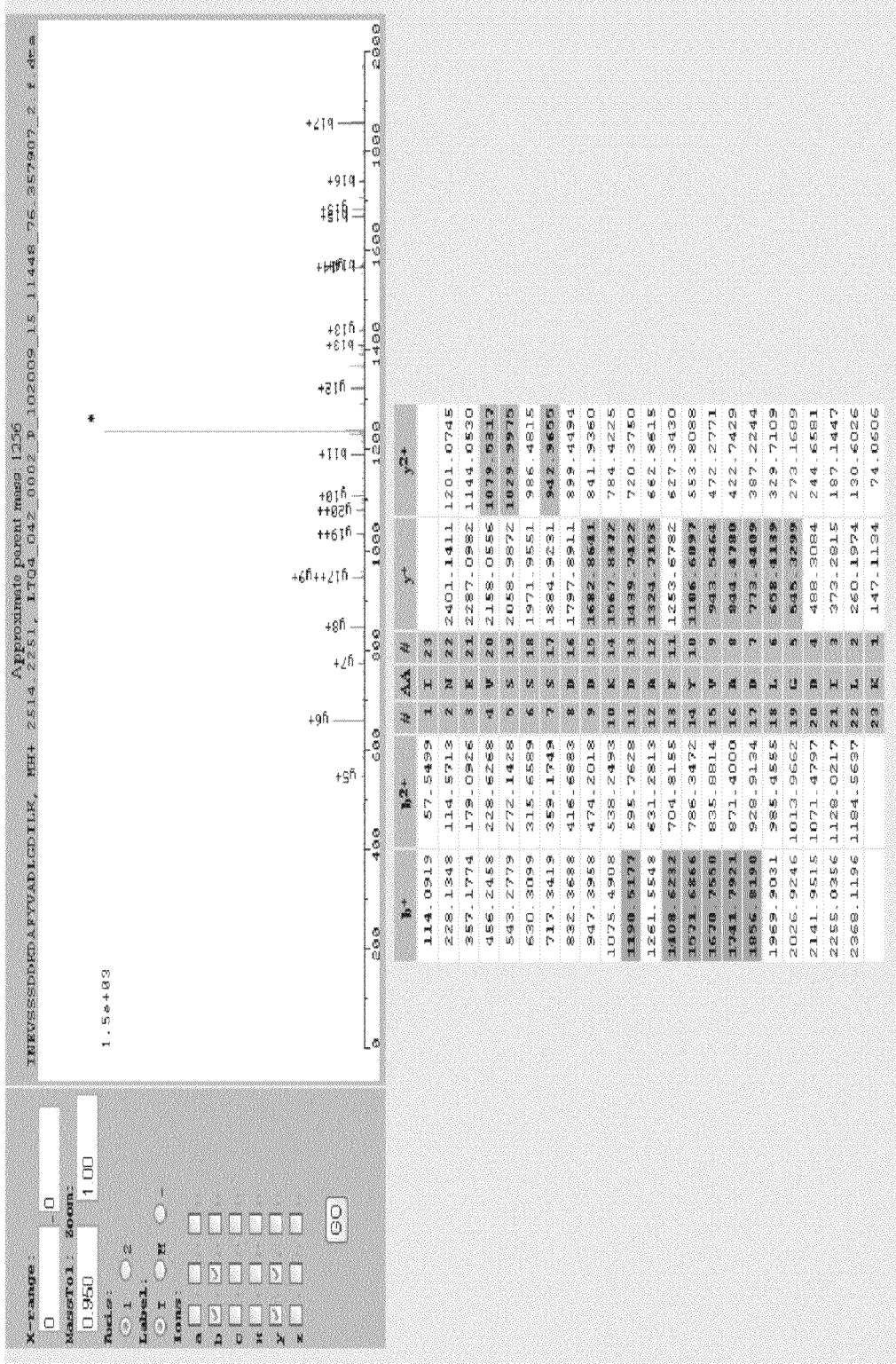
FIG. 1Q cont. -- gi|IPI00008497.1|sp|P11926|rs|NP_002530|NP_002530.1 Ornithine decarboxylase|gs|ODC1
LY400909

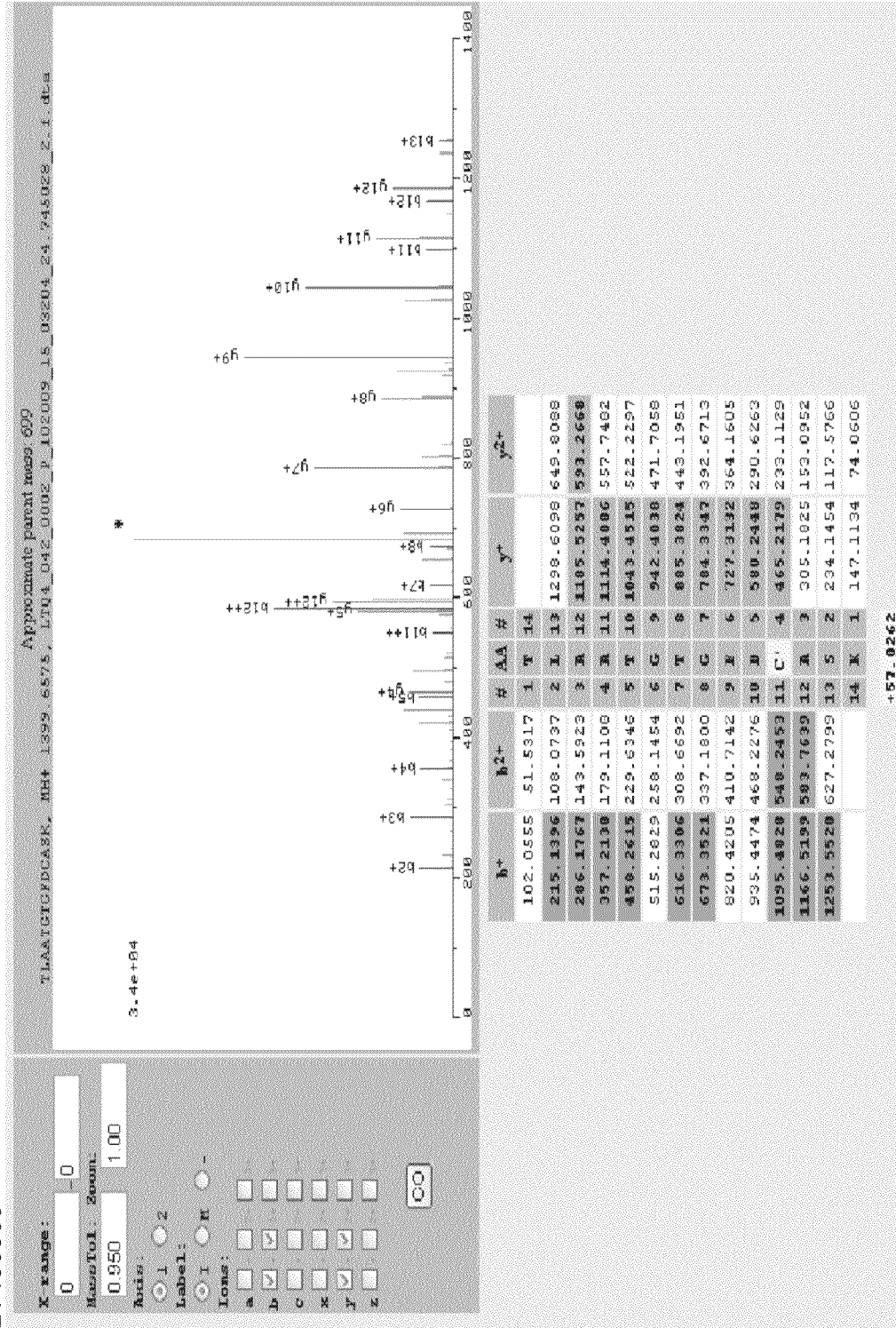
FIG. 1R cont. -- gi|IPI00008497.1|sp|P11926|rs|NP_002530|NP_002530.1 Ornithine decarboxylase|gs|ODC1 LY400909

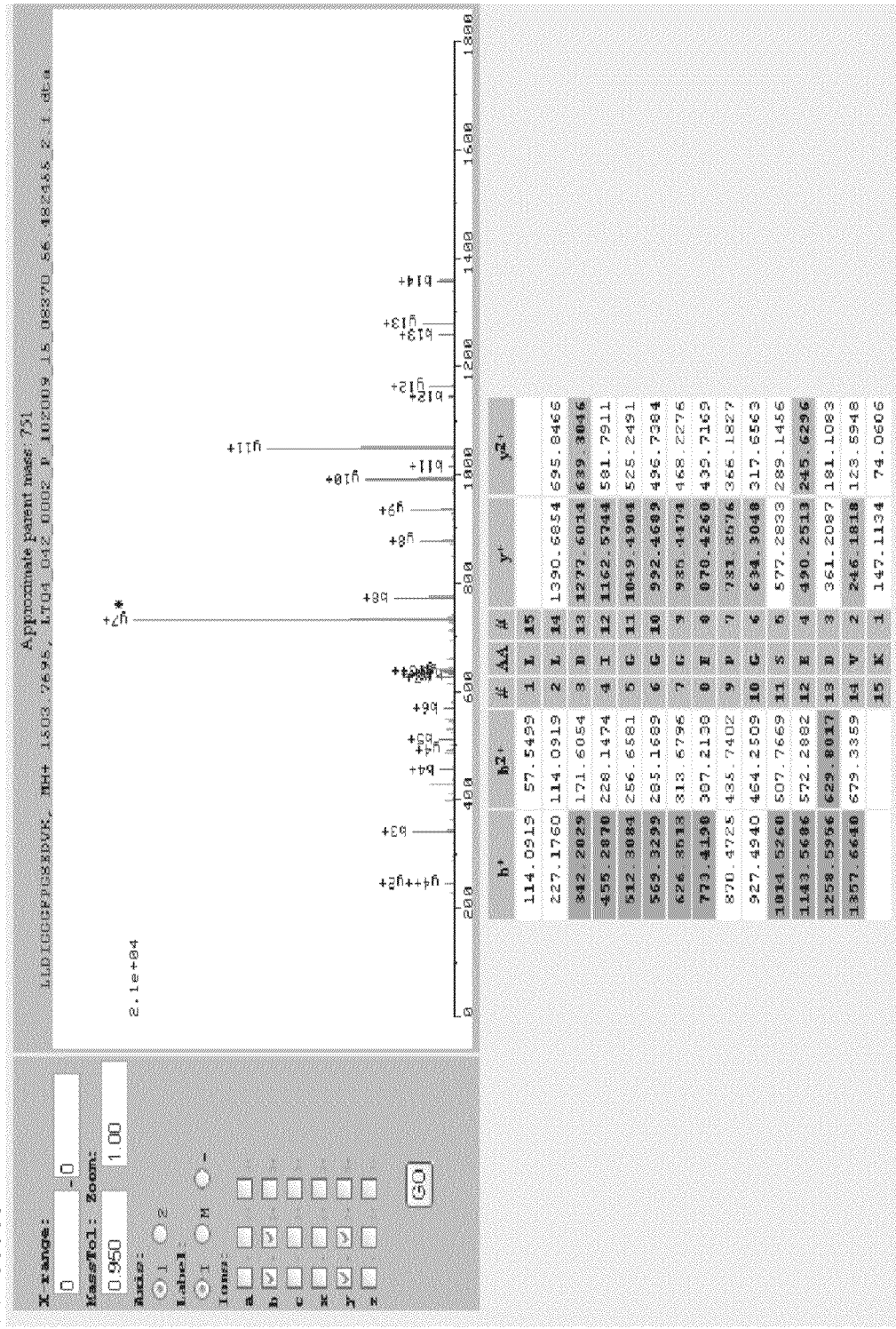
FIG. 1S cont. -- gi|IPI00008497.1|sp|P11926|rs|NP_002530| NP_002530.1 Ornithine decarboxylase|gs|ODC1 LY400909

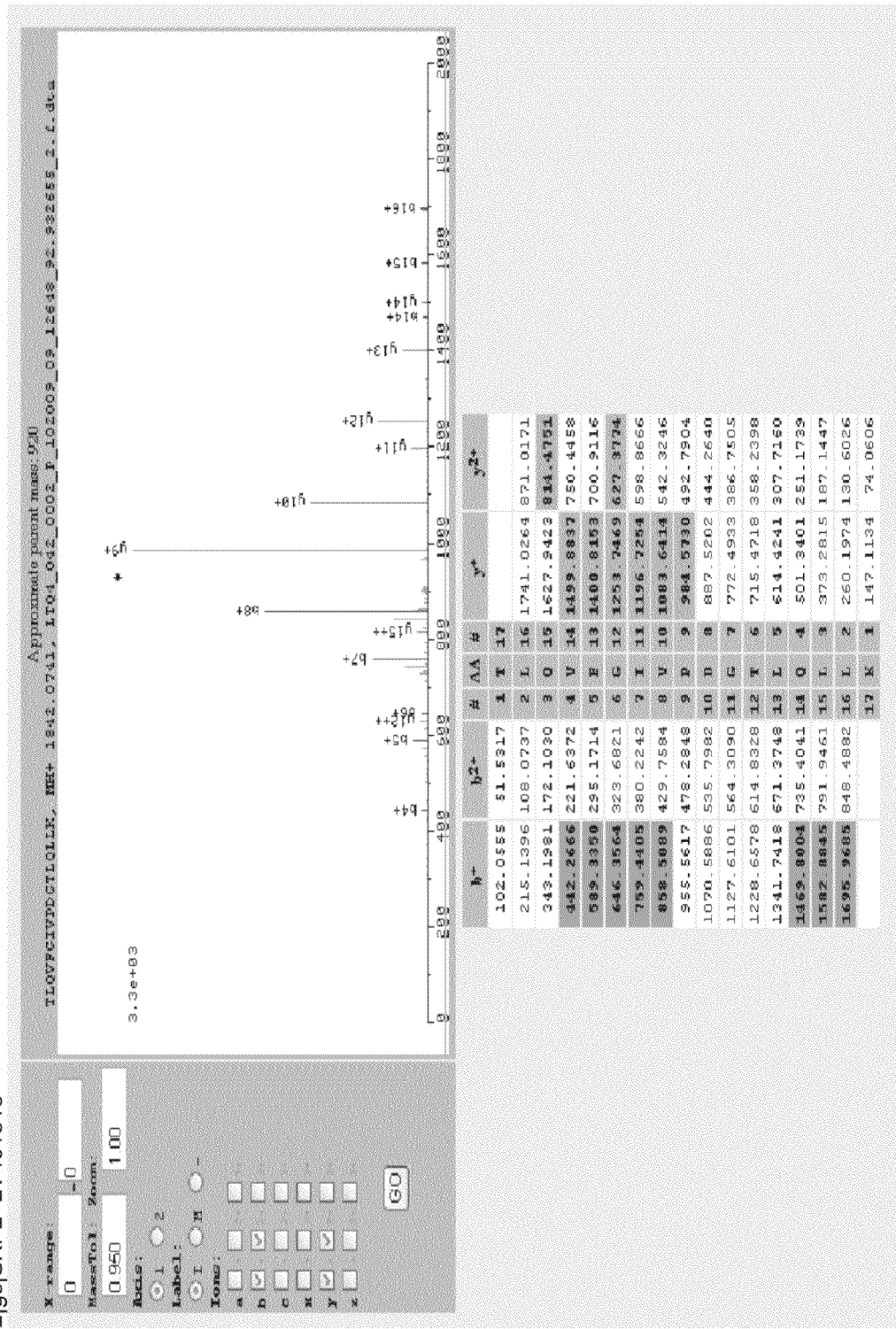
FIG. 1T cont. -- gi|IPI00178899.1|sp|Q13309-1|rs|NP_005974|NP_005974.2 Isoform 1 of S-phase kinase-associated protein 2|gs|SKP2 LY401815

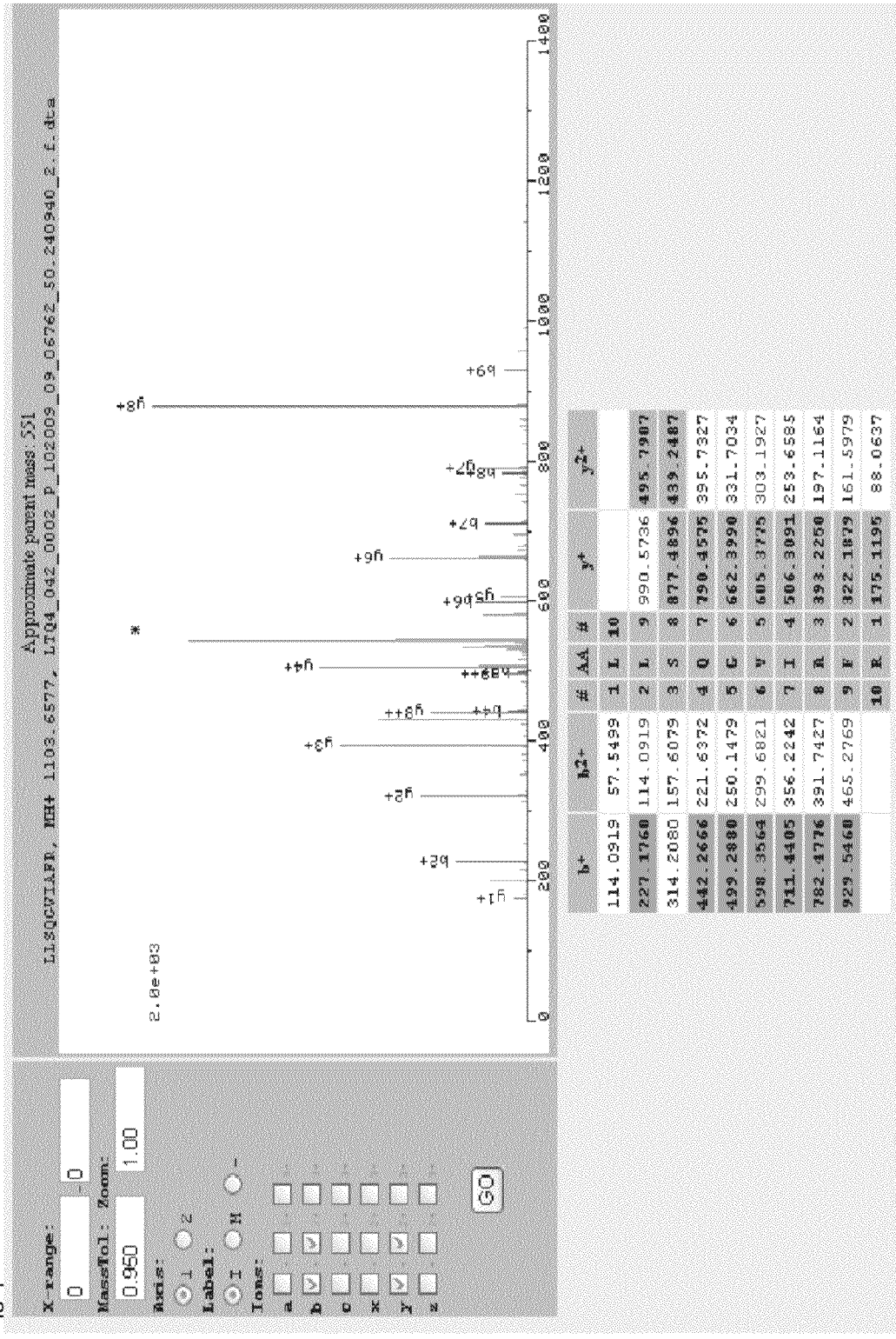
FIG. 1U cont. -- gi|IPI00178899.1|sp|Q13309-1|rs|NP_005974|NP_005974.2 Isoform 1 of S-phase kinase-associated protein 2|gs|SKP2 LY401815

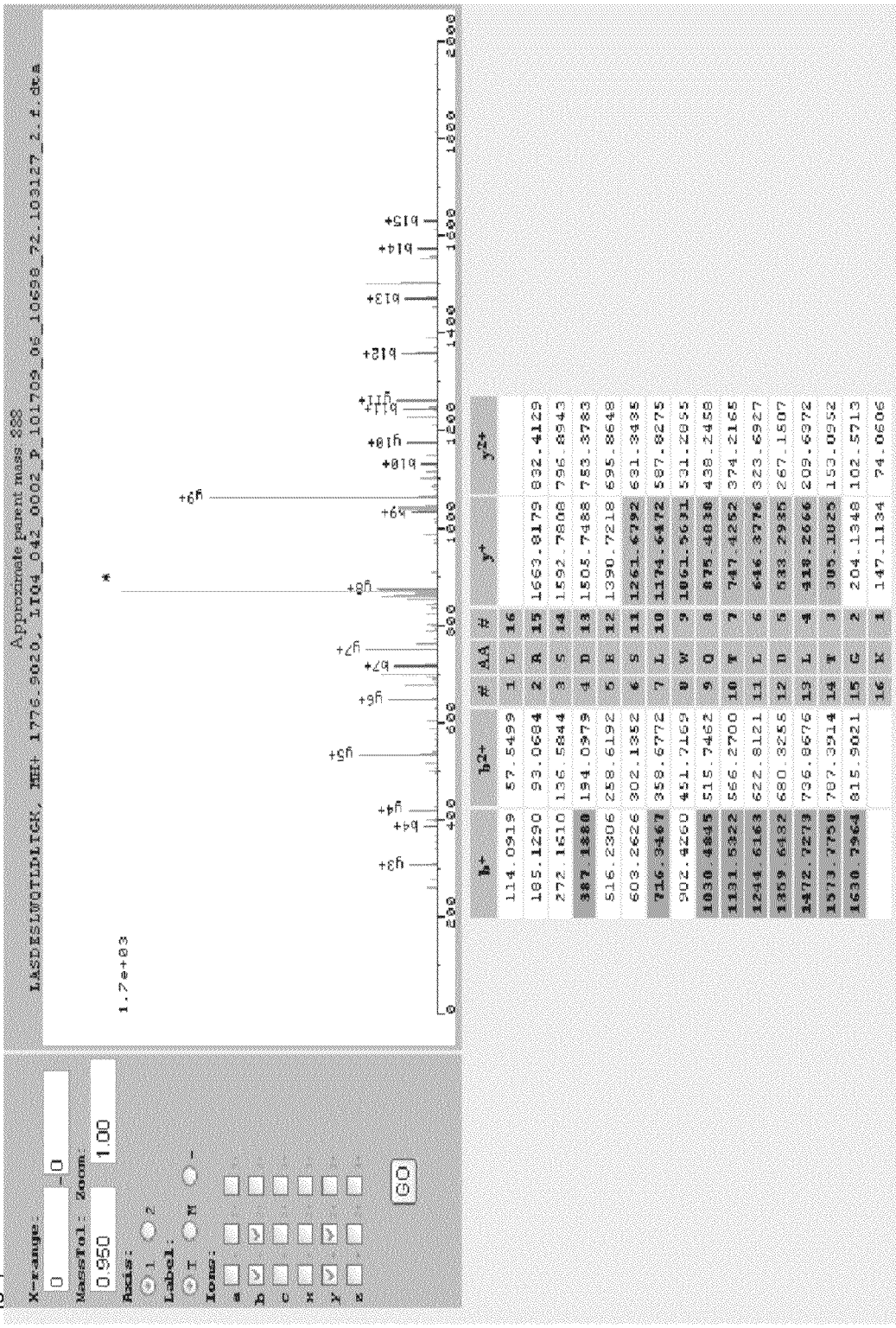
FIG. 1V cont. -- gi|IPI00178899.1|sp|Q13309-1|rs|NP_005974|NP_005974.2 Isoform 1 of S-phase kinase-associated protein 2|gs|SKP2 LY401815

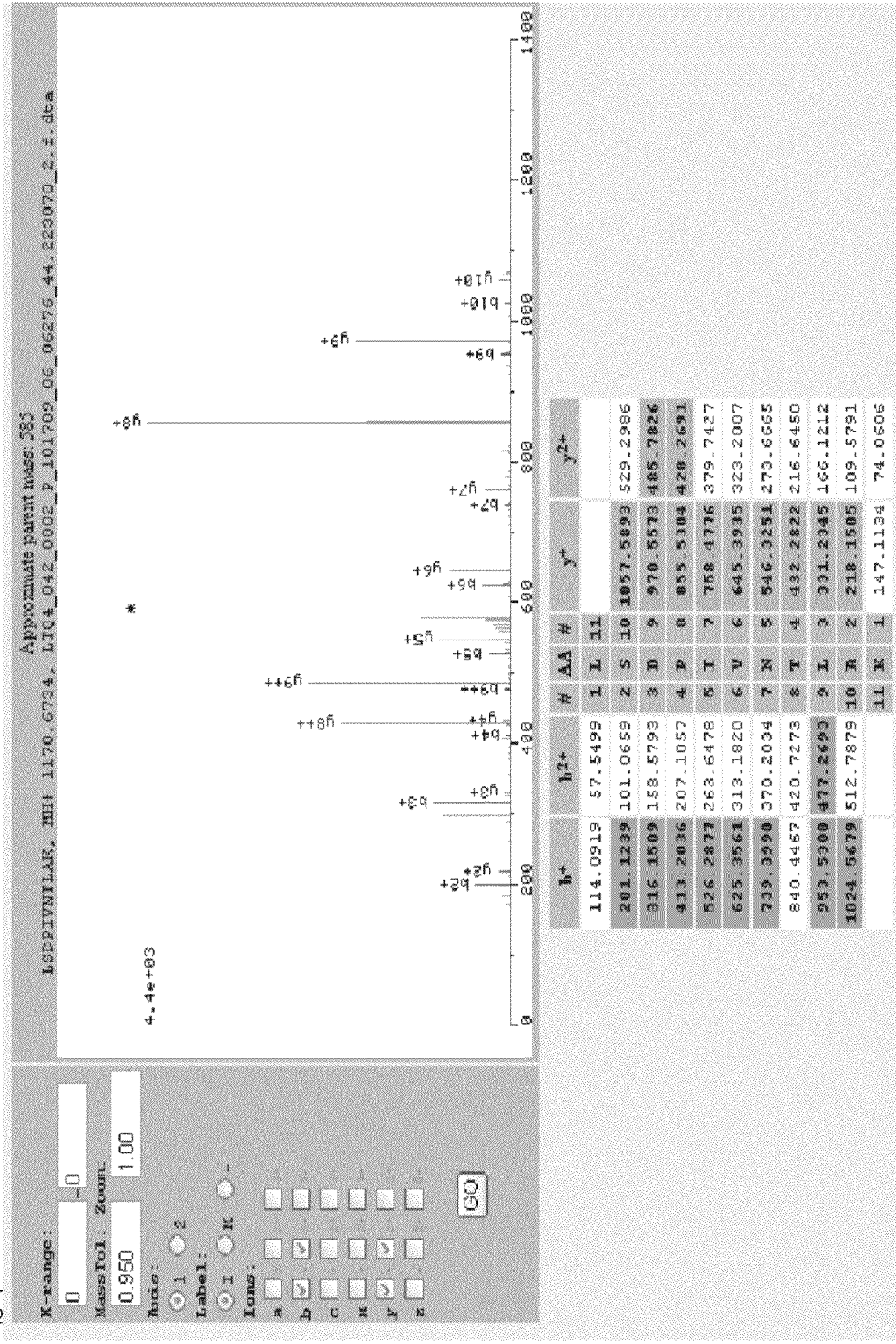
FIG. 1W cont. -- gi|IPI00178899.1|sp|Q13309-1|rs|NP_005974| NP_005974.2 Isoform 1 of S-phase kinase-associated protein 2|gs|SKP2 LY401815

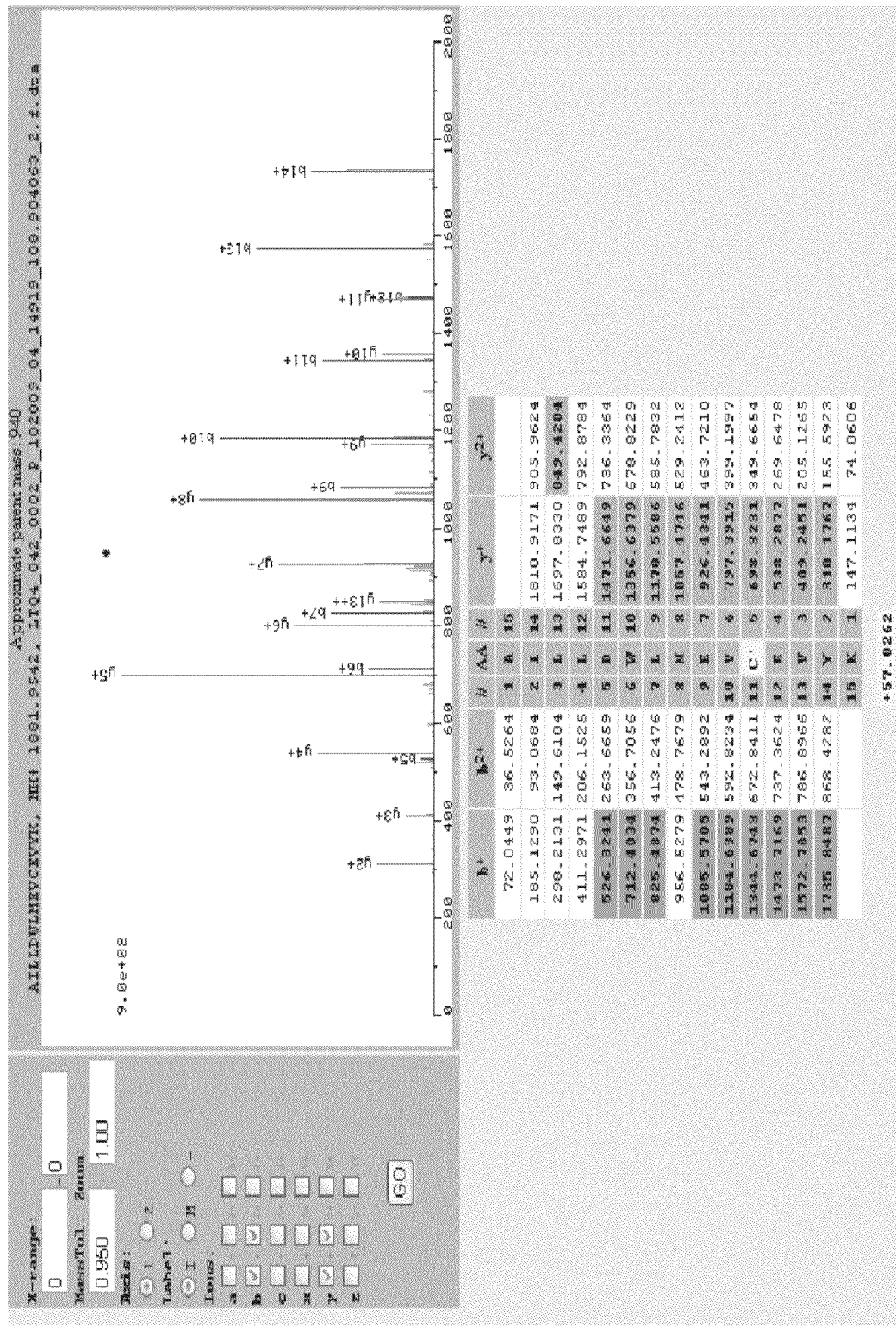
FIG. 1X cont. -- gi|IPI00031077.1|sp|P24864-1|rs|NP_001229|NP_001229.1 Isoform E1L of G1/S-specific cyclin-E1|gs|CCNE1 LY400495

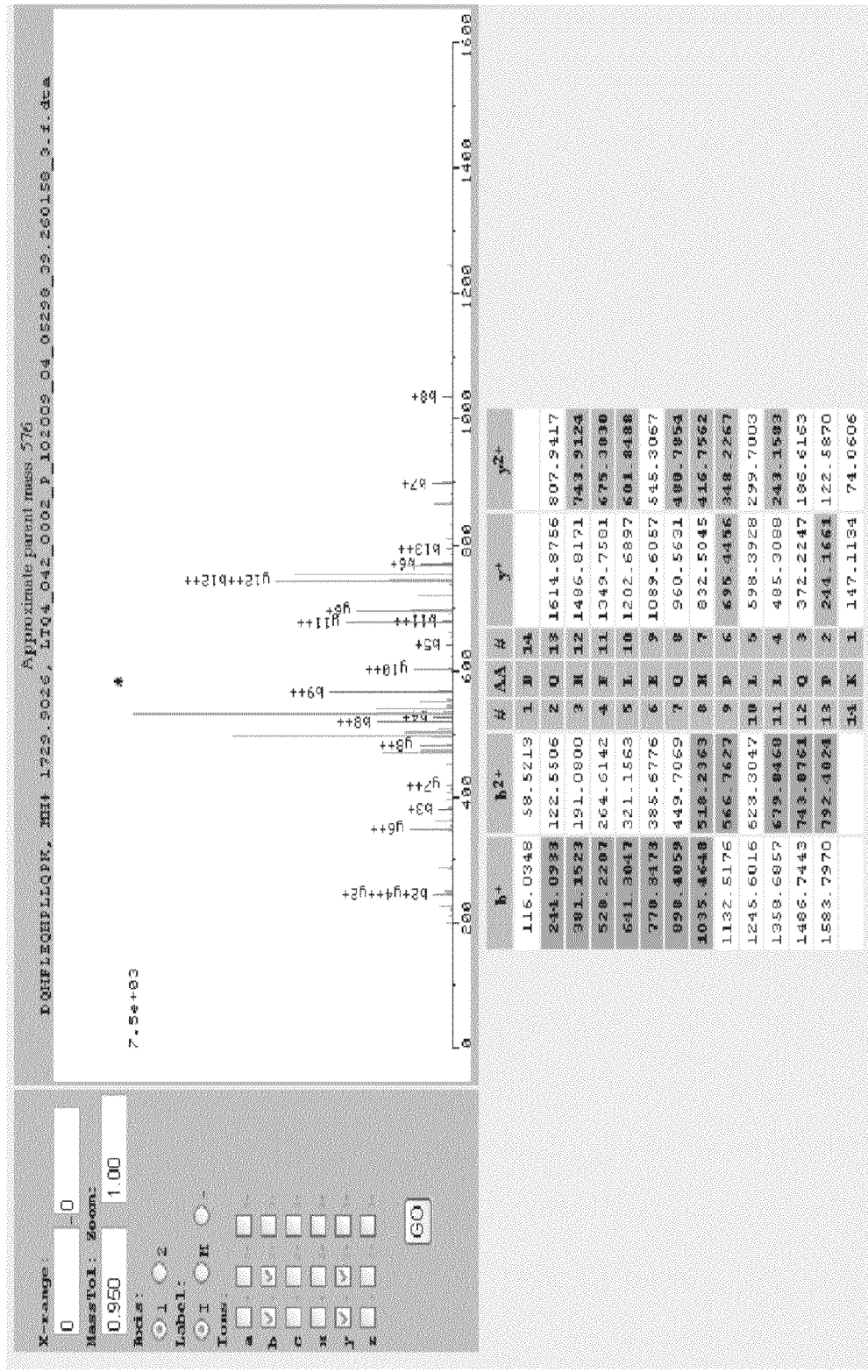
FIG. 1Y cont. -- gi|IPI00031077.1|sp|P24864-1|rs|NP_001229|NP_001229.1_Isoform E1L of G1/S-specific cyclin-E1|gs|CCNE1
LY400495

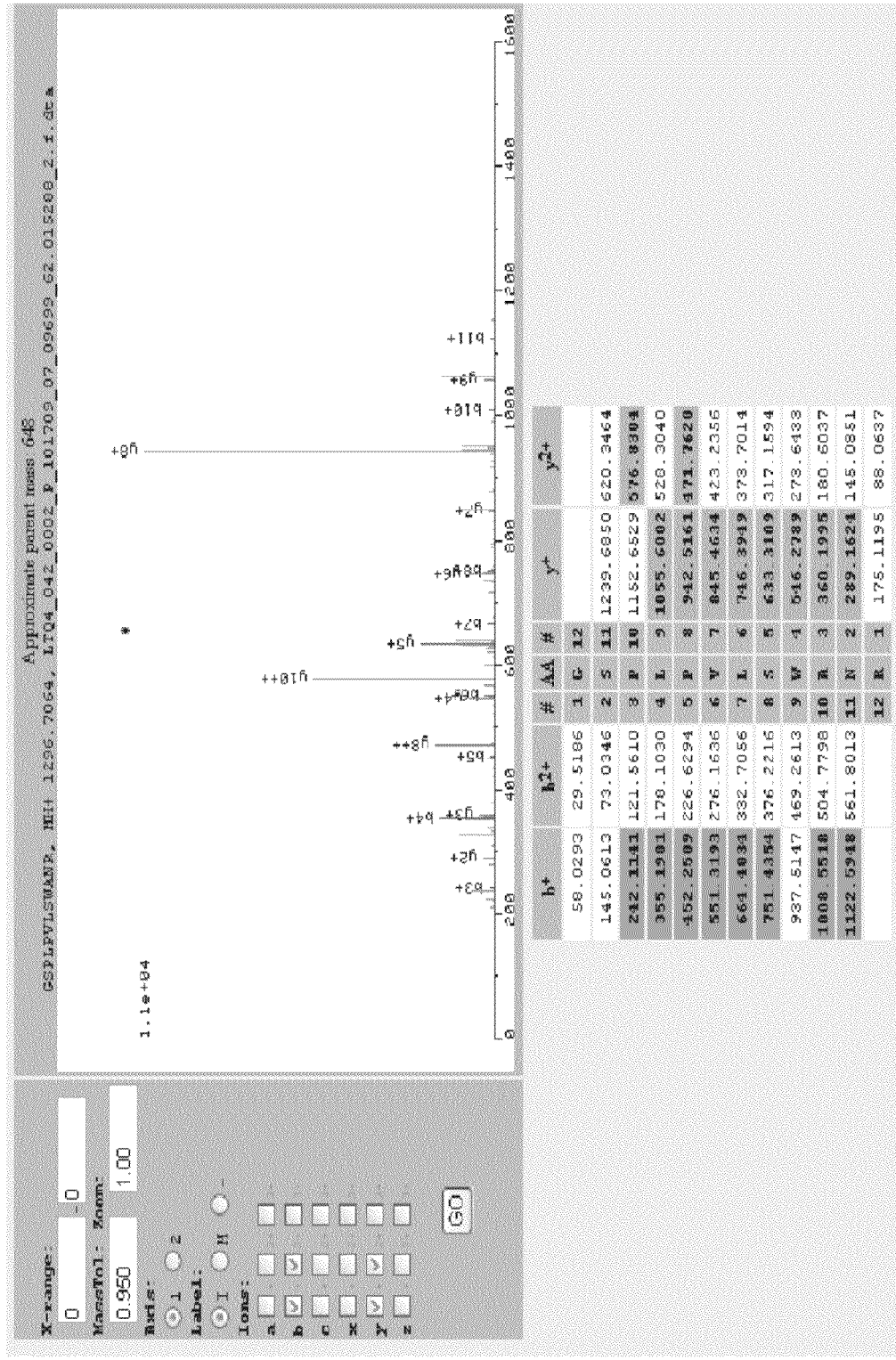
FIG. 1Z cont. -- gi|IPI00031077.1|sp|P24864-1|rs|NP_001229| NP_001229.1 Isoform E1L of G1/S-specific cyclin-E1|gs|CCNE1 LY400495

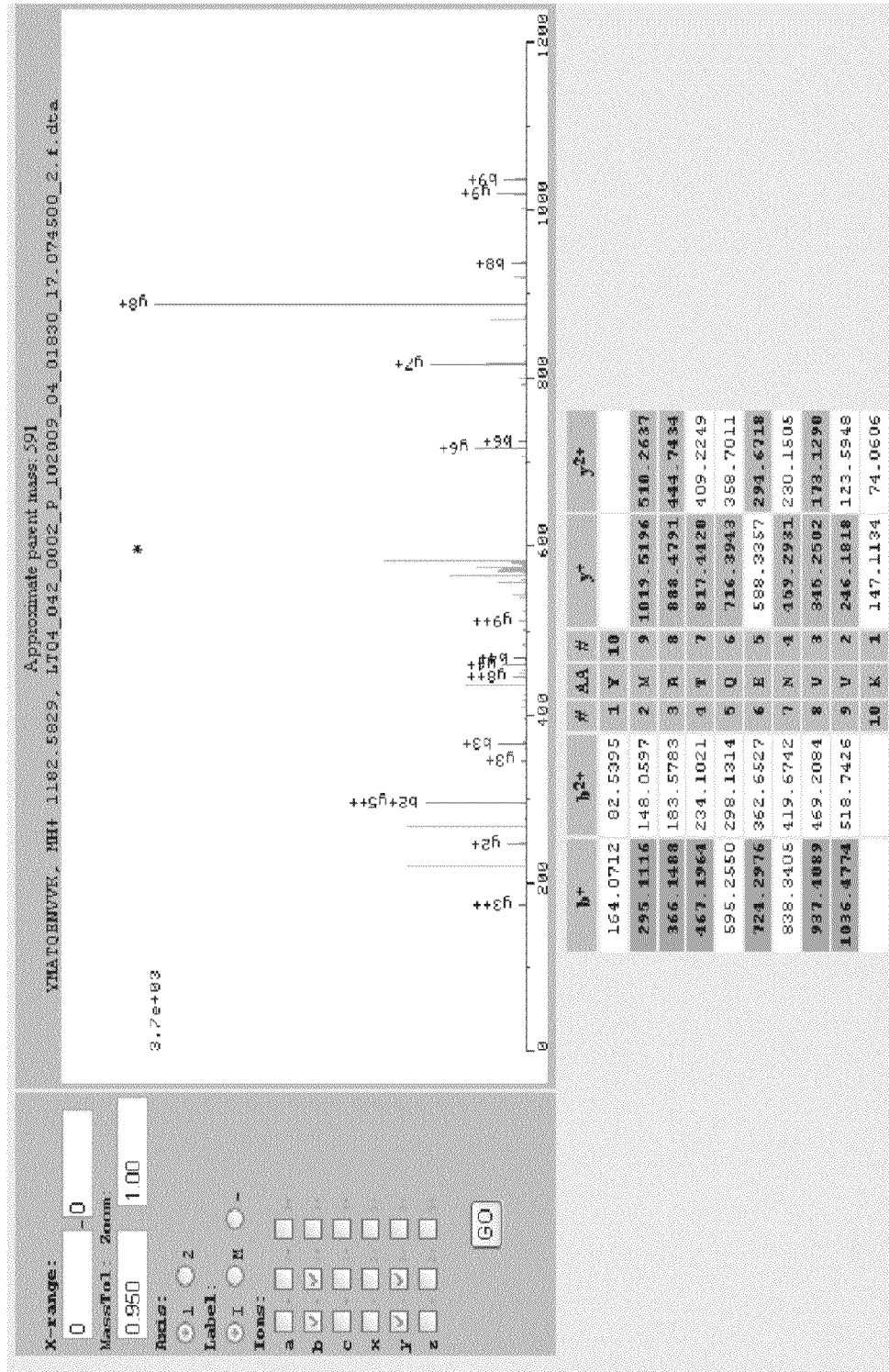
FIG. 1AA cont. -- gi|IPI00031077.1|sp|P24864-1|rs|NP_001229.1  Isoform E1L of G1/S-specific cyclin-E1|gs|CCNE1
LY400495

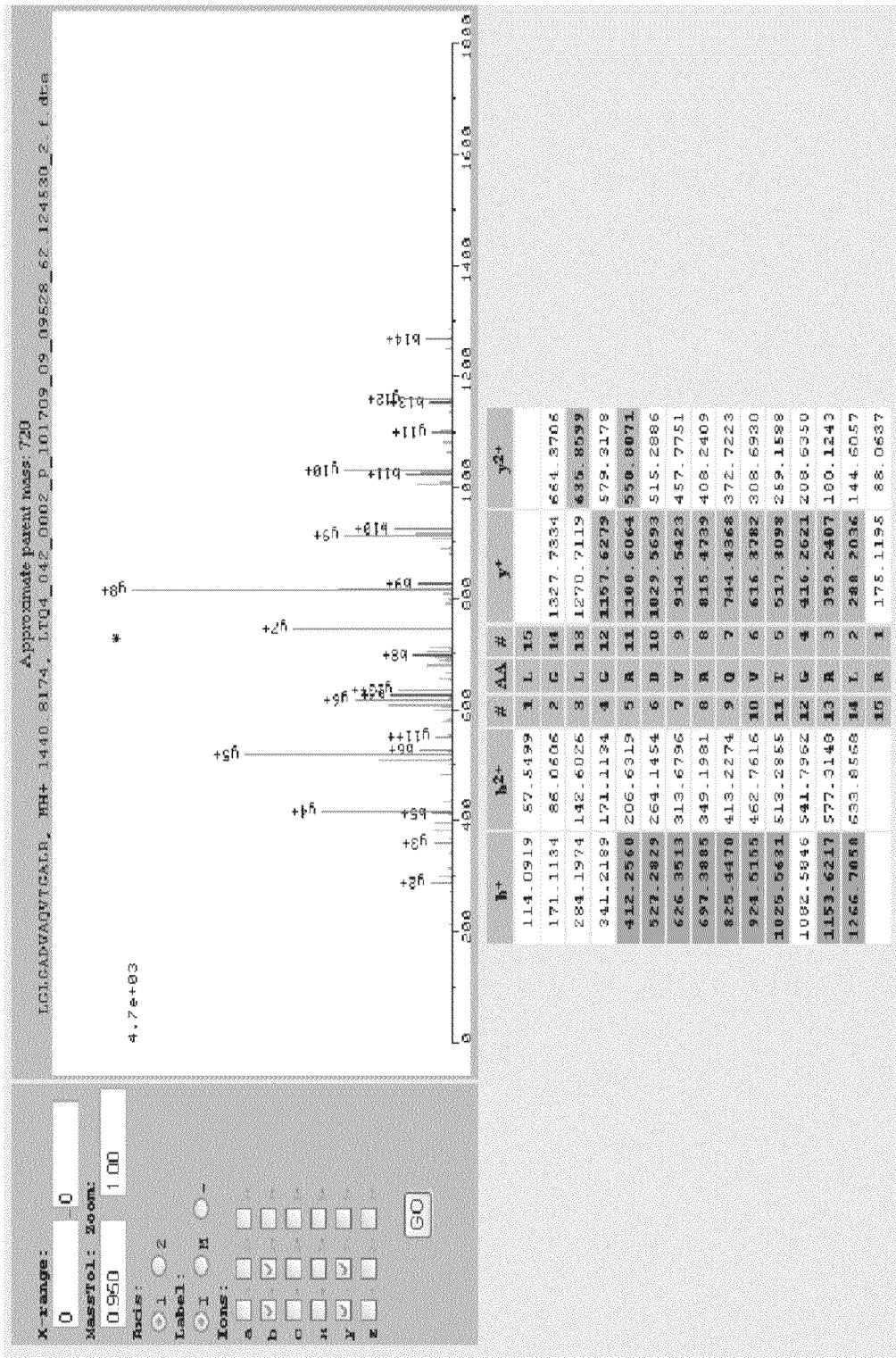
FIG. 1AB cont. -- gi|IPI00027509.4|sp|P14780|rs|NP_004985|NP_004985.2 Matrix metalloproteinase-9|gs|MMP9 LY401553

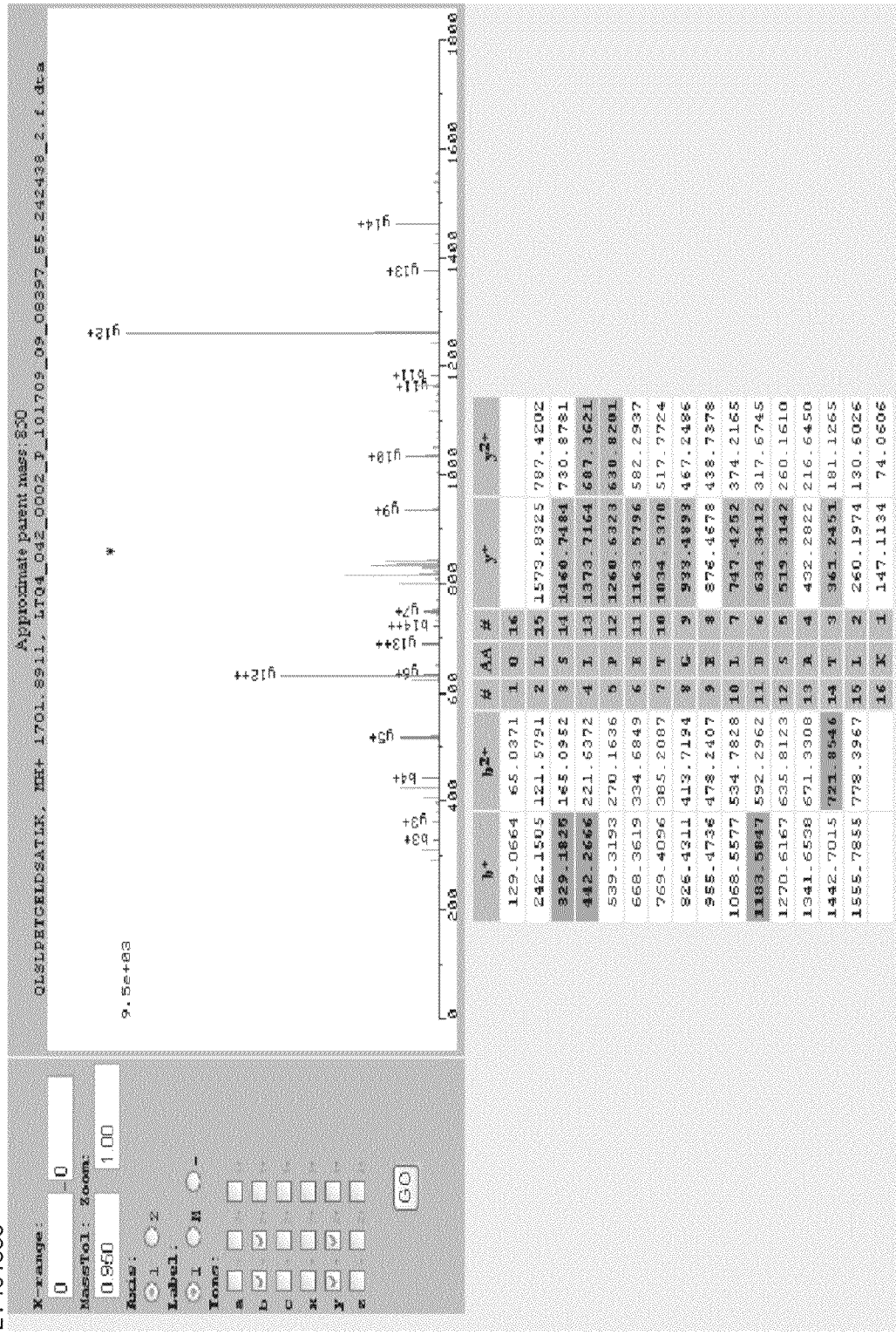
FIG. 1AC cont. -- gi|PI00027509.4|sp|P14780|rs|NP_004985] NP_004985.2 Matrix metalloproteinase-9|gs|MMP9 LY401553

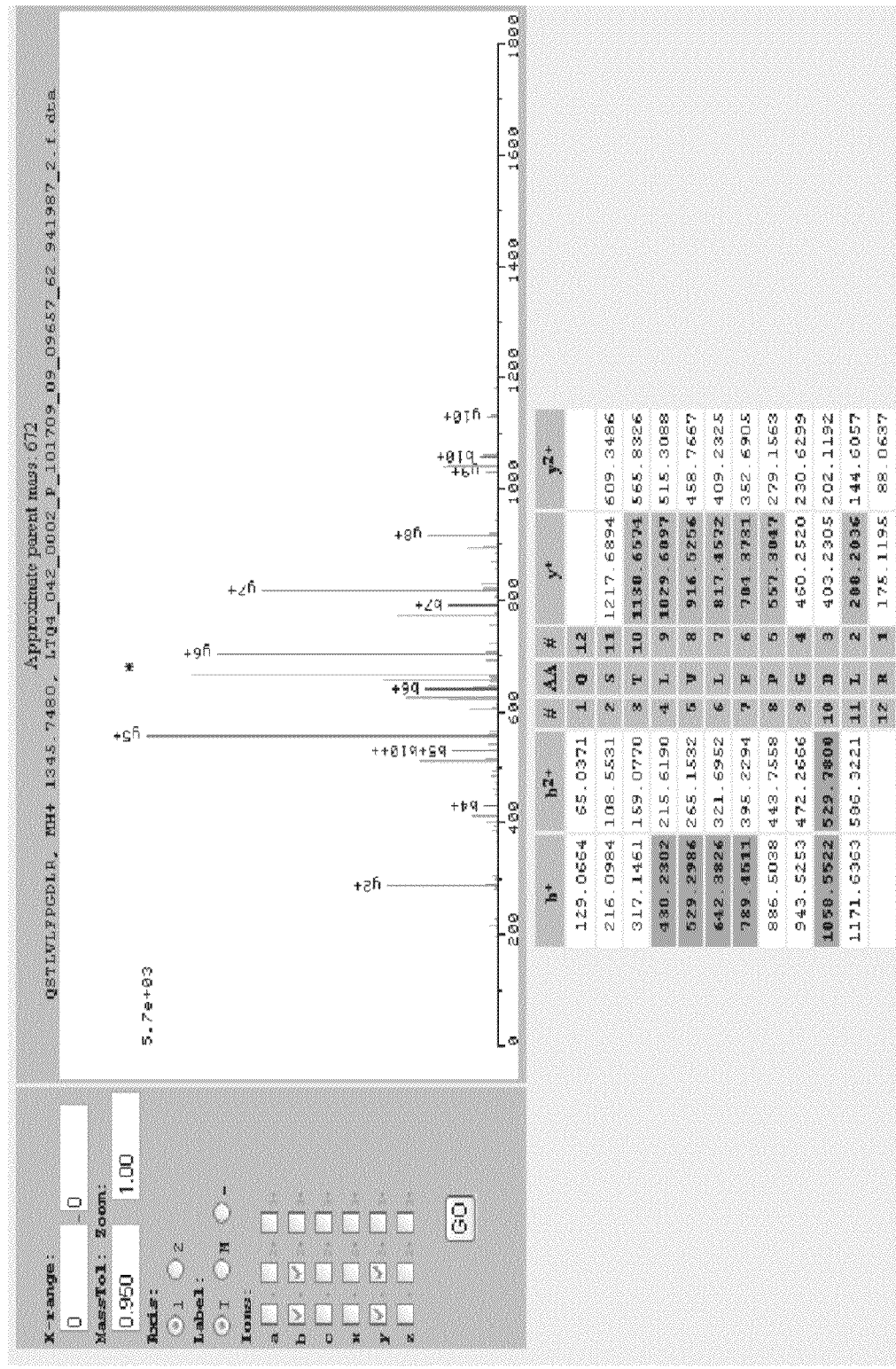
FIG. 1AD cont. -- gi|IPI00027509.4|sp|P14780|rs|NP_004985|NP_004985.2 Matrix metalloproteinase-9|gs|MMP9 LY401553

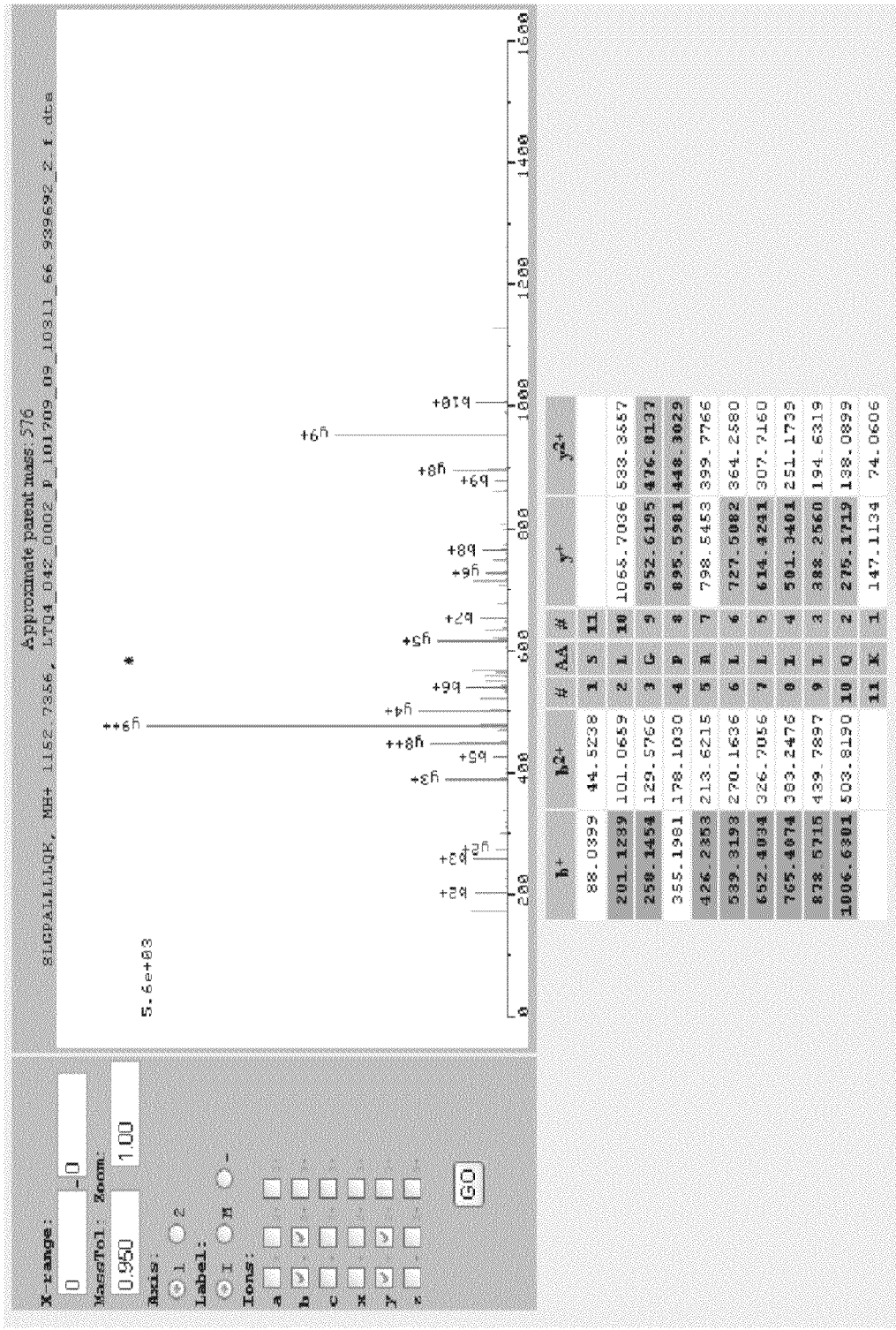
FIG. 1AE cont. -- gi|IPI00027509.4|sp|P14780|rs|NP_004985|NP_004985.2 Matrix metalloproteinase-9|gs|MMP9 LY401553

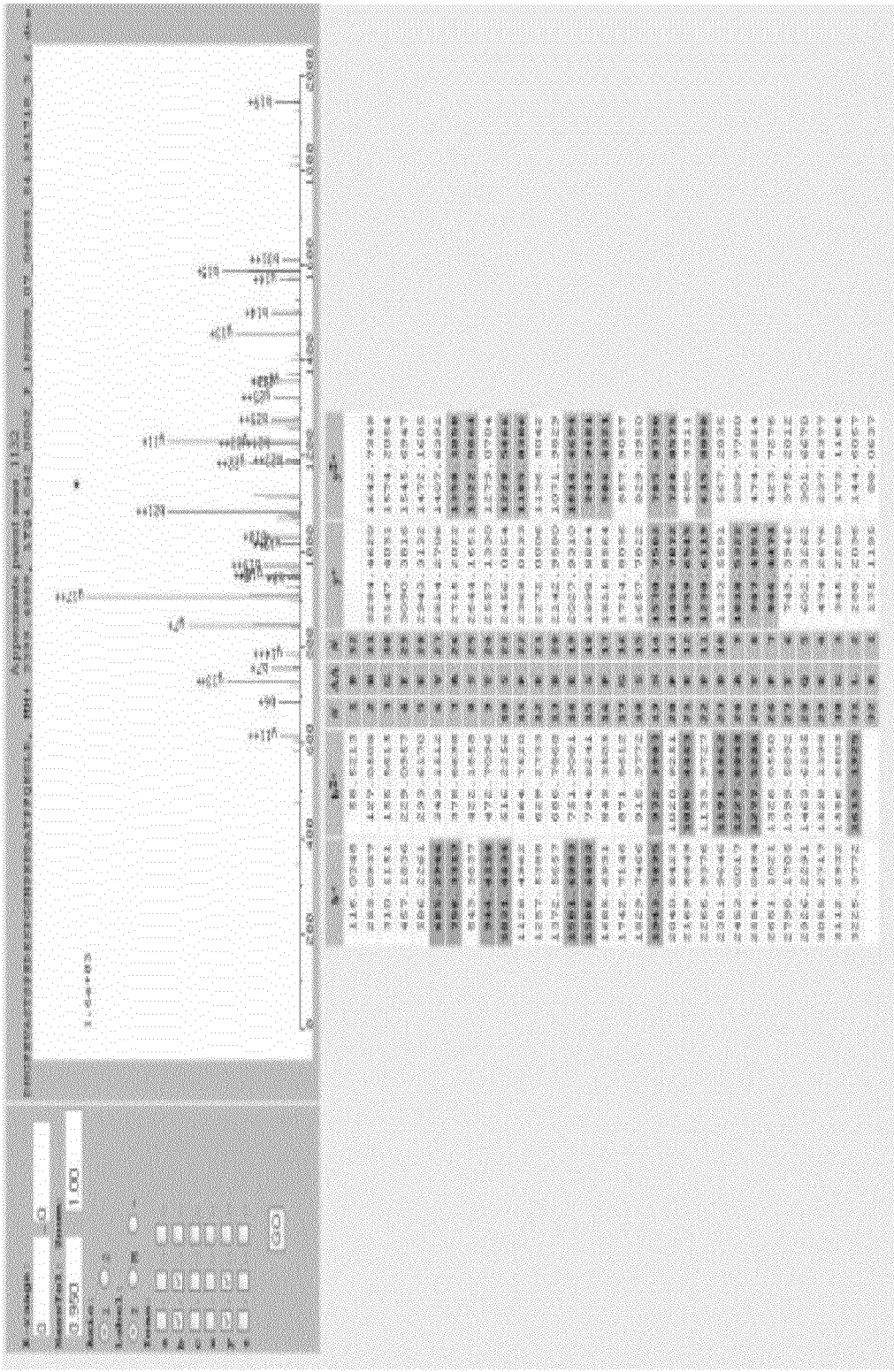
FIG. 1AG cont. -- gi|g ||IPI00216934.1|sp|P55211-2|rs|NP_127463|NP_127463.1 Isoform 2 of Caspase- 9|gs|CASP9 LY409796

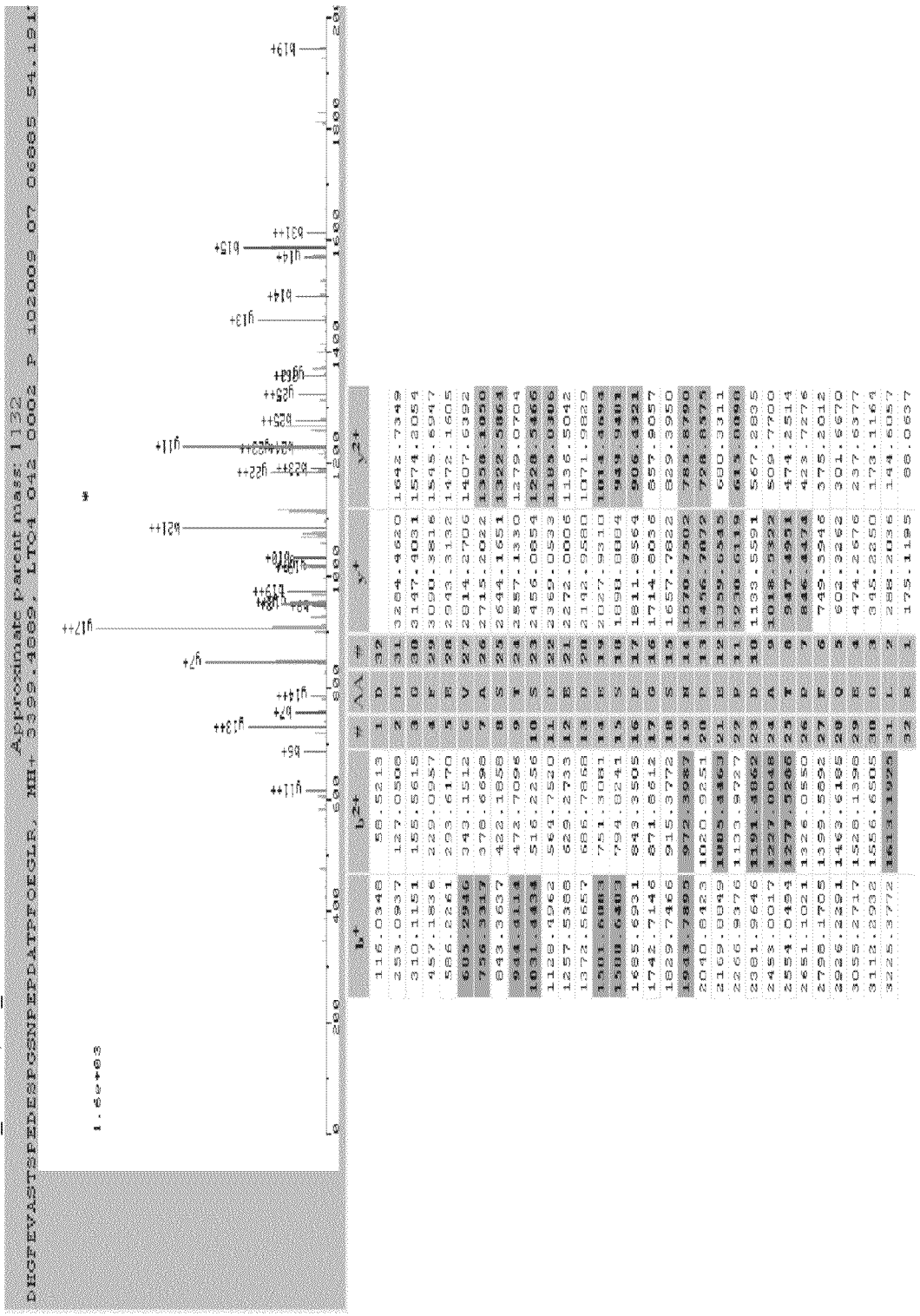
FIG. 1AH cont. NP_127463; NP_127463.1-- DHGFEVASTSPEDESPGSNPEPDATPFQEGLR, MH+ 3399.4889

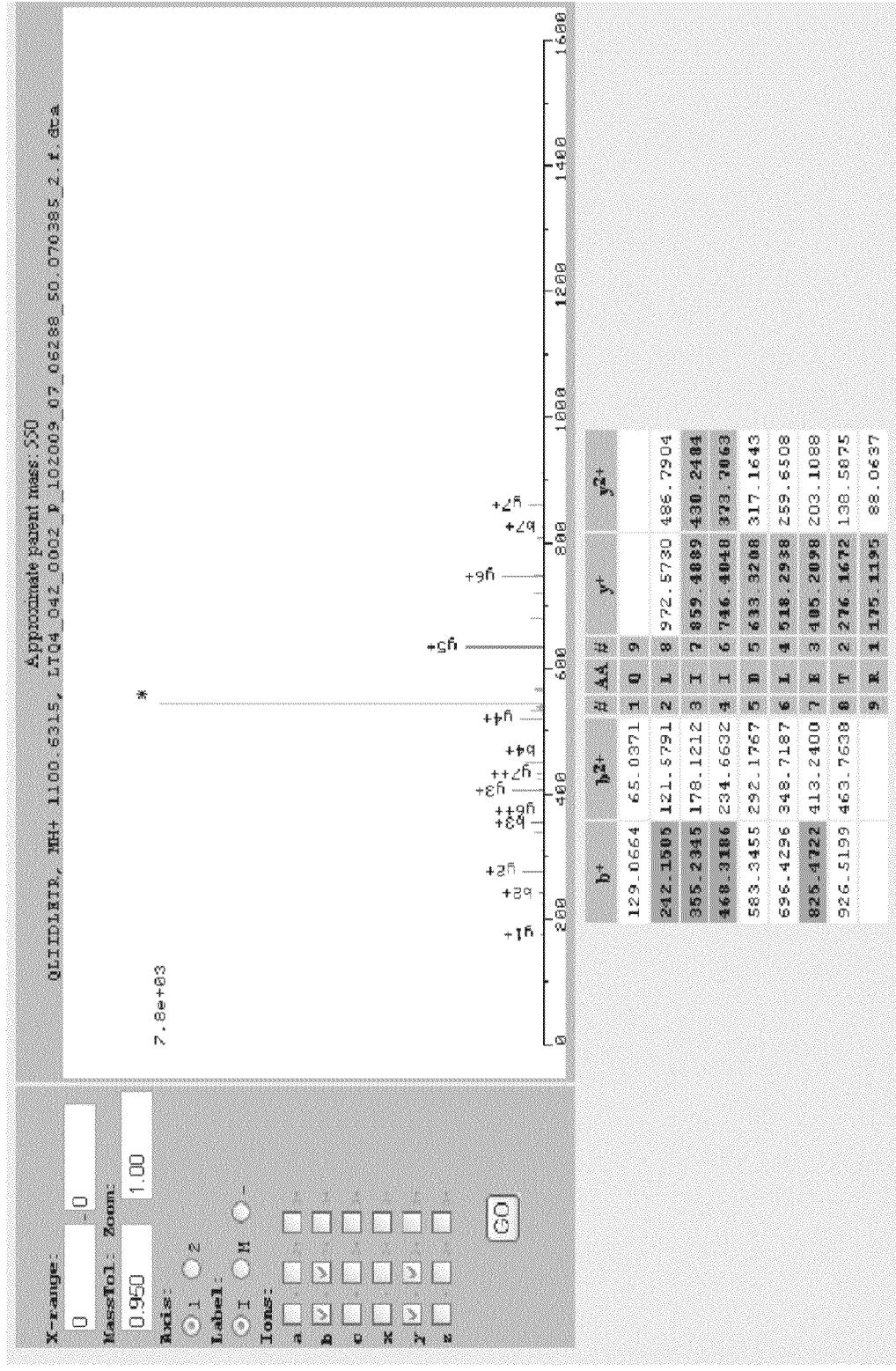
FIG. 1AI cont. -- gi|g |IPI00216934.1|sp|P55211-2|rs|NP_127463|NP_127463.1 Isoform 2 of Caspase-9|gs|CASP9 LY409796

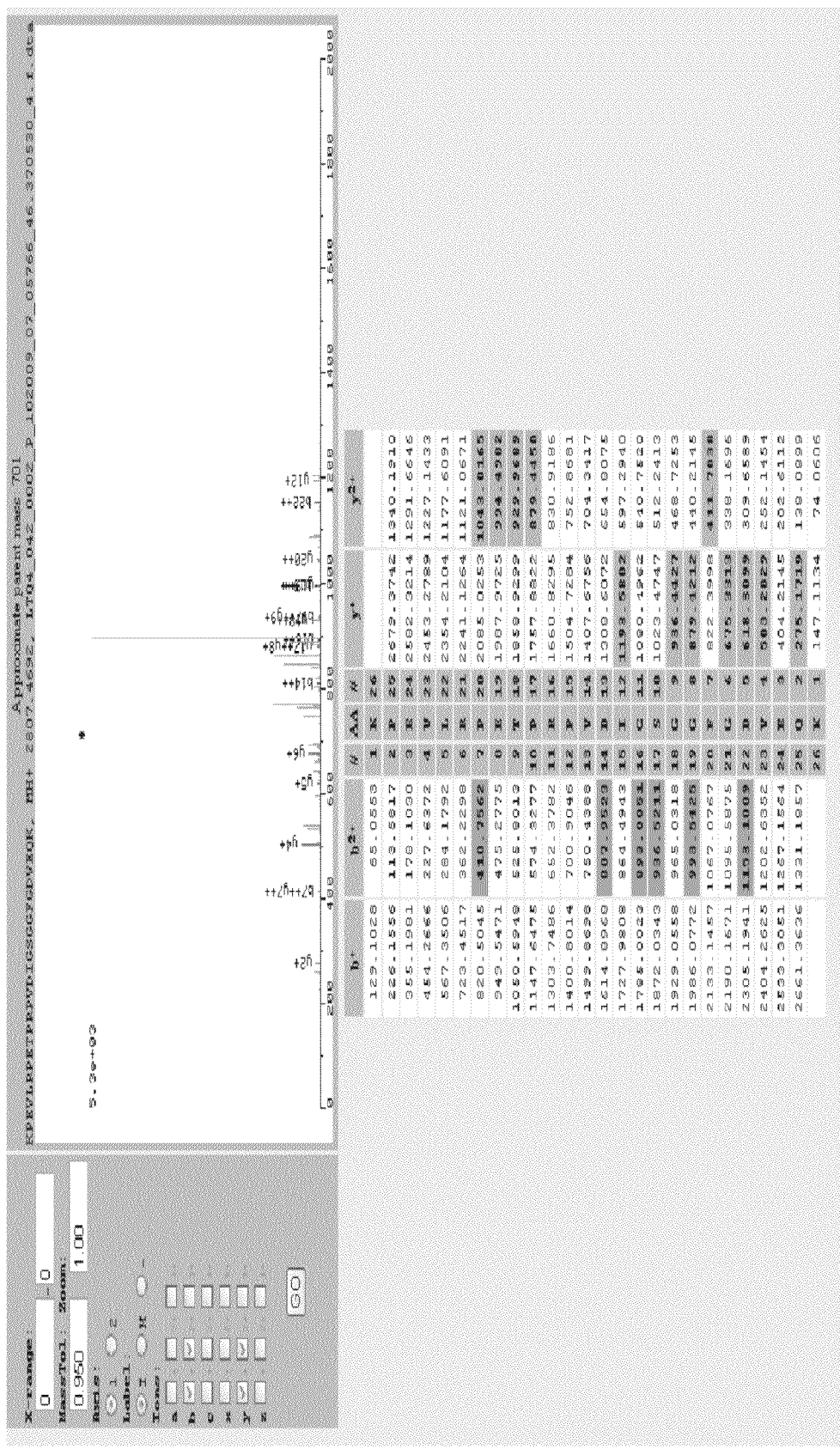
FIG. 1AJ cont. -- gi|g||IPI00216934.1|sp|P55211-2|rs|NP_127463|NP_127463.1 Isoform 2 of Caspase-9|gs|CASP9
LY409796

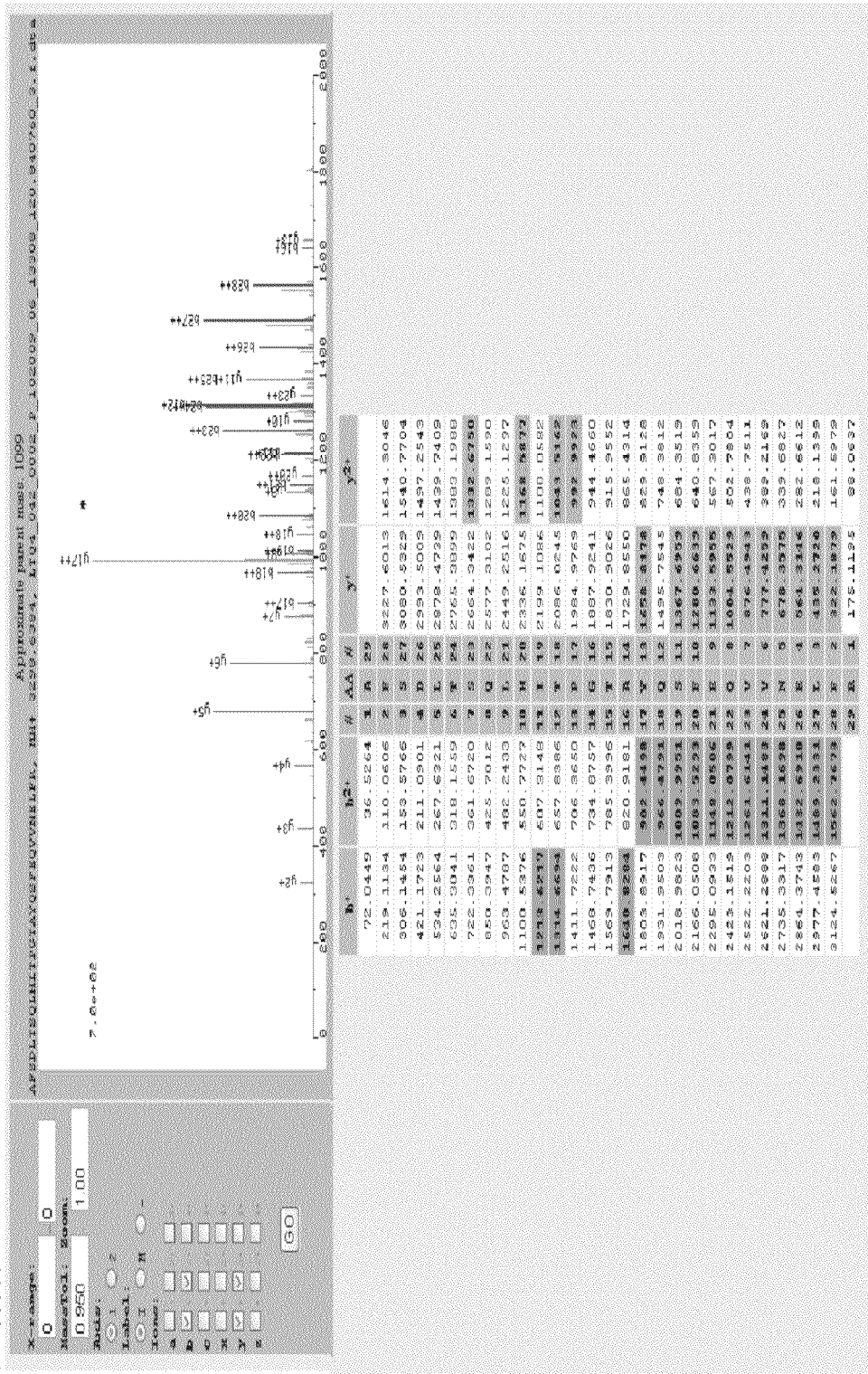
FIG. 1AK cont. -- gi||PI000019983.1|sp|Q07817-1|rs|NP_612815.1|NP_612815.1 Isoform Bcl-X(L) of Bcl-2-like protein 1|gs|BCL2L1 LY403363

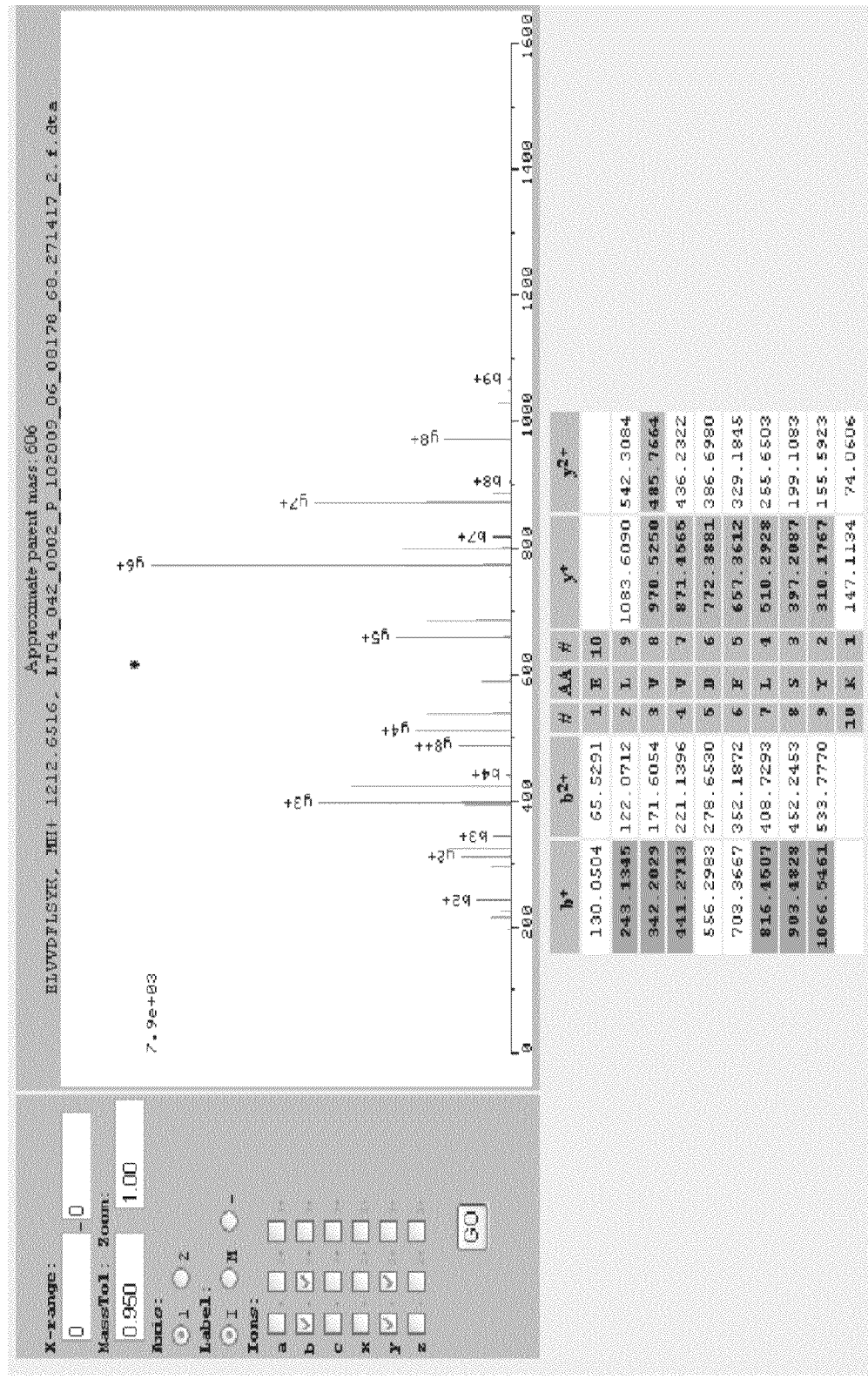
FIG. 1AL cont. -- gi|IPI00019983.1|sp|Q07817-1|rs|NP_612815.1|NP_612815.1 Isoform Bcl-X(L) of Bcl-2-like protein 1|gs|BCL2L1 LY403363

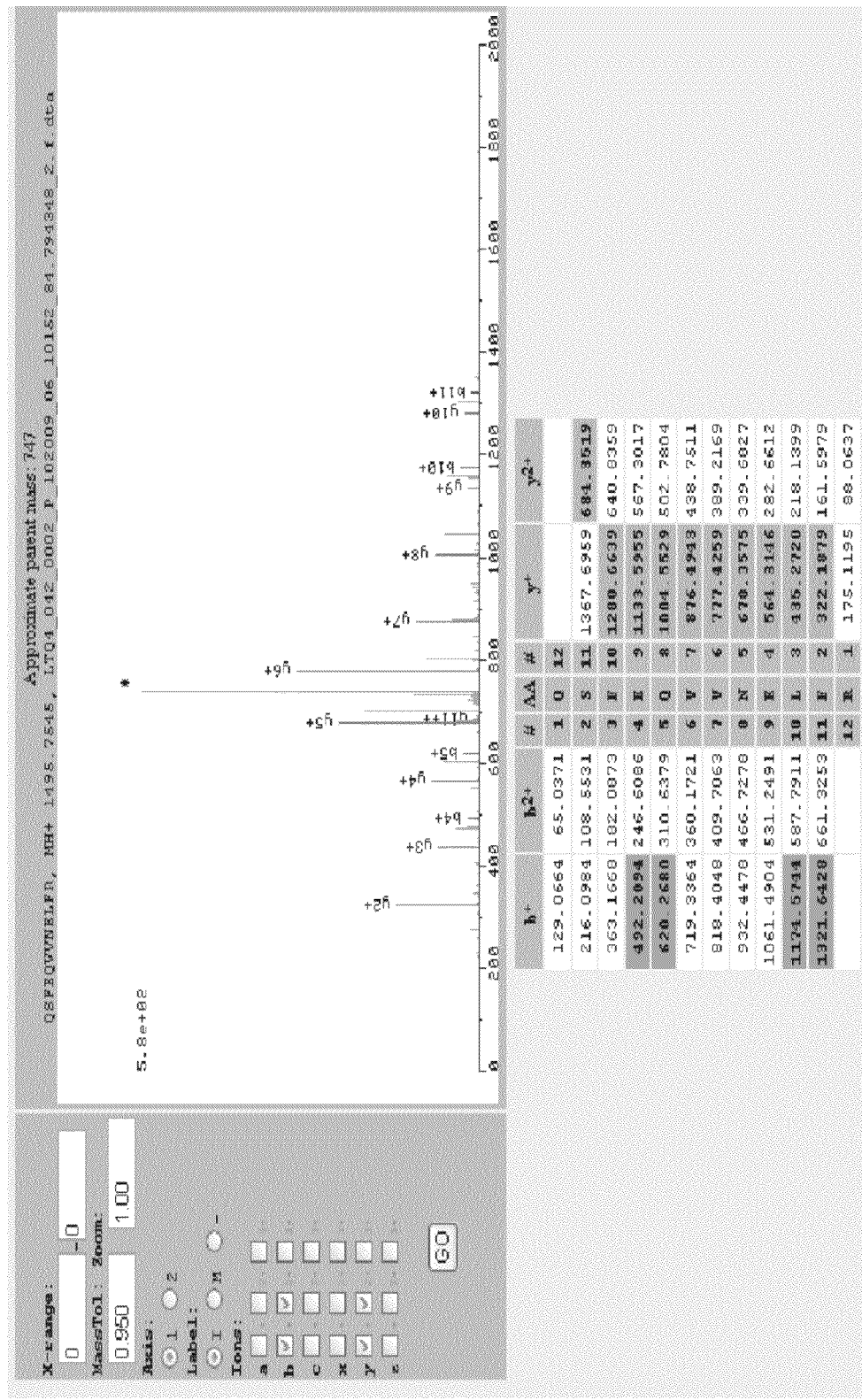
FIG. 1AM cont. -- gi|IPI00019983.1|sp|Q07817-1|rs|NP_612815| NP_612815.1 Isoform Bcl-X(L) of Bcl-2-like protein 1|gs|BCL2L1
LY403363

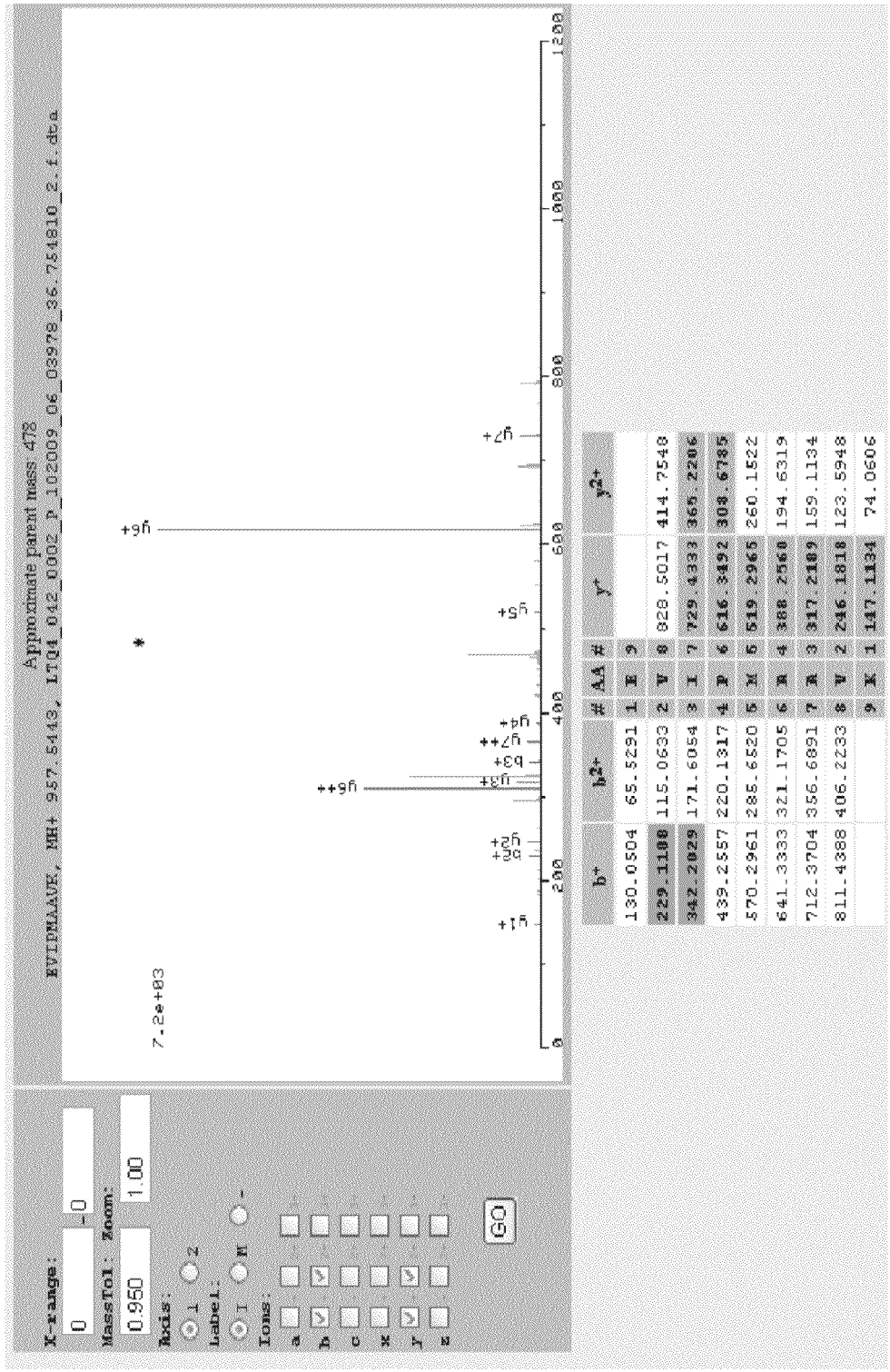
FIG. 1AN cont. -- gi|IPI00019983.1|sp|Q07817-1|rs|NP_612815|NP_612815.1 Isoform Bcl-X(L) of Bcl-2-like protein 1|gs|BCL2L1 LY403363

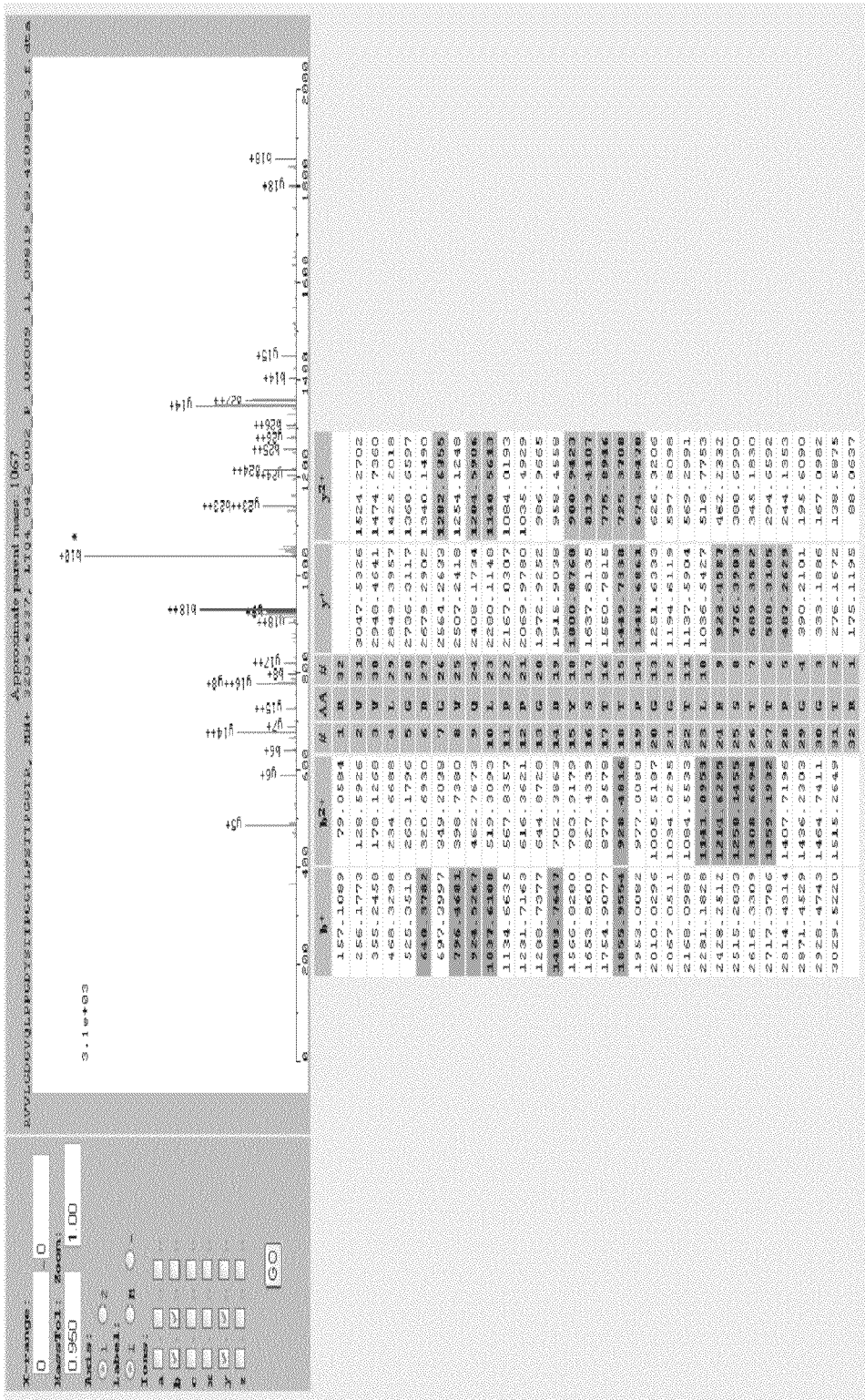
FIG. 1AO cont. -- gi|IPI00002569.3|sp|Q13541|rs|NP_004086|NP_004086.1 Eukaryotic translation initiation factor 4E-binding protein 1|gs|EIF4EBP1 LY401322

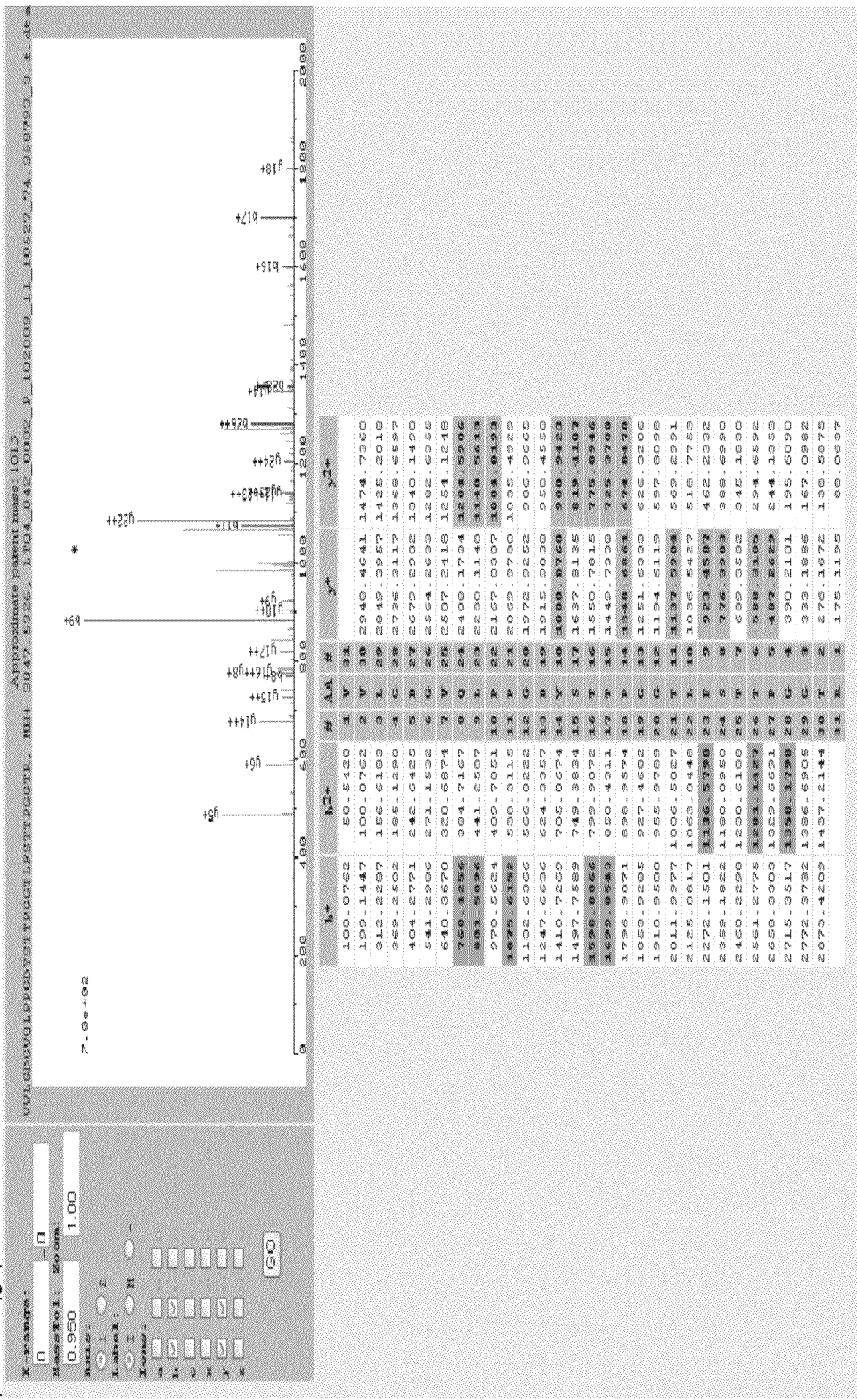
FIG. 1AP cont. -- gi|IPI00002569.3|sp|Q13541|rs|NP_004086| NP_004086.1 Eukaryotic translation initiation factor 4E-binding protein 1|gs|EIF4EBP1 LY401322

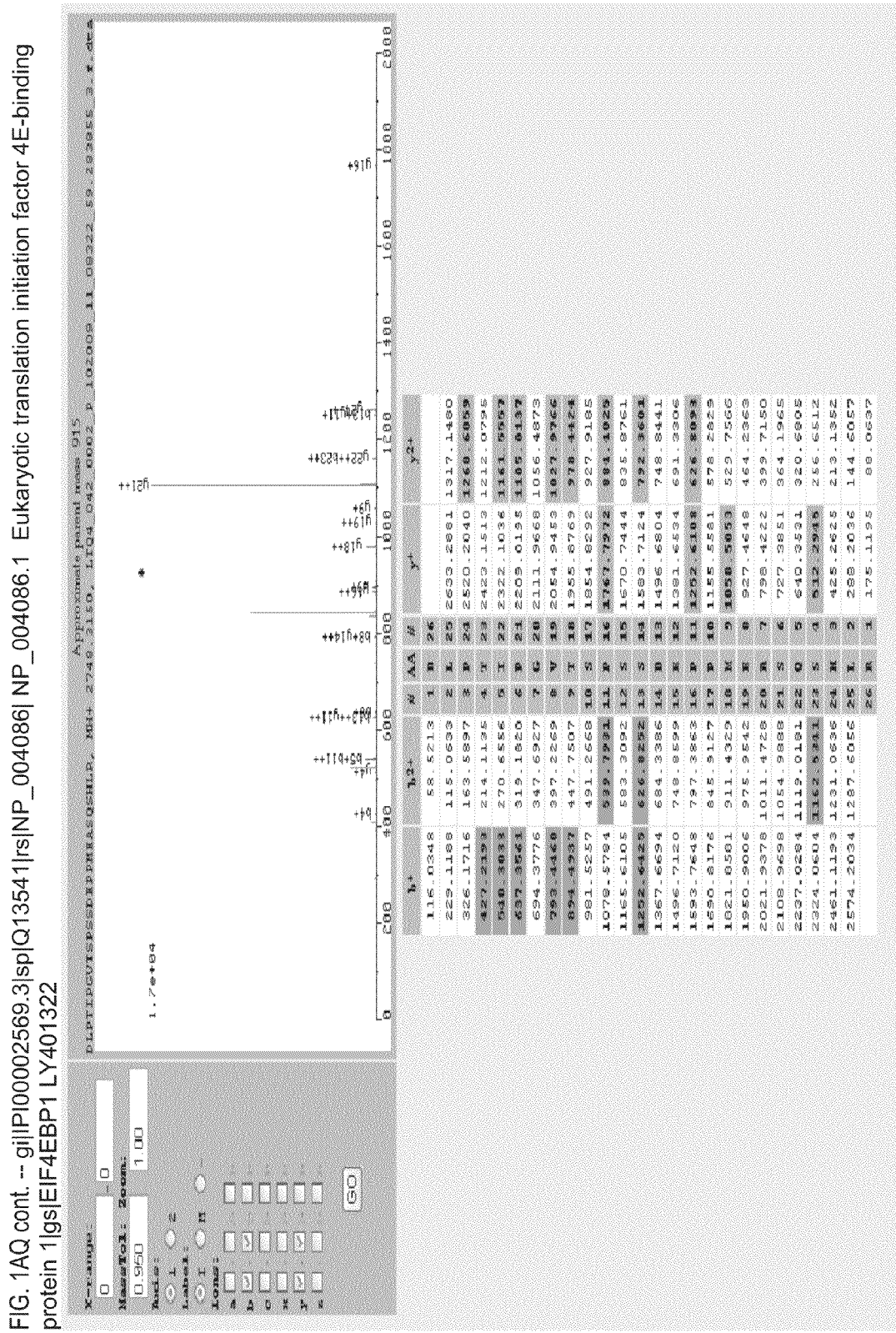
FIG. 1AQ cont. -- gi|IPI00002569.3|sp|Q13541|rs|NP_004086| NP_004086.1 Eukaryotic translation initiation factor 4E-binding protein 1|gs|EIF4EBP1 LY401322

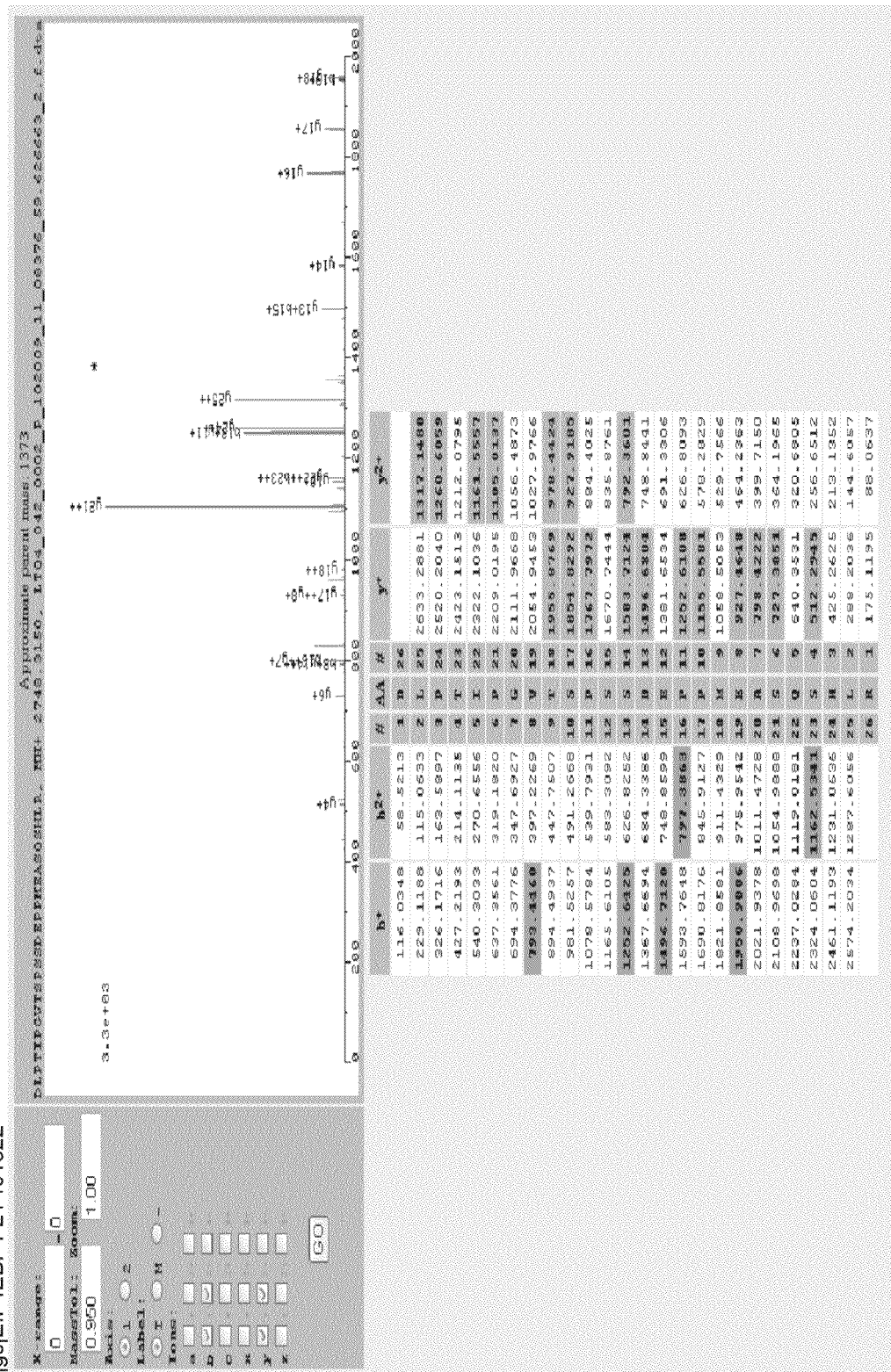
FIG. 1AR cont. -- gi||PI00002569.3|sp|Q13541|rs|NP_004086|NP_004086.1 Eukaryotic translation initiation factor 4E-binding protein 1|gs|EIF4EBP1 LY401322

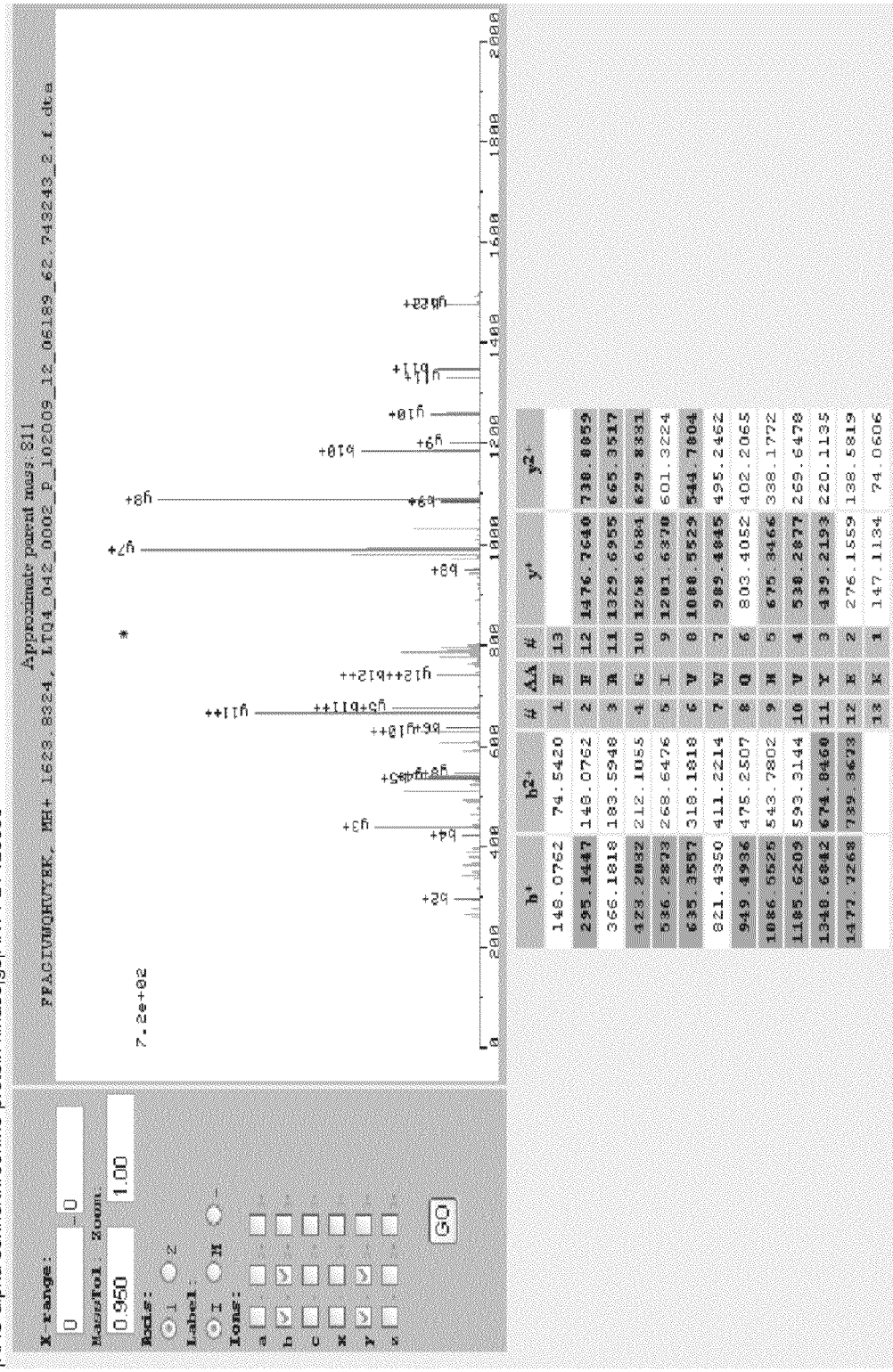
FIG. 1AS cont. -- gi|IPI00012866.2|sp|P31749|rs|NP_001014431|NP_001014431.1;NP_001014432;NP_001014432.1; NP_005154;NP_005154.2 |RAC-alpha serine/threonine-protein kinase|gs|AKT1 LY423056

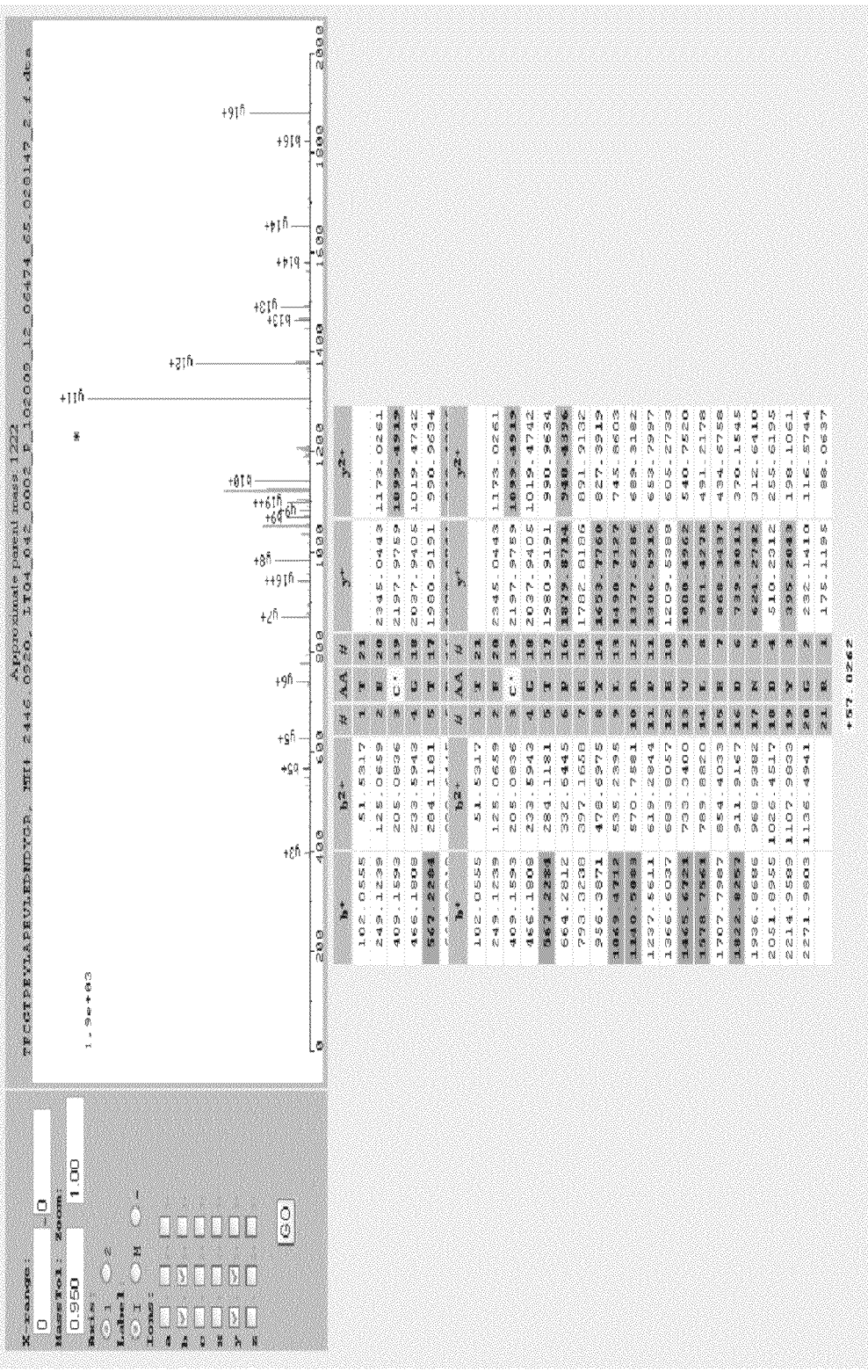
FIG. 1AT cont. --
gi|IPI00012866.2|sp|P31749|rs|NP_0010144431;NP_0010144431.1;NP_0010144432;NP_0010144321.1;NP_005154;NP_005154.2|RAC-alpha serine/threonine-protein kinase|gs|AKT1 LY423056

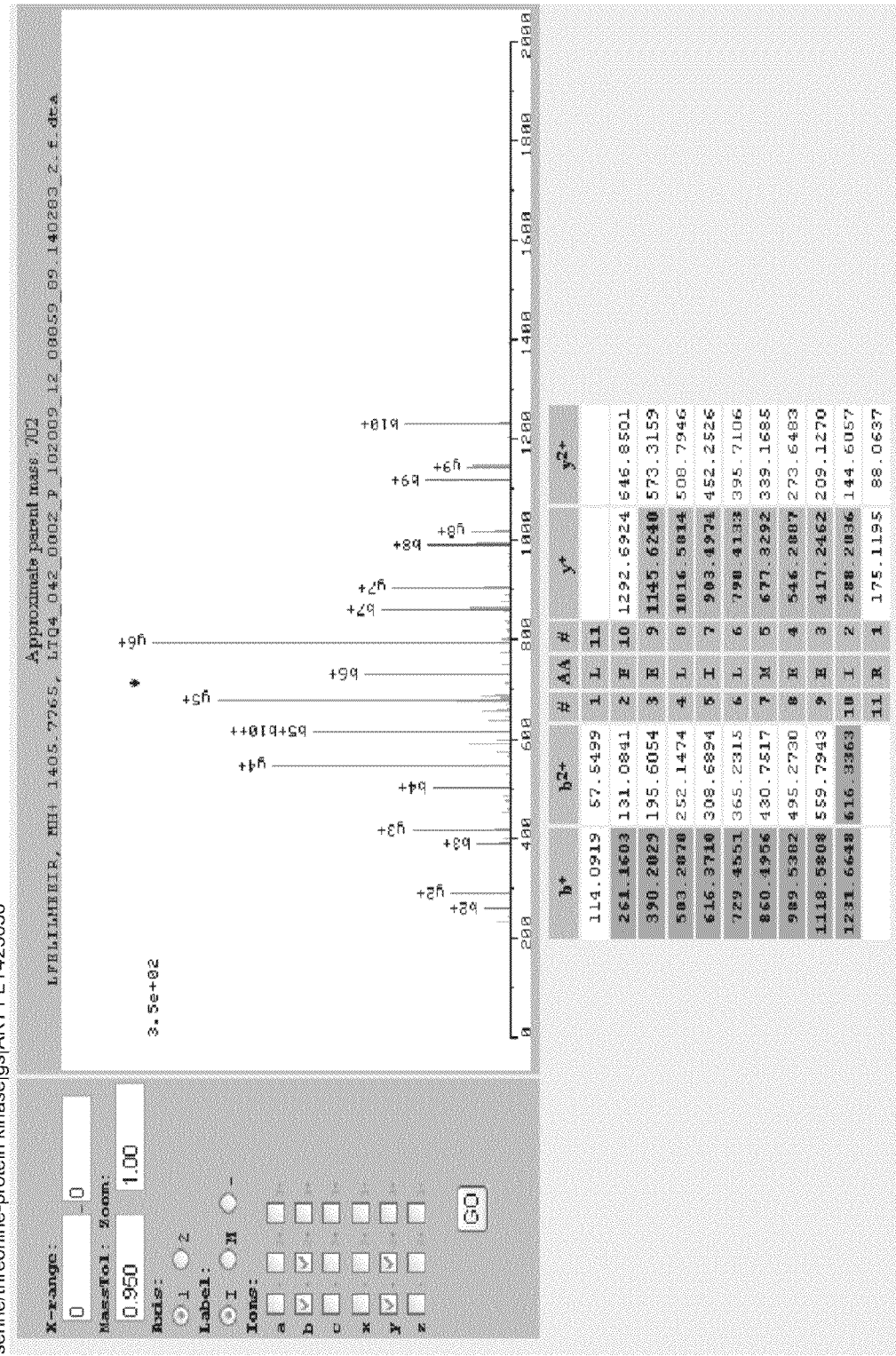
FIG. 1AV cont. --
gi|IPI00012866.2|sp|P31749|rs|NP_001014431;NP_001014431.1;NP_001014432;NP_001014432.1;NP_005154;NP_005154.2|RAC-alpha serine/threonine-protein kinase|gs|AKT1 LY423056

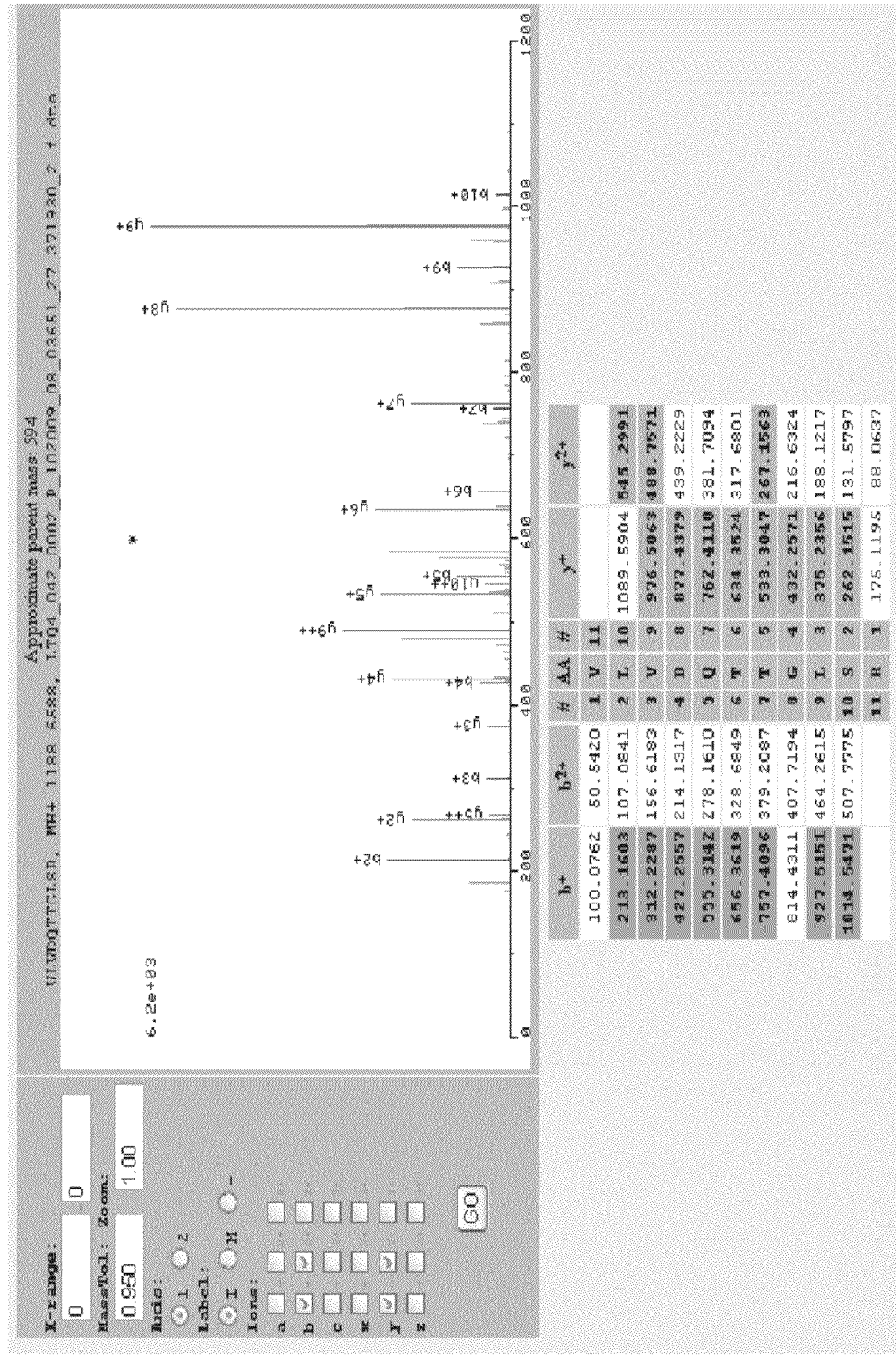
FIG. 1AW cont. -- gi|IPI00301936.4|sp|Q15717|rs|NP_001410;NP_001410.2| cDNA FLJ60076, highly similar to ELAV-like protein 1|gs|ELAVL1 LY400549

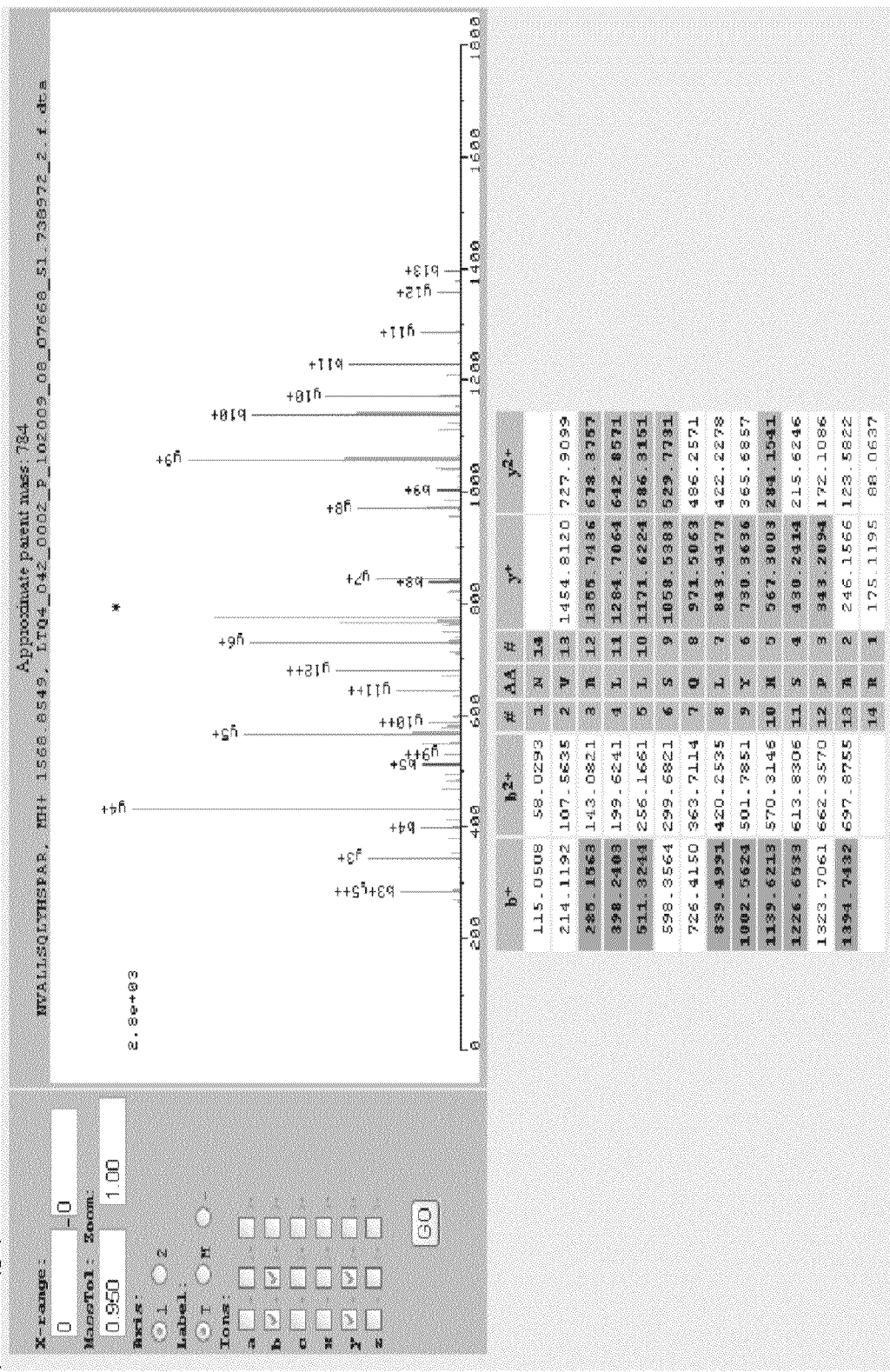
FIG. 1AX cont. — gi|PI00301936.4|sp|Q15717|rs|NP_001410;NP_001410.2| cDNA FLJ60076, highly similar to ELAV-like protein 1|gs|ELAVL1 LY400549

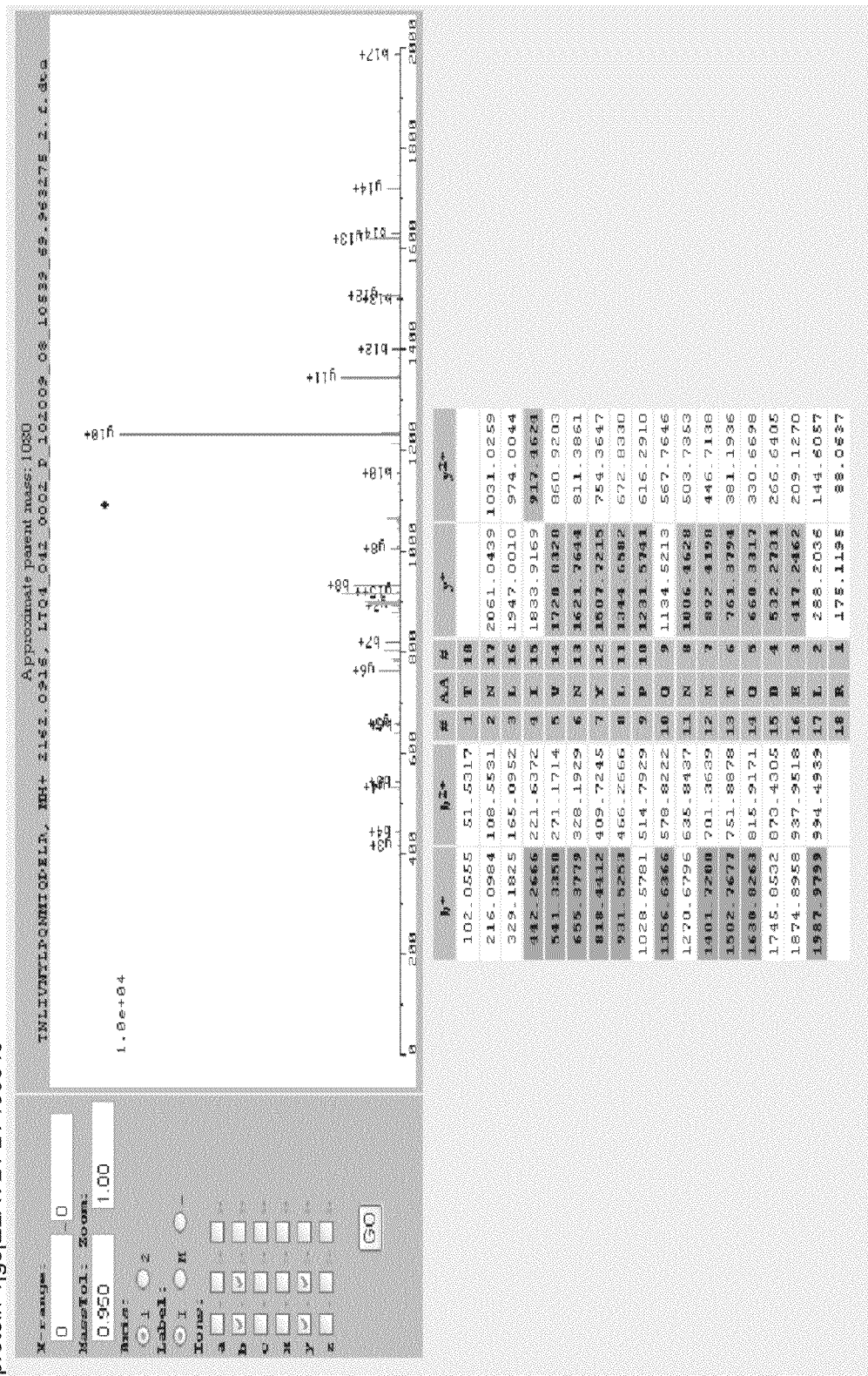
FIG. 1AY cont. -- gi|IPI00301936.4|sp|Q15717|rs|NP_001410; NP_001410.2| cDNA FLJ60076, highly similar to ELAV-like protein 1|gs|ELAVL1 LY400549

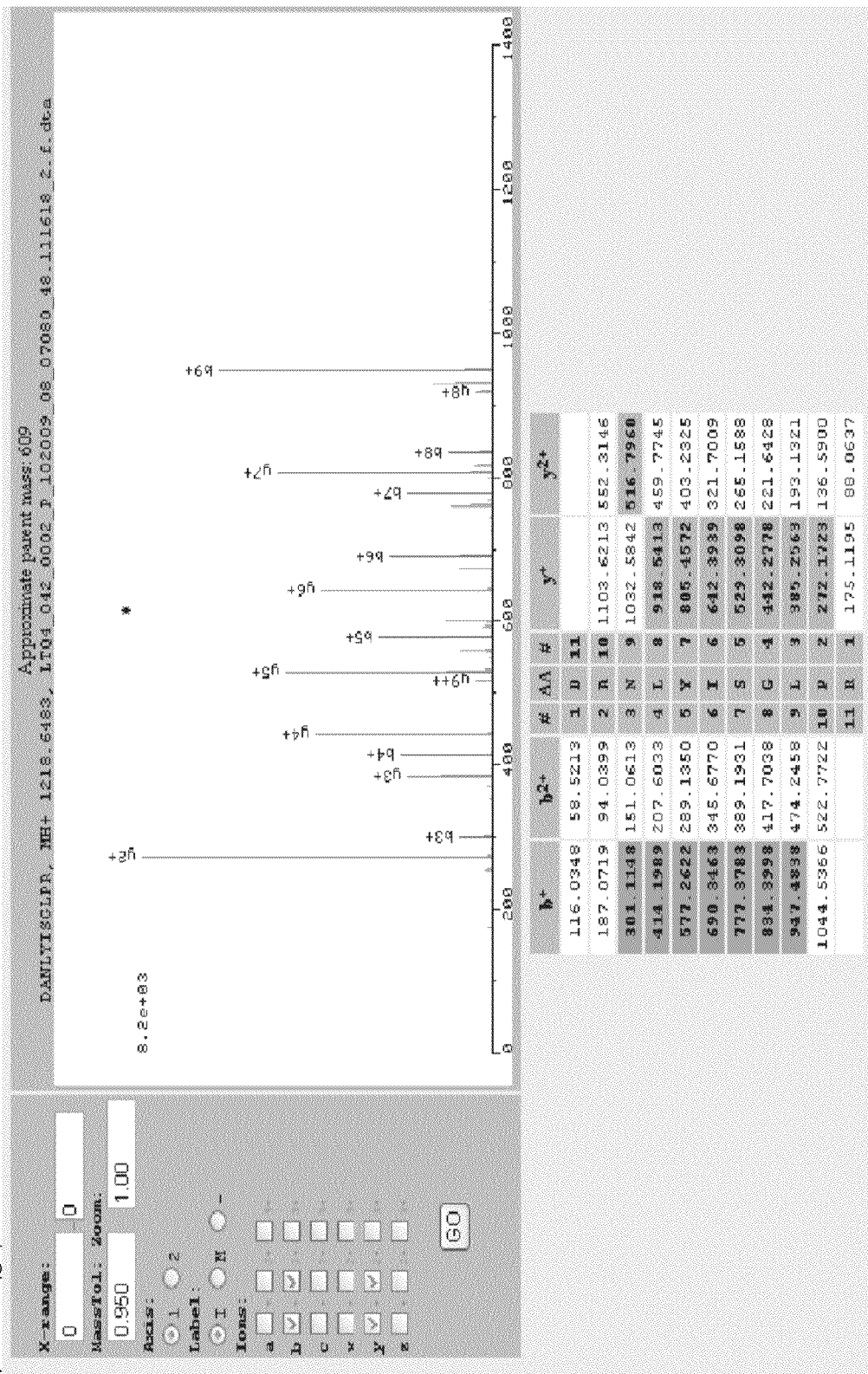
FIG. 1AZ cont. -- gi|IPI00301936.4|sp|Q15717|rs|NP_001410;NP_001410.2| cDNA FLJ60076, highly similar to ELAV-like protein 1|gs|ELAVL1 LY400549

EIF4E .. MS/MS spectra of IVIGYQSMADTATK gi|IPI00020961.1|sp|P10415-1|rs|NP_000624| Isoform Alpha of
Apoptosis regulator Bcl-2|gs|BCL2  NP_000624.2

MS/MS chromatogram of peptide FATVVEELFR gi|IPI00018274.1|sp|P00533-1|rs|NP_005219| Isoform 1 of Epidermal growth factor receptor|gs|EGFR  NP_005219.2

MS/MS chromatogram of peptide GDSFTHTPPLDPQELDILK gi|IPI00018274.1|sp|P00533-1|rs|NP_005219| Isoform 1 of Epidermal growth factor receptor|gs|EGFR  NP_005219.2

MS/MS chromatogram of peptide IPLENLQIIR gi|IPI00020468.4|sp|Q9BQE4|rs|NP_060915;NP_982298|
Selenoprotein S|gs|SELS  NP_060915.2; NP_982298.1

MS/MS chromatogram of peptide AAAAVEPDVVVK

**gi|IPI00020468.4|sp|Q9BQE4|rs|NP_060915;NP_982298|
Selenoprotein S|gs|SELS**   NP_060915.2; NP_982298.1

MS/MS chromatogram of peptide MQEELNAQVEK gi|IPI00154603.3|sp|P09038-1|rs|NP_001997|
fibroblast growth factor 2|gs|FGF2    NP_001997.5

MS/MS chromatogram of peptide CVTDECFFFER

**gi|IPI00154603.3|sp|P09038-1|rs|NP_001997|
fibroblast growth factor 2|gs|FGF2**  NP_001997.5

MS/MS chromatogram of peptide AILFLPMSAK gi|IPI00300384.3|sp|P04626|rs|NP_004439| NP_004439.2
Receptor tyrosine-protein kinase erbB-2|gs|ERBB2

MS/MS chromatogram of peptide GIWIPDGENVK gi|IPI00300384.3|sp|P04626|rs|NP_004439| NP_004439.2
Receptor tyrosine-protein kinase erbB-2|gs|ERBB2

MS/MS chromatogram of peptide VLGSGAFGTVYK gi|IPI00218875.1|sp|P10451-3|rs|NP_001035149|
Isoform C of Osteopontin|gs|SPP1  NP_001035149.1

MS/MS chromatogram of peptide AIPVAQDLNAPSDWDSR

**gi|IPI00218875.1|sp|P10451-3|rs|NP_001035149|
Isoform C of Osteopontin|gs|SPP1** NP_001035149.1

MS/MS chromatogram of peptide GDSVVYGLR

FIGURE 2

```
SEQ ID NO: 3 (cyclin D1 NP_444284.1)
1    mehqllccev etirraypda nllndrvlra mlkaeetcap svsyfkcvqk evlpsmrkiv
61   atwmlevcee qkceeevfpl amnyldrfls lepvkksrlq llgatcmfva skmketiplt
121  aeklciytdn sirpeellqm elllvnklkw nlaamtphdf iehflskmpe aeenkqiirk
181  haqtfvalca tdvkfisnpp smvaagsvva avqglnlrsp nnflsyyrlt rflsrvikcd
241  pdclracqeq ieallesslr qaqqnmdpka aeeeeeeeee vdlactptdv rdvdi SEQ ID NO: 4 (Vascular endothelial growth factor A NP_003367.4)
1    mtdrqtdtap spsyhllpgr rrtvdaaasr gqgpepapgg gvegvgargv alklfvqllg
61   csrfggavvr ageaepsgaa rsassgreep qpeegeeeee keeergpqwr lgarkpgswt
121  geaavcadsa paarapqala rasgrggrva rrgaeesgpp hspsrrgsas ragpgraset
181  mnfllswvhw slalllylhh akwsqaapma egggqnhhev vkfmdvyqrs ychpietlvd
241  ifqeypdeie yifkpscvpl mrcggccnde glecvptees nitmqimrik phqgqhigem
301  sflqhnkcec rpkkdrarqe kksvrgkgkg qkrkrkksry kswsvpcgpc serrkhlfvq
361  dpqtckcsck ntdsrckarq lelnertcrc dkprr SEQ ID NO: 5 (ornithine decarboxylase 1 NP_002530.1)
1    mnnfgneefd chfldegfta kdildqkine vsssddkdaf yvadlgdilk khlrwlkalp
61   rvtpfyavkc ndskaivktl aatgtgfdca skteiqlvqs lgvpperiiy anpckqvsqi
121  kyaanngvqm mtfdsevelm kvarahpkak lvlriatdds kavcrlsvkf gatlrtsrll
181  lerakelnid vvgvsfhvgs gctdpetfvq aisdarcvfd mgaevgfsmy lldigggfpg
241  sedvklkfee itgvinpald kyfpsdsgvr iiaepgryyv asaftlavni iakkivlkeq
301  tgsddedess eqtfmyyvnd gvygsfncil ydhahvkpll qkrpkpdeky ysssiwgptc
361  dgldriverc dlpemhvgdw mlfenmgayt vaaastfngf qrptiyyvms gpawqlmqqf
421  qnpdfppeve eqdastlpvs cawesgmkrh raacasasin v SEQ ID NO: 6: (nibrin NP_002476.2)
1    mwkllpaagp aggepyrllt gveyvvgrkn cailiendqs isrnhavlta nfsvtnlsqt
61   deipvltlkd nskygtfvne ekmqngfsrt lksgdgitfg vfgskfriey eplvacsscl
121  dvsgktalnq ailqlggftv nnwteecthl vmvsvkvtik ticalicgrp ivkpeyftef
181  lkaveskkqp pqiesfyppl depsigsknv dlsgrqerkq ifkgktfifl nakqhkklss
241  avvfgggear liteeneeeh nfflapgtcv vdtgitnsqt lipdcqkkwi qsimdmlqrq
301  glrpipeaei glavifmttk nycdpqghps tglktttpgp slsqgvsvde klmpsapvnt
361  ttyvadtese qadtwdlser pkeikvskme qkfrmlsqda ptvkesckts snnnsmvsnt
421  lakmripnyq lsptklpsin kskdrasqqq qtnsirnyfq pstkkrerde enqemsscks
481  arietscsll eqtqpatpsl wknkeqhlse nepvdtnsdn nlftdtdlks ivknsasksh
541  aaeklrsnkk remddvaied evleqlfkdt kpeleidvkv qkqeedvnvr krprmdietn
601  dtfsdeavpe sskisqenei gkkrelkeds lwsakeisnn dklqddseml pkkllltefr
661  slviknstsr npsginddyg qlknfkkfkk vtypgagklp hiiggsdlia hharkntele
721  ewlrqemevq nqhakeesla ddlfrynpyl krrr SEQ ID NO: 7: (pim-1 oncogene  NP_002639.1)
1    mllskinsla hlraapcndl hatklapgke keplesqyqv gpllgsggfg svysgirvsd
61   nlpvaikhve kdrisdwgel pngtrvpmev vllkkvssgf sgvirlldwf erpdsfvlil
121  erpepvqdlf dfitergalq eelarsffwq vleavrhchn cgvlhrdikd enilidlnrg
181  elklidfgsg allkdtvytd fdgtrvyspp ewiryhryhg rsaavwslgi llydmvcgdi
241  pfehdeeiir gqvffrqrvs secqhlirwc lalrpsdrpt feeiqnhpwm qdvllpqeta
301  eihlhslspg psk
```

FIGURE 2 (continued)

```
SEQ ID NO: 8 (v-akt murine thymoma viral oncogene homolog 1  NP_001014432.1)
1    msdvaivkeg wlhkrgeyik twrpryfllk ndgtfigyke rpqdvdqrea plnnfsvaqc
61   qlmkterprp ntfiirclqw ttviertfhv etpeereewt taiqtvadgl kkqeeeemdf
121  rsgspsdnsg aeemevslak pkhrvtmnef eylkllgkgt fgkvilvkek atgryyamki
181  lkkevivakd evahtltenr vlqnsrhpfl talkysfqth drlcfvmeya nggelffhls
241  rervfsedra rfygaeivsa ldylhseknv vyrdlklenl mldkdghiki tdfglckegi
301  kdgatmktfc gtpeylapev ledndygrav dwwglgvvmy emmcgrlpfy nqdheklfel
361  ilmeeirfpr tlgpeaksll sgllkkdpkq rlgggsedak eimqhrffag ivwqhvyekk
421  lsppfkpqvt setdtryfde eftaqmitit ppdqddsmec vdserrphfp qfsysasgta SEQ ID NO: 9 (Eukaryotic translation initiation factor 4E binding protein 1
NP_004086.1)
1    msggsscsqt psraipatrr vvlgdgvqlp pgdysttpgg tlfsttpggt riiydrkflm
61   ecrnspvtkt pprdlptipg vtspssdepp measqshlrn spedkragge esqfemdi SEQ ID NO: 10 (Cyclin A2  NP_001228.1)
1    mlgnsapgpa treagsalla lqqtalqedq eninpekaap vqqprtraal avlksgnprg
61   laqqqrpktr rvaplkdlpv ndehvtppw kanskqpaft ihvdeaekea qkkpaesqki
121  eredalafns aislpgprkp lvpldypmdg sfesphtmdm sivledekpv svnevpdyhe
181  dihtylreme vkckpkvgym kkqpditnsm railvdwlve vgeeyklqne tlhlavnyid
241  rflssmsvlr gklqlvgtaa mllaskfeei yppevaefvy itddtytkkq vlrmehlvlk
301  vltfdlaapt vnqfltqyfl hqqpanckve slamflgels lidadpylky lpsviagaaf
361  hlalytvtgq swpeslirkt gytleslkpc lmdlhqtylk apqhaqqsir ekyknskyhg
421  vsllnppetl nl SEQ ID NO: 11 (HuR (ELAV-like 1)  NP_001410)
1    msngyedhma edcrgdigrt nlivnylpqn mtqdelrslf ssigevesak lirdkvaghs
61   lgygfvnyvt akdaeraint lnglrlqskt ikvsyarpss evikdanlyi sglprtmtqk
121  dvedmfsrfg riinsrvlvd qttglsrgva firfdkrsea eeaitsfngh kppgssepit
181  vkfaanpnqn knvallsqly hsparrfggp vhhqaqrfrf spmgvdhmsg lsgvnvpgna
241  ssgwcifiyn lgqdadegil wqmfgpfgav tnvkvirdfn tnkckgfgfv tmtnyeeaam
301  aiaslngyrl gdkilqvsfk tnkshk
```

FIGURE 2 (continued)

SKP2 (NP_005974) (NP_005974.2) (NP_116020) (NP_116020.1) – SEQ ID NO. 199

MHRKHLQEIPDLSSNVATSFTWGWDSSKTSELLSGMGVSALEKEEPDSENIPQELLSNLGHPESPPRKRLKSKGSDKDF
VIVRRPKLNRENFPGVSWDSLPDELLLGIFSCLCLPELLKVSGVCKRWYRLASDESLWQTLDLTGKNLHPDVTGRLLSQG
VIAFRCPRSFMDQPLAEHFSPFRVQHMDLSNSVIEVSTLHGILSQCSKLQNLSLEGLRLSDPIVNTLAKNSNLVRLNLSGC
SGFSEFALQTLLSSCSRLDELNLSWCFDFTEKHVQVAVAHVSETITQLNLSGYRKNLQKSDLSTLVRRCPNLVHLDLSDSV
MLKNDCFQEFFQLNYLQHLSLSRCYDIIPETLLELGEIPTLKTLQVFGIVPDGTLQLLKEALPHLQINCSHFTTIARPTIGNKK
NQEIWGIKCRLTLQKPSCL

Cyclin E1 (P24864) (NP_001229) (NP_001229.1) (NP_001220) (NP_001220.1)– SEQ ID NO. 200

MPRERRERDAKERDTMKEDGGAEFSARSRKRKANVTVFLQDPDEEMAKIDRTARDQCGSQPWDNNAVCADPCSLIP
TPDKEDDDRVYPNSTCKPRIIAPSRGSPLPVLSWANREEVWKIMLNKEKTYLRDQHFLEQHPLLQPKMRAILLDWLME
VCEVYKLHRETFYLAQDFFDRYMATQENVVKTLLQLIGISSLFIAAKLEEIYPPKLHQFAYVTDGACSGDEILTMELMIMK
ALKWRLSPLTIVSWLNVYMQVAYLNDLHEVLLPQYPQQIFIQIAELLDLCVLDVDCLEFPYGILAASALYHFSSSELMQKV
SGYQWCDIENCVKWMVPFAMVIRETGSSKLKHFRGVADEDAHNIQTHRDSLDLLDKARAKKAMLSEQNRASPLPSGL
LTPPQSGKKQSSGPEMA

MMP9 (P14780) (NP_004985) (NP_004985.2)– SEQ ID NO. 201

FQTFEGDLKWHHHNITYWIQNYSEDLPRAVIDDAFARAFALWSAVTPLTFTRVYSRDADIVIQFGVAEHGDGYPFDGK
DGLLAHAFPPGPGIQGDAHFDDDELWSLGKGVVVPTRFGNADGAACHFPFIFEGRSYSACTTDGRSDGLPWCSTTAN
YDTDDRFGFCPSERLYTQDGNADGKPCQFPFIFQGQSYSACTTDGRSDGYRWCATTANYDRDKLFGFCPTRADSTVM
GGNSAGELCVFPFTFLGKEYSTCTSEGRGDGRLWCATTSNFDSDKKWGFCPDQGYSLFLVAAHEFGHALGLDHSSVPE
ALMYPMYRFTEGPPLHKDDVNGIRHLYGPRPEPEPRPPTTTTPQPTAPPTVCPTGPPTVHPSERPTAGPTGPPSAGPTG
PPTAGPSTATTVPLSPVDDACNVNIFDAIAEIGNQLYLFKDGKYWRFSEGRGSRPQGPFLIADKWPALPRKLDSVFEERL
SKKLFFFSGRQVWVYTGASVLGPRRLDKLGLGADVAQVTGALRSGRGKMLLFSGRRLWRFDVKAQMVDPRSASEVD
RMFPGVPLDTHDVFQYREKAYFCQDRFYWRVSSRSELNQVDQVGYVTYDILQCPED

CASP9 (P55211) (NP_127463) (NP_127463.1)– SEQ ID NO. 202

MDEADRRLLRRCRLRLVEELQVDQLWDALLSRELFRPHMIEDIQRAGSGSRRDQARQLIIDLETRGSQALPLFISCLEDT
GQDMLASFLRTNRQAAKLSKPTLENLTPVVLRPEIRKPEVLRPETPRPVDIGSGGFGDVGALESLRGNADLAYILSMEPC
GHCLIINNVNFCRESGLRTRTGSNIDCEKLRRRFSSLHFMVEVKGDLTAKKMVLALLELAQQDHGALDCCVVVILSHGC
QASHLQFPGAVYGTDGCPVSVEKIVNIFNGTSCPSLGGKPKLFFIQACGGEQKDHGFEVASTSPEDESPGSNPEPDATPF
QEGLRTFDQLDAISSLPTPSDIFVSYSTFPGFVSWRDPKSGSWYVETLDDIFEQWAHSEDLQSLLLRVANAVSVKGIYKQ
MPGCFNFLRKKLFFKTS

FIGURE 2 (continued)

BCL2L1 (Q07817) (NP_612815) (NP_612815.1) (NP_000648) (NP_000648.2)– SEQ ID NO. 203

MSQSNRELVVDFLSYKLSQKGYSWSQFSDVEENRTEAPEGTESEMETPSAINGNPSWHLADSPAVNGATGHSSSLDA
REVIPMAAVKQALREAGDEFELRYRRAFSDLTSQLHITPGTAYQSFEQVVNELFRDGVNWGRIVAFFSFGGALCVESVD
KEMQVLVSRIAAWMATYLNDHLEPWIQENGGWDTFVELYGNNAAAESRKGQERFNRWFLTGMTVAGVVLLGSLFS
RK

EIF4EBP1 (Q13541) (NP_004086) (NP_004086.1)– SEQ ID NOs. 204, 559

AcSGGSSCSQTPSRAIPATRRVVLGDGVQLPPGDYSTTPGGTLFSTTPGGTRIIYDRKFLMECRNSPVTKTPPRDLPTIPG
VTSPSSDEPPMEASQSHLRNSPEDKRAGGEESQFEMDI

BCL2 (P10415) (NP_000624) (NP_000624.2)– SEQ ID NO. 205

MAHAGRTGYDNREIVMKYIHYKLSQRGYEWDAGDVGAAPPGAAPAPGIFSSQPGHTPHPAASRDPVARTSPLQTPA
APGAAAGPALSPVPPVVHLTLRQAGDDFSRRYRRDFAEMSSQLHLTPFTARGRFATVVEELFRDGVNWGRIVAFFEFG
GVMCVESVNREMSPLVDNIALWMTEYLNRHLHTWIQDNGGWDAFVELYGPSMRPLFDFSWLSLKTLLSLALVGACIT
LGAYLGHK

EGFR (P00533) (NP_005219) (NP_005219.2)– SEQ ID NO. 206

LEEKKVCQGTSNKLTQLGTFEDHFLSLQRMFNNCEVVLGNLEITYVQRNYDLSFLKTIQEVAGYVLIALNTVERIPLENLQI
IRGNMYYENSYALAVLSNYDANKTGLKELPMRNLQEILHGAVRFSNNPALCNVESIQWRDIVSSDFLSNMSMDFQNH
LGSCQKCDPSCPNGSCWGAGEENCQKLTKIICAQQCSGRCRGKSPSDCCHNQCAAGCTGPRESDCLVCRKFRDEATCK
DTCPPLMLYNPTTYQMDVNPEGKYSFGATCVKKCPRNYVVTDHGSCVRACGADSYEMEEDGVRKCKKCEGPCRKVC
NGIGIGEFKDSLSINATNIKHFKNCTSISGDLHILPVAFRGDSFTHTPPLDPQELDILKTVKEITGFLLIQAWPENRTDLHAF
ENLEIIRGRTKQHGQFSLAVVSLNITSLGLRSLKEISDGDVIISGNKNLCYANTINWKKLFGTSGQKTKIISNRGENSCKATG
QVCHALCSPEGCWGPEPRDCVSCRNVSRGRECVDKCNLLEGEPREFVENSECIQCHPECLPQAMNITCTGRGPDNCIQ
CAHYIDGPHCVKTCPAGVMGENNTLVWKYADAGHVCHLCHPNCTYGCTGPGLEGCPTNGPKIPSIATGMVGALLLLL
VVALGIGLFMRRRHIVRKRTLRRLLQERELVEPLTPSGEAPNQALLRILKETEFKKIKVLGSGAFGTVYKGLWIPEGEKVKIP
VAIKELREATSPKANKEILDEAYVMASVDNPHVCRLLGICLTSTVQLITQLMPFGCLLDYVREHKDNIGSQYLLNWCVQI
AKGMNYLEDRRLVHRDLAARNVLVKTPQHVKITDFGLAKLLGAEEKEYHAEGGKVPIKWMALESILHRIYTHQSDVWS
YGVTVWELMTFGSKPYDGIPASEISSILEKGERLPQPPICTIDVYMIMVKCWMIDADSRPKFRELIIEFSKMARDPQRYLV
IQGDERMHLPSPTDSNFYRALMDEEDMDDVVDADEYLIPQQGFFSSPSTSRTPLLSSLSATSNNSTVACIDRNGLQSCPI
KEDSFLQRYSSDPTGALTEDSIDDTFLPVPEYINQSVPKRPAGSVQNPVYHNQPLNPAPSRDPHYQDPHSTAVGNPEYL
NTVQPTCVNSTFDSPAHWAQKGSHQISLDNPDYQQDFFPKEAKPNGIFKGSTAENAEYLRVAPQSSEFIGA

FGF2 (P09038) (NP_001997) (NP_001997.5) (NP_002006) (NP_002006.4)– SEQ ID NO. 207
MVGVGGGDVEDVTPRPGGCQISGRGARGCNGIPGAAAWEAALPRRRPRRHPSVNPRSRAAGSPRTRGRRTEERPSG
SRLGDRGRGRALPGGRLGGRGRGRAPERVGGRGRGRGTAAPRAAPAARGSRPGPAGTMAAGSITTLPALPEDGGSG
AFPPGHFKDPKRLYCKNGGFFLRIHPDGRVDGVREKSDPHIKLQLQAEERGVVSIKGVCANRYLAMKEDGRLLASKCVT
DECFFFERLESNNYNTYRSRKYTSWYVALKRTGQYKLGSKTGPGQKAILFLPMSAKS

FIGURE 2 (continued)

HER2 (P04626) (NP_004439) (NP_004439.2)– SEQ ID NO. 208

TQVCTGTDMKLRLPASPETHLDMLRHLYQGCQVVQGNLELTYLPTNASLSFLQDIQEVQGYVLIAHNQVRQVPLQRLR
IVRGTQLFEDNYALAVLDNGDPLNNTTPVTGASPGGLRELQLRSLTEILKGGVLIQRNPQLCYQDTILWKDIFHKNNQLA
LTLIDTNRSRACHPCSPMCKGSRCWGESSEDCQSLTRTVCAGGCARCKGPLPTDCCHEQCAAGCTGPKHSDCLACLHF
NHSGICELHCPALVTYNTDTFESMPNPEGRYTFGASCVTACPYNYLSTDVGSCTLVCPLHNQEVTAEDGTQRCEKCSKP
CARVCYGLGMEHLREVRAVTSANIQEFAGCKKIFGSLAFLPESFDGDPASNTAPLQPEQLQVFETLEEITGYLYISAWPDS
LPDLSVFQNLQVIRGRILHNGAYSLTLQGLGISWLGLRSLRELGSGLALIHHNTHLCFVHTVPWDQLFRNPHQALLHTAN
RPEDECVGEGLACHQLCARGHCWGPGPTQCVNCSQFLRGQECVEECRVLQGLPREYVNARHCLPCHPECQPQNGSV
TCFGPEADQCVACAHYKDPPFCVARCPSGVKPDLSYMPIWKFPDEEGACQPCPINCTHSCVDLDDKGCPAEQRASPLT
SIISAVVGILLVVVLGVVFGILIKRRQQKIRKYTMRRLLQETELVEPLTPSGAMPNQAQMRILKETELRKVKVLGSGAFGTV
YKGIWIPDGENVKIPVAIKVLRENTSPKANKEILDEAYVMAGVGSPYVSRLLGICLTSTVQLVTQLMPYGCLLDHVRENR
GRLGSQDLLNWCMQIAKGMSYLEDVRLVHRDLAARNVLVKSPNHVKITDFGLARLLDIDETEYHADGGKVPIKWMAL
ESILRRRFTHQSDVWSYGVTVWELMTFGAKPYDGIPAREIPDLLEKGERLPQPPICTIDVYMIMVKCWMIDSECRPRFR
ELVSEFSRMARDPQRFVVIQNEDLGPASPLDSTFYRSLLEDDDMGDLVDAEEYLVPQQGFFCPDPAPGAGGMVHHRH
RSSSTRSGGGDLTLGLEPSEEEAPRSPLAPSEGAGSDVFDGDLGMGAAKGLQSLPTHDPSPLQRYSEDPTVPLPSETDGY
VAPLTCSPQPEYVNQPDVRPQPPSPREGPLPAARPAGATLERPKTLSPGKNGVVKDVFAFGGAVENPEYLTPQGGAAP
QPHPPPAFSPAFDNLYYWDQDPPERGAPPSTFKGTPTAENPEYLGLDVPV

SELS (Q9BQE4) (NP_982298) (NP_982298.1) (NP_060915) (NP_060915.2)– SEQ ID NO. 209

MERQEESLSARPALETEGLRFLHTTVGSLLATYGWYIVFSCILLYVVFQKLSARLRALRQRQLDRAAAAVEPDVVVKRQE
ALAAARLKMQEELNAQVEKHKEKLKQLEEEKRRQKIEMWDSMQEGKSYKGNAKKPQEEDSPGPSTSSVLKRKSDRKP
LRGGGYNPLSGEGGGACSWRPGRRGPSSGGUG

SPP1 (P10451) (NP_001035149) (NP_001035149.1) – SEQ ID NO. 210

IPVKQADSGSSEEKQLYNKYPDAVATWLNPDPSQKQNLLAPQNAVSSEETNDFKQETLPSKSNESHDHMDDMDDED
DDDHVDSQDSIDSNDSDDVDDTDDSHQSDESHHSDESDELVTDFPTDLPATEVFTPVVPTVDTYDGRGDSVVYGLRSK
SKKFRRPDIQYPDATDEDITSHMESEELNGAYKAIPVAQDLNAPSDWDSRGKDSYETSQLDDQSAETHSHKQSRLYKRK
ANDESNEHSDVIDSQELSKVSREFHSHEFHSHEDMLVVDPKSKEEDKHLKFRISHELDSASSEVN

AKT1 (P31749) (NP_00104431, NP_005154, NP_001014432) (NP_00104431.1, NP_005154.2,
NP_001014432.1)– SEQ ID NOs. 211, 560

MSDVAIVKEGWLHKRGEYIKTWRPRYFLLKNDGTFIGYKERPQDVDQREAPLNNFSVAQCQLMKTERPRPNTFIIRCL
QWTTVIERTFHVETPEEREEWTTAIQTVADGLKKQEEEEMDFRSGPSDNSGAEEMEVSLAKPKHRVTMNEFEYLKLL
GKGTFGKVILVKEKATGRYYAMKILKKEVIVAKDEVAHTLTENRVLQNSRHPFLTALKYSFQTHDRLCFVMEYANGGELF
FHLSRERVFSEDRARFYGAEIVSALDYLHSEKNVVYRDLKLENLMLDKDGHIKITDFGLCKEGIKDGATMKTFCGTPEYLA
PEVLEDNDYGRAVDWWGLGVVMYEMMCGRLPFYNQDHEKLFELILMEEIRFPRTLGPEAKSLLSGLLKKDPKQRLGG
GSEDAKEIMQHRFFAGIVWQHVYEKKLSPPFKPQVTSETDTRYFDEEFTAQMITITPPDQDDSMECVDSERRPHFPQFS
YSASGTA

FIGURE 3A

Akt

| | | | | |
|---|---|---|---|---|
| 1014.103 | 1013.481 | 31 | 39 | 0 NDGTFIGYK (SEQ ID No. 12) |
| 1053.099 | 1052.467 | 215 | 222 | 0 YSFQTHDR (SEQ ID No.13) |
| 1142.194 | 1141.547 | 40 | 48 | 0 ERPQDVDQR (SEQ ID No.14) |
| 1212.259 | 1211.476 | 113 | 121 | 0 QEEEEMDFR (SEQ ID No.15) |
| 1244.326 | 1243.583 | 87 | 96 | 0 TFHVETPEER (SEQ ID No.16) |
| 1273.472 | 1272.606 | 145 | 154 | 0 VTMNEFEYLK (SEQ ID No.17) |
| 1284.348 | 1283.610 | 190 | 200 | 0 DEVAHTLTENR (SEQ ID No.18) |
| 1290.398 | 1289.604 | 347 | 356 | 0 LPFYNQDHEK (SEQ ID No.19) |
| 1305.521 | 1304.654 | 77 | 86 | 0 CLQWTTVIER (SEQ ID No.20) |
| | | | | (1)+C2H3ON@C |
| 1405.722 | 1404.768 | 357 | 367 | 0 LFELILMEEIR (SEQ ID No.21) |
| 1499.736 | 1498.836 | 65 | 76 | 0 TERPRPNTFIIR (SEQ ID No. 22) |
| 1623.874 | 1622.824 | 407 | 419 | 0 FFAGIVWQHVYEK (SEQ ID No. 23) |
| 1652.787 | 1651.774 | 466 | 480 | 0 RPHFPQFSYSASGTA (SEQ ID No. 24) |
| 1661.829 | 1660.830 | 97 | 111 | 0 EEWTTAIQTVADGLK (SEQ ID No. 25) |
| 1803.002 | 1801.921 | 421 | 436 | 0 LSPPFKPQVTSETDTR (SEQ ID No. 26) |
| 1850.150 | 1848.886 | 49 | 64 | 0 EAPLNNFSVAQCQLMK (SEQ ID No. 27) |
| | | | | (1)+C2H3ON@C |
| 1942.156 | 1940.951 | 252 | 268 | 0 FYGAEIVSALDYLHSEK (SEQ ID No. 28) |
| 2120.279 | 2118.973 | 122 | 142 | 0 SGSPSDNSGAEEMEVSLAKPK (SEQ ID No.29) |
| 2160.594 | 2158.946 | 329 | 346 | 0 AVDWWGLGVVMYEMMCGR (SEQ ID No. 30) |
| | | | | (1)+C2H3ON@C |
| 2290.652 | 2289.071 | 223 | 241 | 0 LCFVMEYANGGELFFHLSR (SEQ ID No. 31) |
| | | | | (1)+C2H3ON@C |
| 2446.634 | 2445.079 | 308 | 328 | 0 TFCGTPEYLAPEVLEDNDYGR (SEQ ID No. 32) |
| | | | | (1)+C2H3ON@C |
| 3470.728 | 3468.431 | 437 | 465 | 0 YFDEEFTAQMITITPPDQDDSMECVDSER (SEQ ID No. 33) |
| | | | | (1)+C2H3ON@C |

Pim1

| | | | | |
|---|---|---|---|---|
| 1008.142 | 1007.539 | 96 | 105 | 0 VSSGFSGVIR (SEQ ID No.34) |
| 1027.337 | 1026.614 | 86 | 94 | 0 VPMEVVLLK (SEQ ID No. 35) |
| 1055.239 | 1054.602 | 58 | 67 | 0 VSDNLPVAIK (SEQ ID No. 36) |
| 1133.353 | 1132.649 | 184 | 194 | 0 LIDFGSGALLK (SEQ ID No. 37) |
| 1146.311 | 1145.586 | 206 | 214 | 0 VYSPPEWIR (SEQ ID No. 38) |
| 1197.337 | 1196.560 | 14 | 24 | 0 AAPCNDLHATK (SEQ ID No. 39) |
| | | | | (1)+C2H3ON@C |
| 1214.341 | 1213.630 | 170 | 179 | 0 DENILIDLNR (SEQ ID No. 40) |
| 1228.395 | 1227.602 | 259 | 268 | 0 VSSECQHLIR (SEQ ID No. 41) |
| | | | | (1)+C2H3ON@C |
| 1289.321 | 1288.557 | 195 | 205 | 0 DTVYTDFDGTR (SEQ ID No. 42) |
| 1289.468 | 1288.566 | 157 | 166 | 0 HCHNCGVLHR (SEQ ID No. 43) |
| | | | | (2)+C2H3ON@C |
| 1344.447 | 1343.646 | 74 | 85 | 0 ISDWGELPNGTR (SEQ ID No. 44) |
| 1381.597 | 1380.719 | 146 | 156 | 0 SFFWQVLEAVR (SEQ ID No. 45) |
| 2697.985 | 2696.344 | 32 | 57 | 0 EPLESQYQVGPLLGSGGFGSVYSGIR (SEQ ID No.46) |
| 3349.834 | 3347.620 | 222 | 250 | 0 SAAVWSLGILLYDMVCGDIPFEHDEEIIR (SEQ ID No. 47) |
| | | | | (1)+C2H3ON@C |
| 3836.360 | 3833.966 | 106 | 136 | 0 LLDWFERPDSFVLILERPEPVQDLFDFITER (SEQ ID No. 48) |

FIGURE 3B

```
Nibrin
1017.104  1016.513  532  540  0ISQENEIGK (SEQ ID No. 49)
1089.278  1088.553  313  322  0MLSQDAPTVK (SEQ ID No. 50)
1160.335  1159.623  344  353  0IPNYQLSPTK (SEQ ID No. 51)
1175.325  1174.553  561  570  0LQDDSEMLPK (SEQ ID No. 52)
1189.290  1188.577  634  642  0NTELEEWLR (SEQ ID No. 53)
1194.263  1193.556  654  663  0EESLADDLFR (SEQ ID No. 54)
1249.389  1248.646  156  168  0LSSAVVFGGGEAR (SEQ ID No. 55)
1260.329  1259.621  364  374  0ASQQQQTNSIR (SEQ ID No. 56)
1271.392  1270.619   11   23  0SGDGITFGVFGSK (SEQ ID No.57)
1286.445  1285.676  487  497  0DTKPELEIDVK (SEQ ID No. 58)
1341.468  1340.614  643  653  0QEMEVQNQHAK (SEQ ID No. 59)
1356.411  1355.496  387  397  0DEENQEMSSCK (SEQ ID No. 60)
                              (1)+C2H3ON@C
1420.499  1419.663  589  601  0NPSGINDDYGQLK (SEQ ID No. 61)
1420.720  1419.700  207  217  0WIQSIMDMLQR (SEQ ID No. 62)
1567.697  1566.730  327  341  0TSSNNNSMVSNTLAK (SEQ ID No. 63)
1573.707  1572.699  239  252  0NYCDPQGHPSTGLK (SEQ ID No. 64)
                              (1)+C2H3ON@C
1702.836  1701.842  253  269  0TTTPGPSLSQGVSVDEK (SEQ ID No. 65)
1706.969  1705.937  617  632  0LPHIIGGSDLIAHHAR (SEQ ID No. 66)
2023.245  2021.950  470  486  0EMDDVAIEDEVLEQLFK (SEQ ID No. 67)
2027.304  2025.938   26   43  0IEYEPLVACSSCLDVSGK (SEQ ID No. 68)
                              (2)+C2H3ON@C
2115.213  2113.899  513  531  0MDIETNDTFSDEAVPESSK (SEQ ID No. 69)
2229.472  2228.100  107  126  0QPPQIESFYPPLDEPSIGSK (SEQ ID No. 70)
2284.749  2283.266  218  238  0QGLRPIPEAEIGLAVIFMTTK (SEQ ID No. 71)
2289.592  2288.135  401  420  0IETSCSLLEQTQPATPSLWK (SEQ ID No. 72)
                              (1)+C2H3ON@C
2656.209  2654.396   79  100  0TICALICGRPIVKPEYFTEFLK (SEQ ID No. 73)
                              (2)+C2H3ON@C
2875.954  2874.279  423  447  0EQHLSENEPVDTNSDNNLFTDTDLK (SEQ ID No. 74)
3453.743  3451.608  270  300  0LMPSAPVNTTTYVADTESEQADTWDLSERPK (SEQ ID No. 75)
3475.008  3472.748   44   74  0TALNQAILQLGGFTVNNWTEECTHLVMVSVK (SEQ ID No. 76)
                              (1)+C2H3ON@C
```

FIGURE 3C

ODC

| | | | | |
|---|---|---|---|---|
| 1027.101 | 1026.477 | 262 | 270 | 0 YFPSDSGVR (SEQ ID No. 77) |
| 1093.112 | 1092.493 | 28 | 37 | 0 INEVSSSDDK (SEQ ID No. 78) |
| 1399.544 | 1398.644 | 79 | 92 | 0 TLAATGTGFDCASK (SEQ ID No. 79) |
| | | | | (1)+C2H3ON@C |
| 1439.628 | 1438.734 | 38 | 50 | 0 DAFYVADLGDILK (SEQ ID No. 80) |
| 1545.753 | 1544.808 | 248 | 261 | 0 FEEITGVINPALDK (SEQ ID No. 81) |
| 1665.907 | 1664.909 | 93 | 107 | 0 TEIQLVQSLGVPPER (SEQ ID No. 82) |
| 1744.064 | 1742.960 | 278 | 293 | 0 YYVASAFTLAVNIIAK (SEQ ID No. 83) |
| 1877.021 | 1875.809 | 350 | 365 | 0 YYSSSIWGPTCDGLDR (SEQ ID No. 84) |
| | | | | (1)+C2H3ON@C |
| 2278.613 | 2277.011 | 122 | 141 | 0 YAANNGVQMMTFDSEVELMK (SEQ ID No. 85) |
| 2522.715 | 2521.031 | 1 | 21 | 0 MNNFGNEEFDCHFLDEGFTAK (SEQ ID No. 86) |
| | | | | (1)+C2H3ON@C |
| 3098.526 | 3096.391 | 217 | 245 | 0 CVFDMGAEVGFSMYLLDIGGGFPGSEDVK (SEQ ID No. 87) |
| | | | | (1)+C2H3ON@C |
| 3320.642 | 3318.582 | 186 | 216 | 0 ELNIDVVGVSFHVGSGCTDPETFVQAISDAR (SEQ ID No. 88) |
| | | | | (1)+C2H3ON@C |

VEGF

| | | | | |
|---|---|---|---|---|
| 1015.048 | 1014.473 | 71 | 81 | 0 AGEAEPSGAAR (SEQ ID No. 89) |
| 1192.448 | 1191.643 | 54 | 63 | 0 LFVQLLGCSR (SEQ ID No. 90) |
| | | | | (1)+C2H3ON@C |
| 1307.342 | 1306.590 | 153 | 165 | 0 GAEESGPPHSPSR (SEQ ID No. 91) |
| 1333.425 | 1332.518 | 319 | 329 | 0 QENPCGPCSER (SEQ ID No. 92) |
| | | | | (2)+C2H3ON@C |
| 1372.568 | 1371.660 | 332 | 342 | 0 HLFVQDPQTCK (SEQ ID No. 93) |
| | | | | (1)+C2H3ON@C |
| 1591.701 | 1590.775 | 31 | 48 | 0 GQGPEPAPGGGVEGVGAR (SEQ ID No. 94) |
| 1687.645 | 1686.674 | 88 | 101 | 0 EEPQPEEGEEEEEK (SEQ ID No. 95) |
| 1739.906 | 1738.863 | 5 | 20 | 0 QTDTAPSPSYHLLPGR (SEQ ID No. 96) |
| 2002.195 | 2000.937 | 115 | 134 | 0 KPGSWTGEAAVCADSAPAAR (SEQ ID No. 97) |
| | | | | (1)+C2H3ON@C |
| 2133.332 | 2131.985 | 203 | 222 | 0 WSQAAPMAEGGGQNHHEVVK (SEQ ID No. 98) |
| 2229.551 | 2228.127 | 289 | 307 | 0 IKPHQGQHIGEMSFLQHNK (SEQ ID No. 99) |
| 3061.448 | 3059.222 | 263 | 288 | 0 CGGCCNDEGLECVPTEESNITMQIMR (SEQ ID No. 100) |
| | | | | (4)+C2H3ON@C |
| 3081.635 | 3079.610 | 177 | 202 | 0 ASETMNFLLSWVHWSLALLLYLHHAK (SEQ ID No. 101) |

FIGURE 3D

Cyclin D1

| | | | | | |
|---|---|---|---|---|---|
| 1001.145 | 1000.544 | 115 | 123 | 0 | ETIPLTAEK (SEQ ID No. 102) |
| 1059.168 | 1058.481 | 261 | 269 | 0 | QAQQNMDPK (SEQ ID No. 103) |
| 1260.372 | 1259.593 | 219 | 228 | 0 | SPNNFLSYYR (SEQ ID No. 104) |
| 1261.357 | 1260.609 | 16 | 26 | 0 | AYPDANLLNDR (SEQ ID No. 105) |
| 1488.638 | 1487.660 | 34 | 46 | 0 | AEETCAPSVSYFK (SEQ ID No. 106) |
| | | | | | (1)+C2H3ON@C |
| 1538.896 | 1537.799 | 99 | 112 | 0 | LQLLGATCMFVASK (SEQ ID No. 107) |
| | | | | | (1)+C2H3ON@C |
| 1560.794 | 1559.776 | 181 | 194 | 0 | HAQTFVALCATDVK (SEQ ID No. 108) |
| | | | | | (1)+C2H3ON@C |
| 1736.043 | 1734.832 | 59 | 72 | 0 | IVATWMLEVCEEQK (SEQ ID No. 109) |
| | | | | | (1)+C2H3ON@C |
| 1746.959 | 1745.861 | 246 | 260 | 0 | ACQEQIEALLESSLR (SEQ ID No. 110) |
| | | | | | (1)+C2H3ON@C |
| 1818.129 | 1816.826 | 1 | 14 | 0 | MEHQLLCCEVETIR (SEQ ID No. 111) |
| | | | | | (2)+C2H3ON@C |
| 1886.137 | 1884.838 | 73 | 87 | 0 | CEEEVFPLAMNYLDR (SEQ ID No. 112) |
| | | | | | (1)+C2H3ON@C |
| 2157.481 | 2156.051 | 150 | 167 | 0 | WNLAAMTPHDFIEHFLSK (SEQ ID No. 113) |
| 2398.813 | 2397.283 | 195 | 218 | 0 | FISNPPSMVAAGSVVAAVQGLNLR (SEQ ID No. 114) |
| 2550.604 | 2549.059 | 270 | 291 | 0 | AAEEEEEEEEEVDLACTPTDVR (SEQ ID No. 115) |
| | | | | | (1)+C2H3ON@C |
| 2905.430 | 2903.513 | 124 | 147 | 0 | LCIYTDNSIRPEELLQMELLLVNK (SEQ ID No. 116) |
| | | | | | (1)+C2H3ON@C |

FIGURE 3E eIF4E-BP1

| | | | | |
|---|---|---|---|---|
| 1312.376 | 1311.528 | 107 | 118 | 0AGGEESQFEMDI (SEQ ID No. 117) |
| 1341.446 | 1340.544 | 1 | 13 | 0MSGGSSCSQTPSR (SEQ ID No. 118) |
| | | | | (1)+C2H3ON@C |
| 2749.008 | 2747.307 | 74 | 99 | 0DLPTIPGVTSPSSDEPPMEASQSHLR (SEQ ID No. 119) |
| 3048.357 | 3046.524 | 21 | 51 | 0VVLGDGVQLPPGDYSTTPGGTLFSTTPGGTR (SEQ ID No. 120) |

Cyclin A2

| | | | | |
|---|---|---|---|---|
| 1025.176 | 1024.577 | 60 | 68 | 0GLAQQQRPK (SEQ ID No. 121) |
| 1039.264 | 1038.553 | 242 | 250 | 0FLSSMSVLR (SEQ ID No. 122) |
| 1061.184 | 1060.497 | 203 | 211 | 0QPDITNSMR (SEQ ID No. 123) |
| 1135.248 | 1134.589 | 401 | 410 | 0APQHAQQSIR (SEQ ID No. 124) |
| 1171.343 | 1170.581 | 1 | 12 | 0MLGNSAPGPATR (SEQ ID No. 125) |
| 1415.761 | 1414.821 | 253 | 266 | 0LQLVGTAAMLLASK (SEQ ID No. 126) |
| 1484.629 | 1483.730 | 96 | 108 | 0QPAFTIHVDEAEK (SEQ ID No. 127) |
| 1657.844 | 1656.847 | 123 | 138 | 0EDALAFNSAISLPGPR (SEQ ID No. 128) |
| 1666.895 | 1665.872 | 418 | 432 | 0YHGVSLLNPPETLNL (SEQ ID No. 129) |
| 1745.953 | 1744.878 | 77 | 91 | 0DLPVNDEHVTVPPWK (SEQ ID No. 130) |
| 1763.020 | 1761.918 | 212 | 226 | 0AILVDWLVEVGEEYK (SEQ ID No. 131) |
| 1799.017 | 1797.937 | 227 | 241 | 0LQNETLHLAVNYIDR (SEQ ID No. 132) |
| 2324.721 | 2323.202 | 329 | 349 | 0VESLAMFLGELSLIDADPYLK (SEQ ID No. 133) |
| 2511.946 | 2510.254 | 380 | 400 | 0TGYTLESLKPCLMDLHQTYLK (SEQ ID No. 134) |
| | | | | (1)+C2H3ON@C |
| 2669.921 | 2668.247 | 267 | 288 | 0FEEIYPPEVAEFVYITDDTYTK (SEQ ID No. 135) |
| 2710.935 | 2709.345 | 13 | 37 | 0EAGSALLALQQTALQEDQENINPEK (SEQ ID No. 136) |
| 3161.652 | 3159.675 | 350 | 378 | 0YLPSVIAGAAFHLALYTVTGQSWPESLIR (SEQ ID No. 137) |
| 3265.741 | 3263.643 | 301 | 328 | 0VLTFDLAAPTVNQFLTQYFLHQQPANCK (SEQ ID No. 138) |
| | | | | (1)+C2H3ON@C |

FIGURE 3F

Hur

| | | | | |
|---|---|---|---|---|
| 998.081 | 997.417 | 121 | 128 | 0DVEDMFSR (SEQ ID No. 139) |
| 1003.083 | 1002.488 | 183 | 191 | 0FAANPNQNK (SEQ ID No. 140) |
| 1188.346 | 1187.651 | 137 | 147 | 0VLVDQTTGLSR (SEQ ID No. 141) |
| 1218.375 | 1217.640 | 105 | 115 | 0DANLYISGLPR (SEQ ID No. 142) |
| 1233.355 | 1232.616 | 207 | 217 | 0FGGPVHHQAQR (SEQ ID No. 143) |
| 1335.523 | 1334.719 | 93 | 104 | 0VSYARPSSEVIK (SEQ ID No. 144) |
| 1353.492 | 1352.682 | 38 | 50 | 0SLFSSIGEVESAK (SEQ ID No. 145) |
| 1568.796 | 1567.847 | 192 | 205 | 0NVALLSQLYHSPAR (SEQ ID No. 146) |
| 1714.835 | 1713.618 | 1 | 14 | 0MSNGYEDHMAEDCR (SEQ ID No. 147) (1)+C2H3ON@C |
| 1783.017 | 1781.910 | 56 | 72 | 0VAGHSLGYGFVNYVTAK (SEQ ID No. 148) |
| 2162.452 | 2161.083 | 20 | 37 | 0TNLIVNYLPQNMTQDELR (SEQ ID No. 149) |
| 2612.833 | 2611.276 | 158 | 182 | 0SEAEEAITSFNGHKPPGSSEPITVK (SEQ ID No. 150) |
| 2613.955 | 2612.203 | 286 | 309 | 0GFGFVTMTNYEEAAMAIASLNGYR (SEQ ID No. 151) |

4E

| | | | | |
|---|---|---|---|---|
| 997.207 | 996.522 | 43 | 49 | 0WALWFFK (SEQ ID No. 2) |
| 1348.453 | 1347.565 | 96 | 106 | 0DGIEPMWEDEK (SEQ ID No. 152) |
| 1392.556 | 1391.650 | 163 | 173 | 0IAIWTTECENR (SEQ ID No. 153) (1)+C2H3ON@C |
| 1503.675 | 1502.772 | 193 | 206 | 0IVIGYQSHADTATK (SEQ ID No. 154) |
| 1758.862 | 1757.822 | 22 | 36 | 0TESNQEVANPEHYIK (SEQ ID No. 155) |
| 2299.495 | 2298.057 | 1 | 21 | 0MATVEPETTPTPNPPTTEEEK (SEQ ID No. 156) |
| 3393.800 | 3391.574 | 129 | 157 | 0FWLETLLCLIGESFDDYSDDVCGAVVNVR (SEQ ID No. 157) (2)+C2H3ON@C |
| 3612.058 | 3609.658 | 66 | 95 | 0FDTVEDFWALYNHIQLSSNLMPGCDYSLFK (SEQ ID No. 158) (1)+C2H3ON@C |

Figure 3G

SKP2

| | | | | | | |
|---|---|---|---|---|---|---|
| 648.781 | 648.326 | 120 | 125 | 0 | VSCVCK (1)+C2H3ON8C | SEQ ID No. 212 |
| 701.781 | 701.382 | 223 | 234 | 0 | NSNLVR | SEQ ID No. 213 |
| 747.892 | 747.427 | 78 | 83 | 0 | DPVIVR | SEQ ID No. 214 |
| 890.004 | 889.486 | 300 | 307 | 0 | SULSTIVR | SEQ ID No. 215 |
| 987.123 | 986.518 | 406 | 412 | 0 | NQEIWGIK | SEQ ID No. 216 |
| 1008.102 | 1007.514 | 146 | 154 | 0 | NLRFDVYGK | SEQ ID No. 217 |
| 1059.295 | 1058.579 | 416 | 424 | 0 | DYLQKPSCL | SEQ ID No. 218 |
| | | | | | (1)+C2H3ON8C | |
| 1103.330 | 1102.669 | 155 | 164 | 0 | LLSQEVIAPK | SEQ ID No. 219 |
| 1142.321 | 1141.649 | 208 | 217 | 0 | LQNLSLEGLR | SEQ ID No. 220 |
| 1170.371 | 1169.665 | 218 | 228 | 0 | LSDPIVNYLAK | SEQ ID No. 221 |
| 1521.752 | 1520.775 | 29 | 43 | 0 | TSELLSGMGVSALEK | SEQ ID No. 222 |
| 1776.961 | 1775.894 | 130 | 145 | 0 | LASDESLWQTLDLTSF | SEQ ID No. 223 |
| 1809.035 | 1807.835 | 168 | 182 | 0 | SFMDQFLAKHFSPFR | SEQ ID No. 224 |
| 1841.183 | 1839.922 | 309 | 324 | 0 | CPNLVRLDLSDSVMLR | SEQ ID No. 225 |
| | | | | | (1)+C2H3ON8C | |
| 1842.209 | 1841.066 | 364 | 380 | 0 | TLQVFGLVPDGTLQLLK | SEQ ID No. 226 |
| 1917.126 | 1915.866 | 258 | 272 | 0 | LDGLNLSWCYDPYEK | SEQ ID No. 227 |
| | | | | | (1)+C2H3ON8C | |
| 2217.609 | 2216.169 | 345 | 363 | 0 | CYDIIPETLLELGEIPTLK | SEQ ID No. 228 |
| | | | | | (1)+C2H3ON8C | |
| 2422.727 | 2421.276 | 273 | 294 | 0 | HVQVAVANVSETITQLRLSGYR | SEQ ID No. 229 |
| 2534.854 | 2533.194 | 235 | 257 | 0 | LRLSGCSGFSKFALQTLLSSCSR | SEQ ID No. 230 |
| | | | | | (2)+C2H3ON8C | |
| 2559.845 | 2558.291 | 325 | 344 | 0 | NDCFQEFFQLNYLQHLSLSR | SEQ ID No. 231 |
| | | | | | (1)+C2H3ON8C | |
| 2684.857 | 2683.272 | 44 | 67 | 0 | KRPDSENIPQELLSNLGHPE3P#R | SEQ ID No. 232 |
| 2705.921 | 2704.276 | 5 | 28 | 0 | HLQEIPDLSSNVATSFTWGNDSSK | SEQ ID No. 233 |
| 2719.121 | 2717.407 | 381 | 404 | 0 | EALPHLQIDCSHFFTIARFTGNK | SEQ ID No. 234 |
| | | | | | (1)+C2H3ON8C | |
| 2783.180 | 2781.370 | 183 | 207 | 0 | VQHMDLSRSVIRVSTLRGILSQCSK | SEQ ID No. 235 |
| | | | | | (1)+C2H3ON8C | |
| 3463.033 | 3460.729 | 90 | 119 | 0 | ENFPGVSNEGLPDKLLIGIFSCLCLSELLK | SEQ ID No. 236 |
| | | | | | (2)+C2H3ON8C | |

Figure 3H

Cyclin E1

| | | | | | | |
|---|---|---|---|---|---|---|
| 607.618 | 607.281 | 340 | 345 | 0 | STGSSK | SEQ ID No. 237 |
| 617.810 | 617.357 | 119 | 123 | 0 | DKLNK | SEQ ID No. 238 |
| 848.584 | 848.235 | 81 | 85 | 0 | EDDDR | SEQ ID No. 239 |
| 855.795 | 855.401 | 96 | 101 | 0 | IIAPSR | SEQ ID No. 240 |
| 689.766 | 689.338 | 114 | 118 | 0 | REVWK | SEQ ID No. 241 |
| 805.864 | 805.327 | 403 | 410 | 0 | QSSGPNMA | SEQ ID No. 242 |
| 918.012 | 917.470 | 365 | 372 | 0 | DSLDLIDK | SEQ ID No. 243 |
| 948.060 | 947.449 | 378 | 385 | 0 | AMLSEQNR | SEQ ID No. 244 |
| 968.140 | 967.527 | 202 | 209 | 0 | LEEIYPPK | SEQ ID No. 245 |
| 1036.039 | 1037.441 | 18 | 27 | 0 | EDGGAEFSAR | SEQ ID No. 246 |
| 1182.363 | 1181.575 | 176 | 185 | 0 | YMATQENVVS | SEQ ID No. 247 |
| 1221.403 | 1220.597 | 86 | 95 | 0 | VYPNGTCKR | SEQ ID No. 248 |
| | | | | | (1)+C2H3ONC | |
| 1249.610 | 1248.651 | 330 | 339 | 0 | WNVPEAMVIR | SEQ ID No. 249 |
| 1296.492 | 1295.698 | 102 | 113 | 0 | GSPLPVLSWANR | SEQ ID No. 250 |
| 1549.788 | 1548.851 | 386 | 401 | 0 | ASPLPSGLLTPPQSGK | SEQ ID No. 252 |
| 1551.675 | 1550.704 | 164 | 175 | 0 | ETYYLAQDFFSP | SEQ ID No. 253 |
| 1562.619 | 1561.723 | 351 | 364 | 0 | GVADEDARNIQTHR | SEQ ID No. 254 |
| 1688.084 | 1687.028 | 186 | 201 | 0 | TLLQLIGISSLFIAAK | SEQ ID No. 255 |
| 1729.956 | 1728.894 | 130 | 143 | 0 | DQRFLEQRFLQPK | SEQ ID No. 256 |
| 1757.966 | 1756.754 | 316 | 329 | 0 | VSGYQWCDIENCVK | |
| | | | | | (2)+C2H3ONC | |
| 1807.011 | 1805.850 | 33 | 48 | 0 | ASVTVFLQDPDEEMAK | SEQ ID No. 257 |
| 1882.275 | 1880.941 | 146 | 160 | 0 | AILDWLMEVCEVYK | SEQ ID No. 258 |
| | | | | | (1)+C2H3ONC | |
| 2946.206 | 2944.242 | 55 | 80 | 0 | DQCGSQPWDNNAVCADPCSLIPTPDK | SEQ ID No. 259 |
| | | | | | (3)+C2H3ONC | |
| 2974.495 | 2972.379 | 210 | 235 | 0 | LIQFAYVTDGACSDDKILEELMIK | SEQ ID No. 260 |
| | | | | | (1)+C2H3ONC | |

Figure 3I

MMP9

| | | | | | | |
|---|---|---|---|---|---|---|
| 594.635 | 594.276 | 435 | 440 | 0 | PSEGR | SEQ ID No. 261 |
| 596.597 | 596.255 | 202 | 206 | 0 | SDGYR | SEQ ID No. 262 |
| 678.768 | 678.322 | 573 | 578 | 0 | PYWK | SEQ ID No. 263 |
| 726.874 | 726.438 | 109 | 115 | 0 | GVVYPTR | SEQ ID No. 264 |
| 738.887 | 738.417 | 454 | 459 | 0 | WPALER | SEQ ID No. 265 |
| 762.774 | 762.350 | 540 | 546 | 0 | SASEVDR | SEQ ID No. 266 |
| 787.828 | 787.382 | 328 | 334 | 0 | DDVNGIR | SEQ ID No. 267 |
| 815.949 | 815.395 | 533 | 539 | 0 | AQMVQPN | SEQ ID No. 268 |
| 823.027 | 822.443 | 518 | 524 | 0 | MLLFSGR | SEQ ID No. 269 |
| 873.022 | 872.454 | 473 | 479 | 0 | LDFTSGR | SEQ ID No. 270 |
| 959.050 | 958.396 | 565 | 571 | 0 | AYFCQDR (1)+C2H3ON1C | SEQ ID No. 271 |
| 977.085 | 976.497 | 29 | 37 | 0 | AVIDDAFAR | SEQ ID No. 272 |
| 994.069 | 993.476 | 461 | 468 | 0 | LDGYPKER | SEQ ID No. 273 |
| 997.186 | 996.485 | 219 | 226 | 0 | LRGPEPTR | SEQ ID No. 274 |
| 999.115 | 998.437 | 162 | 169 | 0 | PGFCFSER (1)+C2H3ON1C | SEQ ID No. 275 |
| 1035.173 | 1024.534 | 319 | 327 | 0 | FTEGPPLHK | SEQ ID No. 276 |
| 1084.194 | 1083.523 | 1 | 9 | 0 | FQTFEGDLK | SEQ ID No. 277 |
| 1117.161 | 1116.450 | 134 | 143 | 0 | SYSACTTDGR | SEQ ID No. 278 |
| 1189.225 | 1188.471 | 251 | 260 | 0 | EYCTCTSGCR (1)+C2H3ON1C | SEQ ID No. 279 |
| 1257.349 | 1256.524 | 207 | 216 | 0 | WCATTANYDR (1)+C2H3ON1C | SEQ ID No. 280 |
| 1385.586 | 1384.746 | 441 | 453 | 0 | GSRPQGPFLIADK | SEQ ID No. 281 |
| 1440.663 | 1439.809 | 498 | 512 | 0 | LGLGADVAQVTGALR | SEQ ID No. 282 |
| 1532.763 | 1531.814 | 480 | 493 | 0 | QVWVYTGASVLGPR | SEQ ID No. 283 |
| 1544.662 | 1543.661 | 265 | 277 | 0 | LKCATTSNFDSDK (1)+C2H3ON1C | SEQ ID No. 284 |
| 1680.967 | 1679.903 | 39 | 52 | 0 | AFALWSAVTPLTFTR | SEQ ID No. 285 |
| 1923.198 | 1920.919 | 547 | 563 | 0 | MFPGVPLDTHDVFQYR | SEQ ID No. 286 |
| 2013.224 | 2011.899 | 116 | 133 | 0 | FGRADGAACHFPFIFEGR | SEQ ID No. 287 |
| 2074.126 | 2072.838 | 144 | 161 | 0 | SLGLDHCITTANYDTDDR (1)+C2H3ON1C | SEQ ID No. 288 |
| 2350.527 | 2349.091 | 57 | 78 | 0 | DADIVIQFGVAEHGDSYPFDGK | SEQ ID No. 289 |
| 2506.658 | 2504.171 | 227 | 250 | 0 | ADGYPMQGCSAGELCVFPFTFLGK (1)+C2H3ON1C | SEQ ID No. 290 |
| 2509.726 | 2508.172 | 10 | 28 | 0 | NHIRFTYWIQNYSEDLPR | SEQ ID No. 291 |
| 2585.785 | 2584.183 | 580 | 601 | 0 | SELNQVDQVGYVTYDILQCPED (1)+C2H3ON1C | SEQ ID No. 292 |
| 3176.449 | 3174.504 | 79 | 108 | 0 | DGLLAHAFPPGPGIQGDAHFDDDELWSLGK | SEQ ID No. 293 |
| 3630.935 | 3628.598 | 170 | 201 | 0 | LYTQHGNADGKPCQFPFIFQGQSYSACTTDGR (1)+C2H3ON1C | SEQ ID No. 294 |

Figure 3J

CASP9

| | | | | | | |
|---|---|---|---|---|---|---|
| 533.342 | 533.255 | 46 | 51 | 0 | AGSGSR | SEQ ID No. 295 |
| | | | | | | SEQ ID No. 296 |
| 553.702 | 553.326 | 411 | 414 | 0 | LPTR | SEQ ID No. 297 |
| 560.808 | 560.291 | 174 | 178 | 0 | SSGLR | SEQ ID No. 298 |
| 603.673 | 603.322 | 205 | 210 | 0 | GGLPAK | SEQ ID No. 299 |
| 735.773 | 735.285 | 1 | 6 | 0 | MDEADR | SEQ ID No. 300 |
| 786.927 | 786.459 | 387 | 394 | 0 | VANAVSVK | SEQ ID No. 301 |
| 1023.089 | 1022.433 | 181 | 189 | 0 | PGSNIDCEK (1)+C2H3ON8C | SEQ ID No. 302 |
| 1100.280 | 1099.623 | 57 | 65 | 0 | QLIIDLETR | SEQ ID No. 303 |
| 1269.514 | 1268.579 | 399 | 408 | 0 | QMPGCFNFLR (1)+C2H3ON8C | SEQ ID No. 304 |
| 1323.579 | 1322.669 | 194 | 204 | 0 | FSSLRFMVEVK | SEQ ID No. 305 |
| 1397.619 | 1396.680 | 281 | 292 | 0 | LFIQACQGEQK (1)+C2H3ON8C | SEQ ID No. 306 |
| 1683.952 | 1682.856 | 33 | 45 | 0 | ELFRPNMTEDIQP | SEQ ID No. 307 |
| 1889.386 | 1887.987 | 263 | 280 | 0 | IVNIFNGTSCPSLGGKPK (1)+C2H3ON8C | SEQ ID No. 308 |
| 2027.385 | 2026.073 | 16 | 32 | 0 | LVRELQVDQLNDALLSR | SEQ ID No. 309 |
| 2175.600 | 2174.278 | 98 | 116 | 0 | LSKPTLENLTPVVLRPEIR | SEQ ID No. 310 |
| 2770.180 | 2768.351 | 66 | 90 | 0 | GSQALDLFISCLEDTGQNLASFLR (1)+C2H3ON8C | SEQ ID No. 311 |
| 3149.555 | 3147.667 | 117 | 146 | 0 | KPKVLRPETPRPVDIGSGGFGDVGALESLR | SEQ ID No. 312 |
| 3152.651 | 3150.450 | 147 | 173 | 0 | GRADLAYILSMEPCGHCLIIHNVSCR (3)+C2H3ON8C | SEQ ID No. 313 |
| 3338.635 | 3336.593 | 355 | 386 | 0 | SGSWYVETLDDIFEQWAHSEDLQSLLLR | SEQ ID No. 314 |
| 3400.488 | 3398.481 | 293 | 324 | 0 | DHGFEVASTSPEDESPGSNPEPDATPFQEGLR | |
| 3481.864 | 3479.692 | 325 | 355 | 0 | TFDQLDAISSLPTPSDIFVSYSTFPGFVSWR | SEQ ID No. 315 |
| 5552.402 | 5549.670 | 213 | 262 | 0 | RVLALLELAQQDHGALDCCVVVILSHGCQA SHLQFPGAVYGTDGCPVSVEK (4)+C2H3ON8C | SEQ ID No. 316 |

Figure 3K

BCL2L1

| | | | | | | |
|---|---|---|---|---|---|---|
| 721.792 | 721.317 | 1 | 6 | 0 | MSQSNR | SEQ ID No. 317 |
| 802.645 | 802.372 | 133 | 139 | 0 | DSVNWGR | SEQ ID No. 318 |
| 957.203 | 956.536 | 79 | 87 | 0 | EVIPMDAVK | SEQ ID No. 319 |
| 961.150 | 960.506 | 158 | 165 | 0 | RMQVLVSR | SEQ ID No. 320 |
| 1065.109 | 1064.477 | 92 | 100 | 0 | RAGDEFELR | SEQ ID No. 321 |
| 1212.408 | 1211.643 | 7 | 16 | 0 | ELVVDFLSYK | SEQ ID No. 322 |
| 1703.743 | 1702.722 | 21 | 34 | 0 | GYSWSQFSDVEENR | SEQ ID No. 323 |
| 1946.255 | 1944.965 | 140 | 157 | 0 | LVAFFSFGGALCVESVDK (1)402K3CFST | SEQ ID No. 324 |
| 2154.605 | 2153.170 | 213 | 232 | 0 | NPLTGMTVAGVVLLGSLFSR | SEQ ID No. 325 |
| 3299.645 | 3297.630 | 104 | 132 | 0 | AFSDLTSQLHITPGTAYQSFEQVVNELFR | SEQ ID No. 326 |
| 4454.861 | 4452.954 | 166 | 204 | 0 | LAAWMATYLNDHLEPWIQENGGWDTFVELY GNNAAAESR | SEQ ID No. 327 |
| 4479.690 | 4477.000 | 35 | 78 | 0 | TEAPEGTESEMETPSAINGNPSWHLADSPA VNGATGHSSSLDAP | SEQ ID No. 328 |

Figure 3L

EIF4EBP1

| | | | | | | |
|---|---|---|---|---|---|---|
| 627.741 | 627.378 | 15 | 20 | 0 | SLPATR | SEQ ID No. 329 |
| 644.726 | 644.349 | 65 | 70 | 0 | NSPVTK | SEQ ID No. 330 |
| 679.786 | 679.378 | 53 | 57 | 0 | IIYDR | SEQ ID No. 331 |
| 688.692 | 688.302 | 101 | 106 | 0 | NSSEDK | SEQ ID No. 332 |
| 855.049 | 854.377 | 59 | 64 | 0 | FLMECR | SEQ ID No. 333 |
| | | | | | (1)+C2H3ON8C | |
| 1312.375 | 1311.526 | 108 | 119 | 0 | AGGEESQFEMDI | SEQ ID No. 334 |
| 1441.523 | 1440.572 | 1 | 14 | 0 | ACSGSSCSQTPSR | SEQ ID No. 335 |
| | | | | | (3)+C2H3ON8C | |
| 2749.006 | 2747.307 | 75 | 100 | 0 | ELPTIPGVTSPSSDEPPMEASQSHLR | SEQ ID No. 336 |
| 3048.337 | 3046.524 | 22 | 52 | 0 | YVLGDGVQLPPGDYSTTPGGTLPSTIPGGT R | SEQ ID No. 337 |

Figure 3M

BCL2

| | | | | | | |
|---|---|---|---|---|---|---|
| 618.795 | 618.341 | 13 | 17 | 0 | SIVMK | SEQ ID No. 338 |
| 641.792 | 641.306 | 1 | 6 | 0 | MAHAGR | SEQ ID No. 339 |
| 722.842 | 722.375 | 18 | 22 | 0 | YIHYK | SEQ ID No. 340 |
| 724.728 | 724.314 | 7 | 12 | 0 | TGYDNR | SEQ ID No. 341 |
| 802.845 | 802.372 | 140 | 146 | 0 | DGVNWGR | SEQ ID No. 342 |
| 894.896 | 894.383 | 99 | 106 | 0 | QAGDDFSR | SEQ ID No. 343 |
| 1210.395 | 1209.639 | 130 | 139 | 0 | SATVVEELRT | SEQ ID No. 344 |
| 1951.190 | 1949.930 | 111 | 127 | 0 | DPAEMSQLHLTPFTAR | SEQ ID No. 345 |
| 2061.413 | 2059.985 | 147 | 164 | 0 | IVAFFSYGGVMCVESVNR | SEQ ID No. 346 |
| 2171.633 | 2170.218 | 219 | 239 | 0 | (1)+C2H2ONO TLLSLALVGACITLGAYLGHK | SEQ ID No. 347 |
| 2295.666 | 2294.107 | 165 | 183 | 0 | (1)+C2H2ONO EMGPLVDNIALWMTEYLNR | SEQ ID No. 348 |
| 2987.376 | 2985.612 | 69 | 98 | 0 | TSPLQTPAAPGAAAGPALSPVPPVVHLTLR | SEQ ID No. 349 |
| 3597.866 | 3595.606 | 27 | 63 | 0 | GYEWDAGDVGAAPPGAAPAPGIFSSQPGHT PHPAASR | SEQ ID No. 350 |
| 4164.717 | 4162.013 | 184 | 218 | 0 | HLETWIQDNGGWDAFVELYGPSMRPLFDFS WLSLK | SEQ ID No. 351 |

Figure 3N

SELS

| | | | | | | |
|---|---|---|---|---|---|---|
| | | | | | | SEQ ID No. 352 |
| 517.496 | 517.213 | 182 | 189 | 0 | QFSSGGUG | SEQ ID No. 353 |
| 530.581 | 530.281 | 62 | 65 | 0 | QLDB | SEQ ID No. 354 |
| 774.826 | 774.375 | 106 | 111 | 0 | QLEEEK | SEQ ID No. 355 |
| 828.924 | 828.445 | 79 | 86 | 0 | QEALAAK | SEQ ID No. 356 |
| 1168.356 | 1167.649 | 66 | 77 | 0 | AAAAVEPDVVVK | SEQ ID No. 357 |
| 1318.471 | 1317.623 | 89 | 99 | 0 | MQEELNAQVEK | SEQ ID No. 358 |
| 1353.540 | 1352.574 | 116 | 126 | 0 | IEMWDSMQEGK | SEQ ID No. 359 |
| 1785.926 | 1784.879 | 134 | 150 | 0 | KPQEEDSPGPSTSSVLK | SEQ ID No. 360 |
| 1886.049 | 1884.954 | 4 | 20 | 0 | QEPSLSARPALETBGLP | SEQ ID No. 361 |
| 2092.239 | 2090.934 | 160 | 180 | 0 | GQGYNPLSGEGGGACSWRPGR | |
| 3549.230 | 3547.877 | 21 | 50 | 0 | FLRTTVGSLLATYGNYIVESCILLYVFQK | SEQ ID No. 362 |

Figure 3O

SPP1

| | | | | | | |
|---|---|---|---|---|---|---|
| 684.753 | 684.354 | 15 | 19 | 0 | QLYNK | SEQ ID No. 363 |
| 801.895 | 801.423 | 55 | 61 | 0 | QETLPSK | SEQ ID No. 364 |
| 955.074 | 964.497 | 144 | 152 | 0 | GDSVVYGLR | SEQ ID No. 365 |
| 1037.005 | 1036.430 | 5 | 14 | 0 | QADSGSSEEK | SEQ ID No. 366 |
| 1387.423 | 1386.626 | 286 | 298 | 0 | ISHELDSASSEVN | SEQ ID No. 367 |
| 1801.974 | 1800.868 | 20 | 35 | 0 | YPDAVATWLNPDPSQK | SEQ ID No. 368 |
| 1854.994 | 1853.890 | 189 | 204 | 0 | AIPVAQDLNAPSDWDSR | SEQ ID No. 369 |
| 2105.246 | 2104.007 | 36 | 54 | 0 | QELLAPQNAVSSEETNDFK | SEQ ID No. 370 |
| 2117.125 | 2115.919 | 234 | 252 | 0 | ANDESNEHSDVIDSQELSK | SEQ ID No. 371 |
| 2178.167 | 2176.914 | 207 | 225 | 0 | DSYETSQLDDQSAETHSHK | SEQ ID No. 372 |
| 2320.527 | 2319.037 | 256 | 274 | 0 | KFRSHELNSHRSHELMLVVDPK | SEQ ID No. 373 |
| 3225.406 | 3223.425 | 160 | 187 | 0 | KPDIQYPDATDEDITSHMESEELNGAYK | SEQ ID No. 374 |

Figure 3P

FGF2

| | | | | | | |
|---|---|---|---|---|---|---|
| 595.635 | 595.312 | 119 | 124 | 0 | AAPAAR | SEQ ID No. 375 |
| 557.607 | 557.293 | 59 | 64 | 0 | AAGSPR | SEQ ID No. 376 |
| 569.661 | 569.328 | 87 | 92 | 0 | ALPSGR | SEQ ID No. 377 |
| 571.634 | 571.307 | 113 | 118 | 0 | GTAAPR | SEQ ID No. 378 |
| 582.721 | 582.283 | 165 | 168 | 0 | LYCK (1)+C2H3ON0C | SEQ ID No. 379 |
| 586.646 | 586.307 | 272 | 277 | 0 | TGPGQK | SEQ ID No. 380 |
| 595.653 | 595.296 | 263 | 267 | 0 | TSQYK | SEQ ID No. 381 |
| 601.744 | 601.379 | 203 | 208 | 0 | GVVSIK | SEQ ID No. 382 |
| 624.802 | 624.330 | 215 | 219 | 0 | YLAMK | SEQ ID No. 383 |
| 675.767 | 675.312 | 209 | 214 | 0 | GVCANR (1)+C2H3ON0C | SEQ ID No. 384 |
| 693.760 | 693.355 | 176 | 181 | 0 | IHPDGR | SEQ ID No. 385 |
| 695.773 | 695.360 | 189 | 194 | 0 | SDPHIK | SEQ ID No. 386 |
| 805.892 | 805.419 | 50 | 56 | 0 | HESVHPR | SEQ ID No. 387 |
| 809.923 | 809.418 | 169 | 175 | 0 | NGGFFLR | SEQ ID No. 388 |
| 986.093 | 985.519 | 195 | 202 | 0 | LQLQAEER | SEQ ID No. 389 |
| 1018.051 | 1017.483 | 70 | 78 | 0 | TEKRPSCSR | SEQ ID No. 390 |
| 1090.395 | 1089.625 | 278 | 287 | 0 | AILFLPMSAK | SEQ ID No. 391 |
| 1130.309 | 1129.580 | 253 | 261 | 0 | YTSWYVALK | SEQ ID No. 392 |
| 1273.325 | 1272.573 | 240 | 249 | 0 | LESNNYNTYR | SEQ ID No. 393 |
| 1509.683 | 1508.606 | 229 | 239 | 0 | CVTDECFFFER (1)+C2H3ON0C | SEQ ID No. 394 |
| 1710.934 | 1709.830 | 28 | 44 | 0 | GCNGIPGAAANEAALPR (1)+C2H3ON0C | SEQ ID No. 395 |
| 2400.679 | 2399.132 | 1 | 24 | 0 | MVGVGGGDVEDVTPRPGGCQISGR | SEQ ID No. 396 |
| 3407.812 | 3405.677 | 125 | 160 | 0 | GSRPGPAGTNAAGSITTLPALPEDGGSGAF PPGHFK | SEQ ID No. 397 |

Figure 3Q

EGFR

| | | | | | | |
|---|---|---|---|---|---|---|
| 631.683 | 631.317 | 725 | 730 | 0 | KATSPK | SEQ ID No. 398 |
| 639.836 | 639.431 | 716 | 721 | 0 | IPVAIK | SEQ ID No. 399 |
| 644.793 | 644.331 | 110 | 114 | 0 | ELPMR | SEQ ID No. 400 |
| 649.723 | 649.274 | 510 | 514 | 0 | SCVDK (1)+C2H3ON&C | SEQ ID No. 401 |
| 652.762 | 652.306 | 685 | 689 | 0 | KTPPK | SEQ ID No. 402 |
| 657.769 | 657.380 | 658 | 662 | 0 | LLQER | SEQ ID No. 403 |
| 693.735 | 693.275 | 471 | 476 | 0 | GENSCK (1)+C2H3ON&C | SEQ ID No. 404 |
| 708.815 | 708.391 | 823 | 829 | 0 | TPQHVK | SEQ ID No. 405 |
| 722.774 | 722.290 | 232 | 237 | 0 | DEADCK (1)+C2H3ON&C | SEQ ID No. 406 |
| 758.870 | 758.417 | 837 | 843 | 0 | LLGAEEK | SEQ ID No. 407 |
| 777.880 | 777.289 | 305 | 310 | 0 | CEGPCR (2)+C2H3ON&C | SEQ ID No. 408 |
| 795.896 | 795.300 | 498 | 503 | 0 | DCVSCR (2)+C2H3ON&C | SEQ ID No. 409 |
| 836.943 | 836.439 | 456 | 463 | 0 | LFGTSGQK | SEQ ID No. 410 |
| 864.009 | 863.475 | 829 | 836 | 0 | IYDFGLAK | SEQ ID No. 411 |
| 889.920 | 889.392 | 844 | 851 | 0 | EYHAEGGK | SEQ ID No. 412 |
| 892.988 | 892.407 | 6 | 13 | 0 | VCQGTSNK (1)+C2H3ON&C | SEQ ID No. 413 |
| 893.952 | 893.424 | 1038 | 1044 | 0 | SDSFLQR | SEQ ID No. 414 |
| 978.153 | 977.543 | 939 | 946 | 0 | ELIIEFSK | SEQ ID No. 415 |
| 997.097 | 996.433 | 800 | 807 | 0 | OMNYLEDR | SEQ ID No. 416 |
| 999.131 | 998.507 | 49 | 56 | 0 | NYDLSFLK | SEQ ID No. 417 |
| 1003.166 | 1002.549 | 1156 | 1164 | 0 | SAKPNGIFK | SEQ ID No. 418 |
| 1016.186 | 1015.512 | 1029 | 1037 | 0 | NGLQSCPIK (1)+C2H3ON&C | SEQ ID No. 419 |
| 1028.173 | 1027.533 | 705 | 713 | 0 | GLWIPEGEK | SEQ ID No. 420 |
| 1032.185 | 1031.474 | 261 | 269 | 0 | YSFGATCVK (1)+C2H3ON&C | SEQ ID No. 421 |
| 1038.171 | 1037.426 | 221 | 228 | 0 | ESDCLVCR (3)+C2H3ON&C | SEQ ID No. 422 |
| 1087.222 | 1086.512 | 515 | 523 | 0 | CNLLEGEPR (1)+C2H3ON&C | SEQ ID No. 423 |
| 1092.217 | 1091.561 | 954 | 962 | 0 | YLVIQGDER | SEQ ID No. 424 |
| 1106.213 | 1104.545 | 1176 | 1186 | 0 | VAPQSSEFIGA | SEQ ID No. 425 |
| 1175.304 | 1174.619 | 323 | 333 | 0 | QSLSINATNIK | SEQ ID No. 426 |
| 1192.386 | 1191.548 | 189 | 198 | 0 | IICAQQCSGR (2)+C2H3ON&C | SEQ ID No. 427 |
| 1193.389 | 1192.591 | 312 | 322 | 0 | VCNGIGIGEEK (1)+C2H3ON&C | SEQ ID No. 428 |
| 1198.384 | 1197.639 | 693 | 704 | 0 | VLGSGAFGTVYK | SEQ ID No. 429 |
| 1208.467 | 1207.728 | 75 | 84 | 0 | IPLENLQIIR | SEQ ID No. 430 |
| 1210.266 | 1209.562 | 1165 | 1175 | 0 | GSTAENAEYLR | SEQ ID No. 431 |
| 1249.436 | 1248.693 | 115 | 125 | 0 | NLQEILNGAVR | SEQ ID No. 432 |
| 1255.507 | 1254.664 | 858 | 868 | 0 | WMALESILHR | SEQ ID No. 433 |
| 1346.457 | 1345.672 | 431 | 443 | 0 | EISDGDVIISGNK | SEQ ID No. 434 |
| 1378.596 | 1377.616 | 926 | 936 | 0 | CWMIDADSRPK (1)+C2H3ON&C | SEQ ID No. 435 |
| 1396.590 | 1395.660 | 444 | 454 | 0 | NLCYANTINWK (1)+C2H3ON&C | SEQ ID No. 436 |
| 1406.543 | 1405.640 | 274 | 285 | 0 | NYVVTDHGSCVR (1)+C2H3ON&C | SEQ ID No. 437 |
| 1564.742 | 1563.714 | 963 | 973 | 0 | MHLPSPTDSNFYR | SEQ ID No. 438 |
| 1570.766 | 1569.815 | 391 | 403 | 0 | TDLHAFENLEIIR | SEQ ID No. 439 |
| 1688.770 | 1687.645 | 286 | 300 | 0 | ACGADSYEMEEDGVR | SEQ ID No. 440 |
| 1777.058 | 1775.833 | 570 | 585 | 0 | TCPAGVMGENNTLVWK (1)+C2H3ON&C | SEQ ID No. 441 |
| 1797.049 | 1795.941 | 376 | 390 | 0 | EITGFLLIQAWPENR | SEQ ID No. 442 |
| 1900.189 | 1898.967 | 337 | 353 | 0 | NCTSISGDLHILPVAFR (1)+C2H3ON&C | SEQ ID No. 443 |

Figure 3R

EGFR (cont.)

| | | | | | | |
|---|---|---|---|---|---|---|
| 1905.141 | 1903.979 | 14 | 29 | 0 | LEQLFTFEDHFLSLQR | SEQ ID No. 444 |
| 1935.151 | 1933.910 | 126 | 141 | 0 | PSNHALCNVESIQWR (1)+C2H3ON&C | SEQ ID No. 445 |
| 1989.300 | 1988.094 | 57 | 74 | 0 | DTQEVAGYVLIALNTVER | SEQ ID No. 446 |
| 2018.857 | 2017.045 | 909 | 925 | 0 | LFGPPICTIDVYMIMVK (1)+C2H3ON&C | SEQ ID No. 447 |
| 2022.313 | 2021.004 | 783 | 799 | 0 | DNIGSQYLLNWCVQIAK (1)+C2H3ON&C | SEQ ID No. 448 |
| 2034.297 | 2033.079 | 663 | 681 | 0 | ELVEPLTPSGEAPNQALLR | SEQ ID No. 449 |
| 2035.211 | 2033.756 | 203 | 220 | 0 | SPSDCCHNQCAAGCTGPR (4)+C2H3ON&C | SEQ ID No. 450 |
| 2123.349 | 2122.058 | 354 | 372 | 0 | GDSFTHTPPLDPQELDILK | SEQ ID No. 451 |
| 2140.471 | 2139.180 | 408 | 427 | 0 | QRQQFSLAVVSLNITSLGLR | SEQ ID No. 452 |
| 2207.447 | 2206.089 | 1009 | 1028 | 0 | TPLLSSLSATSNNSTVACIDR (1)+C2H3ON&C | SEQ ID No. 453 |
| 2218.497 | 2217.019 | 734 | 752 | 0 | HYLLEAYVMASVDNPHVCR (1)+C2H3ON&C | SEQ ID No. 454 |
| 2236.382 | 2235.023 | 1137 | 1155 | 0 | GSHQISLDNPDYQQDFFPK | SEQ ID No. 455 |
| 2241.517 | 2239.956 | 553 | 569 | 0 | GPDNCIQCAHYIDGPHCVK (3)+C2H3ON&C | SEQ ID No. 456 |
| 2299.657 | 2298.113 | 30 | 46 | 0 | MFNNCEVVLGNLEITYVQR (1)+C2H3ON&C | SEQ ID No. 457 |
| 2313.472 | 2311.835 | 166 | 185 | 0 | QHPGCPNGSCWGAGEENCQK (4)+C2H3ON&C | SEQ ID No. 458 |
| 2369.648 | 2368.014 | 477 | 497 | 0 | ATGQVCHALCSPEGCWGPEPR (3)+C2H3ON&C | SEQ ID No. 459 |
| 2399.635 | 2398.225 | 1076 | 1097 | 0 | RPAGSVQNPVYHNQPLNPAPSR | SEQ ID No. 460 |
| 2400.608 | 2399.073 | 85 | 105 | 0 | GNMYYENSYALAVLSNYDANK | SEQ ID No. 461 |
| 2685.032 | 2683.196 | 238 | 260 | 0 | DTCPPLMLYNPTTYQMDVNPEGK (1)+C2H3ON&C | SEQ ID No. 462 |
| 2739.513 | 2737.636 | 619 | 645 | 0 | IPSIATGMVGALLLLLVVALGIGLFMR | SEQ ID No. 463 |
| 2761.067 | 2759.198 | 142 | 165 | 0 | DIVSSDFLSNMSMDFQNHLGSCQK (1)+C2H3ON&C | SEQ ID No. 464 |
| 3125.812 | 3123.653 | 753 | 779 | 0 | LLGICLTSTVQLITQLMPFGCLLDYVR (2)+C2H3ON&C | SEQ ID No. 465 |
| 3281.701 | 3279.387 | 534 | 560 | 0 | KPVRGSECIQCHPECLPQAMNITCTGR (4)+C2H3ON&C | SEQ ID No. 466 |
| 3399.667 | 3397.608 | 1045 | 1075 | 0 | YSSDPTGALTEDSIDDTFLPVPEYINQSVPK | SEQ ID No. 467 |
| 3608.874 | 3606.565 | 976 | 1007 | 0 | ALMDEEDMDDVVDADEYLIPQQGFFSSPSTSR | SEQ ID No. 468 |
| 3659.064 | 3656.511 | 586 | 618 | 0 | YADAGHVCHLCHPNCTYGCTGPGLEGCPTNGPK (5)+C2H3ON&C | SEQ ID No. 469 |
| 4410.721 | 4407.967 | 1098 | 1136 | 0 | DPHYQDPHSTAVGNPEYLNTVQPTCVNSTFDSPAHWAQK (1)+C2H3ON&C | SEQ ID No. 470 |
| 4536.696 | 4533.209 | 866 | 905 | 0 | IYTHQSDVWSYGVTVWELMTFGSKPYDGIPASEISSILEK | SEQ ID No. 471 |

Figure 3S

HER2

| | | | | | | |
|---|---|---|---|---|---|---|
| | | | | | | SEQ ID No. 472 |
| 601.700 | 601.343 | 1150 | 1155 | 0 | YLSPGK | SEQ ID No. 473 |
| 639.336 | 639.431 | 726 | 731 | 0 | IPVAIK | SEQ ID No. 474 |
| 646.698 | 646.328 | 695 | 699 | 0 | ETELR | SEQ ID No. 475 |
| 657.768 | 657.380 | 117 | 121 | 0 | ELQLR | SEQ ID No. 476 |
| 658.755 | 658.343 | 149 | 153 | 0 | DIFHK | SEQ ID No. 477 |
| 674.708 | 674.323 | 735 | 740 | 0 | KNTSPK | SEQ ID No. 478 |
| 680.762 | 680.360 | 833 | 838 | 0 | SKNSVK | SEQ ID No. 479 |
| 739.873 | 739.434 | 71 | 76 | 0 | QVPLQR | SEQ ID No. 480 |
| 741.869 | 741.449 | 129 | 135 | 0 | GGVLIQR | SEQ ID No. 481 |
| 750.809 | 750.366 | 531 | 536 | 0 | EYVRAR | SEQ ID No. 482 |
| 781.953 | 781.481 | 524 | 530 | 0 | VLQGLPR | SEQ ID No. 483 |
| 802.966 | 802.480 | 122 | 128 | 0 | SLTEILK | SEQ ID No. 484 |
| 803.913 | 803.417 | 1209 | 1216 | 0 | GAPPSTFK | SEQ ID No. 485 |
| 816.993 | 816.354 | 619 | 625 | 0 | GCPAEQR | |
| 878.944 | 877.389 | 312 | 318 | 0 | CSKPCAR (1)+C2H3ON@C | SEQ ID No. 486 |
| 892.023 | 891.481 | 839 | 846 | 0 | IIDTGKLAR | SEQ ID No. 487 |
| 951.095 | 950.406 | 198 | 204 | 0 | TVCAGGCAR (2)+C2H3ON@C | SEQ ID No. 488 |
| 956.104 | 955.522 | 908 | 915 | 0 | EIPDLLEK | SEQ ID No. 489 |
| 961.109 | 960.448 | 570 | 577 | 0 | DPPFCVAR (1)+C2H3ON@C | SEQ ID No. 490 |
| 966.059 | 965.481 | 949 | 956 | 0 | ELVSEFSR | SEQ ID No. 491 |
| 1069.203 | 1068.491 | 610 | 618 | 0 | QMSTLRVR | SEQ ID No. 492 |
| 1118.365 | 1117.595 | 866 | 874 | 0 | WMALESILR | SEQ ID No. 493 |
| 1140.304 | 1139.495 | 1 | 10 | 0 | TQVCTGTDMK (1)+C2H3ON@C | SEQ ID No. 494 |
| 1166.258 | 1165.449 | 515 | 523 | 0 | GQECVEECR (2)+C2H3ON@C | SEQ ID No. 495 |
| 1198.384 | 1197.639 | 703 | 714 | 0 | VLGSGAFGTVYK | SEQ ID No. 496 |
| 1227.383 | 1226.629 | 715 | 725 | 0 | GIWIPDGENVK | SEQ ID No. 497 |
| 1247.510 | 1246.471 | 169 | 178 | 0 | ACRPCSPMCK (3)+C2H3ON@C | SEQ ID No. 498 |
| 1334.586 | 1333.627 | 319 | 329 | 0 | VCYGLGMEHLR (1)+C2H3ON@C | SEQ ID No. 499 |
| 1479.720 | 1478.755 | 13 | 25 | 0 | LPASPETHLDMLR | SEQ ID No. 500 |
| 1485.661 | 1484.794 | 154 | 166 | 0 | HNQLALTLIDTNR | SEQ ID No. 501 |
| 1495.677 | 1494.713 | 333 | 346 | 0 | AVTSANIQEFAGCK (1)+C2H3ON@C | SEQ ID No. 502 |
| 1509.754 | 1508.632 | 936 | 946 | 0 | CWNIDSGCPPR (2)+C2H3ON@C | SEQ ID No. 503 |
| 1645.836 | 1644.858 | 1075 | 1089 | 0 | GLQSLPTHDPSPLQR | SEQ ID No. 504 |
| 1675.769 | 1674.773 | 847 | 861 | 0 | LLDIDETEYHADGGK | SEQ ID No. 505 |
| 1678.929 | 1677.818 | 136 | 148 | 0 | NPQLCYQDTILWK | SEQ ID No. 506 |
| 1714.811 | 1713.672 | 182 | 195 | 0 | CWGESSEDCQSLTR (2)+C2H3ON@C | SEQ ID No. 507 |
| 1771.942 | 1770.867 | 1217 | 1233 | 0 | GTPTAENPEYLGLDVPV | SEQ ID No. 508 |
| 1777.099 | 1775.869 | 795 | 809 | 0 | LGSQDLLNWCMQIAK (1)+C2H3ON@C | SEQ ID No. 509 |
| 1831.106 | 1830.011 | 1132 | 1149 | 0 | EGPLPAARPAGATLERPK | SEQ ID No. 510 |
| 1876.247 | 1876.921 | 578 | 593 | 0 | CPSGVKPDLSYMPIWK (1)+C2H3ON@C | SEQ ID No. 511 |
| 1914.013 | 1912.901 | 1033 | 1050 | 0 | SGGGDLTLGLEPSEEEAPR | SEQ ID No. 512 |
| 2018.537 | 2017.046 | 919 | 935 | 0 | LPQPPICTIDVYMIMVK | SEQ ID No. 513 |
| 2056.324 | 2054.998 | 744 | 762 | 0 | EILDEAYVMAGVGSPYVSR | SEQ ID No. 514 |
| 2215.486 | 2214.691 | 207 | 226 | 0 | GPLPTDCCHEQCAAGCTGPK (4)+C2H3ON@C | SEQ ID No. 515 |
| 2249.440 | 2248.031 | 1051 | 1074 | 0 | SPLAPSEGAGSDVFDGDLGMGAAK | SEQ ID No. 516 |
| 2261.554 | 2259.972 | 496 | 514 | 0 | GSCWGPGPTQCVNCSQFLR (2)+C2H3ON@C | SEQ ID No. 517 |

Figure 3T

HER2 (cont.)

| | | | | | | |
|---|---|---|---|---|---|---|
| 2368.629 | 2367.176 | 964 | 984 | 0 | FVVIQNEDLGPASPLDSTFYR | SEQ ID No. 518 |
| 2382.792 | 2381.321 | 413 | 434 | 0 | ILHNGAYSLTLQGLGISWLGLR | SEQ ID No. 519 |
| 2654.061 | 2652.325 | 668 | 691 | 0 | LLQETELVEPLTPSGAMPNQAQMR | SEQ ID No. 520 |
| 2891.699 | 2889.829 | 626 | 654 | 0 | ASPLTSIISAVVGILLVVLGVVFGILIK | SEQ ID No. 521 |
| 2965.230 | 2963.182 | 594 | 618 | 0 | FPDEEGACQPCPINCTHSCVDLDDK (4)+C2H3ONC | SEQ ID No. 522 |
| 3101.750 | 3099.629 | 763 | 789 | 0 | LLGICLTSTVQLVTQLMPYGCLLDHVR (2)+C2H3ONC | SEQ ID No. 523 |
| 3298.779 | 3296.686 | 438 | 465 | 0 | PLSSLSLIHHNTHLCFVHTVPWDQLFR (1)+C2H3ONC | SEQ ID No. 524 |
| 3454.857 | 3452.588 | 466 | 495 | 0 | NPEGALLHTANRPEDECVGEGLACHQLCAR (3)+C2H3ONC | SEQ ID No. 525 |
| 3560.007 | 3557.707 | 877 | 907 | 0 | FTHQSDVWSYGVTVWELMTFGAKPYDGIPAR | SEQ ID No. 526 |
| 3588.891 | 3586.753 | 82 | 116 | 0 | GTQLFEDNYALAVLDNGDPLNNTTPVTGASPGGLR | SEQ ID No. 527 |
| 3916.377 | 3913.594 | 537 | 569 | 0 | HCLPCHPECQPQNGSVTCFGPEADQCVACAHYK (6)+C2H3ONC | SEQ ID No. 528 |
| 4386.629 | 4383.951 | 985 | 1024 | 0 | GLEPSEEDGSVPEREYLVPQQGFFCPDPAPGAGGMVHHR (1)+C2H3ONC | SEQ ID No. 529 |

FIGURE 4 eIF4E
- EAVTHIGR
- WALWFFK

Cyclin D1
- WNLAAMTPHDFIEHFLSK
- ACQEQIEALLESSLR
- AEETCAPSVSYFK
- LCIYTDNSIRPEELLQMELLLVNK

Nibrin/NBS-1
- NPSGINDDYGQLK
- EMDDVAIEDEVLEQLFK
- LLPAAGPAGGEPYR
- KQPPQIESFYPPLDEPSIGSK

Pim-1
- ISDWGELPNGTR
- DTVYTDFDGTR
- LIDFGSGALLK
- SLGILLYDMVCGDIPFEHDEEIIR

ODC
- FEEITGVINPALDK
- INEVSSSDDKDAFYVADLGDILK
- TLAATGTGFDCASK
- LLDIGGGFPGSEDVK

SKP2
- TLQVFGIVPDGTLQLLK
- LLSQGVIAFR
- LASDESLWQTLDLTGK
- LSDPIVNTLAK

Cyclin E1
- AILLDWLMEVCEVYK
- DQHFLEQHPLLQPK
- GSPLPVLSWANR
- YMATQENVVK

MMP9
- LGLGADVAQVTGALR
- QLSLPETGELDSATLK
- QSTLVLFPGDLR
- SLGPALLLLQK

Caspase 9
- LVEELQVDQLWDVLLSR
- DHGFEVASTSPEDESPGSNPEPDATPFQEGLR
- QLIIDLETR
- KPEVLRPETPRPVDIGSGGFGDVEQK

Bcl-X(L)
- AFSDLTSQLHITPGTAYQSFEQVVNELFR
- ELVVDFLSYK
- QSFEQVVNELFR
- EVIPMAAVK eIF4E-BP1
- RVVLGDGVQLPPGDYSTTPGGTLFSTTPGGTR
- VVLGDGVQLPPGDYSTTPGGTLFSTTPGGTR
- DLPTIPGVTSPSSDEPPMEASQSHLR
- DLPTIPGVTSPSSDEPPMEASQSHLR

AKT1
- FFAGIVWQHVYEK
- TFCGTPEYLAPEVLEDNDYGR
- EEWTTAIQTVADGLK
- LFELILMEEIR

ELAVL1/HuR
- DANLYISGLPR
- VLVDQTTGLSR
- NVALLSQLYHSPAR
- TNLIVNYLPQNMTQDELR

FIGURE 4 CONT.

Target peptides for MRM listed below

| Protein/Gene | Peptide Sequence |
|---|---|
| AKT1 | EEWTTAIQTVADGLK (SEQ ID NO: 25) |
| AKT1 | FFAGIVWQHVYEK (SEQ ID NO: 531) |
| BCL2 | FATVVEELFR (SEQ ID NO: 532) |
| BCL2L1 | ELVVDFLSYK (SEQ ID NO: 533) |
| BCL2L1 | EVIPMAAVK (SEQ ID NO: 534) |
| CASP9 | DHGFEVASTSPEDESPGSNPEPDATPFQEGLR (SEQ ID NO: 535) |
| CASP9 | QLIIDLETR (SEQ ID NO: 536) |
| CCND1 | ACQEQIEALLESSLR (SEQ ID NO: 537) |
| CCND1 | AEETCAPSVSYFK (SEQ ID NO: 538) |
| EGFR | GDSFTHTPPLDPQELDILK (SEQ ID NO: 539) |
| EGFR | IPLENLQIIR (SEQ ID NO: 540) |
| EIF4E | IVIGYQSHADTATK (SEQ ID NO: 541) |
| EIF4E | WALWFFK (SEQ ID NO: 542) |
| ELAVL1 | DANLYISGLPR (SEQ ID NO: 543) |
| ELAVL1 | VLVDQTTGLSR (SEQ ID NO: 544) |
| FGF2 | AILFLPMSAK (SEQ ID NO: 545) |
| FGF2 | CVTDECFFFER (SEQ ID NO: 546) |
| HER2 | GIWIPDGENVK (SEQ ID NO: 547) |
| HER2 | VLGSGAFGTVYK (SEQ ID NO: 548) |
| ODC1 | FEEITGVINPALDK (SEQ ID NO: 549) |
| ODC1 | LLDIGGGFPGSEDVK (SEQ ID NO: 550) |
| PIM1 | DTVYTDFDGTR (SEQ ID NO: 551) |
| PIM1 | ISDWGELPNGTR (SEQ ID NO: 552) |
| SELS | AAAAVEPDVVVK (SEQ ID NO: 553) |
| SELS | MQEELNAQVEK (SEQ ID NO: 554) |
| SKP2 | LSDPIVNTLAK (SEQ ID NO: 555) |
| SKP2 | TLQVFGIVPDGTLQLLK (SEQ ID NO: 556) |
| SPP1 | AIPVAQDLNAPSDWDSR (SEQ ID NO: 557) |
| SSP1 | GDSVVYGLR (SEQ ID NO: 558) |

Figure 5

EIF4EBP1 (Q13541) (NP_004086) NP_004086.1) – SEQ ID NO. 559

AcSGGSSCSQTPSRAIPATRRVVLGDGVQLPPGDYSTTPGGTLFSTTPGGTRIIYDRKFLMECRNSPVTKTPPRDLP
TIPGVTSPSSDEPPMEASQSHLRNSPEDKRAGGEESQFEMDI

AKT1 (P31749) (NP_001014431, NP_005154, NP_001014432) (NP_001014431.1, NP_005154.2, NP_001014432.1) – SEQ ID NOs. 211, 560

MSDVAIVKEGWLHKRGEYIKTWRPRYFLLKNDGTFIGYKERPQDVDQREAPLNNFSVAQCQLMKTERPRPNTFIIRCL
QWTTVIERTFHVETPEEREEWTTAIQTVADGLKKQEEEEMDFRSGSPSDNSGAEEMEVSLAKPKHRVTMNEFEYLKLL
GKGTFGKVILVKEKATGRYYAMKILKKEVIVAKDEVAHTLTENRVLQNSRHPFLTALKYSFQTHDRLCFVMEYANGGELF
FHLSRERVFSEDRARFYGAEIVSALDYLHSEKNVVYRDLKLENLMLDKDGHIKITDFGLCKEGIKDGATMKTFCGTPEYLA
PEVLEDNDYGRAVDWWGLGVVMYEMMCGRLPFYNQDHEKLFELILMEEIRFPRTLGPEAKSLLSGLLKKDPKQRLGG
GSEDAKEIMQHRFFAGIVWQHVYEKKLSPPFKPQVTSETDTRYFDEEFTAQMITITPPDQDDSMECVDSERRPHFPQF
SYSASGTA

MASS SPECTROMETRY ASSAY FOR *EIF4E* AND *EIF4E* REGULON ACTIVITY

CROSS-REFERENCE TO RELATED APPLICATIONS

This application is a continuation-in-part of U.S. patent application Ser. No. 12/775,013, filed May 6, 2010, now U.S. Pat. No. 8,604,692, which is a continuation-in-part of PCT/U.S. Ser. No. 08/082,611, filed Nov. 6, 2008, which claims priority to U.S. Provisional Patent Application No. 60/985,787, filed Nov. 6, 2007. The entire contents of each of these applications are hereby incorporated herein by reference in their entireties.

SEQUENCE LISTING

The instant application contains a Sequence Listing which has been submitted via EFS-Web and is hereby incorporated by reference in its entirety. Said ASCII copy is named TXZ00226.txt and is 208,810 bytes in size.

BACKGROUND

Mass spectrometry (MS) is well established as a robust assay platform for small molecules, but it is often considered only as an exploratory research tool for proteins and peptides. This is partly because of the limited throughput of mass spectrometry-based assays and the need for extensive sample processing for most target peptides and proteins especially when the concentration of the target molecule is low. If this limitation can be overcome, mass spectrometry-based assays have advantages relative to antibody-based assays. For example, synthesis of a reference peptide can be done within a few days when the amino acid sequence of the target protein is known, compared to the many months that it takes to generate an antibody against a peptide. Once the reference peptide is available, setting up mass spectrometric conditions to measure the target peptide takes less than a week. When multiple cycles of reagent generation and evaluation are involved, the difference in time to set up a mass spectrometry based assay and antibody-based assay can be even more significant. Despite these advantages, many target proteins are beyond the reach of mass spectrometry because of the need for target enrichment before analysis. The most commonly used method of target enrichment is the use of antibody, which negates the advantage of the mass spectrometry-based assay unless the desired antibodies are already available.

The eukaryotic translation initiation factor eIF4E ("4E") is involved in the modulation of cellular growth. Moderate overexpression of 4E leads to dysregulated growth and malignant transformation. Both the nuclear and cytoplasmic function of 4E contribute to its ability to transform cells. Overexpression of 4E in vivo results in frank tumor formation, and the onset of tumor formation is greatly enhanced when 4E overexpression is placed within the context of a myc mouse background, suggesting again that 4E acts in concert with other oncogenes to promote neoplastic transformation. 4E is believed to represent one of the seven genes whose expression, when up-regulated in cancers, is predictive of metastatic disease. A variety of studies have been done demonstrating that existence of elevated 4E activity within surgical margins is a poor prognosis factor.

In the nucleus, 4E is a critical node in an RNA regulon that impacts nearly every stage of cell cycle progression (Culjkovic, B., Topisirovic, I. and K. L. B. Borden (2007) Controlling gene expression through RNA regulons. *Cell Cycle* 6: 65-69; Culjkovic, B., Topisirovic, I., Skranbanek, L., Ruiz-Gutierrez, M., and K. L. B. Borden (2006) eIF4E is a central node of an RNA regulon that governs cellular proliferation. *J Cell Biol* 175: 415-426; Keene, J. D. (2007) RNA regulons: Coordination of post-transcriptional events. *Nature Reviews Genetics* 8: 533-543). Specifically, 4E coordinately promotes the mRNA export, and in some cases also translation, of several genes involved in cell cycle progression. For example, 4E functions to promote export from the nucleus to the cytoplasm of at least two mRNAs, cyclin D1 and ornithine decarboxylase (ODC), while having no impact on the nuclear to cytoplasmic transport of GAPDH or actin mRNAs. Moreover, there is evidence that the mRNA export function of 4E is linked to its oncogenic transformation activity. Dysregulated expression of tumor suppressors and oncogenes that maintain and enhance the malignant phenotype have been described. Among these molecules are tumor suppressors like p53, Rb, and APC and oncogenes such as myc, cyclin D1 and 4E. Their interaction constitute a network of self-reinforcing feedback loops wherein inactivation of principal elements can lead to the reversal and at times even the sustained loss of the neoplastic phenotype.

4E is overexpressed in a wide variety of malignant cell lines and primary human tumors including tumors of the breast, colon, head and neck, thyroid, lung, non-Hodgkin's lymphoma, prostate, cervix, bladder and chronic and acute myelogenous leukemias. Consistently, even moderate overexpression of 4E in rodent cells leads to deregulated proliferation and malignant transformation.

Despite being essential for growth and survival of eukaryotes by acting at a critical step of cap-dependent translation and recruiting transcripts to the ribosome as a result of its specific interaction with the 5'-7-methylguanosine (m7G) mRNA cap structure, up-regulation of 4E does not increase translation of all cap-dependent transcripts, but only of a specific subset of 4E-sensitive transcripts.

As much as 70% of 4E is present in the nuclei of mammalian cells, where it associates with nuclear bodies in a wide variety of organism, including yeast, Xenopus and humans. Here, 4E promotes transport of mRNAs of a specific subset of transcripts such as cyclin D1, but not of housekeeping genes such as B-actin and GAPDH. Post-transcriptional regulation of gene expression at the level of 4E mediated mRNA transport and translation exhibits different gene specificities, with some gene being regulated at the level of transport (e.g. cyclin D1) and some at the level of translation (VEGF), others at both levels (ODC), and still yet others at neither level (GAPDH). Binding to the m7G cap is required both for mRNA transport and translation by 4E, both of which contribute to this ability to transform cells.

Past observation indicates that 4E's capacity to discriminate between cyclin D1 and GAPDH is surprising seeing that the traditional view is that 4E binds the m7G cap found on all mRNAs regardless of other sequence specific features. Thus, this functional discrimination presents a conundrum in terms of our understanding of 4E mRNA recognition in the nucleus.

Elevated 4E activity has been observed to mediate selectively the translation (but not transcription) of a subset of the total collection of mRNAs expressed within cells, tissues, organs. Specifically, within cells, tumors and/or cancers where 4E activity is present at elevated levels, the translation of mRNA transcripts possessing complex 5'UTR regions is selectively upregulated. The repertoire of genes whose translation is thereby upregulated in circumstances where elevated 4E activity exists is a who's who of genes known to be involved in the regulation of the cell cycle, angiogenesis, proliferation and the like. However, the molecular mechanisms that regulate 4E transport, and how regulation of 4E activity could be used to modulate such processes, is not well-characterized.

Current diagnostic, segmentation and stratification methodologies do not provide for the enhanced detection, analysis and therapeutic monitoring of 4E and 4E regulon activity.

SUMMARY

Provided are highly sensitive high throughput mass spectrometry-based quantitative assays that provide for the single sample multiplexed analysis of at least one target protein, as well as in certain embodiments the simultaneous analysis of phosphorylation states of the at least one target protein. The mass spectrometry-based assays employ an enrichment method for the target protein(s), which allows the construction of highly sensitive, high-throughput assays without the use of an antibody. The assays can be adapted to detect 4E and 4E regulon component levels and phosphorylation states, and when so adapted becomes the first single sample analytical method of the 4E/4E regulon biological pathway.

This method may be incorporated into any of a variety of methods for compositions for the identification, diagnosis and monitoring of 4E and 4E regulon component activity and for the discovery of agents that modulate 4E and 4E regulon component activity.

This method may also be incorporated into any of a variety of methods for compositions for the identification, diagnosis and monitoring of 4E and 4E regulon component and additional oncogenic element levels and/or activity for the discovery of agents that modulate 4E and 4E regulon component and additional oncogenic element activity.

Kits for the practice of the methods are also described herein.

These embodiments of the present invention, other embodiments, and their features and characteristics will be apparent from the description, drawings, and claims that follow.

BRIEF DESCRIPTION OF THE DRAWINGS

FIG. 1 discloses SEQ ID NOS: 2, 159, 2, 113, 110, 106, 116, 61, 67, 160, 161, 44, 42, 37, 162, 81, 163, 79, 164-178, 178, 178-185, 120, 119, 119, 32, 25, 23, 186, 141, 146, 149, 142, 154, and 188-198, respectively, in order of appearance.

FIG. 2 depicts sequences of 4E regulon components and additional oncogenic elements that may be detected using the assays described herein. FIG. 2 discloses SEQ ID NOS: 3-11 and 199-204, 559, 205-211, and 560, respectively, in order of appearance.

FIG. 3 contains twenty panels, A-T depicting potential fragments of 4E regulon components produced using trypsin digestion that may be used to analyze the 4E regulon components using the assay described herein. The columns from left to right are as follows: monoisotopic mass, average mass, starting residue, ending residue, tryptic peptide sequence. FIG. 3 discloses the "Akt" sequences as SEQ ID NOS: 12-33, respectively, in order of appearance, the "Pim1" sequences as SEQ ID NOS: 34-48, respectively, in order of appearance, the "Nibrin" sequences as SEQ ID NOS: 49-76, respectively, in order of appearance, the "ODC" sequences as SEQ ID NOS: 77-88, respectively, in order of appearance, the "VEGF" sequences as SEQ ID NOS: 89-101, respectively, in order of appearance, the "Cyclin D1" sequences as SEQ ID NOS: 102-116, respectively, in order of appearance the "eIF4E-BP1" sequences as SEQ ID NOS: 117-120, respectively, in order of appearance, the "Cyclin A2" sequences as SEQ ID NOS: 121-138, respectively, in order of appearance, the "Hur" sequence as SEQ ID NOS: 139-151, respectively, in order of appearance and the "4E" sequences as SEQ ID NOS: 2 and 152-158, respectively, in order of appearance, the "Skp2" sequences as SEQ ID NOS: 212-236, respectively, in order of appearance, the "Cyclin E1" sequences as SEQ ID NOS: 237-260, respectively, in order of appearance, the "MMP9" sequences as SEQ ID NOS: 261-294, respectively, in order of appearance, the "Casp9" sequences as SEQ ID NOS: 295-316, respectively, in order of appearance, the "BCL2L1" sequences as SEQ ID NOS: 317-328, respectively, in order of appearance, the "EIF4EBP1" sequences as SEQ ID NOS: 329-337, respectively, in order of appearance, the "BCL2" sequences as SEQ ID NOS: 338-351, respectively, in order of appearance, the "SELS" sequences as SEQ ID NOS: 352-362, respectively, in order of appearance, the "SPP1" sequences as SEQ ID NOS: 363-374, respectively, in order of appearance, the "FGF2" sequences as SEQ ID NOS: 375-397, respectively, in order of appearance, the "EGFR" sequences as SEQ ID NOS: 398-471, respectively, in order of appearance, the "HER2" sequences as SEQ ID NOS: 472-529, respectively, in order of appearance.

FIG. 4 presents 4E and 4E Regulon component mass-selective mass spectrometry detection analytes as provided by the Example below. FIG. 4 discloses the "eIF4E" sequences as SEQ ID NOS: 159 and 2, respectively, in order of appearance, the "Cyclin D1" sequences as SEQ ID NOS: 113, 110, 106 and 116, respectively, in order of appearance, the "Nibrin/NBS-1" sequences as SEQ ID NOS: 61, 67, 160 and 161, respectively, in order of appearance, the "Pim-1" sequences as SEQ ID NOS: 44, 42, 37 and 162, respectively, in order of appearance, the "ODC" sequences as SEQ ID NOS: 81, 163, 79 and 164, respectively, in order of appearance, the "SKP2" sequences as SEQ ID NOS: 165-168, respectively, in order of appearance, the "Cyclin E1" sequences as SEQ ID NOS: 169-172, respectively, in order of appearance, the "MMP9" sequences as SEQ ID NOS: 173-176, respectively, in order of appearance, the "Caspase 9" sequences as SEQ ID NOS: 177-180, respectively, in order of appearance, the "Bcl-X(L)" sequences as SEQ ID NOS: 181-184, the "eIF4E-BP1" sequences as SEQ ID NOS: 185, 120, 119 and 119, respectively, in order of appearance, the "AKT1" sequences as SEQ ID NOS: 23, 32, 25 and 186, respectively, in order of appearance, and the "ELAVL1/HuR" sequences as SEQ ID NOS: 142, 141, 146 and 149, respectively, in order of appearance.

FIG. 5 depicts potential phosphopeptide fragments of representative and exemplary eIF4E regulon elements, eIF4EBP1 and Akt1. The position of phosphorylation sites [Ser (S), Thr (T) and Tyr (Y)] are indicated by enlarged font and peptide analyte fragments are indicated by shading. FIG. 5 discloses the "EIF4EBP1" sequences as SEQ ID NO: 559 and the "AKT1" sequences as SEQ ID NOS: 211 and 560, respectively, in order of appearance.

DETAILED DESCRIPTION

Figure 1:
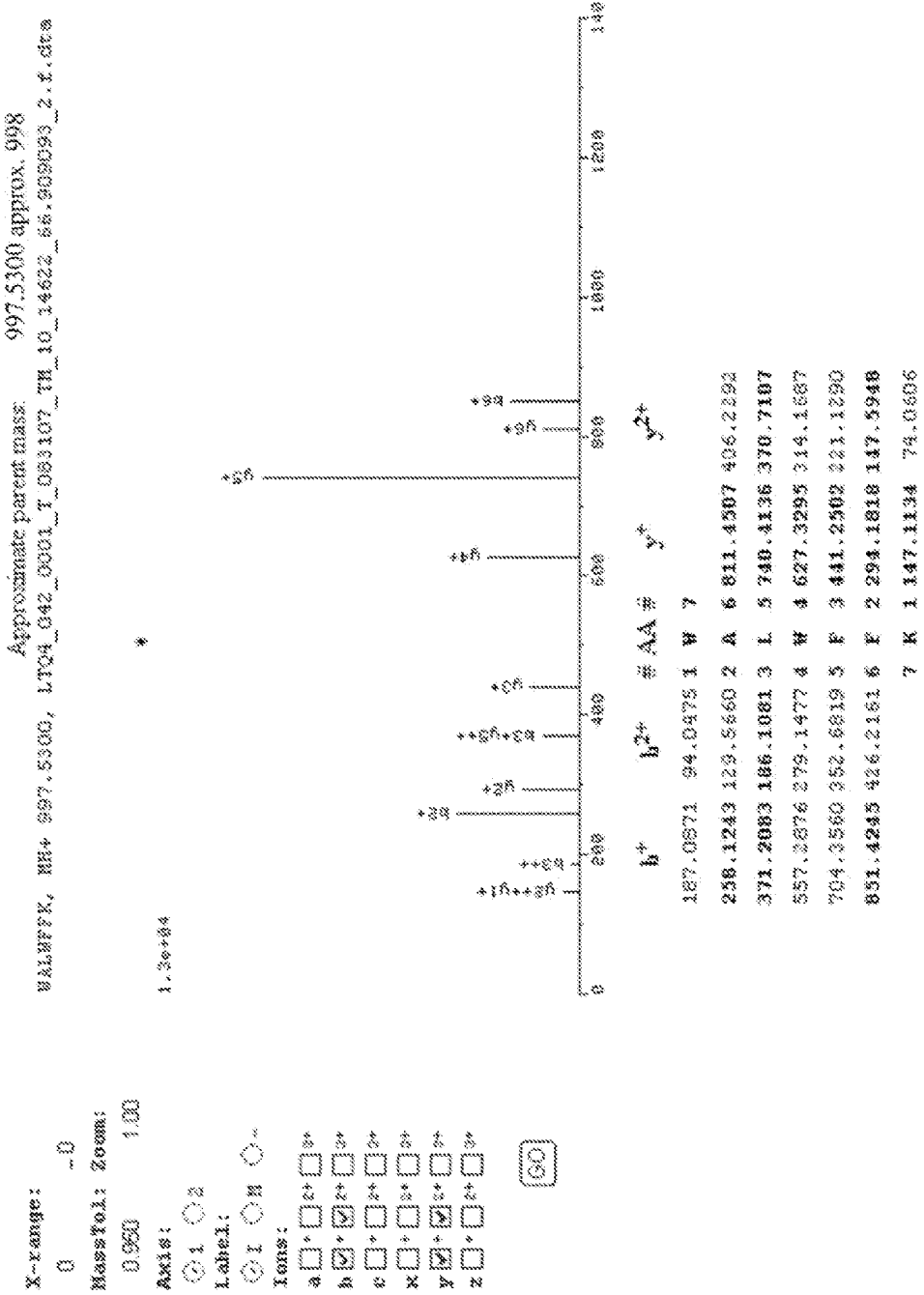
FIG. 1 contains sixty-four panels, A-BL depicting the mass spectra obtained by an embodiment of an assay for detection of 4E and 4E regulon component levels as described in the Example below.
Figure 1B:
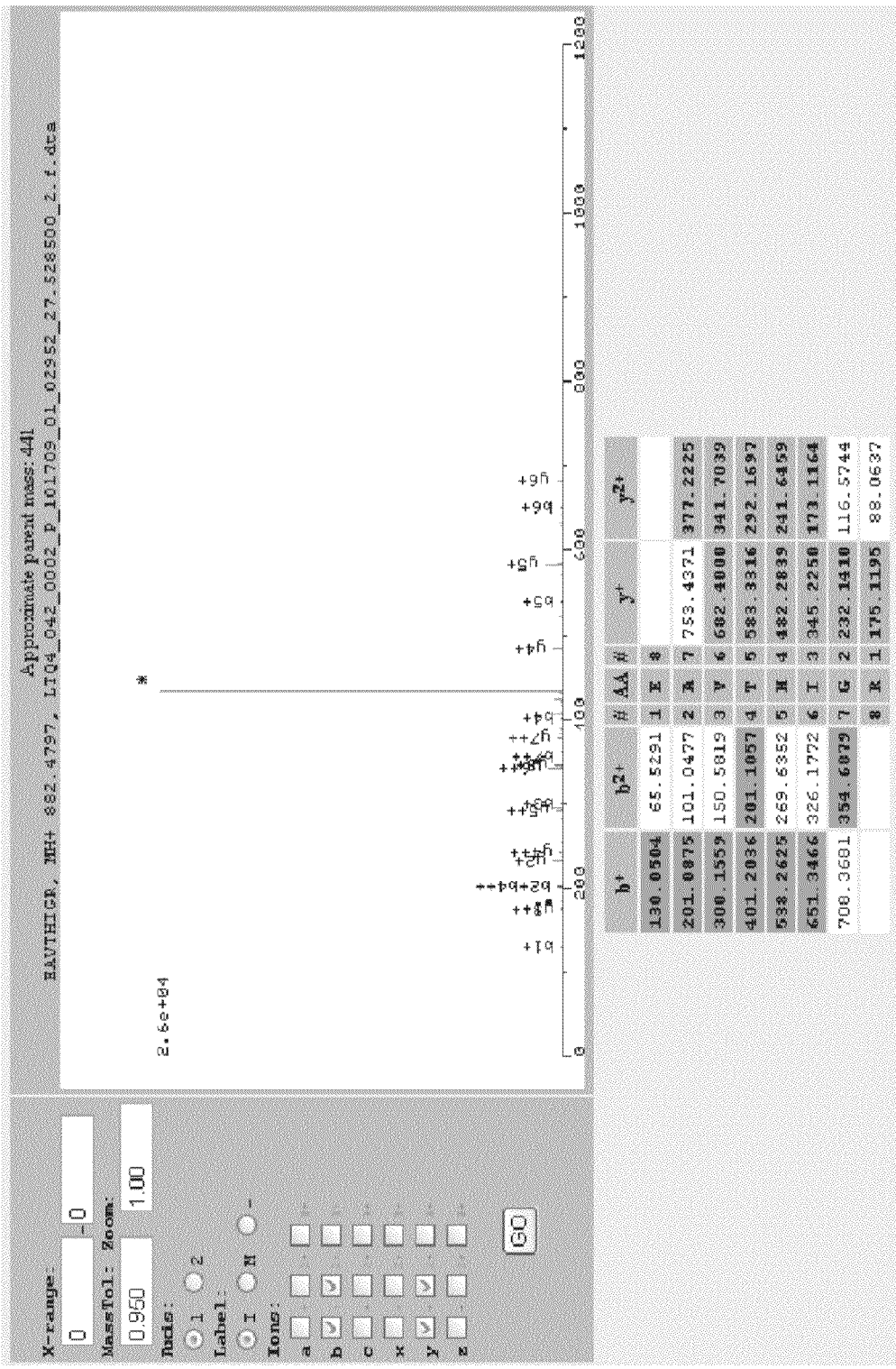
Figure 1L:
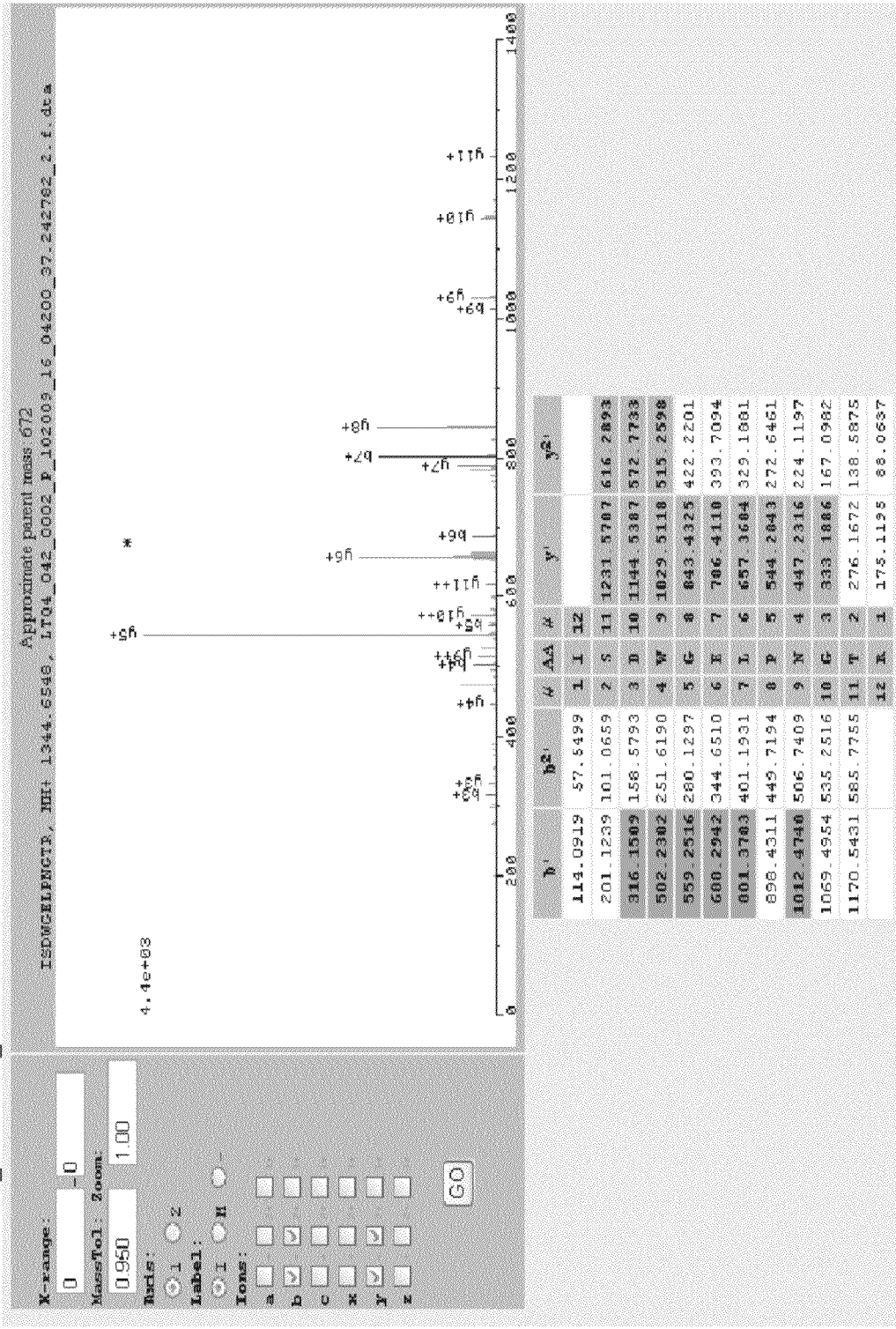
Figure 1A:
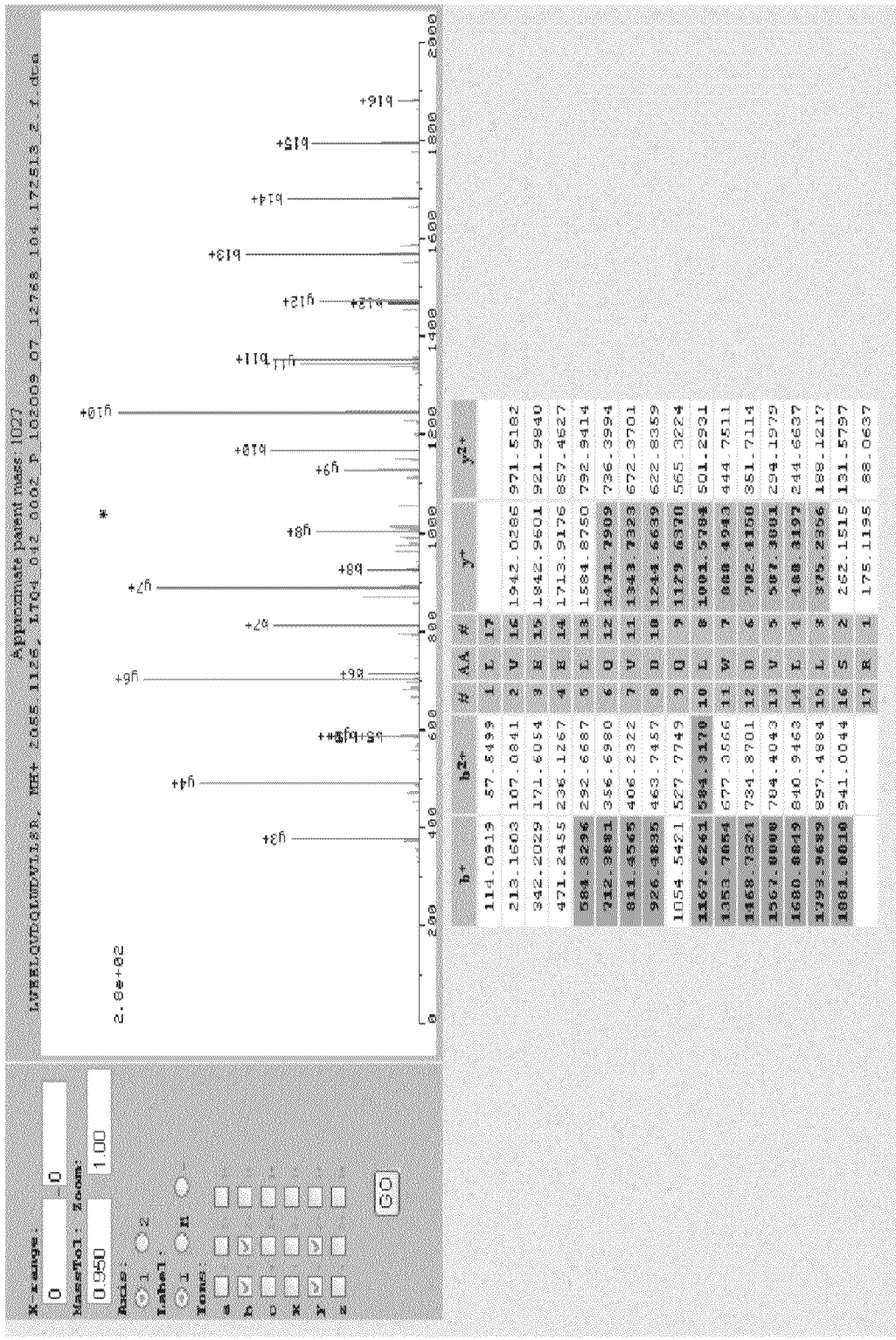
Figure 1A:
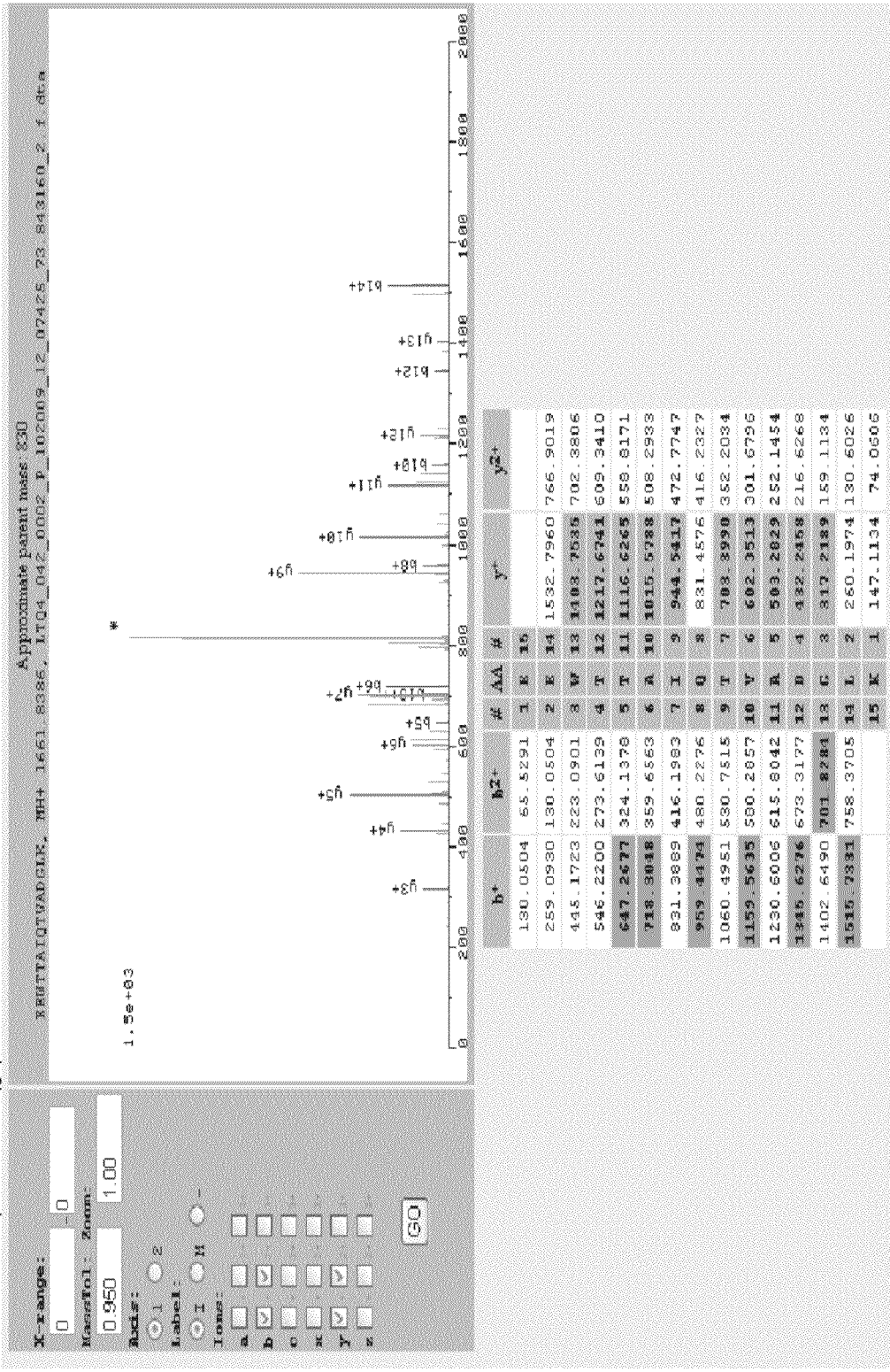
Figure 1B:
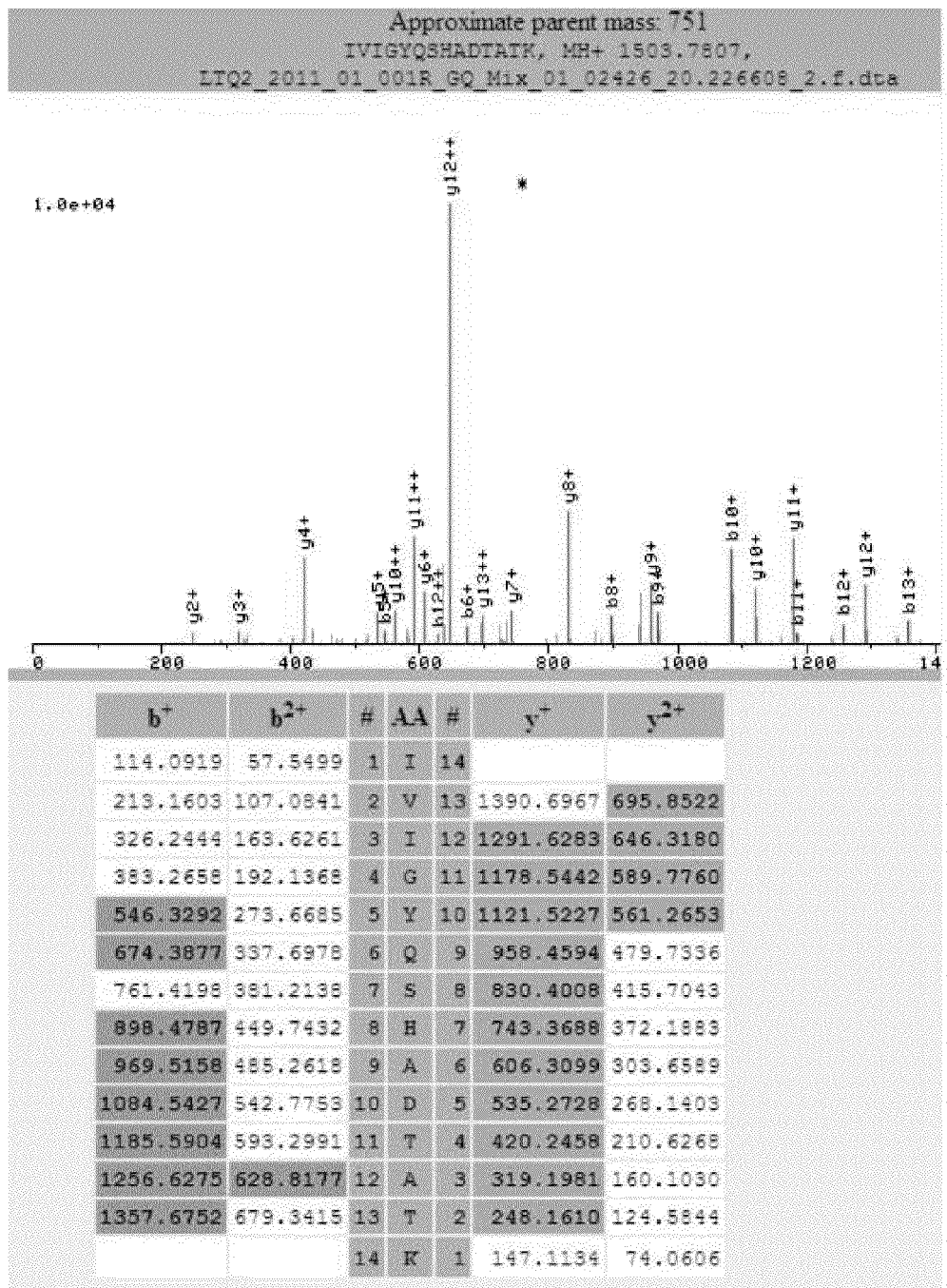
Figure 1B:
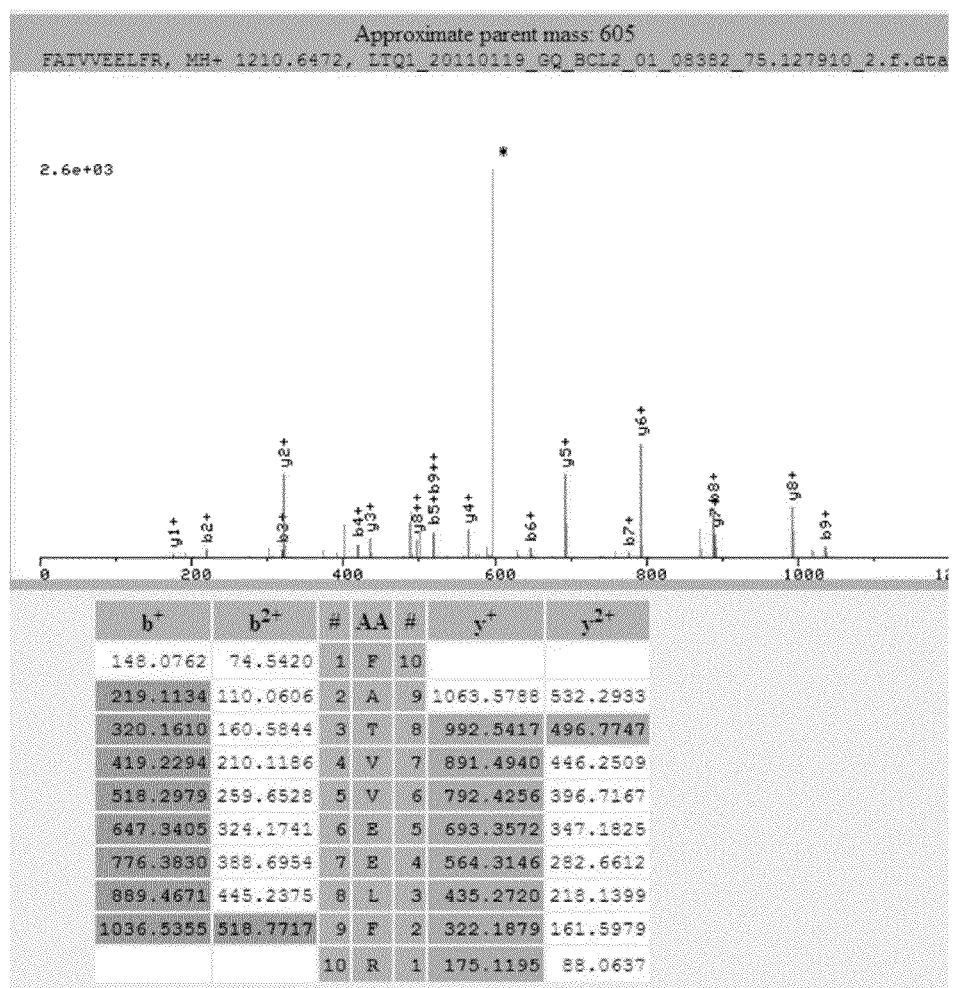
Figure 1B:
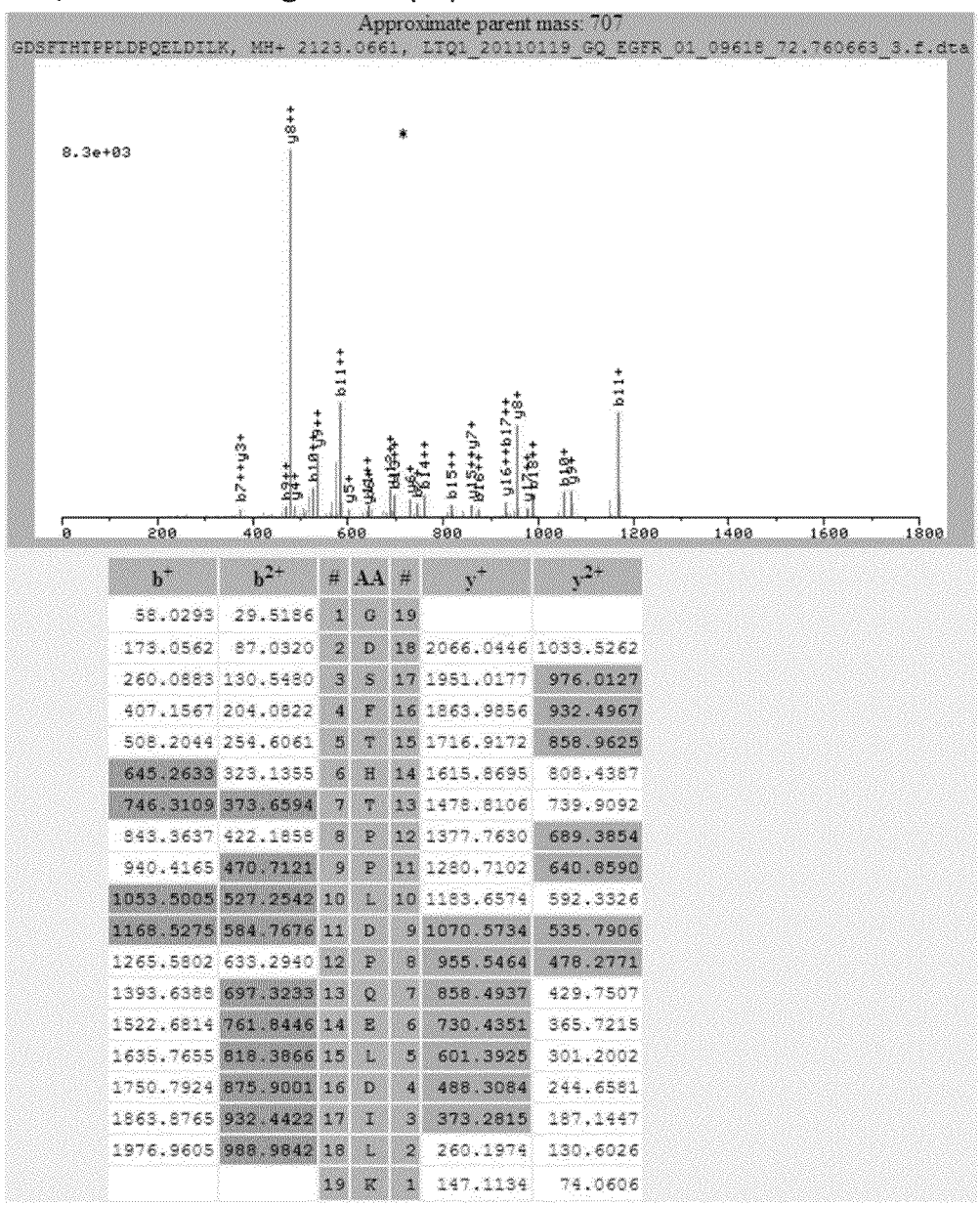
Figure 1B:
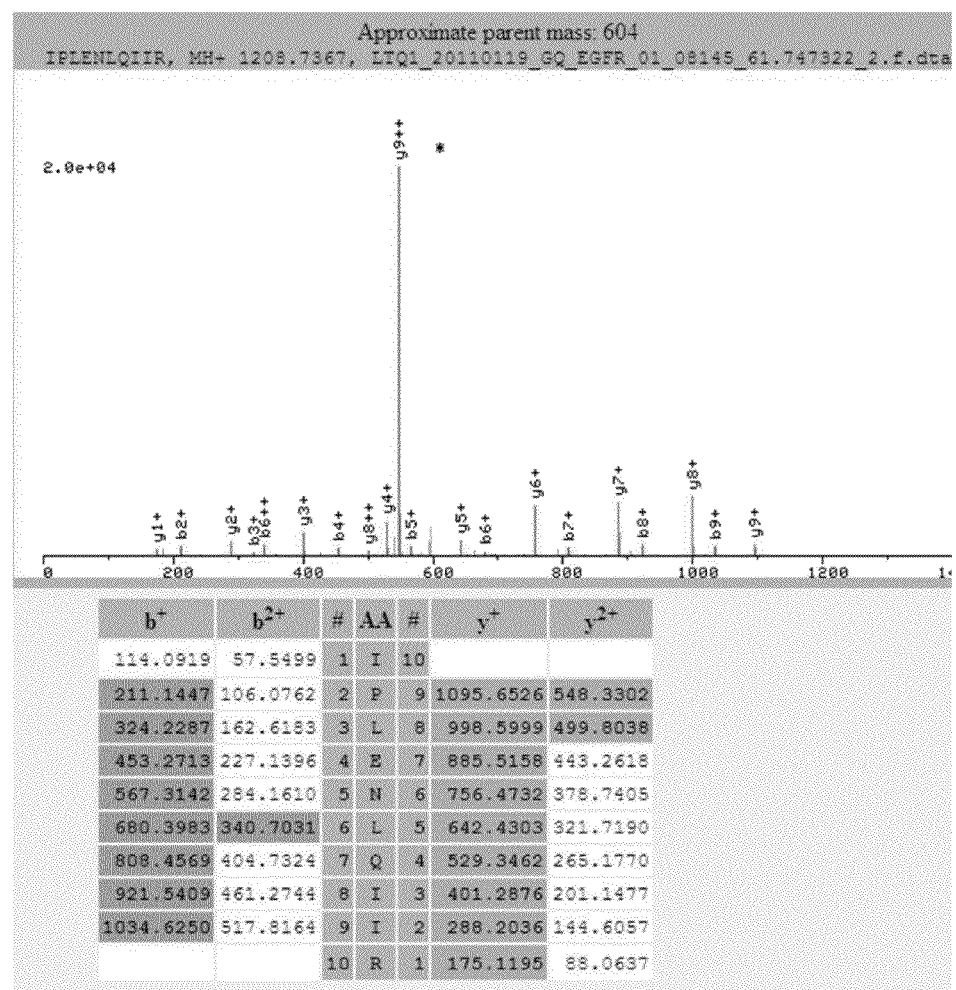
Figure 1B:
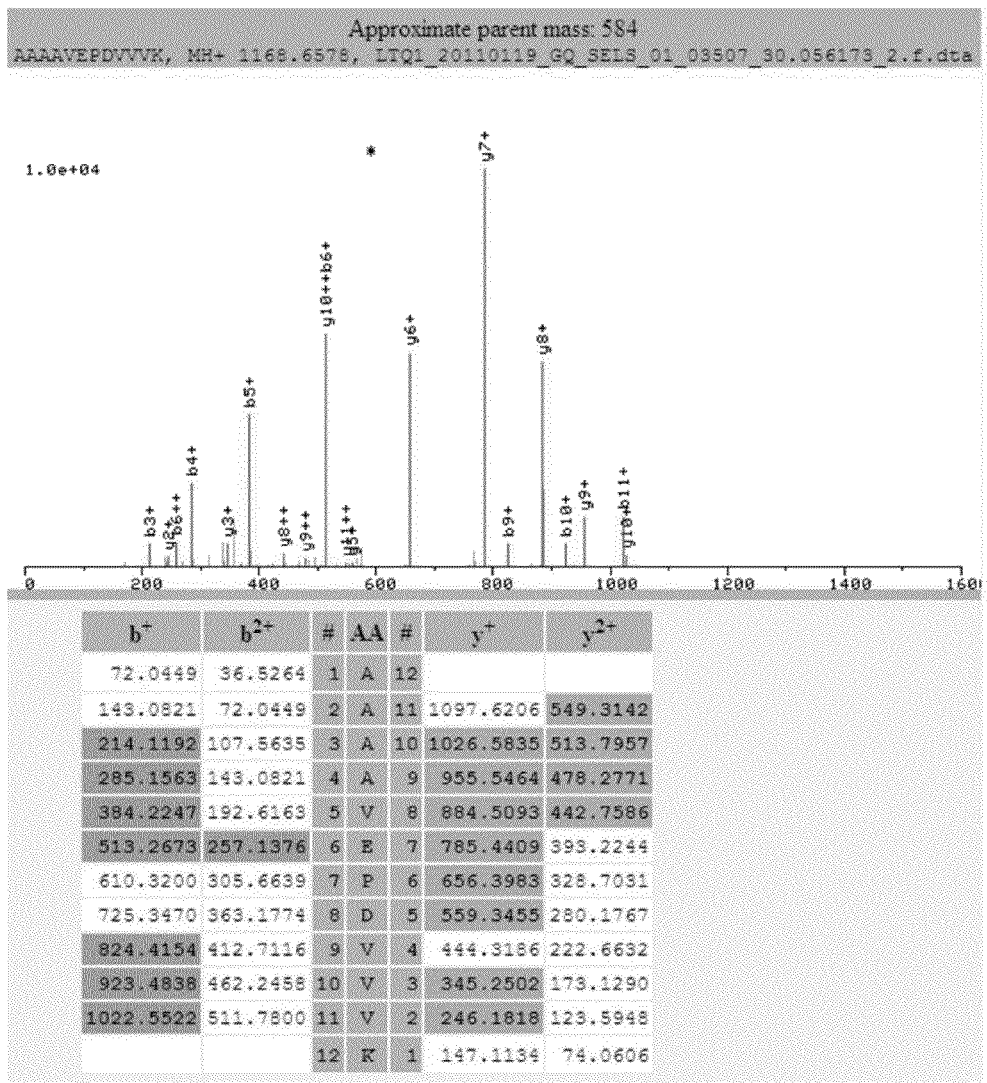
Figure 1B:
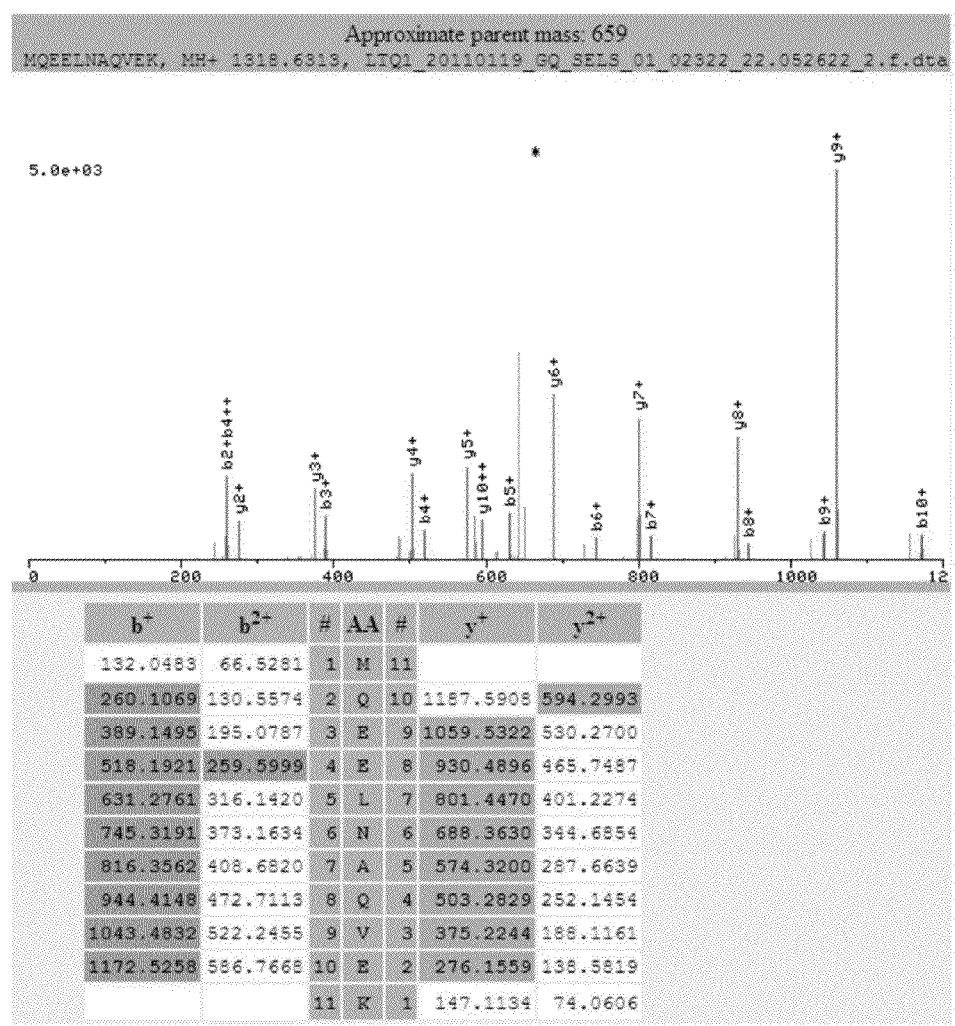
Figure 1B:
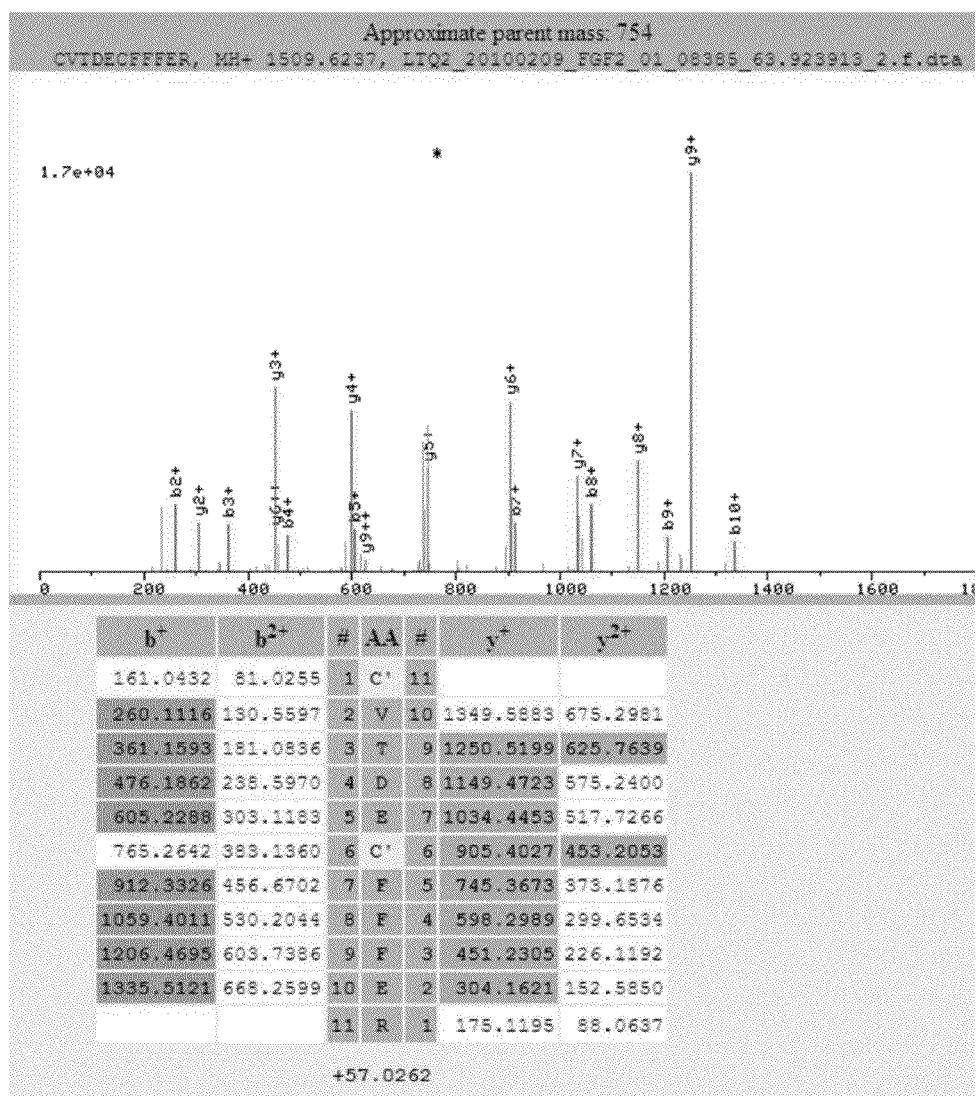
Figure 1B:
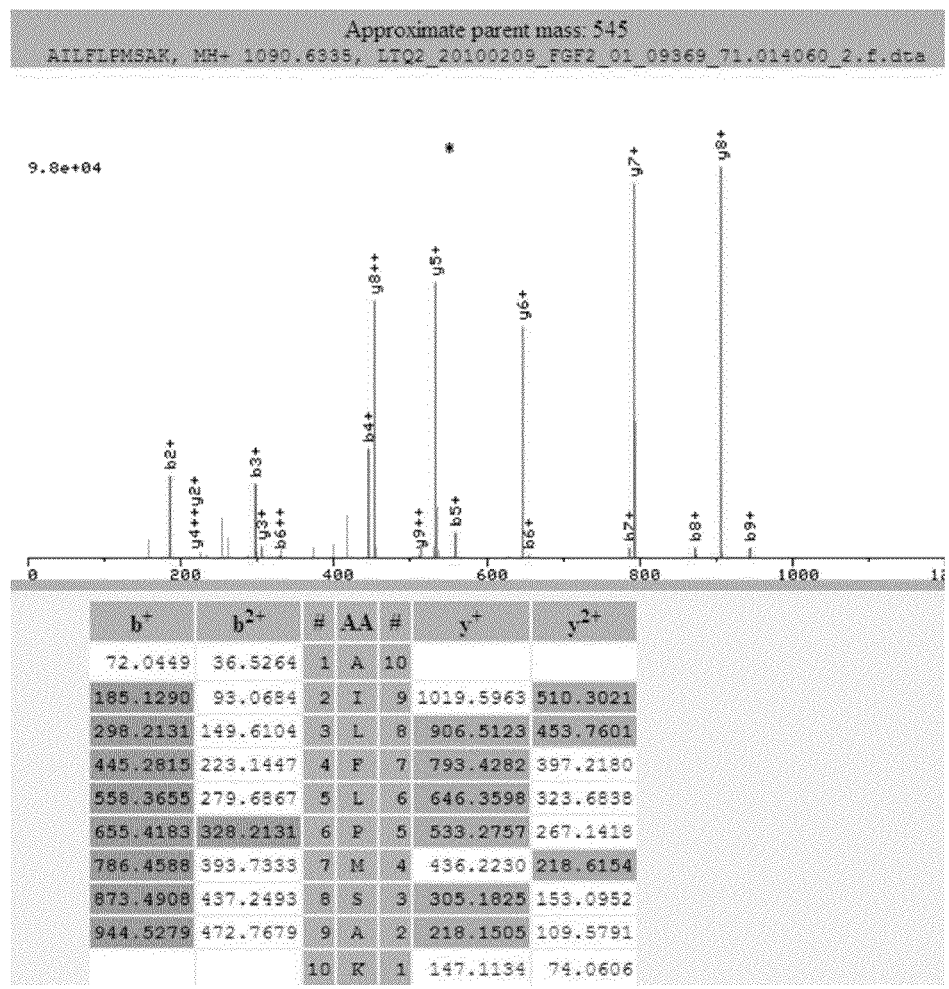
Figure 1B:
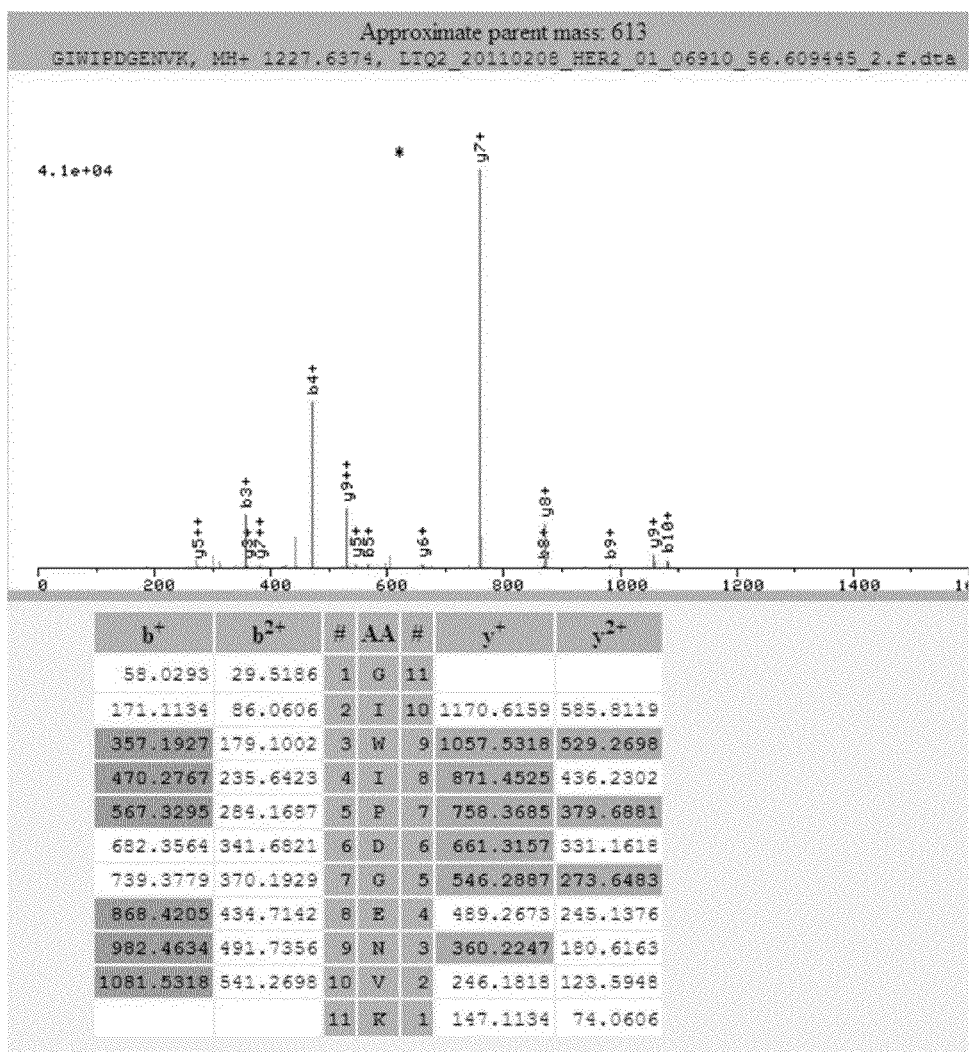
Figure 1B:
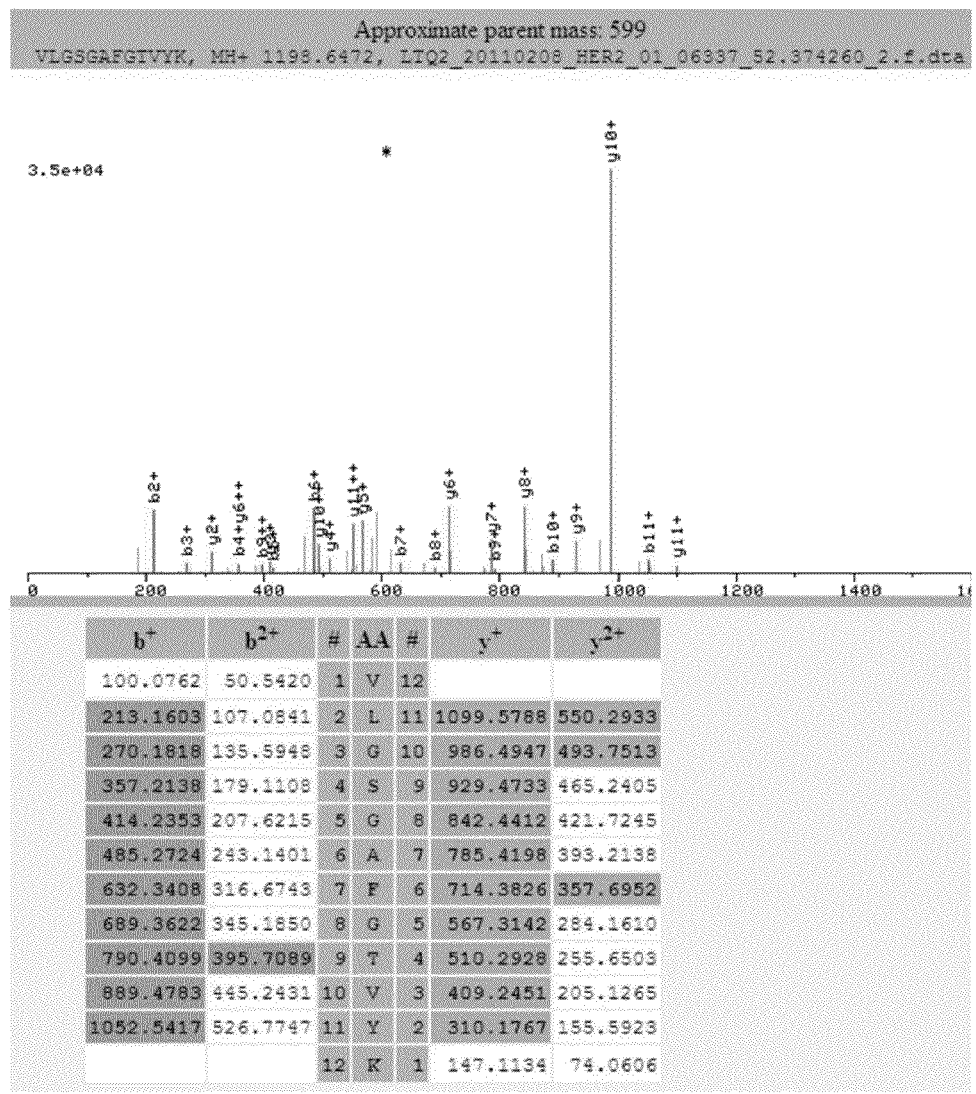
Figure 1B:
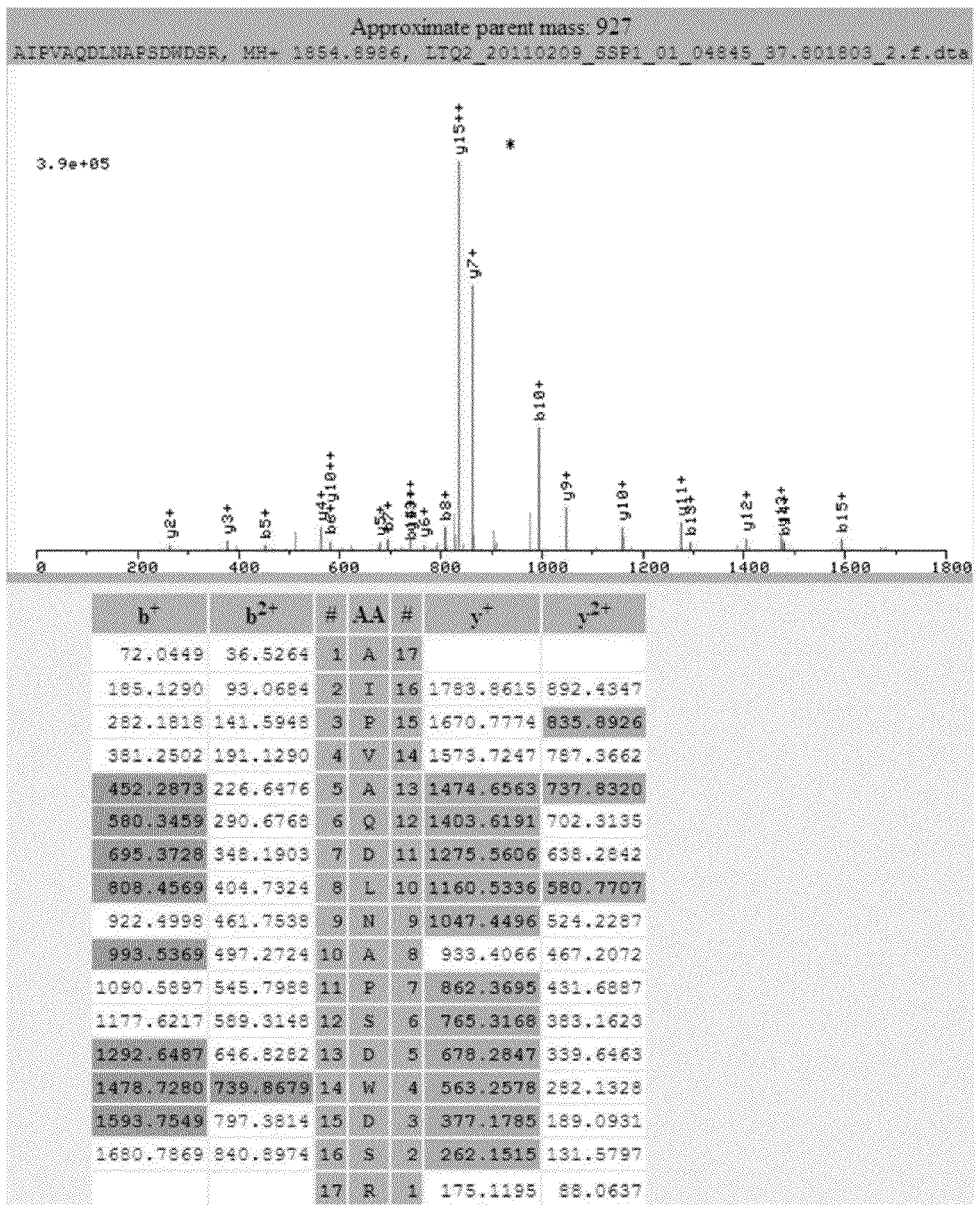
Figure 1B:
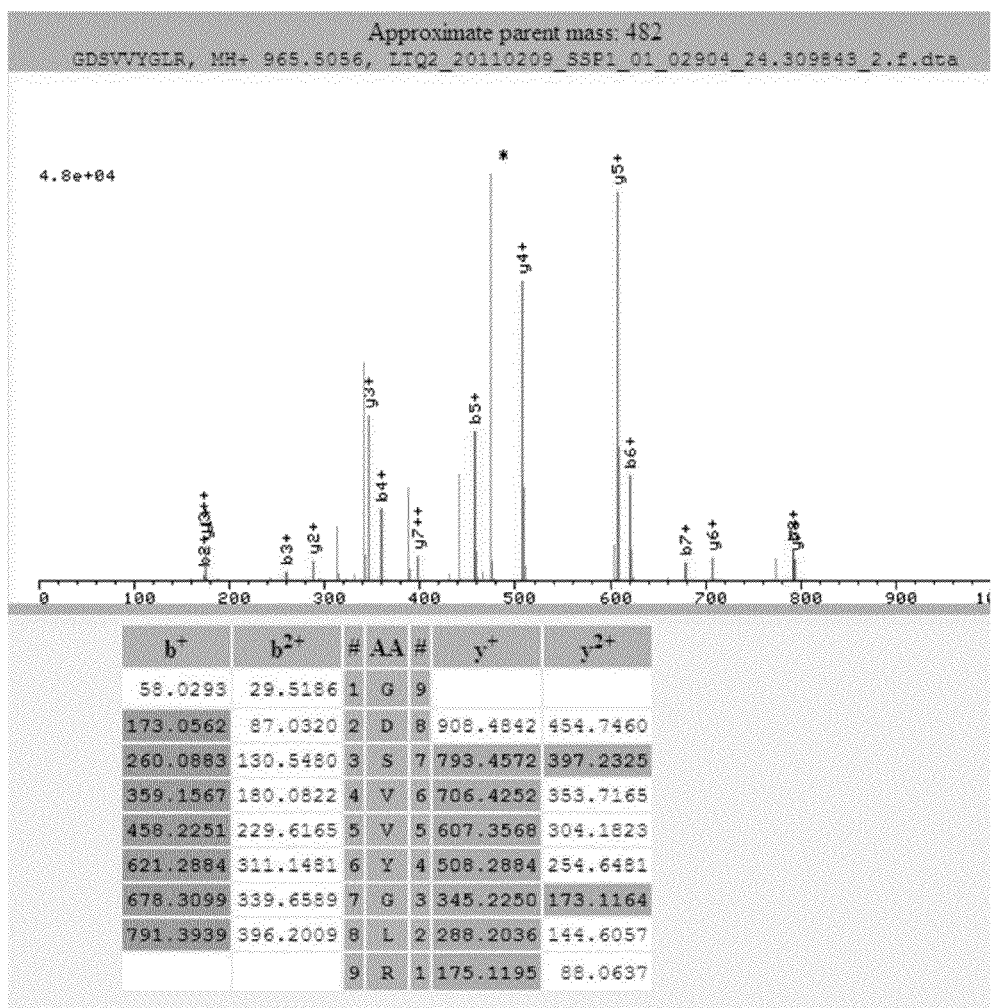

For convenience, certain terms employed in the specification, examples, and appended claims are collected here. Unless defined otherwise, all technical and scientific terms used herein have the same meaning as commonly understood by one of ordinary skill in the art to which this invention belongs.

The term "4E activity" or "activity of 4E" includes any of the biological effects of the 4E gene or protein, including but not limited to elevated expression of 4E, elevated protein levels of 4E, and/or activation of 4E regulon components, and phosphorylation state of 4E.

The term "4E regulon activity" or "4E regulon component activity" or "activity of a 4E regulon component" refers the activity of 4E as a mediator of the 4E regulon and also includes 4E regulon activation, expression, transport and/or activity of the 4E regulon components.

The term "4E regulon component" refers to 4E (SEQ ID NO: 1 MATVEPETTPTPNPPTTEEEKTESNQE-VANPEHYIKHPLQNRWALWFFKNDKSKTWQANL RLISKFDTVEDFWALYNHIQLSSN-LMPGCDYSLFKDGIEPMWEDEKNKRGGR-WLITLNKQ QRRSDLDRFWLETLLCLIGESFDDYSD-DVCGAVVNVRAKGDKIAIWTTECENREAVTHIGR VYKERLGLPPKIVIGYQSHADTATKSGSTTKNRFVV), any of the components of its regulon, and any modifier of the regulon such as HuR. Exemplary 4E regulon components include: eIF4E (gi: 54873625) (NP_001959, NP_001959.1); Cyclin D1 (gi: 77628152) (NP_444284, NP_444284.1); NBS/Nibrin (gi: 67189763) (NP_002476, NP_002476.2); Pim-1 (gi: 31543400) (NP_002639, NP_002639.1); Cyclin B1 (gi: 34304372) (NP_114172, NP_114172.1); Cyclin A2 (gi: 16950653) (NP_001228, NP_001228.1); ODC (gi: 4505488) (NP_002530, NP_002530.1); VEGF (gi: 71051577) (NP_003367, NP_003367.4); Skp2 (gi: 16306594, 16306593) (NP_005974, NP_005974.2, NP_116026, NP_116026.1); Cyclin E1 (gi: 17318558) (NP_001229, NP_001229.1); c-myc (gi: 71774082) (NP_002458, NP_002458.2); FGF2 (gi: 153285460, 153285461) (NP_2006, NP_2006.4, NP_001997, NP_001997.5); MMP-9 (gi: 74272286) (NP_004985, NP_004985.2); mdm2 (gi: 46488903) (NP_002383, NP_002383.2); caspase-9 (gi: 14790123, 14790127) (NP_001220, NP_001220.2, NP_127463, NP_127463.1); bc12 (gi: 72198188, 72198345) (NP_000624, NP_000624.2, NP_000648, NP_000648.2); Bcl/xL (gi: 20336334) (NP_612815, NP_612815.1); Fbox1 (gi: 16306583); CGGbp1 (gi: 56550052); P54nrb/NONO.1 (gi: 34932413); Selenoprotein S (gi: 33285002, 45439347) (NP_060915, NP_060915.2, NP_018445, NP_018445.4); eIF4E-BP1 (gi: 117938308) (NP_004086, NP_004086.1); Akt1 (gi: 62241012, 62241010, 62241014) (NP_001014431, NP_001014431.1, NP_005154, NP_005154.2, NP_001014432, NP_001014432.1); PI3K (gi: 54792081, 21237724) (NP_006209, NP_006209.2, NP_002640, NP_002640.2); GSK3B (gi: 21361339) (NP_002084, NP_002084.2); HuR (gi: 38201714) (NP_001410, NP_001410.2); and mTOR/FRAP1 (gi: 19924298) (NP_004949, NP_004949.1). Preferred 4E regulon components (components) to be used in certain of the below-described methods are 4E, 4E-BP1, NBS/Nibrin, Pim-1, VEGF, Cyclin D1, Cyclin A2, ODC and HuR. A "regulon" is a family of multiple mRNAs that are coordinately regulated in a sequence specific fashion by one or more RNA binding proteins that orchestrate and control their splicing, export, stability, localization and/or translation.

The articles "a" and "an" are used herein to refer to one or to more than one (i.e., to at least one) of the grammatical object of the article. By way of example, "an component" means one component or more than one component.

As used herein, the term "amino acid" is intended to mean both naturally occurring and non-naturally occurring amino acids as well as amino acid analogs and mimetics. Naturally occurring amino acids include the 20 (L)-amino acids utilized during protein biosynthesis as well as others such as 4-hydroxyproline, hydroxylysine, desmosine, isodesmosine, homocysteine, citrulline and ornithine, for example. Non-naturally occurring amino acids include, for example, (D)-amino acids, norleucine, norvaline, p-fluorophenylalanine, ethionine and the like. Amino acid analogs include modified forms of naturally and non-naturally occurring amino acids. Such modifications can include, for example, substitution or replacement of chemical groups and moieties on the amino acid or by derivitization of the amino acid. Amino acid mimetics include, for example, organic structures which exhibit functionally similar properties such as charge and charge spacing characteristic of the reference amino acid. For example, an organic structure which mimics arginine (Arg or R) would have a positive charge moiety located in similar molecular space and having the same degree of mobility as the .epsilon.-amino group of the side chain of the naturally occurring Arg amino acid. Mimetics also include constrained structures so as to maintain optimal spacing and charge interactions of the amino acid or of the amino acid functional groups. Those skilled in the art know or can determine what structures constitute functionally equivalent amino acid analogs and amino acid mimetics.

The term "biological sample", or "sample" as used herein, refers to a sample obtained from an organism or from components (e.g., cells) of an organism. The sample may be of any biological tissue or fluid. Frequently the sample will be a "clinical sample" which is a sample derived from a patient. Such samples include, but are not limited to, sputum, blood, blood cells (e.g., white cells), tissue or fine needle biopsy samples, urine, peritoneal fluid, and pleural fluid, or cells therefrom. Biological samples may also include sections of tissues such as frozen sections taken for histological purposes.

The terms "comprise" and "comprising" are used in the inclusive, open sense, meaning that additional components may be included.

As used herein, the term "fragment" when used in reference to a polypeptide or parent polypeptide is intended to mean any truncated or smaller mass form, corresponding to either carboxyl-terminal, amino-terminal, or both regions, of a reference polypeptide or parent polypeptide. Accordingly, a deletion of a single amino acid from the carboxyl- or amino-terminus is considered a fragment of a parent polypeptide. The term fragment therefore includes deletion of amino acids at the amino- and/or carboxyl-terminus as well as modifications where, for example, an amino acid side chain is removed but the peptide bond remains. A fragment includes a truncated polypeptide that is generated, for example, by polypeptide cleavage using a chemical reagent, enzyme, or energy input. A fragment can result from a sequence-specific or sequence independent cleavage event. Examples of reagents commonly used for cleaving polypeptides include enzymes, for example, proteases, such as thrombin, trypsin, chymotrypsin and the like, and chemicals, such as cyanogen bromide, acid, base, and o-iodobenzoic acid. A fragment can also be generated by a mass spectrometry method including, for example, all types of fragmentation methods and collision induced dissociation. Furthermore, a fragment can also result from multiple cleavage events such that a truncated polypeptide resulting from one cleavage event can be further truncated by additional cleavage events.

The term "including" is used to mean "including but not limited to". "Including" and "including but not limited to" are used interchangeably.

"Protein" and "polypeptide" are used interchangeably herein when referring to a gene product, e.g., as may be encoded by a coding sequence. By "gene product" it is meant a molecule that is produced as a result of transcription of a gene. Gene products include RNA molecules transcribed from a gene, as well as proteins translated from such transcripts.

Provided, in one aspect, is a method for determining the level of and/or phosphorylation state of at least one target protein, in some embodiments simultaneously, in a single sample, comprising: (a) adding at least one internal standard protein or peptide corresponding to each target protein to the sample; (b) reducing and alkylating the at least one target protein and internal standard in the sample without the use of urea; (c) digesting the at least one target protein and the at least one internal standard protein or peptide by contacting the sample with at least one protease; (d) analyzing the fragments of said digesting by a mass spectrometry-based method; and (e) determining the level of and/or phosphorylation state of the at least one target protein using the results of the analysis of the fragments.

In certain embodiments, there are at least two, three, four, five, ten or more target proteins for which the level and/or phosphorylation state are determined. In certain embodiments the level and/or phosphorylation state of the target protein are determined simultaneously, i.e., in a multiplexed fashion.

The internal standard protein or peptide corresponds to the target protein (or a fragment of it), but includes appropriate corresponding internal marker amino acids (e.g. Leu residue with the molecular weight 7 amu higher than the natural counterpart) to modify the mass of the internal standard protein or peptide to make it distinguishable from the target protein. The protein may be modified by naturally occurring modifications such as post-translational modifications, including phosphorylation, lipidation, prenylation, sulfation, hydroxylation, acetylation, ubiquitination, glycosylation, methylation, palmitoylation, myristylation, addition of carbohydrate, addition of prosthetic groups or cofactors, formation of disulfide bonds, proteolysis, assembly into macromolecular complexes, and the like.

A modification of a protein can also include non-naturally occurring derivatives, analogues and functional mimetics thereof generated by, for example, chemical synthesis. For example, derivatives can include chemical modifications of the protein such as alkylation, acylation, carbamylation, iodination, or any modification that derivatizes the protein. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups can be derivatized to form salts, methyl and ethyl esters or other types of esters or hydrazides. Free hydroxyl groups can be derivatized to form O-acyl or O-alkyl derivatives. The imidazole nitrogen of histidine can be derivatized to form N-im-benzylhistidine. Also included as derivatives or analogues are those proteins which contain one or more naturally occurring amino acid derivatives of the twenty standard amino acids, for example, 4-hydroxyproline, 5-hydroxylysine, 3-methylhistidine, homoserine, ornithine or carboxyglutamate, and can include amino acids that are not linked by peptide bonds. Another specific example of a modification of a protein includes modification of proteins in a sample with a moiety having a stable isotope. For example, two different proteins can be separately labeled with moieties that are isotopically distinct, and such differentially labeled proteins can be compared. Modification of proteins with stable isotopes can be used for both quantitating the relative amount of one or more proteins in a sample.

Polypeptides can be differentially labeled by a variety of methods well known to those skilled in the art, for example, a label can be included at any position within a polypeptide for which specific chemistries or biochemical methods are available. Such positions include, for example, carboxyl and amino terminal, and amino acid side chains. A specific example of labeling carboxyl moieties, including the carboxyl terminus of a polypeptide and side chains is the esterification using methanol. Additionally cysteine can be used to attach labels through, for example, an iodoacetamide reactive group. Polypeptides in a sample can also be labeled with a moiety having a stable isotope. A moiety can be produced that is enriched or depleted in a particular stable isotope, for example, a stable isotope of an element can contain trace amounts of a different atomic weight isotope of that element which can be depleted before incorporating into the labeling moiety. Isotopic labels that can be used to label amino acids include, for example, isotopically heavy and light versions of hydrogen, carbon, oxygen, nitrogen, sulfur and selenium. The corresponding heavy isotopes of these light atoms include: $^{2}H$, $^{13}C$, $^{17}O$, $^{18}O$, $^{15}N$, $^{33}S$, $^{34}S$ and $^{35}S$.

Differentially labeled polypeptides are useful for determining the relative abundance of a polypeptide, or polypeptides, in two different samples. Changes in abundance of a particular polypeptide between two samples can indicate a role for that polypeptide in a biological process. For example, polypeptides from one sample can be labeled with a light isotope containing label while polypeptides from another sample are labeled with a heavy isotope containing label. The two different samples can be, for example, polypeptides extracted from a normal cell and a cancerous cell. A particular polypeptide species that is present in both samples will be chemically the same in the two samples except for the mass of the label or the chemistry used to attach the label. Because the differentially labeled polypeptides behave physicochemically the same, the same polypeptides in the two samples will ionize or fragment similarly, but still be distinguishable by MS due to the isotopic difference in the differential label. Accordingly, the relative amounts of the same polypeptides can be readily compared and quantitated.

Reduction and alkylation of the target proteins and internal standard proteins may be performed essentially as described earlier (Hale J E et al (2004) Anal Biochem 333:174-181) with the modifications described in the example. A key modification is that no urea should be used in this step.

The reduced and alkylated target proteins and internal standard proteins or peptides are then fragmented. Polypeptides can be fragmented by a number of methods including polypeptide cleavage using a chemical reagent, enzyme, or energy input. A fragment can result from a sequence-specific or sequence independent cleavage event. Examples of reagents commonly used for cleaving polypeptides include enzymes, for example, proteases, such as thrombin, trypsin, chymotrypsin and the like, and chemicals, such as cyanogen bromide, acid, base, and o-iodobenzoic acid. A fragment can also be generated by a mass spectrometry method including, for example, all types of fragmentation methods and collision induced dissociation (CID). Furthermore, a fragment can also result from multiple cleavage events such that a truncated polypeptide resulting from one cleavage event can be further truncated by additional cleavage events. Several identical or different fragments can be obtained from the original, or parent, polypeptide. The methods of the invention can use one or more polypeptide fragments from a population of polypeptide fragments.

Analysis of the digested fragments may be by any mass spectrometry-based method that allows high-throughput multiplexed analysis. Mass spectrometry is a sensitive and accurate technique for separating and identifying molecules. Generally, mass spectrometers have two main components, an ion source for the production of ions and a mass-selective analyzer for measuring the mass-to-charge ratio of ions, which is and converted into a measurement of mass for these ions. Several ionization methods are known in the art and described herein. Different mass spectrometry methods, for example, quadrupole mass spectrometry, ion trap mass spectrometry, time-of-flight mass spectrometry and tandem mass spectrometry can utilize various combinations of ion sources and mass analyzers which allows for flexibility in designing customized detection protocols. In addition, mass spectrometers can be programmed to transmit all ions from the ion source into the mass spectrometer either sequentially or at the same time. Furthermore, a mass spectrometer can be programmed to select ions of a particular mass for transmission into the mass spectrometer while blocking other ions. The ability to precisely control the movement of ions in a mass spectrometer allows for greater options in detection protocols which can be advantageous when a large number of fragments, for example, from a multiplex experiment, are being analyzed. Mass spectrometry methods are well known in the art (see Burlingame et al. Anal. Chem. 70:647 R-716R (1998); Kinter and Sherman, Protein Sequencing and Identification Using Tandem Mass Spectrometry Wiley-Interscience, New York (2000)). The basic processes associated with a mass spectrometry method are the generation of gas-phase ions derived from the sample, and the measurement of their mass. Mass spectrometry technology exists by which several thousands of protein species can be separated, detected and quantified in a single operation.

The mass spectrometry may be preceded by a chromatography step. New chromatography based methods for the identification of the proteins contained in complex mixtures without the need for separation of the mixture into individual protein components are available. A separation step can also be used to remove salts, enzymes, or other buffer components. Several methods well known in the art, such as chromatography, gel electrophoresis, or precipitation, can be used to clean up the sample. For example, size exclusion chromatography or affinity chromatography can be used to remove salt from a sample. The choice of separation method can depend on the amount of a sample. For example, when small amounts of sample are available or a miniturized apparatus is used, a micro-affinity chromatography separation step can be used. In addition, whether a separation step is desired, and the choice of separation method, can depend on the detection method used. For example, the efficiency of matrix-assisted laser desorption/ionization and electrospray ionization can be improved by removing salts from a sample. For example, salts can absorb energy from the laser in matrix-assisted laser desorption/ionization and result in lower ionization efficiency.

In a preferred embodiment, the method is LC-MS/MS. Currently, up to 10,000 sequencing runs can be recorded in a single LC-MS analysis of 60 minutes duration. Often the duty cycle of the mass spectrometer is the rate limiting step, however, as mass spectrometers continue to improve, the number of polypeptides that can be detected and/or sequenced in one run will continue to increase. Further automation and on-line analysis will greatly improve the efficiency of mass spectrometry. Therefore, as the instrumentation increases in efficiency the rate of polypeptides that can be detected and/or sequenced with the methods of the invention will also concurrently increase.

In certain embodiments, the above-described methods may be adapted for specifically detecting the level and/or phosphorylation state of 4E and/or at least one 4E regulon component. In one embodiment, the at least one target protein is 4E is at least in part on the analysis of the fragment SEQ ID NO: 2 WALWFFK which has a parent mass of 998 Da. The transitions from the parent mass used in the determination are 998→740, 998→627 and 998→371. In other embodiments, the at least one target protein is a 4E regulon component and is selected from the group consisting of: eIF4E (gi: 54873625) (NP_001959, NP_001959.1); Cyclin D1 (gi: 77628152) (NP_444284, NP_444284.1); NBS/Nibrin (gi: 67189763) (NP_002476, NP_002476.2); Pim-1 (gi: 31543400) (NP_002639, NP_002639.1); Cyclin B1 (gi: 34304372) (NP_114172, NP_114172.1); Cyclin A2 (gi: 16950653) (NP_001228, NP_001228.1); ODC (gi: 4505488) (NP_002530, NP_002530.1); VEGF (gi: 71051577) (NP_003367, NP_003367.4); Skp2 (gi: 16306594, 16306593) (NP_005974, NP_005974.2, NP_116026, NP_116026.1); Cyclin E1 (gi: 17318558) (NP_001229, NP_001229.1); c-myc (gi: 71774082) (NP_002458, NP_002458.2); FGF2 (gi: 153285460, 153285461) (NP_2006, NP_2006.4, NP_001997, NP_001997.5); MMP-9 (gi: 74272286) (NP_004985, NP_004985.2); mdm2 (gi: 46488903) (NP_002383, NP_002383.2); caspase-9 (gi: 14790123, 14790127) (NP_001220, NP_001220.2, NP_127463, NP_127463.1); bcl2 (gi: 72198188, 72198345) (NP_000624, NP_000624.2, NP_000648, NP_000648.2); Bcl/xL (gi: 20336334) (NP_612815, NP_612815.1); Fbox1 (gi: 16306583); CGGbp1 (gi: 56550052); P54nrb/NONO.1 (gi: 34932413); Selenoprotein S (gi: 33285002, 45439347) (NP_060915, NP_060915.2, NP_018445, NP_018445.4); eIF4E-BP1 (gi: 117938308) (NP_004086, NP_004086.1); Akt1 (gi: 62241012, 62241010, 62241014) (NP_001014431, NP_001014431.1, NP_005154, NP_005154.2, NP_001014432, NP_001014432.1); PI3K (gi: 54792081, 21237724) (NP_006209, NP_006209.2, NP_002640, NP_002640.2); GSK3B (gi: 21361339) (NP_002084, NP_002084.2); HuR (gi: 38201714) (NP_001410, NP_001410.2); and mTOR/FRAP1 (gi: 19924298) (NP_004949, NP_004949.1). Preferred 4E regulon components (components) to be used in certain of the below-described methods are 4E, 4E-BP1, NBS/Nibrin, Pim-1, VEGF, Cyclin D1, Cyclin A2, ODC and HuR. Preferred regulon components include 4E regulon component and is selected from the group consisting of: 4E, 4E-BP1, NBS/Nibrin, Pim-1, VEGF, Cyclin D1, Cyclin A2, ODC, Akt and HuR.

The assays for detecting the level and/or phosphorylation state of 4E and/or at least one 4E regulon component described above may be incorporated into any of a variety of methods for compositions for the identification, diagnosis and monitoring of 4E and 4E regulon component activity and for the discovery of agents that modulate 4E and 4E regulon component activity. Such methods are described extensively in PCT Application US06/049450, filed Dec. 28, 2006 and PCT Application U.S. 07/021,167 filed Oct. 1, 2007, both of which applications are hereby incorporated by reference in their entireties. Exemplary phosphopeptide analytes for two eIF4E regulon element (eIF4EBP1 and Akt1) are presented in FIG. 5.

In certain embodiments, assays and/or methods may incorporate the detection of analytes useful in determining the level/phosphorylation state and activity of additional oncogenic elements, as defined in PCT/US07/021,167, including epidermal growth factor receptor (EGFR), HER2/neu, estrogen receptor (ER), progesterone receptor (PR), additional oncogenic elements, and combinations thereof. Such assays and/or methods may present the ability to use the assay methodologies defined herein as a pan-cancer diagnostic, i.e. a single diagnostic that would be capable of detecting cancers driven by eIF4E alone or in conjunction with EGFR, Her2/neu, ER, PR and additional oncogenic elements, thereby helping to aid and direct the use of targeted therapeutic regimens that permit clinicians to develop personalized therapeutic regimens for the treatment of a wide range and variety of human cancers.

In certain embodiments, the level of and/or phosphorylation state of 4E or a 4E regulon component may be compared to the level of and/or phosphorylation state of a control, such as actin or GADPH.

The present invention provides kits for practice of any of the aforedescribed methods. In certain embodiments, kits may comprise internal protein standards and reagents for creating fragments of the standards and target proteins. A kit may further comprise controls, buffers, and instructions for use. Kit components may be packaged for either manual or partially or wholly automated practice of the foregoing methods. Such kits may have a variety of uses, including, for example, imaging, diagnosis, therapy, and other applications.

EXAMPLE

The present invention is further illustrated by the following example which should not be construed as limiting in any way. The contents of all cited references including literature references, issued patents, published or non published patent applications as cited throughout this application are hereby expressly incorporated by reference.

A highly sensitive high throughput mass spectrometry-based quantitative assay for 4E and 4E regulon components has been developed which provides for the single sample multiplexed analysis of 4E and 4E regulon component levels, as well as the potential simultaneous analysis of 4E and 4E regulon component phosphorylation states, providing for the first single sample analysis of the 4E/4E regulon biological pathway.

The mass spectrometry-based assay employs an enrichment method for the target protein(s), which allows the construction of a highly sensitive, high-throughput assay without the use of an antibody. The enrichment step was built into the reduction/alkylation step so that the enrichment method did not introduce any extra steps or reagents to sample preparation. A similar approach may be applicable to development of mass spectrometry-based assay for many other proteins. Other types of non-antibody based enrichment methods have been successfully adopted to develop mass spectrometry-based assay for a variety of different proteins. The throughput of the assay was comparable to or higher than most antibody-based assays. For example, one person processed more than a thousand samples in a week in duplicate without use of a robotic system.

Reagents: Trypsin-gold was purchased from Promega (Cat # V5280). Ammonium carbonate, ammonium bicarbonate, 2-iodoethanol, and triethylphosphine were from Sigma. Mass-spectrometry grade formic acid was from Sigma. Water with 0.1% formic acid was from Fisher Scientific. Acetonitrile (CAN) was from Burdick & Jackson. Synthetic peptides were from Midwest Biotech (Fishers, Ind.).

Sample preparation: Proteins were digested with trypsin before analysis by tandem mass spectrometry coupled in line with high performance liquid chromatography (LC-MS/MS). When target peptide(s) contain a Cys residue, serum/plasma proteins were first reduced and alkylated prior to trypsin digestion. Reduction and alkylation of the serum or plasma proteins was done in one step essentially as described earlier (Hale J E et al (2004) Anal Biochem 333:174-181) with the following modifications. Most importantly, urea was omitted during the coupled reduction/alkylation step. Typically, 10 µL of serum or plasma sample was diluted with 50 µL of ammonium carbonate solution (0.1 M, pH 11) in a polypropylene container and kept on ice followed by mixing with 80 uL of reduction/alkylation cocktail (R/A cocktail) at room temperature. The R/A cocktail was prepared by mixing 0.5 mL 2-iodoethanol, 0.125 mL triethylphosphine, and 24.375 mL of acetonitrile (2-Iodoethanol comes with copper granules as a stabilizer and was filtered through 0.45 µm spin filter (Millipore UFC30HV00) immediately prior to preparation of the R/A cocktail). For smaller volume of samples, total volume was maintained the same by prediluting the serum with phosphate buffered saline (PBS). For larger volume of samples, each reagent volume was increased accordingly. After adding the R/A cocktail to the diluted sample in alkaline pH, the samples were mixed thoroughly and incubated for 1 h at 37° C. with constant shaking Reduced and alkylated samples were centrifuged at 4000 rpm for 4 min then filtered through Solvinert filter plates (Millipore, MSRLN0450) to remove precipitated proteins. Solvents as well as the remaining reduction/alkylation reagents were removed from the filtrate by SpeedVac (miVac DUO concentrator from GeneVac Cat #DUC-12060-000) typically under high heat (75° C.) for 6 h followed by an additional 12-18 h at room temperature. Dried samples were dissolved in 100 µL of 100 mM ammonium bicarbonate solution (ABC) containing trypsin (1 µg of Trypsin-gold per 10 µL initial plasma or serum volume). The best results were obtained when samples were reconstituted with Trypsin-gold immediately after removal from the SpeedVac. Plates were sealed using pierceable heat-sealing aluminum foil (ABgene Cat # AB-0757) using a heat sealer (Eppendorf, Cat #5390) and incubated with trypsin for 6 h to overnight then filtered through Solvinert filter plates (Millipore, MSRLN0450) before injecting 50 µL to the LC-MS/MS system.

Optimization of the Sample Preparation Procedure for High-Throughput Handling: Reduction/alkylation reaction was performed in 96-well PCR plates with a tall raised-rim around individual wells (Robbins, Surrey UK, Cat #1055-00-0). A precursor of an internal standard peptide includes appropriate corresponding internal marker amino acids (e.g. Leu residue with the molecular weight 7 amu higher than the natural counterpart) was prepared in ice-cold ammonium carbonate buffer at 50 nM concentration. Fifty microliter of this solution was dispensed into the PCR plates using a Multiprop (Thermo). The PCR plates were kept chilled on ice while 10 µL of serum or plasma samples were transferred and mixed in duplicate. The R/A cocktail was added at room temperature using an eight-channel multidispense pipet. Prerinsing of the pipet tips was important for accurate delivery of the reagent due to high vapor pressure of the acetonitrile in the solution. Plates were sealed using pierceable heat-sealing aluminum foil (ABgene Cat # AB-0757) using a heat sealer (Eppendorf, Cat #5390) then mixed thoroughly. Plates were incubated at 37° C. for 1 h with moderate shaking Plates were centrifuged for 4 min at 4000 rpm before peeling the sealing foil. The filtration assembly was prepared by putting a Solvinert filter plate from Millipore (MSRLN0450) on top of the tall raised-rim PCR plate (TempPlate II from USA Scientific, Cat #1402-9600) as a receiving plate in a locking position. The outlet of this filter plate fits into the raised rim of the receiving plate. The filtration assembly was placed over the sample plate in an upside-down position to form a filtration sandwich so that the raised rim of the sample plate is inserted into individual well of the filter plate. The filtration sandwich was inverted and centrifuged for 1 min at 1000 rpm followed by 4 min at 4000 rpm. The filtrates were dried by SpeedVac as described above and then samples were reconstituted with Trypsin gold, the plates sealed and samples digested at 37° C. overnight. Because the sample preparation method involves two filtration steps, the final sample plate is in the same orientation as the initial reduction/alkylation plate. Enrichment procedures as described above or as suitable for the target protein/peptides are employed as required.

LC-MS/MS of 4E and 4E regulon component peptides: Tryptic peptide derived from 4E and individual 4E regulon components are measured and detected using in-line LC-MS/MS for quantitation of 4E and eIF4E regulon components. In the corresponding standard peptide, the Leu residue (or appropriate internal standard heavy labeled amino acid residue) is uniformly labeled with N15 and C13. Interfering peptides were separated by an HPLC system (Surveyor MS pump from Thermo Finnigan) on a C18 reversed-phase column (XBridge 2.5 um×2.1 mm×50 mm) using the following two-solvent gradient system as required (solvent A, 0.1% formic acid/H2O; solvent B, 0.1% formic acid/acetonitrile). The HPLC column was maintained at 50° C., and the solvents were kept at room temperature and the samples were kept at 4° C. Typically 50 µL of the sample out of total volume of 100 µL was injected using a sample injection loop of 100 µL and peptides was eluted at the times indicated. Two water blank samples were injected before the actual samples so that the HPLC column could reach a steady state. Typical carry-over of pNTTP peptide from previous run was less than 0.1%.

Positive ion mass spectrometry was obtained using an LTQ ion trap quadrupole mass spectrometer equipped with an ESI source (Thermo Finnigan). The entire effluent of the column was directed to the ESI source between 2 and 3 min of HPLC run, whereas the rest was diverted away from the mass spectrometer. To accommodate high flow rate, certain parameters for the instrument had to be adjusted manually including transfer capillary temperature (312° C.) and nitrogen sheath flow.

All microscans were set to one microscan of 50 ms collection of ions for the trap. In the instrument method, the following parameters were used for Mass-selective/Mass spectrometry (MS/MS) conditions; normalized collision energy, 21; activation Q, 0.180; activation time, 50 ms. Three (MS/MS) transitions were measured for both the standard peptide and target 4E and 4E regulon peptides.

Peak Integration and Curve Fitting: Peak integration was done using a processing method within XCaliber software using the following parameters: peak integration method, ICIS; smoothing points, 5; baseline window, 15; area noise factor, 1; peak noise factor, 3 for the standard peptide and 5 for target 4E and 4E regulon peptides; constrain peak width, 5% peak height and 3% tailing factor; advanced option, repetitive noise method. Isotopic distribution and relative intensities among three transitions for each peptide was examined and was confirmed to match with those of synthetic peptides. The ratio between the standard peptide and 4E and 4E regulon target peptides were calculated for each transition then numeric average of the three ratios was obtained. NPI values for the calibration standard samples were fitted to a sigmoidal curve (NPI) Bottom+(Top-Bottom)/(1+10^((log EC50−X)* (Hill Slope))) where X is the logarithm of concentration; Bottom, Top, EC50, and Hill Slope are parameters to be determined by the curve fitting of the data) using a nonlinear curve fitting function of the GraphPad Prism (GraphPad Software, Inc., San Diego, Calif.) with 1/Y^2 as a weighting factor. It was important to use the weighting factor to obtain calibration curve that works over the entire concentration range equally well.

Embodiment of Assay for Detection of 4E Levels and Phosphorylation States: The peptide used to detect 4E was SEQ ID NO: 2: WALWFFK. Its parent mass is 498 and the transitions used were 498→740, 498→627 and 498→371.

The mass spectra determined for eIF4E, eIF4E regulon elements and additional oncogenic elements as described above are shown in FIG. 1.

Other peptides such as those in FIGS. 2 and 3 may be used in the aforedescribed assay to detect the eiF4E and 4E regulon components and additional oncogenic elements from which they are derived Embodiment of Assay for Detection of 4E Regulon Component Levels and Phosphorylation States: The sequences of 4E regulon components and exemplary phosphopeptide sequences of said components that may be detected using the above-described assay are shown in FIG. 2 and FIG. 5. Potential digestion product peptides used to analyze each of the components are shown in FIG. 3 and FIG. 5.

eIF4E Regulon Component Analyte Determination by Mass-Selective Mass Spectrometry: Purified proteins were obtained from a commercial supplier (Origene) and prepared for mass-selective mass-spectrometry using the following procedure. Samples were precipitated with acetone, denatured in 8M urea, reduced with 10 mM DTT in 10 mM ammonium bicarbonate and alkylated with 55 mM iodoacetamide in ammonium bicarbonate. Each sample was then treated with Trypsin (Promega) and incubated overnight at 37 degrees Celsius. The tryptic peptides mixtures obtained using the procedure presented above were injected onto a C18 column (Xbridge C18 2.5 uM-2.1 mm×5 cm). Tryptic peptides were eluted with a linear gradient from 3 to 45% acetonitrile (in water) developed over 120 min at 50 degrees Celsius using a flow rate of 200 uL/min using a Surveyor HPLC pump. Column effluent was electro-sprayed into the LTQ mass spectrometer (Thermo) and peptides detected. Peptides detected were verified by searching against an IPI human database (V360) using Sequest and XITandem algorithms. Peptide analyte identification confidence was calculated using a published method (Higgs, R. E. et al (2007) J Proteome Res. 4: 1758-1767). All peptides presented had identification confidence levels exceeding 99%. A summary of peptide analytes identified for eIF4E Regulon components and additional oncogenic analytes are presented in FIG. 4 and their corresponding mass spectra are presented in FIG. 1.

I claim:

1. A method for identifying a subject who has a disease wherein 4E regulon activity is dysfunctional, said method comprises simultaneously determining the levels of and/or phosphorylation states of a set of target proteins or peptides in a sample obtained from the subject, said target proteins or peptides are eIF4E (NP_001959) (NP_001959.1), HuR (NP_001410) (NP_001410.2), and at least one eIF4E regulon component selected from the group consisting of: Cyclin D1(NP_444284) (NP_444284.1); NBS/Nibrin (NP_002476) (NP_002476.2); Pim-1 (NP_002639) (NP_002639.1); Cyclin B1 (NP_114172) (NP_114172.1); Cyclin A2 (NP_001228) (NP_001228.1); ODC (NP_002530) (NP_002530.1); VEGF (NP_003367) (NP_003367.4); Skp2 (NP_005974, NP_116026) (NP_005974.2, NP_116026.1); Cyclin E1 (P24864) (NP_001229) (NP_001229.1); c-myc (gi: 71774082) (NP_002458) (NP_002458.2); FGF2 (P09038) (NP_002006) (NP_001997) (NP_002006.4) (NP_001997.5); MMP-9 (P14780) (NP_004985) (NP_004985.2); mdm2 (NP_002383) (NP_002383.2); caspase-9 (P55211) (NP_001220, NP_127463) (NP_001220.2, NP_127463.1); bcl2 (P10415) (NP_000624, NP_000648) (NP_000624.2, NP_000648.2); Bcl/xL (Q07817) (NP_612815) (NP_612815.1); Selenoprotein S (Q9BQE4) (NP_060915), (NP_982298) (NP_060915.2), (NP_982298.1); eIF4E-BP1 (Q13541) (NP_004086) (NP_004086.1); Akt1 (P31749) (NP_001014431, NP_005154, NP_001014432) (NP_001014431.1, NP_005154.2, NP_001014432.1); PI3K (NP_006209, NP_002640) (NP_006209.2, NP_002640.2); GSK3B (NP_002084) (NP_002084.2); Osteopontin (P10451) (NP_001035149) (NP_001035149.1) and mTOR/FRAP1 (NP_004949) (NP_004949.1), and at least one non-eIF4E regulon component selected from the group consisting of EGFR (P00533) (NP_005219) (NP_005219.2), HER2/neu (PO4626) (NP_004439) (NP_004439.2), ER (NP_0001116) (NP_000116.2) and PR (AAA60081) (AAA60081.1) in a sample, the method comprising:
- (a) adding at least one internal standard protein or peptide corresponding to each target protein of eIF4E, HuR, and the at least one eIF4E regulon component selected from the group consisting of Cyclin D1, NBS/Nibrin, Pim-1, Cyclin B1, Cyclin A2, ODC, VEGF, Skp2, Cyclin E1, c-myc, FGF2, MMP-9, mdm2, caspase-9, bcl2, Bcl/xL, Selenoprotein S, eIF4E-BP1, Akt1, PI3K, GSK3B, Osteopontin and mTOR/FRAP1, and the at least one non-eIF4E regulon component selected from the group consisting of EGFR, HER2/neu, ER and PR to the sample;
- (b) fragmenting the target proteins or peptides of eIF4E, HuR, the at least one eIF4E regulon component, and the at least one non-eIF4E component and the at least four corresponding internal standard proteins or peptides, thereby generating fragments of the eIF4E, the HuR, the at least one eIF4E regulon component, and the at least one non-eIF4E regulon component, and the at least four corresponding internal standard proteins or peptides;
- (c) analyzing the corresponding parent masses and determining amounts of the resultant fragments from step (b) by a mass spectrometry-based method; and
- (d) using the results from step (c) to determine and quantitate the levels of and/or phosphorylation states of the eIF4E, HuR, the at least one eIF4E regulon component, and the at least one non-eIF4E regulon component.

2. The method of claim 1, wherein:
- (a) the at least one eIF4E regulon component is selected from the group consisting of: Cyclin D1 (NP_444284) (NP_444284.1); NBS/Nibrin (NP_002476) (NP_002476.2); Pim-1 (NP_002639) (NP_002639.1); Cyclin A2 (NP_001228) (NP_001228.1); ODC (NP_002530) (NP_002530.1); VEGF (NP_003367) (NP_003367.4); Skp2 (NP_005974, NP_116026) (NP_005974.2, NP_116026.1); Cyclin E1 (P24864) (NP_001229) (NP_001229.1); FGF2 (P09038) (NP_002006) (NP_001997) (NP_002006.4) (NP_001997) (NP_001997.5); MMP-9 (P14780) (NP_004985) (NP_004985.2); caspase-9 (P55211) (NP_001220, NP_127463) (NP_001220.2, NP_127463.1); bcl2 (P10415) (NP_000624, NP_000648) (NP_000624.2, NP_000648.2); Bcl/xL (Q07817) (NP_612815) (NP_612815.1); Selenoprotein S (Q9BQE4) (NP_060915), (NP_982298) (NP_060915.2), (NP_982298.1); eIF4E-BP1 (Q13541) (NP_004086) (NP_004086.1); Osteopontin (P10451) (NP_001035149) (NP_001035149.1); Akt1 (P31749) (NP_001014431, NP_005154, NP_001014432) (NP_001014431.1, NP_005154.2, NP_001014432.1); and
- (b) the at least one internal standard protein or peptide corresponding to the at least one eIF4E regulon component is selected from the group consisting of: Cyclin D1, NBS/Nibrin, Pim-1, Cyclin A2, ODC, VEGF, Skp2, Cyclin E1, FGF2, MMP-9, caspase-9, bcl2, Bcl/xL, Selenoprotein S, eIF4E-BP1, Osteopontin and Akt1.

3. The method of claim 1, wherein the mass spectrometry-based method is Liquid chromatography-Mass-selective/Mass Spectrometry (LC-MS/MS).

4. The method of claim 1 wherein in step (b), fragmenting is mediated by the addition of and/or exposure to: chemical agents selected from the group consisting of acid, base, cyanogen bromide, and o-iodobenzoic acid; enzymes or proteases selected from the group consisting of thrombin, trypsin, and chymotrypsin; or mass-spectrometry based fragmentation methods or including collision-induced dissociation.

5. The method of claim 4 wherein the fragmenting is mediated by the addition of and/or exposure to an enzyme or protease, and said enzyme or protease is selected from the group consisting of thrombin, trypsin, and chymotrypsin.

6. The method of claim 5 wherein said enzyme or protease is trypsin.

7. The method of claim 1, wherein the levels and/or phosphorylation states of:
- (a) eIF4E is determined at least in part on the analysis of the at least one fragment selected from the group consisting of: WALWFFK (SEQ ID NO.: 2 and 542), DGIEPMWEDEK (SEQ ID NO.: 152), IAIWTTECENR (SEQ ID NO.: 153), IVIGYQSHADTATK (SEQ ID NO.: 154, 187 and 541), TESNQEVANPEHYIK (SEQ ID NO.: 155), MATVEPETTPTPNPPTTEEEK (SEQ ID NO.: 156), FWLETLLCLIGESFDDYSDDVCGAVVNVR (SEQ ID NO.: 157), FDTVEDFWALYNHIQLSSNLMPGCDYSLFK (SEQ ID NO.: 158), and EAVTHIGR (SEQ ID NO.: 159);
- (b) HuR is determined at least in part on the analysis of the at least one fragment selected from the group consisting of: DVEDMFSR (SEQ ID NO.: 139), FAANPNQNK (SEQ ID NO.: 140), VLVDQTTGLSR (SEQ ID NO.: 141 and 544), DANLYISGLPR (SEQ ID NO.: 142 and 543), FGGPVHHQAQR (SEQ ID NO.: 143), VSYARPSSEVIK (SEQ ID NO.: 144), SLFSSIGEVESAK (SEQ ID NO.: 145), NVALLSQLYHSPAR (SEQ ID NO.: 146), MSNGYEDHMAEDCR (SEQ ID NO.: 147), VAGHSLGYGFVNYVTAK (SEQ ID NO.: 148), TNLIVNYLPQNMTQDELR (SEQ ID NO.: 149), SEAEEAITSFNGHKPPGSSEPITVK (SEQ ID NO.: 150), and GFGFVTMTNYEEAAMAIASLNGYR (SEQ ID NO.: 151);
- (c) Cyclin D1 is determined at least in part on the analysis of the at least one fragment selected from the group consisting of: ETIPLTAEK (SEQ ID NO.: 102), QAQQNMDPK (SEQ ID NO.: 103), SPNNFLSYYR (SEQ ID NO.: 104), AYPDANLLNDR (SEQ ID NO.: 105), AEETCAPSVSYFK (SEQ ID NO.: 106 and 538), LQLLGATCMFVASK (SEQ ID NO.: 107), HAQTFVALCATDVK (SEQ ID NO.: 108), IVATWMLEVCEEQK (SEQ ID NO.: 109), ACQEQIEALLESSLR (SEQ ID NO.: 110 and 537), MEHQLLCCEVETIR (SEQ ID NO.: 111), CEEEVFPLAMNYLDR (SEQ ID NO.: 112), WNLAAMTPHDFIEHFLSK (SEQ ID NO.: 113), FISNPPSMVAAGSVVAAVQGLNLR (SEQ ID NO.: 114), AAEEEEEEEEEVDLACTPTDVR (SEQ ID NO.: 115), and LCIYTDNSIRPEELLQMELLLVNK (SEQ ID NO.: 116);
- (d) NBS/Nibrin is determined at least in part on the analysis of the at least one fragment selected from the group consisting of: ISQENEIGK (SEQ ID NO.: 49), MLSQDAPTVK (SEQ ID NO.: 50), IPNYQLSPTK (SEQ ID NO.: 51), LQDDSEMLPK (SEQ ID NO.: 52), NTELEEWLR (SEQ ID NO.: 53), EESLADDLFR (SEQ ID NO.: 54), LSSAVVFGGGEAR (SEQ ID NO.: 55), ASQQQQTNSIR (SEQ ID NO.: 56), SGDGITFGVFGSK (SEQ ID NO.: 57), DTKPELEIDVK (SEQ ID NO.: 58), QEMEVQNQHAK (SEQ ID NO.: 59), DEENQEMSSCK (SEQ ID NO.: 60), NPSGINDDYGQLK (SEQ ID NO.: 61), WIQSIMDMLQR (SEQ ID NO.: 62), TSSNNNSMVSNTLAK (SEQ ID NO.: 63), NYCDPQGHPSTGLK (SEQ ID NO.: 64), TTTPGPSLSQGVSVDEK (SEQ ID NO.: 65), LPHIIGGSDLIAHHAR (SEQ ID NO.: 66), EMDDVAIEDEVLEQLFK (SEQ ID NO.: 67), IEYEPLVACSSCLDVSGK (SEQ ID NO.: 68), MDIETNDTFSDEAVPESSK (SEQ ID NO.: 69), QPPQIESFYPPLDEPSIGSK (SEQ ID NO.: 70), QGLRPIPEAEIGLAVIFMTTK (SEQ ID NO.: 71), IETSCSLLEQTQPATPSLWK (SEQ ID NO.: 72), TICALICGRPIVKPEYFTEFLK (SEQ ID NO.: 73), EQHLSENEPVDTNSDNNLFTDTDLK (SEQ ID NO.: 74), LMPSAPVNTTTYVADTESEQADTWDLSERPK (SEQ ID NO.: 75), TALNQAILQLGGFTVNNWTEECTHLVMVSVK (SEQ ID NO.: 76), LLPAAGPAGGEPYR (SEQ ID NO.: 160), and KQPPQIESFYPPLDEPSIGSK (SEQ ID NO.: 161);

(e) Pim-1 is determined at least in part on the analysis of the at least one fragment selected from the group consisting of: VSSGFSGVIR (SEQ ID NO.: 34), VPMEVVLLK (SEQ ID NO.: 35), VSDNLPVAIK (SEQ ID NO.: 36), LIDFGSGALLK (SEQ ID NO.: 37), VYSPPEWIR (SEQ ID NO.: 38), AAPCNDLHATK (SEQ ID NO.: 39), DENILIDLNR (SEQ ID NO.: 40), VSSECQHLIR (SEQ ID NO.: 41), DTVYTDFDGTR (SEQ ID NO.: 42 and 551), HCHNCGVLHR (SEQ ID NO.: 43), ISDWGELPNGTR (SEQ ID NO.: 44 and 552), SFFWQVLEAVR (SEQ ID NO.: 45), EPLESQYQVGPLLGSGGFGSVYSGIR (SEQ ID NO.: 46), SAAVWSLGILLYDMVCGDIPFEHDEEIIR (SEQ ID NO.: 47), LLDWFERPDSFVLILERPEPVQDLFDFITER (SEQ ID NO.: 48), and SLGILLYDMVCGDIPFEHDEEIIR (SEQ ID NO.: 162);

(f) Cyclin A2 is determined at least in part on the analysis of the at the at least one fragment selected from the group consisting of: GLAQQQRPK (SEQ ID NO.: 121), FLSSMSVLR (SEQ ID NO.: 122), QPDITNSMR (SEQ ID NO.: 123), APQHAQQSIR (SEQ ID NO.: 124), MLGNSAPGPATR (SEQ ID NO.: 125), LQLVGTAAMLLASK (SEQ ID NO.: 126), QPAFTIHVDEAEK (SEQ ID 127), EDALAFNSAISLPGPR (SEQ ID NO.: 128), YHGVSLLNPPETLNL (SEQ ID NO.: 129), DLPVNDEHVTVPPWK (SEQ ID NO.: 130), AILVDWLVEVGEEYK (SEQ ID NO.: 131), LQNETLHLAVNYIDR (SEQ ID NO.: 132), VESLAMFLGELSLIDADPYLK (SEQ ID NO.: 133), TGYTLESLKPCLMDLHQTYLK (SEQ ID NO.: 134), FEEIYPPEVAEFVYITDDTYTK (SEQ ID NO.: 135), EAGSALLALQQTALQEDQENINPEK (SEQ ID NO.: 136), YLPSVIAGAAFHLALYTVTGQSWPESLIR (SEQ ID NO.: 137), and VLTFDLAAPTVNQFLTQYFLHQQPANCK (SEQ ID NO.: 138);

(g) ODC is determined at least in part on the analysis of the at the at least one fragment selected from the group consisting of: YFPSDSGVR (SEQ ID NO.: 77), INEVSSSDDK (SEQ ID NO.: 78), TLAATGTGFDCASK (SEQ ID NO.: 79), DAFYVADLGDILK (SEQ ID NO.: 80), FEEITGVINPALDK (SEQ ID NO.: 81 and 549), TEIQLVQSLGVPPER (SEQ ID NO.: 82), YYVASAFTLAVNIIAK (SEQ ID 83), YYSSSIWGPTCDGLDR (SEQ ID NO.: 84), YAANNGVQMMTFDSEVELMK (SEQ ID NO.: 85), MNNFGNEEFDCHFLDEGFTAK (SEQ ID NO.: 86), CVFDMGAEVGFSMYLLDIGGGFPGSEDVK (SEQ ID NO.: 87), ELNIDVVGVSFHVGSGCTDPETFVQAISDAR (SEQ ID NO.: 88), INEVSSSDDKDAFYVADLGDILK (SEQ ID NO.: 163), and LLDIGGGFPGSEDVK (SEQ ID NO.: 164 and 550);

(h) VEGF is determined at least in part on the analysis of the at least one fragment selected from the group consisting of: AGEAEPSGAAR (SEQ ID NO.: 89), LFVQLLGCSR (SEQ ID NO.: 90), GAEESGPPHSPSR (SEQ ID NO.: 91), QENPCGPCSER (SEQ ID NO.: 92), HLFVQDPQTCK (SEQ ID NO.: 93), GQGPEPAPGGGVEGVGAR (SEQ ID NO.: 94), EEPQPEEGEEEEEK (SEQ ID NO.: 95), QTDTAPSPSYHLLPGR (SEQ ID NO.: 96), KPGSWTGEAAVCADSAPAAR (SEQ ID NO.: 97), WSQAAPMAEGGGQNHHEVVK (SEQ ID NO.: 98), IKPHQGQHIGEMSFLQHNK (SEQ ID NO.: 99), CGGCCNDEGLECVPTEESNITMQIMR (SEQ ID NO.: 100), and ASETMNFLLSWVHWSLALLLYLHHAK (SEQ ID NO.: 101);

(i) Skp2 is determined at least in part on the analysis of the at least one fragment selected from the group consisting of: TLQVFGIVPDGTLQLLK (SEQ ID NO.: 165, 226 and 556), LLSQGVIAFR (SEQ ID NO.: 166 and 219), LASDESLWQTLDLTGK (SEQ ID NO.: 167 and 223), LSDPIVNTLAK (SEQ ID NO.: 168, 221 and 555), VSGVCK (SEQ ID NO.: 212), NSNLVR (SEQ ID NO.: 213), DFVIVR (SEQ ID NO.: 214), SDLSTLVR (SEQ ID NO.: 215), NQEIWGIK (SEQ ID NO.: 216), NLHPDVTGR (SEQID NO.: 217), LTLQKPSCL (SEQ ID NO. 218), LQNLSLEGLR (SEQ ID NO.: 220), TSELLSGMGVSALEK (SEQ ID NO. 222), SFMDQPLAEHFSPFR (SEQ ID NO.: 224), CPNLVHLDLSDSVMLK (SEQ ID NO.: 225), LDELNLSWCFDFTEK (SEQ ID NO.: 227), CYDIIPETLLELGEIPTLK (SEQ ID NO.: 228), HVQVAVAHVSETITQLNLSGYR (SEQ ID NO.: 229), LNLSGCSGFSEFALQTLLSSCSR (SEQ ID NO.: 230), NDCFQEFFQLNYLQHLSLSR (SEQ ID NO.: 231), EEPDSENIPQELLSNLGHPESPPR (SEQ ID NO.: 232), HLQEIPDLSSNVATSFTWGWDSSK (SEQ ID NO.: 233), EALPHLQINCSHFTTIARPTIGNK (SEQ ID NO.: 234), VQHMDLSNSVIEVSTLHGILSQCSK (SEQ ID NO.: 235), and ENFPGVSWDSLPDELLLGIFSCLCLPELLK (SEQ ID NO.: 236);

(j) Cyclin E1 is determined at least in part on the analysis of the at least one fragment selected from the group consisting of: AILLDWLMEVCEVYK (SEQ ID NO.: 169 and 258), DQHFLEQHPLLQPK (SEQ ID NO.: 170 and 259), GSPLPVLSWANR (SEQ ID NO.: 171), and YMATQENVVK (SEQ ID NO.: 172 and 247), ETGSSK (SEQ ID NO.: 237), IMLNK (SEQ ID NO. 238), EDDDR (SEQ ID NO.: 239), IIAPSR (SEQ ID NO.: 240), EEVWK (SEQ ID NO.: 241), QSSGPEMA (SEQ ID NO.: 242), DSLDLLDK (SEQ ID NO.: 243), AMLSEQNR (SEQ ID NO.: 244), LEEIYPPK (SEQ ID NO.: 245), EDGGAEFSAR (SEQ ID NO.: 246), VYPNSTCKPR (SEQ ID NO.: 248), WMVPFAMVIR (SEQ ID NO: 249), GSPLPVLSWANR (SEQ ID NO.: 250), ASPLPSGLLTPPQSGK (SEQ ID NO.: 251), ETFYLAQDFFDR (SEQ ID NO.: 252), GVADEDAHNIQTHR (SEQ ID NO.: 253), TLLQLIGISSLFIAAK (SEQ ID NO. 254), DQHFLEQHPLLQPK (SEQ ID NO.: 255), VSGYQWCDIENCVK (SEQ ID NO.: 256), ANVTVFLQDPDEEMAK (SEQ ID NO.: 257), and LHQFAYVTDGACSGDEILTMELMIMK (SEQ ID NO.: 260);

(k) MMP-9 is determined at least in part on the analysis of the at least one fragment selected from the group consisting of: LGLGADVAQVTGALR (SEQ ID NO.: 173 and 282), QLSLPETGELDSATLK (SEQ ID NO.: 174), QSTLVLFPGDLR (SEQ ID NO.: 175), and SLG- PALLLLQK (SEQ ID NO.: 176), FSEGR (SEQ ID NO.: 261), SDGYR (SEQ ID NO.: 262), FYWR (SEQ ID NO.: 263), GVVVPTR (SEQ ID NO.: 264), WPALPR (SEQ ID NO.: 265), SASEVDR (SEQ ID NO.: 266), DDVNGIR (SEQ ID NO.: 267), AQMVDPR (SEQ ID NO.: 268), MLLFSGR (SEQ ID NO. 269), LFFFSGR (SEQ ID NO. 270), AYFCQDR (SEQ ID NO.: 271), AVIDDAFAR (SEQ ID NO.: 272), LDSVFEER (SEQ ID NO.: 273), LFGFCPTR (SEQ ID NO.: 274), FGFCPSER (SEQ ID NO.: 275), FTEGPPLHK (SEQ ID NO.: 276), FQTFEGDLK (SEQ ID NO.: 277), SYSACTTDGR (SEQ ID NO.: 278), EYSTCTSEGR (SEQ ID NO.: 279), WCATTANYDR (SEQ ID NO.: 280), GSRPQGPFLIADK (SEQ ID NO.: 281), QVWVYTGASVLGPR (SEQ ID NO.: 283), LWCATTSNFDSDK (SEQ ID NO.: 284), AFALWSAVTPLTFTR (SEQ ID NO.: 285), MFPGVPLDTHDVFQYR (SEQ ID NO. 286), FGNADGAACHFPFIFEGR (SEQ ID NO.: 287), SDGLPWCSTTANYDTDDR (SEQ NO.: 288), DADIVIQFGVAEHGDGYPFDGK (SEQ ID NO.: 289), ADSTVMGGNSAGELCVFPFTFLGK (SEQ ID NO.: 290), WHHHNITYWIQNYSEDLPR (SEQ ID NO.: 291), SELNQVDQVGYVTYDILQCPED (SEQ ID NO.: 292), DGLLAHAFPPGPGIQGDAHFDDDELWSLGK (SEQ ID NO.: 293), and LYTQDGNADGKPCQFPFIFQGQSYSACTTDGR (SEQ ID NO.: 294);

(l) Capase-9 is determined at least in part on the analysis of the at least one fragment selected from the group consisting of: LVEELQVDQLWDVLLSR (SEQ ID NO.: 177 and 308), DHGFEVASTSPEDESPGSNPEPDATPFQEGLR (SEQ ID NO.: 178, 314 and 535), QLIIDLETR (SEQ ID NO.: 179, 302 and 536), and KPEVLRPETPRPVDIGSGGFGDVEQK (SEQ ID NO.: 180), AGSGSR (SEQ ID NO.: 295), LFFK (SEQ ID NO.: 296), ESGLR (SEQ ID NO.: 297), GDLTAK (SEQ ID NO.: 298), MDEADR (SEQ ID NO.: 299), VANAVSVK (SEQ ID NO.: 300), TGSNIDCEK (SEQ ID NO.: 301), QMPGCFNFLR (SEQ ID NO.: 303), FSSLHFMVEVK (SEQ ID NO.: 304), LFFIQACGGEQK (SEQ ID NO.: 305), ELFRPHMIEDIQR (SEQ ID NO.: 306), IVNIFNGTSCPSLGGKPK (SEQ ID NO.: 307), LSKPTLENLTPVVLRPEIR (SEQ ID NO.: 309), GSQALPLFISCLEDTGQDMLASFLR SEQ ID NO.: 310), KPEVLRPETPRPVDIGSGGFGDVGALESLR (SEQ ID NO.: 311), GNADLAYILSMEPCGHCLIINNVNFCR (SEQ ID NO.: 312), SGSWYVETLDDIFEQWAHSEDLQSLLLR (SEQ ID NO.: 313), TFDQLDAISSLPTPSDIFVSYSTFPGFVSWR (SEQ ID NO.: 315), and MVLALLELAQQDHGALDCCVVVILSHGCQASHLQFPGAVYGTDGCPVSVEK (SEQ ID NO.: 316);

(m) Bcl/xL is determined at least in part on the analysis of the at least one fragment selected from the group consisting of: AFSDLTSQLHITPGTAYQSFEQVVNELFR (SEQ ID NO.: 181 and 326)), ELVVDFLSYK (SEQ ID NO.: 182, 322 and 533), QSFEQVVNELFR (SEQ ID NO.: 183), EVIPMAAVK (SEQ ID NO.: 184, 319 and 534), MSQSNR (SEQ ID NO.: 317), DGVNWGR (SEQ ID NO. 318), EMQVLVSR (SEQ ID NO.: 320), EAGDEFELR (SEQ ID NO.: 321), GYSWSQFSDVEENR (SEQ ID NO.: 323), IVAFFSFGGALCVESVDK (SEQ ID NO.: 324), WFLTGTVAGVVLLGSLFSR (SEQ ID NO.: 325), IAAWMATYLNDHLEPWIQENGGWDTFVELYGNNAAAESR (SEQ ID NO.: 327), and TEAPEGTESEMETPSAINGNPSWHLADSPAVNGATGHSSSLDAR (SEQ ID NO.: 328);

(n) eIF4E-BP1 is determined at least in part on the analysis of the at least one fragment selected from the group consisting of: AGGEESQFEMDI (SEQ ID NO.: 117 and 334), MSGGSSCSQTPSR (SEQ ID NO.: 118), DLPTIPGVTSPSSDEPPMEASQSHLR (SEQ ID NO.: 119 and 336), VVLGDGVQLPPGDYSTTPGGTLFSTTPGGTR (SEQ ID NO.: 120 and 337), RVVLGDGVQLPPGDYSTTPGGTLFSTTPGGTR (SEQ ID NO.: 185), AIPATR (SEQ ID NO.: 329), NSPVTK (SEQ ID NO.: 330), IIYDR (SEQ ID NO.: 331), NSPEDK (SEQ ID NO.: 332), FLMECR (SEQ ID NO.: 333), and ACSGGSSCSQTPSR (SEQ ID NO.: 335), (o) Akt1 is determined at least in part on the analysis of the at least one fragment selected from the group consisting of: NDGTFIGYK (SEQ ID NO.: 12), YSFQTHDR (SEQ ID NO.: 13), ERPQDVDQR (SEQ ID NO.: 14), QEEEEMDFR (SEQ ID NO.: 15), TFHVETPEER (SEQ ID NO.: 16), VTMNEFEYLK (SEQ ID NO.: 17), DEVAHTLTENR (SEQ ID NO.: 18), LPFYNQDHEK (SEQ ID NO.: 19), CLQWTTVIER (SEQ ID NO.: 20), LFELILMEEIR (SEQ ID NO.: 21), TERPRPNTFIIR (SEQ ID NO.: 22), FFAGIVWQHVYEK (SEQ ID NO.: 23 and 531), RPHFPQFSYSASGTA (SEQ ID NO.: 24), EEWTTAIQTVADGLK (SEQ ID NO.: 25 and 530), LSPPFKPQVTSETDTR (SEQ ID NO.: 26), EAPLNNFSVAQCQLMK (SEQ ID NO.: 27), FYGAEIVSALDYLHSEK (SEQ ID NO.: 28), SGSPSDNSGAEEMEVSLAKPK (SEQ ID NO.: 29), AVDWWGLGVVMYEMMCGR (SEQ ID NO.: 30), LCFVMEYANGGELFFHLSR (SEQ ID NO.: 31), TFCGTPEYLAPEVLEDNDYGR (SEQ ID NO.: 32), YFDEEFTAQMITITPPDQDDSMECVDSER (SEQ ID NO.: 33), and LFELILLMEEIR (SEQ ID NO.: 186), (p) Bcl2 is determined at least in part on the analysis of the at least one fragment selected from the group consisting of: FATVVEELFR (SEQ ID NO.: 188, 344 and 532), EIVMK (SEQ ID NO.: 338), MAHAGR (SEQ ID NO.: 339), YIHYK (SEQ ID NO.: 340), TGYDNR (SEQ ID NO.: 341), DGVNWGR (SEQ ID NO.: 342), QAGDDFSR (SEQ ID NO.: 343), DFAEMSSQLHLTPFTAR (SEQ ID NO.: 345), IVAFFEFGGVMCVESVNR (SEQ ID NO. 346), TLLSLALVGACITLGAYLGHK (SEQ ID NO.: 347), EMSPLVDNIALWMTEYLNR (SEQ ID NO.: 348), TSPLQTPAAPGAAAGPALSPVPPVVHLTLR (SEQ ID NO.: 349), GYEWDAGDVGAAPPGAAPAPGIFSSQPGHTPHPAASR (SEQ ID NO.: 350), and HLHTWIQDNGGWDAFVELYGPSMRPLFDFSWLSLK (SEQ ID NO.: 351);

(q) EGFR is determined at least in part on the analysis of the at least one fragment selected from the group consisting of: GDSFTHTPPLDPQELDILK (SEQ ID NO. 189, 451 and 539), IPLENLQIIR (SEQ ID NO.: 190, 430 and 540), EATSPK (SEQ ID NO.: 398), IPVAIK (SEQ ID NO.: 399), ELPMR (SEQ ID NO.: 400), ECVDK (SEQ ID NO.: 401), ETEFK (SEQ ID NO. 402), LLQER (SEQ ID NO.: 403), GENSCK (SEQ ID NO. 404), TPQHVK (SEQ ID NO.: 405), DEATCK (SEQ ID NO.: 406), LLGAEEK (SEQ ID NO.: 407), CEGPCR (SEQ ID NO.: 408), DCVSCR (SEQ ID NO. 409), LFGTSGQK (SEQ ID NO.: 410), ITDFGLAK (SEQ ID NO.: 411), EYHAEGGK (SEQ ID NO.: 412), VCQGTSNK (SEQ ID NO.: 413), EDSFLQR (SEQ ID NO.: 414), ELIIEFSK (SEQ ID NO. 415), GMNYLEDR (SEQ ID NO.: 416), NYDLSFLK (SEQ ID NO.: 417), EAKPNGIFK (SEQ ID NO.: 418), NGLQSCPIK (SEQ ID NO.: 419), GLWIPEGEK (SEQ ID NO. 420), YSFGATCVK (SEQ ID NO.: 421), ESDCLVCR (SEQ ID NO.: 422), CNLLEGEPR (SEQ ID NO.: 423), YLVIQGDER (SEQ ID NO.: 424), VAPQSSEFIGA (SEQ ID NO.: 425), DSLSINATNIK (SEQ ID NO.: 426), IICAQQCSGR (SEQ ID NO.: 427), VCNGIGIGEFK (SEQ ID NO. 428), VLGSGAFGTVYK (SEQ ID NO.: 429), GSTAENAEYLR (SEQ ID NO.: 431), NLQEILHGAVR (SEQ ID NO.: 432), WMALESILHR (SEQ ID NO.: 433), EISDGDVIISGNK (SEQ ID NO. 434), CWMIDADSRPK SEQ ID NO. 435), NLCYANTINWK (SEQ ID NO.: 436), NYVVTDHGSCVR (SEQ ID NO. 437), MHLPSPTDSNFYR (SEQ ID NO.: 438), TDLHAFENLEIIR (SEQ ID NO.: 439), ACGADSYEMEEDGVR (SEQ ID NO.: 440), TCPAGVMGENNTLVWK (SEQ ID NO.: 441), EITGFLLIQAWPENR (SEQ ID NO.: 442), NCTSISGDLHILPVAFR (SEQ ID NO.: 443), LTQLGTFEDHFLSLQR (SEQ ID NO.: 444), FSNNPALCNVESIQWR (SEQ ID NO.: 445), TIQEVAGYVLIALNTVER (SEQ ID NO.: 446), LPQPPICTIDVYMIMVK (SEQ ID NO.: 447), DNIGSQYLLNWCVQIAK (SEQ ID NO.: 448), ELVEPLTPSGEAPNQALLR (SEQ ID NO.: 449), SPSDCCHNQCAAGCTGPR (SEQ ID NO.: 450), QHGQFSLAVVSLNITSLGLR (SEQ ID NO.: 452), TPLLSSLSATSNNSTVACIDR (SEQ ID NO.: 453), EILDEAYVMASVDNPHVCR (SEQ ID NO.: 454), GSHQISLDNPDYQQDFFPK (SEQ ID NO.: 455), GPDNCIQCAHYIDGPHCVK (SEQ ID NO.: 456), MFNNCEVVLGNLEITYVQR (SEQ ID NO.: 457), CDPSCPNGSCWGAGEENCQK (SEQ ID NO.: 458), ATGQVCHALCSPEGCWGPEPR (SEQ ID NO.: 459), RPAGSVQNPVYHNQPLNPAPSR (SEQ ID NO.: 460), GNMYYENSYALAVLSNYDANK (SEQ ID NO.: 461), DTCPPLMLYNPTTYQMDVNPEGK (SEQ ID NO.: 462), IPSIATGMVGALLLLLVVALGIGLFMR (SEQ ID NO.: 463), DIVSSDFLSNMSMDFQNHLGSCQK (SEQ ID NO.: 464), LLGICLTSTVQLITQLMPFGCLLDYVR (SEQ ID NO.: 465), EFVENSECIQCHPECLPQAMNITCTGR (SEQ ID NO. 466), YSSDPTGALTEDSIDDTFLPVPEYINQSVPK (SEQ ID NO.: 467), ALMDEEDMDDVVDADEYLIPQQGFFSSPSTSR (SEQ ID NO.: 468), YADAGHVCHLCHPNCTYGCTPGLEGCPTNGPK (SEQ ID NO.: 469), DPHYQDPHSTAVGNPEYLNTVQPTCVNSTFDSPAHWAQK (SEQ ID NO.: 470), and IYTHQSDVWSYGVTVWELMTFGSKPYDGIPASEISSILEK (SEQ ID NO.: 471);

(r) Selenoprotein S is determined at least in part on the analysis of the at least one fragment selected from the group consisting of: AAAAVEPDVVVK (SEQ ID NO.: 191, 356 and 553), MQEELNAQVEK (SEQ ID NO.: 192, 357 and 554), GPSSGGUG (SEQ ID NO.: 352), QLDR (SEQ ID NO.: 353), QLEEEK (SEQ ID NO.: 354), QEALAAAR (SEQ ID NO. 355), IEMWDSMQEGK (SEQ ID NO.: 358), KPQEEDSPGPSTSSVLK (SEQ ID NO.: 359), QEESLSARPALETEGLR (SEQ ID NO.: 360), GGGYNPLSGEGGGACSWRPGR (SEQ ID NO.: 361), and FLHTTVGSLLATYGWYIVFSCILLYVVFQK (SEQ ID NO.: 362);

(s) FGF2 is determined at least in part on the analysis of the at least one fragment selected from the group consisting of: CVTDECFFFER (SEQ ID NO.: 193, 394 and 546), AILFLPMSAK (SEQ ID NO.: 194, 391 and 545), AAPAAR (SEQ ID NO: 375), AAGSPR (SEQ ID NO.: 376), ALPGGR (SEQ ID NO.: 377), GTAAPR (SEQ ID NO.: 378), LYCK (SEQ ID NO.: 379), TGPGQK (SEQ ID NO.: 380), TGQYK (SEQ ID NO.: 381), GVVSIK (SEQ ID NO. 382), YLAMK (SEQ ID NO.: 383), GVCANR (SEQ ID NO.: 384), IHPDGR (SEQ ID NO.: 385), SDPHIK (SEQ ID NO. 386), HPSVNPR (SEQ ID NO.: 387), NGGFFLR (SEQ ID NO.: 388), LQLQAEER (SEQ ID NO.: 389), TEERPSGSR (SEQ ID NO.: 390), YTSWYVALK (SEQ ID NO.: 392), LESNNYNTYR (SEQ ID NO. 393), GCNGIPGAAAWEAALPR (SEQ ID NO.: 395), MVGVGGGDVEDVTPRPGGCQISGR (SEQ ID NO.: 396), and GSRPGPAGTMAAGSITTLPALPEDGGSGAFPPGHFK (SEQ ID NO.: 397);

(t) HER2/neu is determined at least in part on the analysis of the at least one fragment selected from the group consisting of: GIWIPDGENVK (SEQ ID NO.: 195, 497 and 547), VLGSGAFGTVYK (SEQ ID NO.: 196 and 548), TLSPGK (SEQ ID NO.: 472), IPVAIK (SEQ ID NO.: 473), ETELR (SEQ ID NO.: 474), ELQLR (SEQ ID No.: 475), DIFHK (SEQ ID NO.: 476), ENTSPK (SEQ ID NO.: 477), SPNHVK (SEQ ID NO. 478), QVPLQR (SEQ ID NO.: 479), GGVLIQR (SEQ ID NO.: 480), EYVNAR (SEQ ID NO.: 481), VLQGLPR (SEQ ID NO.: 482), SLTEILK (SEQ ID NO.: 483), GAPPSTFK (SEQ ID NO.: 484), GCPAEQR (SEQ ID NO.: 485), CSKPCAR (SEQ ID NO.: 486), ITDFGLAR (SEQ ID NO.: 487), TVCAGGCAR (SEQ ID NO.: 488), EIPDLLEK (SEQ ID NO.: 489), DPPFCVAR (SEQ ID NO.: 490), ELVSEFSR (SEQ ID NO.: 491), GMSYLEDVR (SEQ ID NO.: 492), WMALESILR (SEQ ID No.: 493), TQVCTGTDMK (SEQ ID NO.: 494), GQECVEECR (SEQ ID NO.: 495), VLGSGAFGTVYK (SEQ ID NO.: 496), ACHPCSPMCK (SEQ ID No.: 498), VCYGLGMEHLR (SEQ ID NO.: 499), LPASPETHLDMLR (SEQ ID NO.: 500), NNQLALTLIDTNR (SEQ ID NO.: 501), AVTSANIQEFAGCK (SEQ ID NO.: 502), CWMIDSECRPR (SEQ ID NO.: 503), GLQSLPTHDPSPLQR, (SEQ ID NO.: 504), LLDIDETEYHADGGK (SEQ ID NO.: 505), NPQLCYQDTILWK (SEQ ID NO.: 506), CWGESSEDCQSLTR (SEQ ID NO.: 507), GTPTAENPEYLGLDVPV (SEQ ID NO.: 508), LGSQDLLNWCMQIAK (SEQ ID No.: 509), EGPLPAARPAGATLERPK (SEQ ID NO.: 510), CPSGVKPDLSYMPIWK (SEQ ID NO.: 511), SGGGDLTLGLEPSEEEAPR (SEQ ID NO.: 512), LPQPPICTIDVYMIMVK (SEQ ID NO.: 513), EILDEAYVMAGVGSPYVSR (SEQ ID NO.: 514), GPLPTDCCHEQCAAGCTGPK (SEQ ID NO.: 515), SPLAPSEGAGSDVFDGDLGMGAAK (SEQ ID NO.: 516), GHCWGPGPTQCVNCSQFLR (SEQ ID NO.: 517), FVVIQNEDLGPASPLDSTFYR (SEQ ID NO.: 518), ILHNGAYSLTLQGLGISWLGLR (SEQ ID NO.: 519), LLQETELVEPLTPSGAMPNQAQMR (SEQ ID NO.: 520), ASPLTSIISAVVGILLVVVLGVVFGILIK (SEQ ID NO.: 521), FPDEEGACQPCPINCTHSCVDLDDK (SEQ ID NO.: 522), LLGICLTSTVQLVTQLMPYGCLLDHVR (SEQ ID NO.: 523), ELGSGLALIHHNTHLCFVHTVPWDQLFR (SEQ ID NO.: 524), NPHQALLHTANRPEDECVGEGLACHQLCAR (SEQ ID NO.: 525), FTHQSDVWSYGVTVWELMTFGAKPYDGIPAR (SEQ ID NO.: 526), GTQLFEDNYALAVLDNGDPLNNTTPVTGASPGGLR (SEQ ID NO.: 527), HCLPCHPECQPQNGSVTCFGPEADQCVACAHYK (SEQ ID NO.: 528), and SLLEDDDMGDLVDAEEYLVPQQGFFCPDPAPGAGGMVHHR (SEQ ID NO.: 529);

(u) Osteopontin is determined at least in part on the analysis of the at least one fragment selected from the group consisting of: AIPVAQDLNAPSDWDSR (SEQ ID NO.: 197, 369 and 557), GDSVVYGLR (SEQ ID NO.: 198, 365 and 558), QLYNK (SEQ ID NO. 363), QETLPSK (SEQ ID NO.: 364), QADSGSSEEK (SEQ ID NO.: 366), ISHELDSASSEVN (SEQ ID NO.: 367), YPDAVATWLNPDPSQK (SEQ ID NO.: 368), QNLLAPQNAVSSEETNDFK (SEQ ID NO.: 370), ANDESNEHSDVIDSQELSK (SEQ ID NO.: 371), DSYETSQLDDQSAETHSHK (SEQ Id No. 372), EFHSHEFHSHEDMLVVDPK (SEQ ID NO.: 373), and RPDIQYPDATDEDITSHMESEELNGAYK (SEQ ID NO.: 374).

\* \* \* \* \*

SEQUENCE LISTING

<160> NUMBER OF SEQ ID NOS: 560

<210> SEQ ID NO 1
<211> LENGTH: 217
<212> TYPE: PRT

```
<213> ORGANISM: Unknown
<220> FEATURE:
<223> OTHER INFORMATION: Description of Unknown: 4E regulon component
      polypeptide

<400> SEQUENCE: 1

Met Ala Thr Val Glu Pro Glu Thr Thr Pro Thr Pro Asn Pro Pro Thr
1               5                   10                  15

Thr Glu Glu Lys Thr Glu Ser Asn Gln Glu Val Ala Asn Pro Glu
            20                  25                  30

His Tyr Ile Lys His Pro Leu Gln Asn Arg Trp Ala Leu Trp Phe Phe
            35                  40                  45

Lys Asn Asp Lys Ser Lys Thr Trp Gln Ala Asn Leu Arg Leu Ile Ser
50                  55                  60

Lys Phe Asp Thr Val Glu Asp Phe Trp Ala Leu Tyr Asn His Ile Gln
65                  70                  75                  80

Leu Ser Ser Asn Leu Met Pro Gly Cys Asp Tyr Ser Leu Phe Lys Asp
                85                  90                  95

Gly Ile Glu Pro Met Trp Glu Asp Glu Lys Asn Lys Arg Gly Gly Arg
            100                 105                 110

Trp Leu Ile Thr Leu Asn Lys Gln Gln Arg Arg Ser Asp Leu Asp Arg
            115                 120                 125

Phe Trp Leu Glu Thr Leu Leu Cys Leu Ile Gly Glu Ser Phe Asp Asp
130                 135                 140

Tyr Ser Asp Asp Val Cys Gly Ala Val Val Asn Val Arg Ala Lys Gly
145                 150                 155                 160

Asp Lys Ile Ala Ile Trp Thr Thr Glu Cys Glu Asn Arg Glu Ala Val
                165                 170                 175

Thr His Ile Gly Arg Val Tyr Lys Glu Arg Leu Gly Leu Pro Pro Lys
            180                 185                 190

Ile Val Ile Gly Tyr Gln Ser His Ala Asp Thr Ala Thr Lys Ser Gly
            195                 200                 205

Ser Thr Thr Lys Asn Arg Phe Val Val
        210                 215

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Trp Ala Leu Trp Phe Phe Lys
1               5

<210> SEQ ID NO 3
<211> LENGTH: 295
<212> TYPE: PRT
<213> ORGANISM: Homo sapiens

<400> SEQUENCE: 3

Met Glu His Gln Leu Leu Cys Cys Glu Val Glu Thr Ile Arg Arg Ala
1               5                   10                  15

Tyr Pro Asp Ala Asn Leu Leu Asn Asp Arg Val Leu Arg Ala Met Leu
            20                  25                  30

Lys Ala Glu Glu Thr Cys Ala Pro Ser Val Ser Tyr Phe Lys Cys Val
            35                  40                  45
```

-continued

```
Gln Lys Glu Val Leu Pro Ser Met Arg Lys Ile Val Ala Thr Trp Met
 50                  55                  60

Leu Glu Val Cys Glu Glu Gln Lys Cys Glu Glu Val Phe Pro Leu
 65                  70                  75                  80

Ala Met Asn Tyr Leu Asp Arg Phe Leu Ser Leu Glu Pro Val Lys Lys
                 85                  90                  95

Ser Arg Leu Gln Leu Leu Gly Ala Thr Cys Met Phe Val Ala Ser Lys
            100                 105                 110

Met Lys Glu Thr Ile Pro Leu Thr Ala Glu Lys Leu Cys Ile Tyr Thr
        115                 120                 125

Asp Asn Ser Ile Arg Pro Glu Glu Leu Leu Gln Met Glu Leu Leu Leu
    130                 135                 140

Val Asn Lys Leu Lys Trp Asn Leu Ala Ala Met Thr Pro His Asp Phe
145                 150                 155                 160

Ile Glu His Phe Leu Ser Lys Met Pro Glu Ala Glu Glu Asn Lys Gln
                165                 170                 175

Ile Ile Arg Lys His Ala Gln Thr Phe Val Ala Leu Cys Ala Thr Asp
            180                 185                 190

Val Lys Phe Ile Ser Asn Pro Pro Ser Met Val Ala Ala Gly Ser Val
        195                 200                 205

Val Ala Ala Val Gln Gly Leu Asn Leu Arg Ser Pro Asn Asn Phe Leu
    210                 215                 220

Ser Tyr Tyr Arg Leu Thr Arg Phe Leu Ser Arg Val Ile Lys Cys Asp
225                 230                 235                 240

Pro Asp Cys Leu Arg Ala Cys Gln Glu Gln Ile Glu Ala Leu Leu Glu
                245                 250                 255

Ser Ser Leu Arg Gln Ala Gln Gln Asn Met Asp Pro Lys Ala Ala Glu
            260                 265                 270

Glu Glu Glu Glu Glu Glu Glu Val Asp Leu Ala Cys Thr Pro Thr
        275                 280                 285

Asp Val Arg Asp Val Asp Ile
    290                 295

<210> SEQ ID NO 4
<211> LENGTH: 395
<212> TYPE: PRT
<213> ORGANISM: Homo sapiens

<400> SEQUENCE: 4

Met Thr Asp Arg Gln Thr Asp Thr Ala Pro Ser Pro Ser Tyr His Leu
 1               5                  10                  15

Leu Pro Gly Arg Arg Thr Val Asp Ala Ala Ala Ser Arg Gly Gln
                 20                  25                  30

Gly Pro Glu Pro Ala Pro Gly Gly Val Glu Gly Val Gly Ala Arg
            35                  40                  45

Gly Val Ala Leu Lys Leu Phe Val Gln Leu Leu Gly Cys Ser Arg Phe
 50                  55                  60

Gly Gly Ala Val Val Arg Ala Gly Glu Ala Glu Pro Ser Gly Ala Ala
 65                  70                  75                  80

Arg Ser Ala Ser Ser Gly Arg Glu Glu Pro Gln Pro Glu Glu Gly Glu
                 85                  90                  95

Glu Glu Glu Glu Lys Glu Glu Glu Arg Gly Pro Gln Trp Arg Leu Gly
            100                 105                 110

Ala Arg Lys Pro Gly Ser Trp Thr Gly Glu Ala Ala Val Cys Ala Asp
```

```
                  115                 120                 125
        Ser Ala Pro Ala Ala Arg Ala Pro Gln Ala Leu Ala Arg Ala Ser Gly
            130                 135                 140

Arg Gly Gly Arg Val Ala Arg Gly Ala Glu Ser Gly Pro Pro
        145                 150                 155                 160

His Ser Pro Ser Arg Gly Ser Ala Ser Arg Ala Gly Pro Gly Arg
                            165                 170                 175

Ala Ser Glu Thr Met Asn Phe Leu Leu Ser Trp Val His Trp Ser Leu
                        180                 185                 190

Ala Leu Leu Leu Tyr Leu His His Ala Lys Trp Ser Gln Ala Ala Pro
                    195                 200                 205

Met Ala Glu Gly Gly Gly Gln Asn His His Glu Val Val Lys Phe Met
                210                 215                 220

Asp Val Tyr Gln Arg Ser Tyr Cys His Pro Ile Glu Thr Leu Val Asp
        225                 230                 235                 240

Ile Phe Gln Glu Tyr Pro Asp Glu Ile Glu Tyr Ile Phe Lys Pro Ser
                            245                 250                 255

Cys Val Pro Leu Met Arg Cys Gly Gly Cys Cys Asn Asp Glu Gly Leu
                        260                 265                 270

Glu Cys Val Pro Thr Glu Glu Ser Asn Ile Thr Met Gln Ile Met Arg
                    275                 280                 285

Ile Lys Pro His Gln Gly Gln His Ile Gly Glu Met Ser Phe Leu Gln
                290                 295                 300

His Asn Lys Cys Glu Cys Arg Pro Lys Lys Asp Arg Ala Arg Gln Glu
        305                 310                 315                 320

Lys Lys Ser Val Arg Gly Lys Gly Lys Gly Gln Lys Arg Lys Arg Lys
                            325                 330                 335

Lys Ser Arg Tyr Lys Ser Trp Ser Val Pro Cys Gly Pro Cys Ser Glu
                        340                 345                 350

Arg Arg Lys His Leu Phe Val Gln Asp Pro Gln Thr Cys Lys Cys Ser
                    355                 360                 365

Cys Lys Asn Thr Asp Ser Arg Cys Lys Ala Arg Gln Leu Glu Leu Asn
                370                 375                 380

Glu Arg Thr Cys Arg Cys Asp Lys Pro Arg Arg
        385                 390                 395

<210> SEQ ID NO 5
<211> LENGTH: 461
<212> TYPE: PRT
<213> ORGANISM: Homo sapiens

<400> SEQUENCE: 5

Met Asn Asn Phe Gly Asn Glu Glu Phe Asp Cys His Phe Leu Asp Glu
        1               5                   10                  15

Gly Phe Thr Ala Lys Asp Ile Leu Asp Gln Lys Ile Asn Glu Val Ser
                            20                  25                  30

Ser Ser Asp Asp Lys Asp Ala Phe Tyr Val Ala Asp Leu Gly Asp Ile
                        35                  40                  45

Leu Lys Lys His Leu Arg Trp Leu Lys Ala Leu Pro Arg Val Thr Pro
                    50                  55                  60

Phe Tyr Ala Val Lys Cys Asn Asp Ser Lys Ala Ile Val Lys Thr Leu
        65                  70                  75                  80

Ala Ala Thr Gly Thr Gly Phe Asp Cys Ala Ser Lys Thr Glu Ile Gln
                            85                  90                  95
```

```
Leu Val Gln Ser Leu Gly Val Pro Pro Glu Arg Ile Ile Tyr Ala Asn
            100                 105                 110

Pro Cys Lys Gln Val Ser Gln Ile Lys Tyr Ala Ala Asn Asn Gly Val
        115                 120                 125

Gln Met Met Thr Phe Asp Ser Glu Val Glu Leu Met Lys Val Ala Arg
130                 135                 140

Ala His Pro Lys Ala Lys Leu Val Leu Arg Ile Ala Thr Asp Asp Ser
145                 150                 155                 160

Lys Ala Val Cys Arg Leu Ser Val Lys Phe Gly Ala Thr Leu Arg Thr
                165                 170                 175

Ser Arg Leu Leu Leu Glu Arg Ala Lys Glu Leu Asn Ile Asp Val Val
            180                 185                 190

Gly Val Ser Phe His Val Gly Ser Gly Cys Thr Asp Pro Glu Thr Phe
        195                 200                 205

Val Gln Ala Ile Ser Asp Ala Arg Cys Val Phe Asp Met Gly Ala Glu
210                 215                 220

Val Gly Phe Ser Met Tyr Leu Leu Asp Ile Gly Gly Gly Phe Pro Gly
225                 230                 235                 240

Ser Glu Asp Val Lys Leu Lys Phe Glu Glu Ile Thr Gly Val Ile Asn
                245                 250                 255

Pro Ala Leu Asp Lys Tyr Phe Pro Ser Asp Ser Gly Val Arg Ile Ile
            260                 265                 270

Ala Glu Pro Gly Arg Tyr Tyr Val Ala Ser Ala Phe Thr Leu Ala Val
        275                 280                 285

Asn Ile Ile Ala Lys Lys Ile Val Leu Lys Gln Thr Gly Ser Asp
290                 295                 300

Asp Glu Asp Glu Ser Ser Glu Gln Thr Phe Met Tyr Tyr Val Asn Asp
305                 310                 315                 320

Gly Val Tyr Gly Ser Phe Asn Cys Ile Leu Tyr Asp His Ala His Val
                325                 330                 335

Lys Pro Leu Leu Gln Lys Arg Pro Lys Pro Asp Glu Lys Tyr Tyr Ser
            340                 345                 350

Ser Ser Ile Trp Gly Pro Thr Cys Asp Gly Leu Asp Arg Ile Val Glu
        355                 360                 365

Arg Cys Asp Leu Pro Glu Met His Val Gly Asp Trp Met Leu Phe Glu
370                 375                 380

Asn Met Gly Ala Tyr Thr Val Ala Ala Ala Ser Thr Phe Asn Gly Phe
385                 390                 395                 400

Gln Arg Pro Thr Ile Tyr Tyr Val Met Ser Gly Pro Ala Trp Gln Leu
                405                 410                 415

Met Gln Gln Phe Gln Asn Pro Asp Phe Pro Pro Glu Val Glu Glu Gln
            420                 425                 430

Asp Ala Ser Thr Leu Pro Val Ser Cys Ala Trp Glu Ser Gly Met Lys
        435                 440                 445

Arg His Arg Ala Ala Cys Ala Ser Ala Ser Ile Asn Val
450                 455                 460

<210> SEQ ID NO 6
<211> LENGTH: 754
<212> TYPE: PRT
<213> ORGANISM: Homo sapiens

<400> SEQUENCE: 6

Met Trp Lys Leu Leu Pro Ala Ala Gly Pro Ala Gly Gly Glu Pro Tyr
1               5                   10                  15
```

-continued

Arg Leu Leu Thr Gly Val Glu Tyr Val Gly Arg Lys Asn Cys Ala
            20                  25                  30
Ile Leu Ile Glu Asn Asp Gln Ser Ile Ser Arg Asn His Ala Val Leu
        35                  40                  45
Thr Ala Asn Phe Ser Val Thr Asn Leu Ser Gln Thr Asp Glu Ile Pro
    50                  55                  60
Val Leu Thr Leu Lys Asp Asn Ser Lys Tyr Gly Thr Phe Val Asn Glu
65                  70                  75                  80
Glu Lys Met Gln Asn Gly Phe Ser Arg Thr Leu Lys Ser Gly Asp Gly
                85                  90                  95
Ile Thr Phe Gly Val Phe Gly Ser Lys Phe Arg Ile Glu Tyr Glu Pro
            100                 105                 110
Leu Val Ala Cys Ser Ser Cys Leu Asp Val Ser Gly Lys Thr Ala Leu
                115                 120                 125
Asn Gln Ala Ile Leu Gln Leu Gly Gly Phe Thr Val Asn Asn Trp Thr
130                 135                 140
Glu Glu Cys Thr His Leu Val Met Val Ser Val Lys Val Thr Ile Lys
145                 150                 155                 160
Thr Ile Cys Ala Leu Ile Cys Gly Arg Pro Ile Val Lys Pro Glu Tyr
                165                 170                 175
Phe Thr Glu Phe Leu Lys Ala Val Glu Ser Lys Lys Gln Pro Pro Gln
            180                 185                 190
Ile Glu Ser Phe Tyr Pro Pro Leu Asp Glu Pro Ser Ile Gly Ser Lys
        195                 200                 205
Asn Val Asp Leu Ser Gly Arg Gln Glu Arg Lys Gln Ile Phe Lys Gly
    210                 215                 220
Lys Thr Phe Ile Phe Leu Asn Ala Lys Gln His Lys Lys Leu Ser Ser
225                 230                 235                 240
Ala Val Val Phe Gly Gly Gly Glu Ala Arg Leu Ile Thr Glu Glu Asn
                245                 250                 255
Glu Glu Glu His Asn Phe Phe Leu Ala Pro Gly Thr Cys Val Val Asp
            260                 265                 270
Thr Gly Ile Thr Asn Ser Gln Thr Leu Ile Pro Asp Cys Gln Lys Lys
        275                 280                 285
Trp Ile Gln Ser Ile Met Asp Met Leu Gln Arg Gln Gly Leu Arg Pro
    290                 295                 300
Ile Pro Glu Ala Glu Ile Gly Leu Ala Val Ile Phe Met Thr Thr Lys
305                 310                 315                 320
Asn Tyr Cys Asp Pro Gln Gly His Pro Ser Thr Gly Leu Lys Thr Thr
                325                 330                 335
Thr Pro Gly Pro Ser Leu Ser Gln Gly Val Ser Val Asp Glu Lys Leu
            340                 345                 350
Met Pro Ser Ala Pro Val Asn Thr Thr Thr Tyr Val Ala Asp Thr Glu
        355                 360                 365
Ser Glu Gln Ala Asp Thr Trp Asp Leu Ser Glu Arg Pro Lys Glu Ile
    370                 375                 380
Lys Val Ser Lys Met Glu Gln Lys Phe Arg Met Leu Ser Gln Asp Ala
385                 390                 395                 400
Pro Thr Val Lys Glu Ser Cys Lys Thr Ser Ser Asn Asn Asn Ser Met
                405                 410                 415
Val Ser Asn Thr Leu Ala Lys Met Arg Ile Pro Asn Tyr Gln Leu Ser
            420                 425                 430

```
Pro Thr Lys Leu Pro Ser Ile Asn Lys Ser Lys Asp Arg Ala Ser Gln
            435                 440                 445

Gln Gln Gln Thr Asn Ser Ile Arg Asn Tyr Phe Gln Pro Ser Thr Lys
        450                 455                 460

Lys Arg Glu Arg Asp Glu Glu Asn Gln Glu Met Ser Ser Cys Lys Ser
465                 470                 475                 480

Ala Arg Ile Glu Thr Ser Cys Ser Leu Leu Glu Gln Thr Gln Pro Ala
                485                 490                 495

Thr Pro Ser Leu Trp Lys Asn Lys Gln His Leu Ser Glu Asn Glu
                500                 505                 510

Pro Val Asp Thr Asn Ser Asp Asn Asn Leu Phe Thr Asp Thr Asp Leu
                515                 520                 525

Lys Ser Ile Val Lys Asn Ser Ala Ser Lys Ser His Ala Ala Glu Lys
            530                 535                 540

Leu Arg Ser Asn Lys Lys Arg Glu Met Asp Asp Val Ala Ile Glu Asp
545                 550                 555                 560

Glu Val Leu Glu Gln Leu Phe Lys Asp Thr Lys Pro Glu Leu Glu Ile
                565                 570                 575

Asp Val Lys Val Gln Lys Gln Glu Asp Val Asn Val Arg Lys Arg
                580                 585                 590

Pro Arg Met Asp Ile Glu Thr Asn Asp Thr Phe Ser Asp Glu Ala Val
            595                 600                 605

Pro Glu Ser Ser Lys Ile Ser Gln Glu Asn Glu Ile Gly Lys Lys Arg
            610                 615                 620

Glu Leu Lys Glu Asp Ser Leu Trp Ser Ala Lys Glu Ile Ser Asn Asn
625                 630                 635                 640

Asp Lys Leu Gln Asp Asp Ser Glu Met Leu Pro Lys Lys Leu Leu Leu
                645                 650                 655

Thr Glu Phe Arg Ser Leu Val Ile Lys Asn Ser Thr Ser Arg Asn Pro
                660                 665                 670

Ser Gly Ile Asn Asp Asp Tyr Gly Gln Leu Lys Asn Phe Lys Lys Phe
            675                 680                 685

Lys Lys Val Thr Tyr Pro Gly Ala Gly Lys Leu Pro His Ile Ile Gly
            690                 695                 700

Gly Ser Asp Leu Ile Ala His His Ala Arg Lys Asn Thr Glu Leu Glu
705                 710                 715                 720

Glu Trp Leu Arg Gln Glu Met Glu Val Gln Asn Gln His Ala Lys Glu
                725                 730                 735

Glu Ser Leu Ala Asp Asp Leu Phe Arg Tyr Asn Pro Tyr Leu Lys Arg
            740                 745                 750

Arg Arg

<210> SEQ ID NO 7
<211> LENGTH: 313
<212> TYPE: PRT
<213> ORGANISM: Homo sapiens

<400> SEQUENCE: 7

Met Leu Leu Ser Lys Ile Asn Ser Leu Ala His Leu Arg Ala Ala Pro
1               5                   10                  15

Cys Asn Asp Leu His Ala Thr Lys Leu Ala Pro Gly Lys Glu Lys Glu
                20                  25                  30

Pro Leu Glu Ser Gln Tyr Gln Val Gly Pro Leu Leu Gly Ser Gly Gly
            35                  40                  45
```

```
Phe Gly Ser Val Tyr Ser Gly Ile Arg Val Ser Asp Asn Leu Pro Val
    50                  55                  60

Ala Ile Lys His Val Glu Lys Asp Arg Ile Ser Asp Trp Gly Glu Leu
 65                  70                  75                  80

Pro Asn Gly Thr Arg Val Pro Met Glu Val Leu Leu Lys Lys Val
                85                  90                  95

Ser Ser Gly Phe Ser Gly Val Ile Arg Leu Leu Asp Trp Phe Glu Arg
                100                 105                 110

Pro Asp Ser Phe Val Leu Ile Leu Glu Arg Pro Glu Pro Val Gln Asp
                115                 120                 125

Leu Phe Asp Phe Ile Thr Glu Arg Gly Ala Leu Gln Glu Glu Leu Ala
130                 135                 140

Arg Ser Phe Phe Trp Gln Val Leu Glu Ala Val Arg His Cys His Asn
145                 150                 155                 160

Cys Gly Val Leu His Arg Asp Ile Lys Asp Glu Asn Ile Leu Ile Asp
                165                 170                 175

Leu Asn Arg Gly Glu Leu Lys Leu Ile Asp Phe Gly Ser Gly Ala Leu
                180                 185                 190

Leu Lys Asp Thr Val Tyr Thr Asp Phe Asp Gly Thr Arg Val Tyr Ser
                195                 200                 205

Pro Pro Glu Trp Ile Arg Tyr His Arg Tyr His Gly Arg Ser Ala Ala
210                 215                 220

Val Trp Ser Leu Gly Ile Leu Leu Tyr Asp Met Val Cys Gly Asp Ile
225                 230                 235                 240

Pro Phe Glu His Asp Glu Glu Ile Ile Arg Gly Gln Val Phe Phe Arg
                245                 250                 255

Gln Arg Val Ser Ser Glu Cys Gln His Leu Ile Arg Trp Cys Leu Ala
                260                 265                 270

Leu Arg Pro Ser Asp Arg Pro Thr Phe Glu Glu Ile Gln Asn His Pro
                275                 280                 285

Trp Met Gln Asp Val Leu Leu Pro Gln Glu Thr Ala Glu Ile His Leu
                290                 295                 300

His Ser Leu Ser Pro Gly Pro Ser Lys
305                 310

<210> SEQ ID NO 8
<211> LENGTH: 480
<212> TYPE: PRT
<213> ORGANISM: Homo sapiens

<400> SEQUENCE: 8

Met Ser Asp Val Ala Ile Val Lys Glu Gly Trp Leu His Lys Arg Gly
 1               5                  10                  15

Glu Tyr Ile Lys Thr Trp Arg Pro Arg Tyr Phe Leu Leu Lys Asn Asp
                20                  25                  30

Gly Thr Phe Ile Gly Tyr Lys Glu Arg Pro Gln Asp Val Asp Gln Arg
                35                  40                  45

Glu Ala Pro Leu Asn Asn Phe Ser Val Ala Gln Cys Gln Leu Met Lys
 50                  55                  60

Thr Glu Arg Pro Arg Pro Asn Thr Phe Ile Ile Arg Cys Leu Gln Trp
 65                  70                  75                  80

Thr Thr Val Ile Glu Arg Thr Phe His Val Glu Thr Pro Glu Glu Arg
                85                  90                  95

Glu Glu Trp Thr Thr Ala Ile Gln Thr Val Ala Asp Gly Leu Lys Lys
                100                 105                 110
```

Gln Glu Glu Glu Glu Met Asp Phe Arg Ser Gly Ser Pro Ser Asp Asn
            115                 120                 125

Ser Gly Ala Glu Glu Met Glu Val Ser Leu Ala Lys Pro Lys His Arg
        130                 135                 140

Val Thr Met Asn Glu Phe Glu Tyr Leu Lys Leu Leu Gly Lys Gly Thr
145                 150                 155                 160

Phe Gly Lys Val Ile Leu Val Lys Glu Lys Ala Thr Gly Arg Tyr Tyr
                165                 170                 175

Ala Met Lys Ile Leu Lys Lys Glu Val Ile Val Ala Lys Asp Glu Val
            180                 185                 190

Ala His Thr Leu Thr Glu Asn Arg Val Leu Gln Asn Ser Arg His Pro
        195                 200                 205

Phe Leu Thr Ala Leu Lys Tyr Ser Phe Gln Thr His Asp Arg Leu Cys
    210                 215                 220

Phe Val Met Glu Tyr Ala Asn Gly Gly Glu Leu Phe Phe His Leu Ser
225                 230                 235                 240

Arg Glu Arg Val Phe Ser Glu Asp Arg Ala Arg Phe Tyr Gly Ala Glu
                245                 250                 255

Ile Val Ser Ala Leu Asp Tyr Leu His Ser Glu Lys Asn Val Val Tyr
            260                 265                 270

Arg Asp Leu Lys Leu Glu Asn Leu Met Leu Asp Lys Asp Gly His Ile
        275                 280                 285

Lys Ile Thr Asp Phe Gly Leu Cys Lys Glu Gly Ile Lys Asp Gly Ala
    290                 295                 300

Thr Met Lys Thr Phe Cys Gly Thr Pro Glu Tyr Leu Ala Pro Glu Val
305                 310                 315                 320

Leu Glu Asp Asn Asp Tyr Gly Arg Ala Val Asp Trp Trp Gly Leu Gly
                325                 330                 335

Val Val Met Tyr Glu Met Met Cys Gly Arg Leu Pro Phe Tyr Asn Gln
            340                 345                 350

Asp His Glu Lys Leu Phe Glu Leu Ile Leu Met Glu Glu Ile Arg Phe
        355                 360                 365

Pro Arg Thr Leu Gly Pro Glu Ala Lys Ser Leu Leu Ser Gly Leu Leu
    370                 375                 380

Lys Lys Asp Pro Lys Gln Arg Leu Gly Gly Gly Ser Glu Asp Ala Lys
385                 390                 395                 400

Glu Ile Met Gln His Arg Phe Phe Ala Gly Ile Val Trp Gln His Val
                405                 410                 415

Tyr Glu Lys Lys Leu Ser Pro Pro Phe Lys Pro Gln Val Thr Ser Glu
            420                 425                 430

Thr Asp Thr Arg Tyr Phe Asp Glu Glu Phe Thr Ala Gln Met Ile Thr
        435                 440                 445

Ile Thr Pro Pro Asp Gln Asp Asp Ser Met Glu Cys Val Asp Ser Glu
    450                 455                 460

Arg Arg Pro His Phe Pro Gln Phe Ser Tyr Ser Ala Ser Gly Thr Ala
465                 470                 475                 480

<210> SEQ ID NO 9
<211> LENGTH: 118
<212> TYPE: PRT
<213> ORGANISM: Homo sapiens

<400> SEQUENCE: 9

Met Ser Gly Gly Ser Ser Cys Ser Gln Thr Pro Ser Arg Ala Ile Pro

```
1               5                   10                  15
Ala Thr Arg Arg Val Val Leu Gly Asp Gly Val Gln Leu Pro Pro Gly
                    20                  25                  30

Asp Tyr Ser Thr Thr Pro Gly Gly Thr Leu Phe Ser Thr Thr Pro Gly
                    35                  40                  45

Gly Thr Arg Ile Ile Tyr Asp Arg Lys Phe Leu Met Glu Cys Arg Asn
                50                  55                  60

Ser Pro Val Thr Lys Thr Pro Pro Arg Asp Leu Pro Thr Ile Pro Gly
65                  70                  75                  80

Val Thr Ser Pro Ser Ser Asp Glu Pro Pro Met Glu Ala Ser Gln Ser
                    85                  90                  95

His Leu Arg Asn Ser Pro Glu Asp Lys Arg Ala Gly Gly Glu Ser
                    100                 105                 110

Gln Phe Glu Met Asp Ile
                    115
```

<210> SEQ ID NO 10
<211> LENGTH: 432
<212> TYPE: PRT
<213> ORGANISM: Homo sapiens

<400> SEQUENCE: 10

```
Met Leu Gly Asn Ser Ala Pro Gly Pro Ala Thr Arg Glu Ala Gly Ser
1               5                   10                  15

Ala Leu Leu Ala Leu Gln Gln Thr Ala Leu Gln Glu Asp Gln Glu Asn
                    20                  25                  30

Ile Asn Pro Glu Lys Ala Ala Pro Val Gln Gln Pro Arg Thr Arg Ala
                    35                  40                  45

Ala Leu Ala Val Leu Lys Ser Gly Asn Pro Arg Gly Leu Ala Gln Gln
                50                  55                  60

Gln Arg Pro Lys Thr Arg Arg Val Ala Pro Leu Lys Asp Leu Pro Val
65                  70                  75                  80

Asn Asp Glu His Val Thr Val Pro Pro Trp Lys Ala Asn Ser Lys Gln
                    85                  90                  95

Pro Ala Phe Thr Ile His Val Asp Glu Ala Lys Glu Ala Gln Lys
                    100                 105                 110

Lys Pro Ala Glu Ser Gln Lys Ile Glu Arg Glu Asp Ala Leu Ala Phe
                    115                 120                 125

Asn Ser Ala Ile Ser Leu Pro Gly Pro Arg Lys Pro Leu Val Pro Leu
    130                 135                 140

Asp Tyr Pro Met Asp Gly Ser Phe Glu Ser Pro His Thr Met Asp Met
145                 150                 155                 160

Ser Ile Val Leu Glu Asp Glu Lys Pro Val Ser Val Asn Glu Val Pro
                    165                 170                 175

Asp Tyr His Glu Asp Ile His Thr Tyr Leu Arg Glu Met Glu Val Lys
                    180                 185                 190

Cys Lys Pro Lys Val Gly Tyr Met Lys Lys Gln Pro Asp Ile Thr Asn
                    195                 200                 205

Ser Met Arg Ala Ile Leu Val Asp Trp Leu Val Glu Val Gly Glu Glu
    210                 215                 220

Tyr Lys Leu Gln Asn Glu Thr Leu His Leu Ala Val Asn Tyr Ile Asp
225                 230                 235                 240

Arg Phe Leu Ser Ser Met Ser Val Leu Arg Gly Lys Leu Gln Leu Val
                    245                 250                 255
```

```
Gly Thr Ala Ala Met Leu Leu Ala Ser Lys Phe Glu Glu Ile Tyr Pro
            260                 265                 270

Pro Glu Val Ala Glu Phe Val Tyr Ile Thr Asp Asp Thr Tyr Thr Lys
            275                 280                 285

Lys Gln Val Leu Arg Met Glu His Leu Val Leu Lys Val Leu Thr Phe
        290                 295                 300

Asp Leu Ala Ala Pro Thr Val Asn Gln Phe Leu Thr Gln Tyr Phe Leu
305                 310                 315                 320

His Gln Gln Pro Ala Asn Cys Lys Val Glu Ser Leu Ala Met Phe Leu
                325                 330                 335

Gly Glu Leu Ser Leu Ile Asp Ala Asp Pro Tyr Leu Lys Tyr Leu Pro
            340                 345                 350

Ser Val Ile Ala Gly Ala Ala Phe His Leu Ala Leu Tyr Thr Val Thr
        355                 360                 365

Gly Gln Ser Trp Pro Glu Ser Leu Ile Arg Lys Thr Gly Tyr Thr Leu
    370                 375                 380

Glu Ser Leu Lys Pro Cys Leu Met Asp Leu His Gln Thr Tyr Leu Lys
385                 390                 395                 400

Ala Pro Gln His Ala Gln Gln Ser Ile Arg Glu Lys Tyr Lys Asn Ser
                405                 410                 415

Lys Tyr His Gly Val Ser Leu Leu Asn Pro Pro Glu Thr Leu Asn Leu
            420                 425                 430

<210> SEQ ID NO 11
<211> LENGTH: 326
<212> TYPE: PRT
<213> ORGANISM: Homo sapiens

<400> SEQUENCE: 11

Met Ser Asn Gly Tyr Glu Asp His Met Ala Glu Asp Cys Arg Gly Asp
1               5                   10                  15

Ile Gly Arg Thr Asn Leu Ile Val Asn Tyr Leu Pro Gln Asn Met Thr
            20                  25                  30

Gln Asp Glu Leu Arg Ser Leu Phe Ser Ser Ile Gly Glu Val Glu Ser
        35                  40                  45

Ala Lys Leu Ile Arg Asp Lys Val Ala Gly His Ser Leu Gly Tyr Gly
    50                  55                  60

Phe Val Asn Tyr Val Thr Ala Lys Asp Ala Glu Arg Ala Ile Asn Thr
65                  70                  75                  80

Leu Asn Gly Leu Arg Leu Gln Ser Lys Thr Ile Lys Val Ser Tyr Ala
                85                  90                  95

Arg Pro Ser Ser Glu Val Ile Lys Asp Ala Asn Leu Tyr Ile Ser Gly
            100                 105                 110

Leu Pro Arg Thr Met Thr Gln Lys Asp Val Glu Asp Met Phe Ser Arg
        115                 120                 125

Phe Gly Arg Ile Ile Asn Ser Arg Val Leu Val Asp Gln Thr Thr Gly
    130                 135                 140

Leu Ser Arg Gly Val Ala Phe Ile Arg Phe Asp Lys Arg Ser Glu Ala
145                 150                 155                 160

Glu Glu Ala Ile Thr Ser Phe Asn Gly His Lys Pro Pro Gly Ser Ser
                165                 170                 175

Glu Pro Ile Thr Val Lys Phe Ala Ala Asn Pro Asn Gln Asn Lys Asn
            180                 185                 190

Val Ala Leu Leu Ser Gln Leu Tyr His Ser Pro Ala Arg Arg Phe Gly
        195                 200                 205
```

```
Gly Pro Val His His Gln Ala Gln Arg Phe Arg Phe Ser Pro Met Gly
    210                 215                 220

Val Asp His Met Ser Gly Leu Ser Gly Val Asn Val Pro Gly Asn Ala
225                 230                 235                 240

Ser Ser Gly Trp Cys Ile Phe Ile Tyr Asn Leu Gly Gln Asp Ala Asp
                245                 250                 255

Glu Gly Ile Leu Trp Gln Met Phe Gly Pro Phe Gly Ala Val Thr Asn
            260                 265                 270

Val Lys Val Ile Arg Asp Phe Asn Thr Asn Lys Cys Lys Gly Phe Gly
        275                 280                 285

Phe Val Thr Met Thr Asn Tyr Glu Glu Ala Ala Met Ala Ile Ala Ser
    290                 295                 300

Leu Asn Gly Tyr Arg Leu Gly Asp Lys Ile Leu Gln Val Ser Phe Lys
305                 310                 315                 320

Thr Asn Lys Ser His Lys
                325

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asn Asp Gly Thr Phe Ile Gly Tyr Lys
1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Tyr Ser Phe Gln Thr His Asp Arg
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Glu Arg Pro Gln Asp Val Asp Gln Arg
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gln Glu Glu Glu Glu Met Asp Phe Arg
```

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Thr Phe His Val Glu Thr Pro Glu Glu Arg
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Val Thr Met Asn Glu Phe Glu Tyr Leu Lys
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asp Glu Val Ala His Thr Leu Thr Glu Asn Arg
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Leu Pro Phe Tyr Asn Gln Asp His Glu Lys
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Cys Leu Gln Trp Thr Thr Val Ile Glu Arg
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 21

Leu Phe Glu Leu Ile Leu Met Glu Glu Ile Arg
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Thr Glu Arg Pro Arg Pro Asn Thr Phe Ile Ile Arg
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Phe Phe Ala Gly Ile Val Trp Gln His Val Tyr Glu Lys
1               5                   10

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Pro His Phe Pro Gln Phe Ser Tyr Ser Ala Ser Gly Thr Ala
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Glu Glu Trp Thr Thr Ala Ile Gln Thr Val Ala Asp Gly Leu Lys
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Leu Ser Pro Pro Phe Lys Pro Gln Val Thr Ser Glu Thr Asp Thr Arg
1               5                   10                  15

<210> SEQ ID NO 27

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Glu Ala Pro Leu Asn Asn Phe Ser Val Ala Gln Cys Gln Leu Met Lys
1               5                   10                  15

<210> SEQ ID NO 28
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Phe Tyr Gly Ala Glu Ile Val Ser Ala Leu Asp Tyr Leu His Ser Glu
1               5                   10                  15

Lys

<210> SEQ ID NO 29
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ser Gly Ser Pro Ser Asp Asn Ser Gly Ala Glu Glu Met Glu Val Ser
1               5                   10                  15

Leu Ala Lys Pro Lys
            20

<210> SEQ ID NO 30
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ala Val Asp Trp Trp Gly Leu Gly Val Val Met Tyr Glu Met Met Cys
1               5                   10                  15

Gly Arg

<210> SEQ ID NO 31
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Leu Cys Phe Val Met Glu Tyr Ala Asn Gly Gly Glu Leu Phe Phe His
1               5                   10                  15

Leu Ser Arg

<210> SEQ ID NO 32
```

```
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Thr Phe Cys Gly Thr Pro Glu Tyr Leu Ala Pro Glu Val Leu Glu Asp
1               5                   10                  15

Asn Asp Tyr Gly Arg
            20

<210> SEQ ID NO 33
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Tyr Phe Asp Glu Glu Phe Thr Ala Gln Met Ile Thr Ile Thr Pro Pro
1               5                   10                  15

Asp Gln Asp Asp Ser Met Glu Cys Val Asp Ser Glu Arg
            20                  25

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Val Ser Ser Gly Phe Ser Gly Val Ile Arg
1               5                   10

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Val Pro Met Glu Val Val Leu Leu Lys
1               5

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Val Ser Asp Asn Leu Pro Val Ala Ile Lys
1               5                   10

<210> SEQ ID NO 37
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 37

Leu Ile Asp Phe Gly Ser Gly Ala Leu Leu Lys
1               5                   10

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Val Tyr Ser Pro Pro Glu Trp Ile Arg
1               5

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ala Ala Pro Cys Asn Asp Leu His Ala Thr Lys
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Asp Glu Asn Ile Leu Ile Asp Leu Asn Arg
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Val Ser Ser Glu Cys Gln His Leu Ile Arg
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Asp Thr Val Tyr Thr Asp Phe Asp Gly Thr Arg
1               5                   10
```

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

His Cys His Asn Cys Gly Val Leu His Arg
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ile Ser Asp Trp Gly Glu Leu Pro Asn Gly Thr Arg
1               5                   10

<210> SEQ ID NO 45
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ser Phe Phe Trp Gln Val Leu Glu Ala Val Arg
1               5                   10

<210> SEQ ID NO 46
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Glu Pro Leu Glu Ser Gln Tyr Gln Val Gly Pro Leu Leu Gly Ser Gly
1               5                   10                  15

Gly Phe Gly Ser Val Tyr Ser Gly Ile Arg
            20                  25

<210> SEQ ID NO 47
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ser Ala Ala Val Trp Ser Leu Gly Ile Leu Leu Tyr Asp Met Val Cys
1               5                   10                  15

Gly Asp Ile Pro Phe Glu His Asp Glu Glu Ile Ile Arg
            20                  25

<210> SEQ ID NO 48
<211> LENGTH: 31

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Leu Leu Asp Trp Phe Glu Arg Pro Asp Ser Phe Val Leu Ile Leu Glu
1               5                   10                  15

Arg Pro Glu Pro Val Gln Asp Leu Phe Asp Phe Ile Thr Glu Arg
            20                  25                  30

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ile Ser Gln Glu Asn Glu Ile Gly Lys
1               5

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Met Leu Ser Gln Asp Ala Pro Thr Val Lys
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ile Pro Asn Tyr Gln Leu Ser Pro Thr Lys
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Leu Gln Asp Asp Ser Glu Met Leu Pro Lys
1               5                   10

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 53

Asn Thr Glu Leu Glu Glu Trp Leu Arg
1               5

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Glu Glu Ser Leu Ala Asp Asp Leu Phe Arg
1               5                   10

<210> SEQ ID NO 55
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Leu Ser Ser Ala Val Val Phe Gly Gly Gly Glu Ala Arg
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ala Ser Gln Gln Gln Gln Thr Asn Ser Ile Arg
1               5                   10

<210> SEQ ID NO 57
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ser Gly Asp Gly Ile Thr Phe Gly Val Phe Gly Ser Lys
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Asp Thr Lys Pro Glu Leu Glu Ile Asp Val Lys
1               5                   10

<210> SEQ ID NO 59
<211> LENGTH: 11
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 59

Gln Glu Met Glu Val Gln Asn Gln His Ala Lys
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Asp Glu Glu Asn Gln Glu Met Ser Ser Cys Lys
1               5                   10

<210> SEQ ID NO 61
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Asn Pro Ser Gly Ile Asn Asp Asp Tyr Gly Gln Leu Lys
1               5                   10

<210> SEQ ID NO 62
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Trp Ile Gln Ser Ile Met Asp Met Leu Gln Arg
1               5                   10

<210> SEQ ID NO 63
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Thr Ser Ser Asn Asn Asn Ser Met Val Ser Asn Thr Leu Ala Lys
1               5                   10                  15

<210> SEQ ID NO 64
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Asn Tyr Cys Asp Pro Gln Gly His Pro Ser Thr Gly Leu Lys
1               5                   10

<210> SEQ ID NO 65
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Thr Thr Thr Pro Gly Pro Ser Leu Ser Gln Gly Val Ser Val Asp Glu
1               5                   10                  15

Lys

<210> SEQ ID NO 66
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Leu Pro His Ile Ile Gly Gly Ser Asp Leu Ile Ala His His Ala Arg
1               5                   10                  15

<210> SEQ ID NO 67
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Glu Met Asp Asp Val Ala Ile Glu Asp Glu Val Leu Glu Gln Leu Phe
1               5                   10                  15

Lys

<210> SEQ ID NO 68
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ile Glu Tyr Glu Pro Leu Val Ala Cys Ser Ser Cys Leu Asp Val Ser
1               5                   10                  15

Gly Lys

<210> SEQ ID NO 69
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Met Asp Ile Glu Thr Asn Asp Thr Phe Ser Asp Glu Ala Val Pro Glu
1               5                   10                  15

Ser Ser Lys

<210> SEQ ID NO 70
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gln Pro Pro Gln Ile Glu Ser Phe Tyr Pro Pro Leu Asp Glu Pro Ser
1               5                   10                  15

Ile Gly Ser Lys
            20

<210> SEQ ID NO 71
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gln Gly Leu Arg Pro Ile Pro Glu Ala Glu Ile Gly Leu Ala Val Ile
1               5                   10                  15

Phe Met Thr Thr Lys
            20

<210> SEQ ID NO 72
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ile Glu Thr Ser Cys Ser Leu Leu Glu Gln Thr Gln Pro Ala Thr Pro
1               5                   10                  15

Ser Leu Trp Lys
            20

<210> SEQ ID NO 73
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Thr Ile Cys Ala Leu Ile Cys Gly Arg Pro Ile Val Lys Pro Glu Tyr
1               5                   10                  15

Phe Thr Glu Phe Leu Lys
            20

<210> SEQ ID NO 74
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

```
Glu Gln His Leu Ser Glu Asn Glu Pro Val Asp Thr Asn Ser Asp Asn
1               5                   10                  15

Asn Leu Phe Thr Asp Thr Asp Leu Lys
            20                  25
```

<210> SEQ ID NO 75
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

```
Leu Met Pro Ser Ala Pro Val Asn Thr Thr Thr Tyr Val Ala Asp Thr
1               5                   10                  15

Glu Ser Glu Gln Ala Asp Thr Trp Asp Leu Ser Glu Arg Pro Lys
            20                  25                  30
```

<210> SEQ ID NO 76
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

```
Thr Ala Leu Asn Gln Ala Ile Leu Gln Leu Gly Gly Phe Thr Val Asn
1               5                   10                  15

Asn Trp Thr Glu Glu Cys Thr His Leu Val Met Val Ser Val Lys
            20                  25                  30
```

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

```
Tyr Phe Pro Ser Asp Ser Gly Val Arg
1               5
```

<210> SEQ ID NO 78
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

```
Ile Asn Glu Val Ser Ser Ser Asp Asp Lys
1               5                   10
```

<210> SEQ ID NO 79
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

```
Thr Leu Ala Ala Thr Gly Thr Gly Phe Asp Cys Ala Ser Lys
1               5                   10
```

<210> SEQ ID NO 80
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

```
Asp Ala Phe Tyr Val Ala Asp Leu Gly Asp Ile Leu Lys
1               5                   10
```

<210> SEQ ID NO 81
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

```
Phe Glu Glu Ile Thr Gly Val Ile Asn Pro Ala Leu Asp Lys
1               5                   10
```

<210> SEQ ID NO 82
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

```
Thr Glu Ile Gln Leu Val Gln Ser Leu Gly Val Pro Pro Glu Arg
1               5                   10                  15
```

<210> SEQ ID NO 83
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

```
Tyr Tyr Val Ala Ser Ala Phe Thr Leu Ala Val Asn Ile Ile Ala Lys
1               5                   10                  15
```

<210> SEQ ID NO 84
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

```
Tyr Tyr Ser Ser Ser Ile Trp Gly Pro Thr Cys Asp Gly Leu Asp Arg
1               5                   10                  15
```

<210> SEQ ID NO 85
<211> LENGTH: 20
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 85

Tyr Ala Ala Asn Asn Gly Val Gln Met Met Thr Phe Asp Ser Glu Val
1               5                   10                  15

Glu Leu Met Lys
            20

<210> SEQ ID NO 86
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Met Asn Asn Phe Gly Asn Glu Glu Phe Asp Cys His Phe Leu Asp Glu
1               5                   10                  15

Gly Phe Thr Ala Lys
            20

<210> SEQ ID NO 87
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Cys Val Phe Asp Met Gly Ala Glu Val Gly Phe Ser Met Tyr Leu Leu
1               5                   10                  15

Asp Ile Gly Gly Gly Phe Pro Gly Ser Glu Asp Val Lys
            20                  25

<210> SEQ ID NO 88
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Glu Leu Asn Ile Asp Val Val Gly Val Ser Phe His Val Gly Ser Gly
1               5                   10                  15

Cys Thr Asp Pro Glu Thr Phe Val Gln Ala Ile Ser Asp Ala Arg
            20                  25                  30

<210> SEQ ID NO 89
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ala Gly Glu Ala Glu Pro Ser Gly Ala Ala Arg
1               5                   10

<210> SEQ ID NO 90
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Leu Phe Val Gln Leu Leu Gly Cys Ser Arg
1               5                   10

<210> SEQ ID NO 91
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gly Ala Glu Glu Ser Gly Pro Pro His Ser Pro Ser Arg
1               5                   10

<210> SEQ ID NO 92
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gln Glu Asn Pro Cys Gly Pro Cys Ser Glu Arg
1               5                   10

<210> SEQ ID NO 93
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

His Leu Phe Val Gln Asp Pro Gln Thr Cys Lys
1               5                   10

<210> SEQ ID NO 94
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gly Gln Gly Pro Glu Pro Ala Pro Gly Gly Val Glu Gly Val Gly
1               5                   10                  15

Ala Arg

<210> SEQ ID NO 95
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95
```

```
Glu Glu Pro Gln Pro Glu Gly Glu Glu Glu Glu Lys
1               5                   10

<210> SEQ ID NO 96
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gln Thr Asp Thr Ala Pro Ser Pro Ser Tyr His Leu Leu Pro Gly Arg
1               5                   10                  15

<210> SEQ ID NO 97
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Lys Pro Gly Ser Trp Thr Gly Glu Ala Ala Val Cys Ala Asp Ser Ala
1               5                   10                  15

Pro Ala Ala Arg
            20

<210> SEQ ID NO 98
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Trp Ser Gln Ala Ala Pro Met Ala Glu Gly Gly Gly Gln Asn His His
1               5                   10                  15

Glu Val Val Lys
            20

<210> SEQ ID NO 99
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ile Lys Pro His Gln Gly Gln His Ile Gly Glu Met Ser Phe Leu Gln
1               5                   10                  15

His Asn Lys

<210> SEQ ID NO 100
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100
```

```
Cys Gly Gly Cys Cys Asn Asp Glu Gly Leu Glu Cys Val Pro Thr Glu
1               5                   10                  15

Glu Ser Asn Ile Thr Met Gln Ile Met Arg
            20                  25

<210> SEQ ID NO 101
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Ala Ser Glu Thr Met Asn Phe Leu Leu Ser Trp Val His Trp Ser Leu
1               5                   10                  15

Ala Leu Leu Leu Tyr Leu His His Ala Lys
            20                  25

<210> SEQ ID NO 102
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Glu Thr Ile Pro Leu Thr Ala Glu Lys
1               5

<210> SEQ ID NO 103
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gln Ala Gln Gln Asn Met Asp Pro Lys
1               5

<210> SEQ ID NO 104
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Ser Pro Asn Asn Phe Leu Ser Tyr Tyr Arg
1               5                   10

<210> SEQ ID NO 105
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ala Tyr Pro Asp Ala Asn Leu Leu Asn Asp Arg
1               5                   10
```

```
<210> SEQ ID NO 106
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Ala Glu Glu Thr Cys Ala Pro Ser Val Ser Tyr Phe Lys
1               5                   10

<210> SEQ ID NO 107
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Leu Gln Leu Leu Gly Ala Thr Cys Met Phe Val Ala Ser Lys
1               5                   10

<210> SEQ ID NO 108
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

His Ala Gln Thr Phe Val Ala Leu Cys Ala Thr Asp Val Lys
1               5                   10

<210> SEQ ID NO 109
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Ile Val Ala Thr Trp Met Leu Glu Val Cys Glu Glu Gln Lys
1               5                   10

<210> SEQ ID NO 110
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Ala Cys Gln Glu Gln Ile Glu Ala Leu Leu Glu Ser Ser Leu Arg
1               5                   10                  15

<210> SEQ ID NO 111
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 111

Met Glu His Gln Leu Leu Cys Cys Glu Val Glu Thr Ile Arg
1               5                   10

<210> SEQ ID NO 112
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Cys Glu Glu Glu Val Phe Pro Leu Ala Met Asn Tyr Leu Asp Arg
1               5                   10                  15

<210> SEQ ID NO 113
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Trp Asn Leu Ala Ala Met Thr Pro His Asp Phe Ile Glu His Phe Leu
1               5                   10                  15

Ser Lys

<210> SEQ ID NO 114
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Phe Ile Ser Asn Pro Pro Ser Met Val Ala Ala Gly Ser Val Val Ala
1               5                   10                  15

Ala Val Gln Gly Leu Asn Leu Arg
            20

<210> SEQ ID NO 115
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Ala Ala Glu Glu Glu Glu Glu Glu Glu Glu Glu Val Asp Leu Ala Cys
1               5                   10                  15

Thr Pro Thr Asp Val Arg
            20

<210> SEQ ID NO 116
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116
```

```
Leu Cys Ile Tyr Thr Asp Asn Ser Ile Arg Pro Glu Glu Leu Leu Gln
1               5                   10                  15

Met Glu Leu Leu Leu Val Asn Lys
            20

<210> SEQ ID NO 117
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Ala Gly Gly Glu Glu Ser Gln Phe Glu Met Asp Ile
1               5                   10

<210> SEQ ID NO 118
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Met Ser Gly Gly Ser Ser Cys Ser Gln Thr Pro Ser Arg
1               5                   10

<210> SEQ ID NO 119
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Asp Leu Pro Thr Ile Pro Gly Val Thr Ser Pro Ser Ser Asp Glu Pro
1               5                   10                  15

Pro Met Glu Ala Ser Gln Ser His Leu Arg
            20                  25

<210> SEQ ID NO 120
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Val Val Leu Gly Asp Gly Val Gln Leu Pro Pro Gly Asp Tyr Ser Thr
1               5                   10                  15

Thr Pro Gly Gly Thr Leu Phe Ser Thr Thr Pro Gly Gly Thr Arg
            20                  25                  30

<210> SEQ ID NO 121
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121
```

```
Gly Leu Ala Gln Gln Gln Arg Pro Lys
1               5
```

<210> SEQ ID NO 122
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

```
Phe Leu Ser Ser Met Ser Val Leu Arg
1               5
```

<210> SEQ ID NO 123
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

```
Gln Pro Asp Ile Thr Asn Ser Met Arg
1               5
```

<210> SEQ ID NO 124
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

```
Ala Pro Gln His Ala Gln Gln Ser Ile Arg
1               5                   10
```

<210> SEQ ID NO 125
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

```
Met Leu Gly Asn Ser Ala Pro Gly Pro Ala Thr Arg
1               5                   10
```

<210> SEQ ID NO 126
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

```
Leu Gln Leu Val Gly Thr Ala Ala Met Leu Leu Ala Ser Lys
1               5                   10
```

<210> SEQ ID NO 127
<211> LENGTH: 13
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 127

Gln Pro Ala Phe Thr Ile His Val Asp Glu Ala Glu Lys
1               5                   10

<210> SEQ ID NO 128
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Glu Asp Ala Leu Ala Phe Asn Ser Ala Ile Ser Leu Pro Gly Pro Arg
1               5                   10                  15

<210> SEQ ID NO 129
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Tyr His Gly Val Ser Leu Leu Asn Pro Pro Glu Thr Leu Asn Leu
1               5                   10                  15

<210> SEQ ID NO 130
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Asp Leu Pro Val Asn Asp Glu His Val Thr Val Pro Pro Trp Lys
1               5                   10                  15

<210> SEQ ID NO 131
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Ala Ile Leu Val Asp Trp Leu Val Glu Val Gly Glu Glu Tyr Lys
1               5                   10                  15

<210> SEQ ID NO 132
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Leu Gln Asn Glu Thr Leu His Leu Ala Val Asn Tyr Ile Asp Arg
1               5                   10                  15
```

<210> SEQ ID NO 133
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Val Glu Ser Leu Ala Met Phe Leu Gly Glu Leu Ser Leu Ile Asp Ala
1               5                   10                  15

Asp Pro Tyr Leu Lys
            20

<210> SEQ ID NO 134
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Thr Gly Tyr Thr Leu Glu Ser Leu Lys Pro Cys Leu Met Asp Leu His
1               5                   10                  15

Gln Thr Tyr Leu Lys
            20

<210> SEQ ID NO 135
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Phe Glu Glu Ile Tyr Pro Pro Glu Val Ala Gly Phe Val Tyr Ile Thr
1               5                   10                  15

Asp Asp Thr Tyr Thr Lys
            20

<210> SEQ ID NO 136
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Glu Ala Gly Ser Ala Leu Leu Ala Leu Gln Gln Thr Ala Leu Gln Glu
1               5                   10                  15

Asp Gln Glu Asn Ile Asn Pro Glu Lys
            20                  25

<210> SEQ ID NO 137
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Tyr Leu Pro Ser Val Ile Ala Gly Ala Ala Phe His Leu Ala Leu Tyr
1               5                   10                  15

Thr Val Thr Gly Gln Ser Trp Pro Glu Ser Leu Ile Arg
            20                  25

<210> SEQ ID NO 138
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Val Leu Thr Phe Asp Leu Ala Ala Pro Thr Val Asn Gln Phe Leu Thr
1               5                   10                  15

Gln Tyr Phe Leu His Gln Gln Pro Ala Asn Cys Lys
            20                  25

<210> SEQ ID NO 139
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Asp Val Glu Asp Met Phe Ser Arg
1               5

<210> SEQ ID NO 140
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Phe Ala Ala Asn Pro Asn Gln Asn Lys
1               5

<210> SEQ ID NO 141
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Val Leu Val Asp Gln Thr Thr Gly Leu Ser Arg
1               5                   10

<210> SEQ ID NO 142
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Asp Ala Asn Leu Tyr Ile Ser Gly Leu Pro Arg
1               5                   10

<210> SEQ ID NO 143
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Phe Gly Gly Pro Val His His Gln Ala Gln Arg
1               5                   10

<210> SEQ ID NO 144
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Val Ser Tyr Ala Arg Pro Ser Ser Glu Val Ile Lys
1               5                   10

<210> SEQ ID NO 145
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Ser Leu Phe Ser Ser Ile Gly Glu Val Glu Ser Ala Lys
1               5                   10

<210> SEQ ID NO 146
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Asn Val Ala Leu Leu Ser Gln Leu Tyr His Ser Pro Ala Arg
1               5                   10

<210> SEQ ID NO 147
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Met Ser Asn Gly Tyr Glu Asp His Met Ala Glu Asp Cys Arg
1               5                   10

<210> SEQ ID NO 148
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 148

Val Ala Gly His Ser Leu Gly Tyr Gly Phe Val Asn Tyr Val Thr Ala
1               5                   10                  15

Lys

<210> SEQ ID NO 149
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Thr Asn Leu Ile Val Asn Tyr Leu Pro Gln Asn Met Thr Gln Asp Glu
1               5                   10                  15

Leu Arg

<210> SEQ ID NO 150
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Ser Glu Ala Glu Glu Ala Ile Thr Ser Phe Asn Gly His Lys Pro Pro
1               5                   10                  15

Gly Ser Ser Glu Pro Ile Thr Val Lys
            20                  25

<210> SEQ ID NO 151
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Gly Phe Gly Phe Val Thr Met Thr Asn Tyr Glu Glu Ala Ala Met Ala
1               5                   10                  15

Ile Ala Ser Leu Asn Gly Tyr Arg
            20

<210> SEQ ID NO 152
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Asp Gly Ile Glu Pro Met Trp Glu Asp Glu Lys
1               5                   10

<210> SEQ ID NO 153
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 153

Ile Ala Ile Trp Thr Thr Glu Cys Glu Asn Arg
1               5                   10

<210> SEQ ID NO 154
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Ile Val Ile Gly Tyr Gln Ser His Ala Asp Thr Ala Thr Lys
1               5                   10

<210> SEQ ID NO 155
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Thr Glu Ser Asn Gln Glu Val Ala Asn Pro Glu His Tyr Ile Lys
1               5                   10                  15

<210> SEQ ID NO 156
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Met Ala Thr Val Glu Pro Glu Thr Thr Pro Thr Pro Asn Pro Pro Thr
1               5                   10                  15

Thr Glu Glu Glu Lys
            20

<210> SEQ ID NO 157
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Phe Trp Leu Glu Thr Leu Leu Cys Leu Ile Gly Glu Ser Phe Asp Asp
1               5                   10                  15

Tyr Ser Asp Asp Val Cys Gly Ala Val Val Asn Val Arg
            20                  25

<210> SEQ ID NO 158
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

```
Phe Asp Thr Val Glu Asp Phe Trp Ala Leu Tyr Asn His Ile Gln Leu
1               5                   10                  15

Ser Ser Asn Leu Met Pro Gly Cys Asp Tyr Ser Leu Phe Lys
            20                  25                  30
```

<210> SEQ ID NO 159
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

```
Glu Ala Val Thr His Ile Gly Arg
1               5
```

<210> SEQ ID NO 160
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

```
Leu Leu Pro Ala Ala Gly Pro Ala Gly Gly Glu Pro Tyr Arg
1               5                   10
```

<210> SEQ ID NO 161
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

```
Lys Gln Pro Pro Gln Ile Glu Ser Phe Tyr Pro Pro Leu Asp Glu Pro
1               5                   10                  15

Ser Ile Gly Ser Lys
            20
```

<210> SEQ ID NO 162
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

```
Ser Leu Gly Ile Leu Leu Tyr Asp Met Val Cys Gly Asp Ile Pro Phe
1               5                   10                  15

Glu His Asp Glu Glu Ile Ile Arg
            20
```

<210> SEQ ID NO 163
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

```
Ile Asn Glu Val Ser Ser Ser Asp Asp Lys Asp Ala Phe Tyr Val Ala
1               5                   10                  15

Asp Leu Gly Asp Ile Leu Lys
            20

<210> SEQ ID NO 164
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Leu Leu Asp Ile Gly Gly Gly Phe Pro Gly Ser Glu Asp Val Lys
1               5                   10                  15

<210> SEQ ID NO 165
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Thr Leu Gln Val Phe Gly Ile Val Pro Asp Gly Thr Leu Gln Leu Leu
1               5                   10                  15

Lys

<210> SEQ ID NO 166
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Leu Leu Ser Gln Gly Val Ile Ala Phe Arg
1               5                   10

<210> SEQ ID NO 167
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Leu Ala Ser Asp Glu Ser Leu Trp Gln Thr Leu Asp Leu Thr Gly Lys
1               5                   10                  15

<210> SEQ ID NO 168
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Leu Ser Asp Pro Ile Val Asn Thr Leu Ala Lys
1               5                   10
```

```
<210> SEQ ID NO 169
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Ala Ile Leu Leu Asp Trp Leu Met Glu Val Cys Glu Val Tyr Lys
1               5                   10                  15

<210> SEQ ID NO 170
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Asp Gln His Phe Leu Glu Gln His Pro Leu Leu Gln Pro Lys
1               5                   10

<210> SEQ ID NO 171
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Gly Ser Pro Leu Pro Val Leu Ser Trp Ala Asn Arg
1               5                   10

<210> SEQ ID NO 172
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Tyr Met Ala Thr Gln Glu Asn Val Val Lys
1               5                   10

<210> SEQ ID NO 173
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Leu Gly Leu Gly Ala Asp Val Ala Gln Val Thr Gly Ala Leu Arg
1               5                   10                  15

<210> SEQ ID NO 174
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174
```

Gln Leu Ser Leu Pro Glu Thr Gly Glu Leu Asp Ser Ala Thr Leu Lys
1               5                   10                  15

<210> SEQ ID NO 175
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Gln Ser Thr Leu Val Leu Phe Pro Gly Asp Leu Arg
1               5                   10

<210> SEQ ID NO 176
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Ser Leu Gly Pro Ala Leu Leu Leu Leu Gln Lys
1               5                   10

<210> SEQ ID NO 177
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Leu Val Glu Glu Leu Gln Val Asp Gln Leu Trp Asp Val Leu Leu Ser
1               5                   10                  15

Arg

<210> SEQ ID NO 178
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Asp His Gly Phe Glu Val Ala Ser Thr Ser Pro Glu Asp Glu Ser Pro
1               5                   10                  15

Gly Ser Asn Pro Glu Pro Asp Ala Thr Pro Phe Gln Glu Gly Leu Arg
                20                  25                  30

<210> SEQ ID NO 179
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Gln Leu Ile Ile Asp Leu Glu Thr Arg
1               5

<210> SEQ ID NO 180
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Lys Pro Glu Val Leu Arg Pro Glu Thr Pro Arg Pro Val Asp Ile Gly
1               5                   10                  15

Ser Gly Gly Phe Gly Asp Val Glu Gln Lys
            20                  25

<210> SEQ ID NO 181
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Ala Phe Ser Asp Leu Thr Ser Gln Leu His Ile Thr Pro Gly Thr Ala
1               5                   10                  15

Tyr Gln Ser Phe Glu Gln Val Val Asn Glu Leu Phe Arg
            20                  25

<210> SEQ ID NO 182
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Glu Leu Val Val Asp Phe Leu Ser Tyr Lys
1               5                   10

<210> SEQ ID NO 183
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Gln Ser Phe Glu Gln Val Val Asn Glu Leu Phe Arg
1               5                   10

<210> SEQ ID NO 184
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Glu Val Ile Pro Met Ala Ala Val Lys
1               5

<210> SEQ ID NO 185
<211> LENGTH: 32

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Arg Val Val Leu Gly Asp Gly Val Gln Leu Pro Pro Gly Asp Tyr Ser
1               5                   10                  15

Thr Thr Pro Gly Gly Thr Leu Phe Ser Thr Thr Pro Gly Gly Thr Arg
            20                  25                  30

<210> SEQ ID NO 186
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Leu Phe Glu Leu Ile Leu Leu Met Glu Glu Ile Arg
1               5                   10

<210> SEQ ID NO 187
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Ile Val Ile Gly Tyr Gln Ser His Ala Asp Thr Ala Thr Lys
1               5                   10

<210> SEQ ID NO 188
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Phe Ala Thr Val Val Glu Glu Leu Phe Arg
1               5                   10

<210> SEQ ID NO 189
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Gly Asp Ser Phe Thr His Thr Pro Pro Leu Asp Pro Gln Glu Leu Asp
1               5                   10                  15

Ile Leu Lys

<210> SEQ ID NO 190
<211> LENGTH: 10
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 190

Ile Pro Leu Glu Asn Leu Gln Ile Ile Arg
1               5                   10

<210> SEQ ID NO 191
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Ala Ala Ala Ala Val Glu Pro Asp Val Val Val Lys
1               5                   10

<210> SEQ ID NO 192
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Met Gln Glu Glu Leu Asn Ala Gln Val Glu Lys
1               5                   10

<210> SEQ ID NO 193
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Cys Val Thr Asp Glu Cys Phe Phe Phe Glu Arg
1               5                   10

<210> SEQ ID NO 194
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Ala Ile Leu Phe Leu Pro Met Ser Ala Lys
1               5                   10

<210> SEQ ID NO 195
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Gly Ile Trp Ile Pro Asp Gly Glu Asn Val Lys
1               5                   10

<210> SEQ ID NO 196

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Val Leu Gly Ser Gly Ala Phe Gly Thr Val Tyr Lys
1               5                   10

<210> SEQ ID NO 197
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Ala Ile Pro Val Ala Gln Asp Leu Asn Ala Pro Ser Asp Trp Asp Ser
1               5                   10                  15

Arg

<210> SEQ ID NO 198
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Gly Asp Ser Val Val Tyr Gly Leu Arg
1               5

<210> SEQ ID NO 199
<211> LENGTH: 424
<212> TYPE: PRT
<213> ORGANISM: Homo sapiens

<400> SEQUENCE: 199

Met His Arg Lys His Leu Gln Glu Ile Pro Asp Leu Ser Ser Asn Val
1               5                   10                  15

Ala Thr Ser Phe Thr Trp Gly Trp Asp Ser Ser Lys Thr Ser Glu Leu
                20                  25                  30

Leu Ser Gly Met Gly Val Ser Ala Leu Glu Lys Glu Glu Pro Asp Ser
            35                  40                  45

Glu Asn Ile Pro Gln Glu Leu Leu Ser Asn Leu Gly His Pro Glu Ser
    50                  55                  60

Pro Pro Arg Lys Arg Leu Lys Ser Lys Gly Ser Asp Lys Asp Phe Val
65                  70                  75                  80

Ile Val Arg Arg Pro Lys Leu Asn Arg Glu Asn Phe Pro Gly Val Ser
                85                  90                  95

Trp Asp Ser Leu Pro Asp Glu Leu Leu Leu Gly Ile Phe Ser Cys Leu
                100                 105                 110

Cys Leu Pro Glu Leu Leu Lys Val Ser Gly Val Cys Lys Arg Trp Tyr
            115                 120                 125

Arg Leu Ala Ser Asp Glu Ser Leu Trp Gln Thr Leu Asp Leu Thr Gly
    130                 135                 140

Lys Asn Leu His Pro Asp Val Thr Gly Arg Leu Leu Ser Gln Gly Val
145                 150                 155                 160
```

Ile Ala Phe Arg Cys Pro Arg Ser Phe Met Asp Gln Pro Leu Ala Glu
            165                 170                 175

His Phe Ser Pro Phe Arg Val Gln His Met Asp Leu Ser Asn Ser Val
        180                 185                 190

Ile Glu Val Ser Thr Leu His Gly Ile Leu Ser Gln Cys Ser Lys Leu
    195                 200                 205

Gln Asn Leu Ser Leu Glu Gly Leu Arg Leu Ser Asp Pro Ile Val Asn
210                 215                 220

Thr Leu Ala Lys Asn Ser Asn Leu Val Arg Leu Asn Leu Ser Gly Cys
225                 230                 235                 240

Ser Gly Phe Ser Glu Phe Ala Leu Gln Thr Leu Leu Ser Ser Cys Ser
                245                 250                 255

Arg Leu Asp Glu Leu Asn Leu Ser Trp Cys Phe Asp Phe Thr Glu Lys
            260                 265                 270

His Val Gln Val Ala Val Ala His Val Ser Glu Thr Ile Thr Gln Leu
        275                 280                 285

Asn Leu Ser Gly Tyr Arg Lys Asn Leu Gln Lys Ser Asp Leu Ser Thr
    290                 295                 300

Leu Val Arg Arg Cys Pro Asn Leu Val His Leu Asp Leu Ser Asp Ser
305                 310                 315                 320

Val Met Leu Lys Asn Asp Cys Phe Gln Glu Phe Phe Gln Leu Asn Tyr
                325                 330                 335

Leu Gln His Leu Ser Leu Ser Arg Cys Tyr Asp Ile Ile Pro Glu Thr
            340                 345                 350

Leu Leu Glu Leu Gly Glu Ile Pro Thr Leu Lys Thr Leu Gln Val Phe
        355                 360                 365

Gly Ile Val Pro Asp Gly Thr Leu Gln Leu Leu Lys Glu Ala Leu Pro
    370                 375                 380

His Leu Gln Ile Asn Cys Ser His Phe Thr Thr Ile Ala Arg Pro Thr
385                 390                 395                 400

Ile Gly Asn Lys Lys Asn Gln Glu Ile Trp Gly Ile Lys Cys Arg Leu
                405                 410                 415

Thr Leu Gln Lys Pro Ser Cys Leu
            420

<210> SEQ ID NO 200
<211> LENGTH: 410
<212> TYPE: PRT
<213> ORGANISM: Homo sapiens

<400> SEQUENCE: 200

Met Pro Arg Glu Arg Arg Glu Arg Asp Ala Lys Glu Arg Asp Thr Met
1               5                   10                  15

Lys Glu Asp Gly Gly Ala Glu Phe Ser Ala Arg Ser Arg Lys Arg Lys
            20                  25                  30

Ala Asn Val Thr Val Phe Leu Gln Asp Pro Asp Glu Glu Met Ala Lys
        35                  40                  45

Ile Asp Arg Thr Ala Arg Asp Gln Cys Gly Ser Gln Pro Trp Asp Asn
    50                  55                  60

Asn Ala Val Cys Ala Asp Pro Cys Ser Leu Ile Pro Thr Pro Asp Lys
65                  70                  75                  80

Glu Asp Asp Asp Arg Val Tyr Pro Asn Ser Thr Cys Lys Pro Arg Ile
                85                  90                  95

Ile Ala Pro Ser Arg Gly Ser Pro Leu Pro Val Leu Ser Trp Ala Asn

```
                100             105             110
Arg Glu Glu Val Trp Lys Ile Met Leu Asn Lys Glu Lys Thr Tyr Leu
            115                 120                 125

Arg Asp Gln His Phe Leu Gln His Pro Leu Leu Gln Pro Lys Met
130                 135                 140

Arg Ala Ile Leu Leu Asp Trp Leu Met Glu Val Cys Glu Val Tyr Lys
145                 150                 155                 160

Leu His Arg Glu Thr Phe Tyr Leu Ala Gln Asp Phe Phe Asp Arg Tyr
                165                 170                 175

Met Ala Thr Gln Glu Asn Val Val Lys Thr Leu Leu Gln Leu Ile Gly
            180                 185                 190

Ile Ser Ser Leu Phe Ile Ala Ala Lys Leu Glu Glu Ile Tyr Pro Pro
        195                 200                 205

Lys Leu His Gln Phe Ala Tyr Val Thr Asp Gly Ala Cys Ser Gly Asp
    210                 215                 220

Glu Ile Leu Thr Met Glu Leu Met Ile Met Lys Ala Leu Lys Trp Arg
225                 230                 235                 240

Leu Ser Pro Leu Thr Ile Val Ser Trp Leu Asn Val Tyr Met Gln Val
                245                 250                 255

Ala Tyr Leu Asn Asp Leu His Glu Val Leu Leu Pro Gln Tyr Pro Gln
            260                 265                 270

Gln Ile Phe Ile Gln Ile Ala Glu Leu Leu Asp Leu Cys Val Leu Asp
        275                 280                 285

Val Asp Cys Leu Glu Phe Pro Tyr Gly Ile Leu Ala Ala Ser Ala Leu
    290                 295                 300

Tyr His Phe Ser Ser Ser Glu Leu Met Gln Lys Val Ser Gly Tyr Gln
305                 310                 315                 320

Trp Cys Asp Ile Glu Asn Cys Val Lys Trp Met Val Pro Phe Ala Met
                325                 330                 335

Val Ile Arg Glu Thr Gly Ser Ser Lys Leu Lys His Phe Arg Gly Val
            340                 345                 350

Ala Asp Glu Asp Ala His Asn Ile Gln Thr His Arg Asp Ser Leu Asp
        355                 360                 365

Leu Leu Asp Lys Ala Arg Ala Lys Lys Ala Met Leu Ser Glu Gln Asn
    370                 375                 380

Arg Ala Ser Pro Leu Pro Ser Gly Leu Leu Thr Pro Pro Gln Ser Gly
385                 390                 395                 400

Lys Lys Gln Ser Ser Gly Pro Glu Met Ala
                405                 410

<210> SEQ ID NO 201
<211> LENGTH: 601
<212> TYPE: PRT
<213> ORGANISM: Homo sapiens

<400> SEQUENCE: 201

Phe Gln Thr Phe Glu Gly Asp Leu Lys Trp His His Asn Ile Thr
1               5                   10                  15

Tyr Trp Ile Gln Asn Tyr Ser Glu Asp Leu Pro Arg Ala Val Ile Asp
            20                  25                  30

Asp Ala Phe Ala Arg Ala Phe Ala Leu Trp Ser Ala Val Thr Pro Leu
        35                  40                  45

Thr Phe Thr Arg Val Tyr Ser Arg Asp Ala Asp Ile Val Ile Gln Phe
    50                  55                  60
```

```
Gly Val Ala Glu His Gly Asp Gly Tyr Pro Phe Asp Gly Lys Asp Gly
 65                  70                  75                  80

Leu Leu Ala His Ala Phe Pro Pro Gly Pro Gly Ile Gln Gly Asp Ala
                 85                  90                  95

His Phe Asp Asp Asp Glu Leu Trp Ser Leu Gly Lys Gly Val Val Val
            100                 105                 110

Pro Thr Arg Phe Gly Asn Ala Asp Gly Ala Ala Cys His Phe Pro Phe
        115                 120                 125

Ile Phe Glu Gly Arg Ser Tyr Ser Ala Cys Thr Thr Asp Gly Arg Ser
    130                 135                 140

Asp Gly Leu Pro Trp Cys Ser Thr Thr Ala Asn Tyr Asp Thr Asp Asp
145                 150                 155                 160

Arg Phe Gly Phe Cys Pro Ser Glu Arg Leu Tyr Thr Gln Asp Gly Asn
                165                 170                 175

Ala Asp Gly Lys Pro Cys Gln Phe Pro Phe Ile Phe Gln Gly Gln Ser
            180                 185                 190

Tyr Ser Ala Cys Thr Thr Asp Gly Arg Ser Asp Gly Tyr Arg Trp Cys
        195                 200                 205

Ala Thr Thr Ala Asn Tyr Asp Arg Asp Lys Leu Phe Gly Phe Cys Pro
    210                 215                 220

Thr Arg Ala Asp Ser Thr Val Met Gly Gly Asn Ser Ala Gly Glu Leu
225                 230                 235                 240

Cys Val Phe Pro Phe Thr Phe Leu Gly Lys Glu Tyr Ser Thr Cys Thr
                245                 250                 255

Ser Glu Gly Arg Gly Asp Gly Arg Leu Trp Cys Ala Thr Thr Ser Asn
            260                 265                 270

Phe Asp Ser Asp Lys Lys Trp Gly Phe Cys Pro Asp Gln Gly Tyr Ser
        275                 280                 285

Leu Phe Leu Val Ala Ala His Glu Phe Gly His Ala Leu Gly Leu Asp
    290                 295                 300

His Ser Ser Val Pro Glu Ala Leu Met Tyr Pro Met Tyr Arg Phe Thr
305                 310                 315                 320

Glu Gly Pro Pro Leu His Lys Asp Asp Val Asn Gly Ile Arg His Leu
                325                 330                 335

Tyr Gly Pro Arg Pro Glu Pro Glu Pro Arg Pro Pro Thr Thr Thr Thr
            340                 345                 350

Pro Gln Pro Thr Ala Pro Pro Thr Val Cys Pro Thr Gly Pro Pro Thr
        355                 360                 365

Val His Pro Ser Glu Arg Pro Thr Ala Gly Pro Thr Gly Pro Pro Ser
370                 375                 380

Ala Gly Pro Thr Gly Pro Pro Thr Ala Gly Pro Ser Thr Ala Thr Thr
385                 390                 395                 400

Val Pro Leu Ser Pro Val Asp Asp Ala Cys Asn Val Asn Ile Phe Asp
                405                 410                 415

Ala Ile Ala Glu Ile Gly Asn Gln Leu Tyr Leu Phe Lys Asp Gly Lys
            420                 425                 430

Tyr Trp Arg Phe Ser Glu Gly Arg Gly Ser Arg Pro Gln Gly Pro Phe
        435                 440                 445

Leu Ile Ala Asp Lys Trp Pro Ala Leu Pro Arg Lys Leu Asp Ser Val
    450                 455                 460

Phe Glu Glu Arg Leu Ser Lys Lys Leu Phe Phe Phe Ser Gly Arg Gln
465                 470                 475                 480

Val Trp Val Tyr Thr Gly Ala Ser Val Leu Gly Pro Arg Arg Leu Asp
```

```
                        485                 490                 495

Lys Leu Gly Leu Gly Ala Asp Val Ala Gln Val Thr Gly Ala Leu Arg
            500                 505                 510

Ser Gly Arg Gly Lys Met Leu Leu Phe Ser Gly Arg Arg Leu Trp Arg
            515                 520                 525

Phe Asp Val Lys Ala Gln Met Val Asp Pro Arg Ser Ala Ser Glu Val
            530                 535                 540

Asp Arg Met Phe Pro Gly Val Pro Leu Asp Thr His Asp Val Phe Gln
545                 550                 555                 560

Tyr Arg Glu Lys Ala Tyr Phe Cys Gln Asp Arg Phe Tyr Trp Arg Val
            565                 570                 575

Ser Ser Arg Ser Glu Leu Asn Gln Val Asp Gln Val Gly Tyr Val Thr
            580                 585                 590

Tyr Asp Ile Leu Gln Cys Pro Glu Asp
            595                 600

<210> SEQ ID NO 202
<211> LENGTH: 416
<212> TYPE: PRT
<213> ORGANISM: Homo sapiens

<400> SEQUENCE: 202

Met Asp Glu Ala Asp Arg Arg Leu Leu Arg Arg Cys Arg Leu Arg Leu
1               5                   10                  15

Val Glu Glu Leu Gln Val Asp Gln Leu Trp Asp Ala Leu Leu Ser Arg
            20                  25                  30

Glu Leu Phe Arg Pro His Met Ile Glu Asp Ile Gln Arg Ala Gly Ser
            35                  40                  45

Gly Ser Arg Arg Asp Gln Ala Arg Gln Leu Ile Ile Asp Leu Glu Thr
        50                  55                  60

Arg Gly Ser Gln Ala Leu Pro Leu Phe Ile Ser Cys Leu Glu Asp Thr
65                  70                  75                  80

Gly Gln Asp Met Leu Ala Ser Phe Leu Arg Thr Asn Arg Gln Ala Ala
                85                  90                  95

Lys Leu Ser Lys Pro Thr Leu Glu Asn Leu Thr Pro Val Val Leu Arg
            100                 105                 110

Pro Glu Ile Arg Lys Pro Glu Val Leu Arg Pro Glu Thr Pro Arg Pro
            115                 120                 125

Val Asp Ile Gly Ser Gly Gly Phe Gly Asp Val Gly Ala Leu Glu Ser
        130                 135                 140

Leu Arg Gly Asn Ala Asp Leu Ala Tyr Ile Leu Ser Met Glu Pro Cys
145                 150                 155                 160

Gly His Cys Leu Ile Ile Asn Asn Val Asn Phe Cys Arg Glu Ser Gly
                165                 170                 175

Leu Arg Thr Arg Thr Gly Ser Asn Ile Asp Cys Glu Lys Leu Arg Arg
            180                 185                 190

Arg Phe Ser Ser Leu His Phe Met Val Glu Val Lys Gly Asp Leu Thr
            195                 200                 205

Ala Lys Lys Met Val Leu Ala Leu Leu Glu Leu Ala Gln Gln Asp His
        210                 215                 220

Gly Ala Leu Asp Cys Cys Val Val Val Ile Leu Ser His Gly Cys Gln
225                 230                 235                 240

Ala Ser His Leu Gln Phe Pro Gly Ala Val Tyr Gly Thr Asp Gly Cys
                245                 250                 255
```

```
Pro Val Ser Val Glu Lys Ile Val Asn Ile Phe Asn Gly Thr Ser Cys
            260                 265                 270

Pro Ser Leu Gly Gly Lys Pro Lys Leu Phe Phe Ile Gln Ala Cys Gly
        275                 280                 285

Gly Glu Gln Lys Asp His Gly Phe Glu Val Ala Ser Thr Ser Pro Glu
    290                 295                 300

Asp Glu Ser Pro Gly Ser Asn Pro Glu Pro Asp Ala Thr Pro Phe Gln
305                 310                 315                 320

Glu Gly Leu Arg Thr Phe Asp Gln Leu Asp Ala Ile Ser Ser Leu Pro
                325                 330                 335

Thr Pro Ser Asp Ile Phe Val Ser Tyr Ser Thr Phe Pro Gly Phe Val
            340                 345                 350

Ser Trp Arg Asp Pro Lys Ser Gly Ser Trp Tyr Val Glu Thr Leu Asp
        355                 360                 365

Asp Ile Phe Glu Gln Trp Ala His Ser Glu Asp Leu Gln Ser Leu Leu
    370                 375                 380

Leu Arg Val Ala Asn Ala Val Ser Val Lys Gly Ile Tyr Lys Gln Met
385                 390                 395                 400

Pro Gly Cys Phe Asn Phe Leu Arg Lys Lys Leu Phe Phe Lys Thr Ser
                405                 410                 415

<210> SEQ ID NO 203
<211> LENGTH: 233
<212> TYPE: PRT
<213> ORGANISM: Homo sapiens

<400> SEQUENCE: 203

Met Ser Gln Ser Asn Arg Glu Leu Val Val Asp Phe Leu Ser Tyr Lys
1               5                   10                  15

Leu Ser Gln Lys Gly Tyr Ser Trp Ser Gln Phe Ser Asp Val Glu Glu
            20                  25                  30

Asn Arg Thr Glu Ala Pro Glu Gly Thr Glu Ser Glu Met Glu Thr Pro
        35                  40                  45

Ser Ala Ile Asn Gly Asn Pro Ser Trp His Leu Ala Asp Ser Pro Ala
    50                  55                  60

Val Asn Gly Ala Thr Gly His Ser Ser Ser Leu Asp Ala Arg Glu Val
65                  70                  75                  80

Ile Pro Met Ala Ala Val Lys Gln Ala Leu Arg Glu Ala Gly Asp Glu
                85                  90                  95

Phe Glu Leu Arg Tyr Arg Arg Ala Phe Ser Asp Leu Thr Ser Gln Leu
            100                 105                 110

His Ile Thr Pro Gly Thr Ala Tyr Gln Ser Phe Glu Gln Val Val Asn
        115                 120                 125

Glu Leu Phe Arg Asp Gly Val Asn Trp Gly Arg Ile Val Ala Phe Phe
    130                 135                 140

Ser Phe Gly Gly Ala Leu Cys Val Glu Ser Val Asp Lys Glu Met Gln
145                 150                 155                 160

Val Leu Val Ser Arg Ile Ala Ala Trp Met Ala Thr Tyr Leu Asn Asp
                165                 170                 175

His Leu Glu Pro Trp Ile Gln Glu Asn Gly Gly Trp Asp Thr Phe Val
            180                 185                 190

Glu Leu Tyr Gly Asn Asn Ala Ala Ala Glu Ser Arg Lys Gly Gln Glu
        195                 200                 205

Arg Phe Asn Arg Trp Phe Leu Thr Gly Met Thr Val Ala Gly Val Val
    210                 215                 220
```

```
Leu Leu Gly Ser Leu Phe Ser Arg Lys
225                 230

<210> SEQ ID NO 204
<211> LENGTH: 117
<212> TYPE: PRT
<213> ORGANISM: Homo sapiens
<220> FEATURE:
<223> OTHER INFORMATION: N-term Ac

<400> SEQUENCE: 204

Ser Gly Gly Ser Ser Cys Ser Gln Thr Pro Ser Arg Ala Ile Pro Ala
1               5                   10                  15

Thr Arg Arg Val Val Leu Gly Asp Gly Val Gln Leu Pro Pro Gly Asp
                20                  25                  30

Tyr Ser Thr Thr Pro Gly Gly Thr Leu Phe Ser Thr Thr Pro Gly Gly
            35                  40                  45

Thr Arg Ile Ile Tyr Asp Arg Lys Phe Leu Met Glu Cys Arg Asn Ser
        50                  55                  60

Pro Val Thr Lys Thr Pro Arg Asp Leu Pro Thr Ile Pro Gly Val
65                  70                  75                  80

Thr Ser Pro Ser Ser Asp Glu Pro Pro Met Glu Ala Ser Gln Ser His
                85                  90                  95

Leu Arg Asn Ser Pro Glu Asp Lys Arg Ala Gly Gly Glu Glu Ser Gln
            100                 105                 110

Phe Glu Met Asp Ile
        115

<210> SEQ ID NO 205
<211> LENGTH: 239
<212> TYPE: PRT
<213> ORGANISM: Homo sapiens

<400> SEQUENCE: 205

Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
                20                  25                  30

Gly Asp Val Gly Ala Ala Pro Pro Gly Ala Ala Pro Ala Pro Gly Ile
            35                  40                  45

Phe Ser Ser Gln Pro Gly His Thr Pro His Pro Ala Ala Ser Arg Asp
        50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Thr
                85                  90                  95

Leu Arg Gln Ala Gly Asp Asp Phe Ser Arg Arg Tyr Arg Arg Asp Phe
            100                 105                 110

Ala Glu Met Ser Ser Gln Leu His Leu Thr Pro Phe Thr Ala Arg Gly
        115                 120                 125

Arg Phe Ala Thr Val Val Glu Glu Leu Phe Arg Asp Gly Val Asn Trp
    130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175
```

```
Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser Met Arg Pro
        195                 200                 205

Leu Phe Asp Phe Ser Trp Leu Ser Leu Lys Thr Leu Leu Ser Leu Ala
210                 215                 220

Leu Val Gly Ala Cys Ile Thr Leu Gly Ala Tyr Leu Gly His Lys
225                 230                 235

<210> SEQ ID NO 206
<211> LENGTH: 1186
<212> TYPE: PRT
<213> ORGANISM: Homo sapiens

<400> SEQUENCE: 206

Leu Glu Glu Lys Lys Val Cys Gln Gly Thr Ser Asn Lys Leu Thr Gln
1               5                   10                  15

Leu Gly Thr Phe Glu Asp His Phe Leu Ser Leu Gln Arg Met Phe Asn
            20                  25                  30

Asn Cys Glu Val Val Leu Gly Asn Leu Glu Ile Thr Tyr Val Gln Arg
        35                  40                  45

Asn Tyr Asp Leu Ser Phe Leu Lys Thr Ile Gln Glu Val Ala Gly Tyr
50                  55                  60

Val Leu Ile Ala Leu Asn Thr Val Glu Arg Ile Pro Leu Glu Asn Leu
65                  70                  75                  80

Gln Ile Ile Arg Gly Asn Met Tyr Tyr Glu Asn Ser Tyr Ala Leu Ala
                85                  90                  95

Val Leu Ser Asn Tyr Asp Ala Asn Lys Thr Gly Leu Lys Glu Leu Pro
            100                 105                 110

Met Arg Asn Leu Gln Glu Ile Leu His Gly Ala Val Arg Phe Ser Asn
        115                 120                 125

Asn Pro Ala Leu Cys Asn Val Glu Ser Ile Gln Trp Arg Asp Ile Val
130                 135                 140

Ser Ser Asp Phe Leu Ser Asn Met Ser Met Asp Phe Gln Asn His Leu
145                 150                 155                 160

Gly Ser Cys Gln Lys Cys Asp Pro Ser Cys Pro Asn Gly Ser Cys Trp
                165                 170                 175

Gly Ala Gly Glu Glu Asn Cys Gln Lys Leu Thr Lys Ile Ile Cys Ala
            180                 185                 190

Gln Gln Cys Ser Gly Arg Cys Arg Gly Lys Ser Pro Ser Asp Cys Cys
        195                 200                 205

His Asn Gln Cys Ala Ala Gly Cys Thr Gly Pro Arg Glu Ser Asp Cys
210                 215                 220

Leu Val Cys Arg Lys Phe Arg Asp Glu Ala Thr Cys Lys Asp Thr Cys
225                 230                 235                 240

Pro Pro Leu Met Leu Tyr Asn Pro Thr Thr Tyr Gln Met Asp Val Asn
                245                 250                 255

Pro Glu Gly Lys Tyr Ser Phe Gly Ala Thr Cys Val Lys Lys Cys Pro
            260                 265                 270

Arg Asn Tyr Val Val Thr Asp His Gly Ser Cys Val Arg Ala Cys Gly
        275                 280                 285

Ala Asp Ser Tyr Glu Met Glu Glu Asp Gly Val Arg Lys Cys Lys Lys
290                 295                 300

Cys Glu Gly Pro Cys Arg Lys Val Cys Asn Gly Ile Gly Ile Gly Glu
305                 310                 315                 320
```

-continued

Phe Lys Asp Ser Leu Ser Ile Asn Ala Thr Asn Ile Lys His Phe Lys
            325                 330                 335

Asn Cys Thr Ser Ile Ser Gly Asp Leu His Ile Leu Pro Val Ala Phe
            340                 345                 350

Arg Gly Asp Ser Phe Thr His Thr Pro Pro Leu Asp Pro Gln Glu Leu
            355                 360                 365

Asp Ile Leu Lys Thr Val Lys Glu Ile Thr Gly Phe Leu Leu Ile Gln
        370                 375                 380

Ala Trp Pro Glu Asn Arg Thr Asp Leu His Ala Phe Glu Asn Leu Glu
385                 390                 395                 400

Ile Ile Arg Gly Arg Thr Lys Gln His Gly Gln Phe Ser Leu Ala Val
                405                 410                 415

Val Ser Leu Asn Ile Thr Ser Leu Gly Leu Arg Ser Leu Lys Glu Ile
                420                 425                 430

Ser Asp Gly Asp Val Ile Ile Ser Gly Asn Lys Asn Leu Cys Tyr Ala
            435                 440                 445

Asn Thr Ile Asn Trp Lys Lys Leu Phe Gly Thr Ser Gly Gln Lys Thr
        450                 455                 460

Lys Ile Ile Ser Asn Arg Gly Glu Asn Ser Cys Lys Ala Thr Gly Gln
465                 470                 475                 480

Val Cys His Ala Leu Cys Ser Pro Glu Gly Cys Trp Gly Pro Glu Pro
                485                 490                 495

Arg Asp Cys Val Ser Cys Arg Asn Val Ser Arg Gly Arg Glu Cys Val
            500                 505                 510

Asp Lys Cys Asn Leu Leu Glu Gly Glu Pro Arg Glu Phe Val Glu Asn
            515                 520                 525

Ser Glu Cys Ile Gln Cys His Pro Glu Cys Leu Pro Gln Ala Met Asn
        530                 535                 540

Ile Thr Cys Thr Gly Arg Gly Pro Asp Asn Cys Ile Gln Cys Ala His
545                 550                 555                 560

Tyr Ile Asp Gly Pro His Cys Val Lys Thr Cys Pro Ala Gly Val Met
                565                 570                 575

Gly Glu Asn Asn Thr Leu Val Trp Lys Tyr Ala Asp Ala Gly His Val
            580                 585                 590

Cys His Leu Cys His Pro Asn Cys Thr Tyr Gly Cys Thr Gly Pro Gly
            595                 600                 605

Leu Glu Gly Cys Pro Thr Asn Gly Pro Lys Ile Pro Ser Ile Ala Thr
        610                 615                 620

Gly Met Val Gly Ala Leu Leu Leu Leu Val Ala Leu Gly Ile
625                 630                 635                 640

Gly Leu Phe Met Arg Arg Arg His Ile Val Arg Lys Arg Thr Leu Arg
                645                 650                 655

Arg Leu Leu Gln Glu Arg Glu Leu Val Glu Pro Leu Thr Pro Ser Gly
            660                 665                 670

Glu Ala Pro Asn Gln Ala Leu Leu Arg Ile Leu Lys Glu Thr Glu Phe
        675                 680                 685

Lys Lys Ile Lys Val Leu Gly Ser Gly Ala Phe Gly Thr Val Tyr Lys
690                 695                 700

Gly Leu Trp Ile Pro Glu Gly Glu Lys Val Lys Ile Pro Val Ala Ile
705                 710                 715                 720

Lys Glu Leu Arg Glu Ala Thr Ser Pro Lys Ala Asn Lys Glu Ile Leu
            725                 730                 735

```
Asp Glu Ala Tyr Val Met Ala Ser Val Asp Asn Pro His Val Cys Arg
            740                 745                 750

Leu Leu Gly Ile Cys Leu Thr Ser Thr Val Gln Leu Ile Thr Gln Leu
            755                 760                 765

Met Pro Phe Gly Cys Leu Leu Asp Tyr Val Arg Glu His Lys Asp Asn
770                 775                 780

Ile Gly Ser Gln Tyr Leu Leu Asn Trp Cys Val Gln Ile Ala Lys Gly
785                 790                 795                 800

Met Asn Tyr Leu Glu Asp Arg Arg Leu Val His Arg Asp Leu Ala Ala
            805                 810                 815

Arg Asn Val Leu Val Lys Thr Pro Gln His Val Lys Ile Thr Asp Phe
            820                 825                 830

Gly Leu Ala Lys Leu Leu Gly Ala Glu Glu Lys Glu Tyr His Ala Glu
            835                 840                 845

Gly Gly Lys Val Pro Ile Lys Trp Met Ala Leu Glu Ser Ile Leu His
            850                 855                 860

Arg Ile Tyr Thr His Gln Ser Asp Val Trp Ser Tyr Gly Val Thr Val
865                 870                 875                 880

Trp Glu Leu Met Thr Phe Gly Ser Lys Pro Tyr Asp Gly Ile Pro Ala
                885                 890                 895

Ser Glu Ile Ser Ser Ile Leu Glu Lys Gly Glu Arg Leu Pro Gln Pro
            900                 905                 910

Pro Ile Cys Thr Ile Asp Val Tyr Met Ile Met Val Lys Cys Trp Met
            915                 920                 925

Ile Asp Ala Asp Ser Arg Pro Lys Phe Arg Glu Leu Ile Ile Glu Phe
930                 935                 940

Ser Lys Met Ala Arg Asp Pro Gln Arg Tyr Leu Val Ile Gln Gly Asp
945                 950                 955                 960

Glu Arg Met His Leu Pro Ser Pro Thr Asp Ser Asn Phe Tyr Arg Ala
                965                 970                 975

Leu Met Asp Glu Glu Asp Met Asp Val Val Asp Ala Asp Glu Tyr
            980                 985                 990

Leu Ile Pro Gln Gln Gly Phe Phe Ser Ser Pro Ser Thr Ser Arg Thr
            995                 1000                1005

Pro Leu Leu Ser Ser Leu Ser Ala Thr Ser Asn Asn Ser Thr Val
    1010                1015                1020

Ala Cys Ile Asp Arg Asn Gly Leu Gln Ser Cys Pro Ile Lys Glu
    1025                1030                1035

Asp Ser Phe Leu Gln Arg Tyr Ser Ser Asp Pro Thr Gly Ala Leu
    1040                1045                1050

Thr Glu Asp Ser Ile Asp Asp Thr Phe Leu Pro Val Pro Glu Tyr
    1055                1060                1065

Ile Asn Gln Ser Val Pro Lys Arg Pro Ala Gly Ser Val Gln Asn
    1070                1075                1080

Pro Val Tyr His Asn Gln Pro Leu Asn Pro Ala Pro Ser Arg Asp
    1085                1090                1095

Pro His Tyr Gln Asp Pro His Ser Thr Ala Val Gly Asn Pro Glu
    1100                1105                1110

Tyr Leu Asn Thr Val Gln Pro Thr Cys Val Asn Ser Thr Phe Asp
    1115                1120                1125

Ser Pro Ala His Trp Ala Gln Lys Gly Ser His Gln Ile Ser Leu
    1130                1135                1140

Asp Asn Pro Asp Tyr Gln Gln Asp Phe Phe Pro Lys Glu Ala Lys
```

```
                 1145                1150                1155

Pro Asn Gly Ile Phe Lys Gly Ser Thr Ala Glu Asn Ala Glu Tyr
            1160                1165                1170

Leu Arg Val Ala Pro Gln Ser Ser Glu Phe Ile Gly Ala
        1175                1180                1185

<210> SEQ ID NO 207
<211> LENGTH: 288
<212> TYPE: PRT
<213> ORGANISM: Homo sapiens

<400> SEQUENCE: 207

Met Val Gly Val Gly Gly Asp Val Glu Asp Val Thr Pro Arg Pro
1               5                   10                  15

Gly Gly Cys Gln Ile Ser Gly Arg Gly Ala Arg Gly Cys Asn Gly Ile
                20                  25                  30

Pro Gly Ala Ala Ala Trp Glu Ala Ala Leu Pro Arg Arg Pro Arg
            35                  40                  45

Arg His Pro Ser Val Asn Pro Arg Ser Arg Ala Ala Gly Ser Pro Arg
        50                  55                  60

Thr Arg Gly Arg Arg Thr Glu Glu Arg Pro Ser Gly Ser Arg Leu Gly
65                  70                  75                  80

Asp Arg Gly Arg Gly Arg Ala Leu Pro Gly Gly Arg Leu Gly Gly Arg
                85                  90                  95

Gly Arg Gly Arg Ala Pro Glu Arg Val Gly Gly Arg Gly Arg Gly Arg
                100                 105                 110

Gly Thr Ala Ala Pro Arg Ala Ala Pro Ala Ala Arg Gly Ser Arg Pro
                115                 120                 125

Gly Pro Ala Gly Thr Met Ala Ala Gly Ser Ile Thr Thr Leu Pro Ala
                130                 135                 140

Leu Pro Glu Asp Gly Gly Ser Gly Ala Phe Pro Pro Gly His Phe Lys
145                 150                 155                 160

Asp Pro Lys Arg Leu Tyr Cys Lys Asn Gly Gly Phe Phe Leu Arg Ile
                165                 170                 175

His Pro Asp Gly Arg Val Asp Gly Val Arg Glu Lys Ser Asp Pro His
                180                 185                 190

Ile Lys Leu Gln Leu Gln Ala Glu Glu Arg Gly Val Val Ser Ile Lys
                195                 200                 205

Gly Val Cys Ala Asn Arg Tyr Leu Ala Met Lys Glu Asp Gly Arg Leu
                210                 215                 220

Leu Ala Ser Lys Cys Val Thr Asp Glu Cys Phe Phe Phe Glu Arg Leu
225                 230                 235                 240

Glu Ser Asn Asn Tyr Asn Thr Tyr Arg Ser Arg Lys Tyr Thr Ser Trp
                245                 250                 255

Tyr Val Ala Leu Lys Arg Thr Gly Gln Tyr Lys Leu Gly Ser Lys Thr
                260                 265                 270

Gly Pro Gly Gln Lys Ala Ile Leu Phe Leu Pro Met Ser Ala Lys Ser
                275                 280                 285

<210> SEQ ID NO 208
<211> LENGTH: 1233
<212> TYPE: PRT
<213> ORGANISM: Homo sapiens

<400> SEQUENCE: 208

Thr Gln Val Cys Thr Gly Thr Asp Met Lys Leu Arg Leu Pro Ala Ser
```

-continued

```
1               5                   10                  15
Pro Glu Thr His Leu Asp Met Leu Arg His Leu Tyr Gln Gly Cys Gln
                20                  25                  30
Val Val Gln Gly Asn Leu Glu Leu Thr Tyr Leu Pro Thr Asn Ala Ser
                35                  40                  45
Leu Ser Phe Leu Gln Asp Ile Gln Glu Val Gln Gly Tyr Val Leu Ile
            50                  55                  60
Ala His Asn Gln Val Arg Gln Val Pro Leu Gln Arg Leu Arg Ile Val
65                  70                  75                  80
Arg Gly Thr Gln Leu Phe Glu Asp Asn Tyr Ala Leu Ala Val Leu Asp
                85                  90                  95
Asn Gly Asp Pro Leu Asn Asn Thr Thr Pro Val Thr Gly Ala Ser Pro
                100                 105                 110
Gly Gly Leu Arg Glu Leu Gln Leu Arg Ser Leu Thr Glu Ile Leu Lys
                115                 120                 125
Gly Gly Val Leu Ile Gln Arg Asn Pro Gln Leu Cys Tyr Gln Asp Thr
            130                 135                 140
Ile Leu Trp Lys Asp Ile Phe His Lys Asn Asn Gln Leu Ala Leu Thr
145                 150                 155                 160
Leu Ile Asp Thr Asn Arg Ser Arg Ala Cys His Pro Cys Ser Pro Met
                165                 170                 175
Cys Lys Gly Ser Arg Cys Trp Gly Glu Ser Ser Glu Asp Cys Gln Ser
                180                 185                 190
Leu Thr Arg Thr Val Cys Ala Gly Gly Cys Ala Arg Cys Lys Gly Pro
                195                 200                 205
Leu Pro Thr Asp Cys Cys His Glu Gln Cys Ala Ala Gly Cys Thr Gly
                210                 215                 220
Pro Lys His Ser Asp Cys Leu Ala Cys Leu His Phe Asn His Ser Gly
225                 230                 235                 240
Ile Cys Glu Leu His Cys Pro Ala Leu Val Thr Tyr Asn Thr Asp Thr
                245                 250                 255
Phe Glu Ser Met Pro Asn Pro Glu Gly Arg Tyr Thr Phe Gly Ala Ser
                260                 265                 270
Cys Val Thr Ala Cys Pro Tyr Asn Tyr Leu Ser Thr Asp Val Gly Ser
                275                 280                 285
Cys Thr Leu Val Cys Pro Leu His Asn Gln Glu Val Thr Ala Glu Asp
            290                 295                 300
Gly Thr Gln Arg Cys Glu Lys Cys Ser Lys Pro Cys Ala Arg Val Cys
305                 310                 315                 320
Tyr Gly Leu Gly Met Glu His Leu Arg Glu Val Arg Ala Val Thr Ser
                325                 330                 335
Ala Asn Ile Gln Glu Phe Ala Gly Cys Lys Lys Ile Phe Gly Ser Leu
                340                 345                 350
Ala Phe Leu Pro Glu Ser Phe Asp Gly Asp Pro Ala Ser Asn Thr Ala
                355                 360                 365
Pro Leu Gln Pro Glu Gln Leu Gln Val Phe Glu Thr Leu Glu Glu Ile
            370                 375                 380
Thr Gly Tyr Leu Tyr Ile Ser Ala Trp Pro Asp Ser Leu Pro Asp Leu
385                 390                 395                 400
Ser Val Phe Gln Asn Leu Gln Val Ile Arg Gly Arg Ile Leu His Asn
                405                 410                 415
Gly Ala Tyr Ser Leu Thr Leu Gln Gly Leu Gly Ile Ser Trp Leu Gly
                420                 425                 430
```

```
Leu Arg Ser Leu Arg Glu Leu Gly Ser Gly Leu Ala Leu Ile His His
        435                 440                 445

Asn Thr His Leu Cys Phe Val His Thr Val Pro Trp Asp Gln Leu Phe
    450                 455                 460

Arg Asn Pro His Gln Ala Leu Leu His Thr Ala Asn Arg Pro Glu Asp
465                 470                 475                 480

Glu Cys Val Gly Glu Gly Leu Ala Cys His Gln Leu Cys Ala Arg Gly
                485                 490                 495

His Cys Trp Gly Pro Gly Pro Thr Gln Cys Val Asn Cys Ser Gln Phe
            500                 505                 510

Leu Arg Gly Gln Glu Cys Val Glu Cys Arg Val Leu Gln Gly Leu
        515                 520                 525

Pro Arg Glu Tyr Val Asn Ala Arg His Cys Leu Pro Cys His Pro Glu
    530                 535                 540

Cys Gln Pro Gln Asn Gly Ser Val Thr Cys Phe Gly Pro Glu Ala Asp
545                 550                 555                 560

Gln Cys Val Ala Cys Ala His Tyr Lys Asp Pro Pro Phe Cys Val Ala
                565                 570                 575

Arg Cys Pro Ser Gly Val Lys Pro Asp Leu Ser Tyr Met Pro Ile Trp
            580                 585                 590

Lys Phe Pro Asp Glu Glu Gly Ala Cys Gln Pro Cys Pro Ile Asn Cys
        595                 600                 605

Thr His Ser Cys Val Asp Leu Asp Asp Lys Gly Cys Pro Ala Glu Gln
    610                 615                 620

Arg Ala Ser Pro Leu Thr Ser Ile Ile Ser Ala Val Val Gly Ile Leu
625                 630                 635                 640

Leu Val Val Val Leu Gly Val Val Phe Gly Ile Leu Ile Lys Arg Arg
                645                 650                 655

Gln Gln Lys Ile Arg Lys Tyr Thr Met Arg Arg Leu Leu Gln Glu Thr
            660                 665                 670

Glu Leu Val Glu Pro Leu Thr Pro Ser Gly Ala Met Pro Asn Gln Ala
        675                 680                 685

Gln Met Arg Ile Leu Lys Glu Thr Glu Leu Arg Lys Val Lys Val Leu
    690                 695                 700

Gly Ser Gly Ala Phe Gly Thr Val Tyr Lys Gly Ile Trp Ile Pro Asp
705                 710                 715                 720

Gly Glu Asn Val Lys Ile Pro Val Ala Ile Lys Val Leu Arg Glu Asn
                725                 730                 735

Thr Ser Pro Lys Ala Asn Lys Glu Ile Leu Asp Glu Ala Tyr Val Met
            740                 745                 750

Ala Gly Val Gly Ser Pro Tyr Val Ser Arg Leu Leu Gly Ile Cys Leu
        755                 760                 765

Thr Ser Thr Val Gln Leu Val Thr Gln Leu Met Pro Tyr Gly Cys Leu
    770                 775                 780

Leu Asp His Val Arg Glu Asn Arg Gly Arg Leu Gly Ser Gln Asp Leu
785                 790                 795                 800

Leu Asn Trp Cys Met Gln Ile Ala Lys Gly Met Ser Tyr Leu Glu Asp
                805                 810                 815

Val Arg Leu Val His Arg Asp Leu Ala Ala Arg Asn Val Leu Val Lys
            820                 825                 830

Ser Pro Asn His Val Lys Ile Thr Asp Phe Gly Leu Ala Arg Leu Leu
        835                 840                 845
```

-continued

```
Asp Ile Asp Glu Thr Glu Tyr His Ala Asp Gly Gly Lys Val Pro Ile
850                 855                 860

Lys Trp Met Ala Leu Glu Ser Ile Leu Arg Arg Phe Thr His Gln
865                 870                 875                 880

Ser Asp Val Trp Ser Tyr Gly Val Thr Val Trp Glu Leu Met Thr Phe
                885                 890                 895

Gly Ala Lys Pro Tyr Asp Gly Ile Pro Ala Arg Glu Ile Pro Asp Leu
            900                 905                 910

Leu Glu Lys Gly Glu Arg Leu Pro Gln Pro Ile Cys Thr Ile Asp
        915                 920                 925

Val Tyr Met Ile Met Val Lys Cys Trp Met Ile Asp Ser Glu Cys Arg
930                 935                 940

Pro Arg Phe Arg Glu Leu Val Ser Glu Phe Ser Arg Met Ala Arg Asp
945                 950                 955                 960

Pro Gln Arg Phe Val Val Ile Gln Asn Glu Asp Leu Gly Pro Ala Ser
                965                 970                 975

Pro Leu Asp Ser Thr Phe Tyr Arg Ser Leu Leu Glu Asp Asp Met
            980                 985                 990

Gly Asp Leu Val Asp Ala Glu Glu Tyr Leu Val Pro Gln Gln Gly Phe
        995                 1000                1005

Phe Cys Pro Asp Pro Ala Pro Gly Ala Gly Gly Met Val His His
    1010                1015                1020

Arg His Arg Ser Ser Ser Thr Arg Ser Gly Gly Gly Asp Leu Thr
    1025                1030                1035

Leu Gly Leu Glu Pro Ser Glu Glu Ala Pro Arg Ser Pro Leu
    1040                1045                1050

Ala Pro Ser Glu Gly Ala Gly Ser Asp Val Phe Asp Gly Asp Leu
    1055                1060                1065

Gly Met Gly Ala Ala Lys Gly Leu Gln Ser Leu Pro Thr His Asp
    1070                1075                1080

Pro Ser Pro Leu Gln Arg Tyr Ser Glu Asp Pro Thr Val Pro Leu
    1085                1090                1095

Pro Ser Glu Thr Asp Gly Tyr Val Ala Pro Leu Thr Cys Ser Pro
    1100                1105                1110

Gln Pro Glu Tyr Val Asn Gln Pro Asp Val Arg Pro Gln Pro Pro
    1115                1120                1125

Ser Pro Arg Glu Gly Pro Leu Pro Ala Ala Arg Pro Ala Gly Ala
    1130                1135                1140

Thr Leu Glu Arg Pro Lys Thr Leu Ser Pro Gly Lys Asn Gly Val
    1145                1150                1155

Val Lys Asp Val Phe Ala Phe Gly Gly Ala Val Glu Asn Pro Glu
    1160                1165                1170

Tyr Leu Thr Pro Gln Gly Gly Ala Ala Pro Gln Pro His Pro Pro
    1175                1180                1185

Pro Ala Phe Ser Pro Ala Phe Asp Asn Leu Tyr Tyr Trp Asp Gln
    1190                1195                1200

Asp Pro Pro Glu Arg Gly Ala Pro Pro Ser Thr Phe Lys Gly Thr
    1205                1210                1215

Pro Thr Ala Glu Asn Pro Glu Tyr Leu Gly Leu Asp Val Pro Val
    1220                1225                1230

<210> SEQ ID NO 209
<211> LENGTH: 189
<212> TYPE: PRT
```

<213> ORGANISM: Homo sapiens
<220> FEATURE:
<221> NAME/KEY: MOD_RES
<222> LOCATION: (188)..(188)
<223> OTHER INFORMATION: Selenocysteine

<400> SEQUENCE: 209

```
Met Glu Arg Gln Glu Ser Leu Ser Ala Arg Pro Ala Leu Glu Thr
1               5                   10                  15

Glu Gly Leu Arg Phe Leu His Thr Thr Val Gly Ser Leu Leu Ala Thr
            20                  25                  30

Tyr Gly Trp Tyr Ile Val Phe Ser Cys Ile Leu Leu Tyr Val Val Phe
            35                  40                  45

Gln Lys Leu Ser Ala Arg Leu Arg Ala Leu Arg Gln Arg Gln Leu Asp
        50                  55                  60

Arg Ala Ala Ala Val Glu Pro Asp Val Val Lys Arg Gln Glu
65                  70                  75                  80

Ala Leu Ala Ala Arg Leu Lys Met Gln Glu Glu Leu Asn Ala Gln
                85                  90                  95

Val Glu Lys His Lys Glu Lys Leu Lys Gln Leu Glu Glu Lys Arg
            100                 105                 110

Arg Gln Lys Ile Glu Met Trp Asp Ser Met Gln Glu Gly Lys Ser Tyr
        115                 120                 125

Lys Gly Asn Ala Lys Lys Pro Gln Glu Glu Asp Ser Pro Gly Pro Ser
    130                 135                 140

Thr Ser Ser Val Leu Lys Arg Lys Ser Asp Arg Lys Pro Leu Arg Gly
145                 150                 155                 160

Gly Gly Tyr Asn Pro Leu Ser Gly Glu Gly Gly Ala Cys Ser Trp
                165                 170                 175

Arg Pro Gly Arg Arg Gly Pro Ser Ser Gly Gly Xaa Gly
            180                 185
```

<210> SEQ ID NO 210
<211> LENGTH: 298
<212> TYPE: PRT
<213> ORGANISM: Homo sapiens

<400> SEQUENCE: 210

```
Ile Pro Val Lys Gln Ala Asp Ser Gly Ser Ser Glu Glu Lys Gln Leu
1               5                   10                  15

Tyr Asn Lys Tyr Pro Asp Ala Val Ala Thr Trp Leu Asn Pro Asp Pro
            20                  25                  30

Ser Gln Lys Gln Asn Leu Leu Ala Pro Gln Asn Ala Val Ser Ser Glu
        35                  40                  45

Glu Thr Asn Asp Phe Lys Gln Glu Thr Leu Pro Ser Lys Ser Asn Glu
    50                  55                  60

Ser His Asp His Met Asp Asp Met Asp Glu Asp Asp Asp His
65                  70                  75                  80

Val Asp Ser Gln Asp Ser Ile Asp Ser Asn Ser Asp Val Asp
                85                  90                  95

Asp Thr Asp Asp Ser His Gln Ser Asp Glu Ser His His Ser Asp Glu
            100                 105                 110

Ser Asp Glu Leu Val Thr Asp Phe Pro Thr Asp Leu Pro Ala Thr Glu
        115                 120                 125

Val Phe Thr Pro Val Val Pro Thr Val Asp Thr Tyr Asp Gly Arg Gly
    130                 135                 140
```

```
Asp Ser Val Val Tyr Gly Leu Arg Ser Lys Ser Lys Phe Arg Arg
145                 150                 155                 160

Pro Asp Ile Gln Tyr Pro Asp Ala Thr Asp Glu Asp Ile Thr Ser His
            165                 170                 175

Met Glu Ser Glu Glu Leu Asn Gly Ala Tyr Lys Ala Ile Pro Val Ala
                180                 185                 190

Gln Asp Leu Asn Ala Pro Ser Asp Trp Asp Ser Arg Gly Lys Asp Ser
            195                 200                 205

Tyr Glu Thr Ser Gln Leu Asp Asp Gln Ser Ala Glu Thr His Ser His
        210                 215                 220

Lys Gln Ser Arg Leu Tyr Lys Arg Lys Ala Asn Asp Glu Ser Asn Glu
225                 230                 235                 240

His Ser Asp Val Ile Asp Ser Gln Glu Leu Ser Lys Val Ser Arg Glu
                245                 250                 255

Phe His Ser His Glu Phe His Ser His Glu Asp Met Leu Val Val Asp
            260                 265                 270

Pro Lys Ser Lys Glu Glu Asp Lys His Leu Lys Phe Arg Ile Ser His
            275                 280                 285

Glu Leu Asp Ser Ala Ser Ser Glu Val Asn
        290                 295

<210> SEQ ID NO 211
<211> LENGTH: 480
<212> TYPE: PRT
<213> ORGANISM: Homo sapiens

<400> SEQUENCE: 211

Met Ser Asp Val Ala Ile Val Lys Glu Gly Trp Leu His Lys Arg Gly
1               5                   10                  15

Glu Tyr Ile Lys Thr Trp Arg Pro Arg Tyr Phe Leu Leu Lys Asn Asp
                20                  25                  30

Gly Thr Phe Ile Gly Tyr Lys Glu Arg Pro Gln Asp Val Asp Gln Arg
            35                  40                  45

Glu Ala Pro Leu Asn Asn Phe Ser Val Ala Gln Cys Gln Leu Met Lys
    50                  55                  60

Thr Glu Arg Pro Arg Pro Asn Thr Phe Ile Ile Arg Cys Leu Gln Trp
65                  70                  75                  80

Thr Thr Val Ile Glu Arg Thr Phe His Val Glu Thr Pro Glu Glu Arg
                85                  90                  95

Glu Glu Trp Thr Thr Ala Ile Gln Thr Val Ala Asp Gly Leu Lys Lys
            100                 105                 110

Gln Glu Glu Glu Glu Met Asp Phe Arg Ser Gly Ser Pro Ser Asp Asn
        115                 120                 125

Ser Gly Ala Glu Glu Met Glu Val Ser Leu Ala Lys Pro Lys His Arg
    130                 135                 140

Val Thr Met Asn Glu Phe Glu Tyr Leu Lys Leu Leu Gly Lys Gly Thr
145                 150                 155                 160

Phe Gly Lys Val Ile Leu Val Lys Glu Lys Ala Thr Gly Arg Tyr Tyr
                165                 170                 175

Ala Met Lys Ile Leu Lys Lys Glu Val Ile Val Ala Lys Asp Glu Val
            180                 185                 190

Ala His Thr Leu Thr Glu Asn Arg Val Leu Gln Asn Ser Arg His Pro
        195                 200                 205

Phe Leu Thr Ala Leu Lys Tyr Ser Phe Gln Thr His Asp Arg Leu Cys
    210                 215                 220
```

```
Phe Val Met Glu Tyr Ala Asn Gly Gly Glu Leu Phe Phe His Leu Ser
225                 230                 235                 240

Arg Glu Arg Val Phe Ser Glu Asp Arg Ala Arg Phe Tyr Gly Ala Glu
                245                 250                 255

Ile Val Ser Ala Leu Asp Tyr Leu His Ser Glu Lys Asn Val Val Tyr
                260                 265                 270

Arg Asp Leu Lys Leu Glu Asn Leu Met Leu Asp Lys Asp Gly His Ile
            275                 280                 285

Lys Ile Thr Asp Phe Gly Leu Cys Lys Glu Gly Ile Lys Asp Gly Ala
        290                 295                 300

Thr Met Lys Thr Phe Cys Gly Thr Pro Glu Tyr Leu Ala Pro Glu Val
305                 310                 315                 320

Leu Glu Asp Asn Asp Tyr Gly Arg Ala Val Asp Trp Trp Gly Leu Gly
                325                 330                 335

Val Val Met Tyr Glu Met Met Cys Gly Arg Leu Pro Phe Tyr Asn Gln
                340                 345                 350

Asp His Glu Lys Leu Phe Glu Leu Ile Leu Met Glu Glu Ile Arg Phe
            355                 360                 365

Pro Arg Thr Leu Gly Pro Glu Ala Lys Ser Leu Leu Ser Gly Leu Leu
        370                 375                 380

Lys Lys Asp Pro Lys Gln Arg Leu Gly Gly Gly Ser Glu Asp Ala Lys
385                 390                 395                 400

Glu Ile Met Gln His Arg Phe Phe Ala Gly Ile Val Trp Gln His Val
                405                 410                 415

Tyr Glu Lys Lys Leu Ser Pro Pro Phe Lys Pro Gln Val Thr Ser Glu
                420                 425                 430

Thr Asp Thr Arg Tyr Phe Asp Glu Glu Phe Thr Ala Gln Met Ile Thr
            435                 440                 445

Ile Thr Pro Pro Asp Gln Asp Asp Ser Met Glu Cys Val Asp Ser Glu
        450                 455                 460

Arg Arg Pro His Phe Pro Gln Phe Ser Tyr Ser Ala Ser Gly Thr Ala
465                 470                 475                 480

<210> SEQ ID NO 212
<211> LENGTH: 6
<212> TYPE: PRT
<213> ORGANISM: Homo sapiens

<400> SEQUENCE: 212

Val Ser Gly Val Cys Lys
1               5

<210> SEQ ID NO 213
<211> LENGTH: 6
<212> TYPE: PRT
<213> ORGANISM: Homo sapiens

<400> SEQUENCE: 213

Asn Ser Asn Leu Val Arg
1               5

<210> SEQ ID NO 214
<211> LENGTH: 6
<212> TYPE: PRT
<213> ORGANISM: Homo sapiens

<400> SEQUENCE: 214
```

Asp Phe Val Ile Val Arg
1               5

<210> SEQ ID NO 215
<211> LENGTH: 8
<212> TYPE: PRT
<213> ORGANISM: Homo sapiens

<400> SEQUENCE: 215

Ser Asp Leu Ser Thr Leu Val Arg
1               5

<210> SEQ ID NO 216
<211> LENGTH: 8
<212> TYPE: PRT
<213> ORGANISM: Homo sapiens

<400> SEQUENCE: 216

Asn Gln Glu Ile Trp Gly Ile Lys
1               5

<210> SEQ ID NO 217
<211> LENGTH: 9
<212> TYPE: PRT
<213> ORGANISM: Homo sapiens

<400> SEQUENCE: 217

Asn Leu His Pro Asp Val Thr Gly Arg
1               5

<210> SEQ ID NO 218
<211> LENGTH: 9
<212> TYPE: PRT
<213> ORGANISM: Homo sapiens

<400> SEQUENCE: 218

Leu Thr Leu Gln Lys Pro Ser Cys Leu
1               5

<210> SEQ ID NO 219
<211> LENGTH: 10
<212> TYPE: PRT
<213> ORGANISM: Homo sapiens

<400> SEQUENCE: 219

Leu Leu Ser Gln Gly Val Ile Ala Phe Arg
1               5                   10

<210> SEQ ID NO 220
<211> LENGTH: 10
<212> TYPE: PRT
<213> ORGANISM: Homo sapiens

<400> SEQUENCE: 220

Leu Gln Asn Leu Ser Leu Glu Gly Leu Arg
1               5                   10

<210> SEQ ID NO 221
<211> LENGTH: 11
<212> TYPE: PRT
<213> ORGANISM: Homo sapiens

<400> SEQUENCE: 221

Leu Ser Asp Pro Ile Val Asn Thr Leu Ala Lys
1               5                   10

<210> SEQ ID NO 222
<211> LENGTH: 15
<212> TYPE: PRT
<213> ORGANISM: Homo sapiens

<400> SEQUENCE: 222

Thr Ser Glu Leu Leu Ser Gly Met Gly Val Ser Ala Leu Glu Lys
1               5                   10                  15

<210> SEQ ID NO 223
<211> LENGTH: 16
<212> TYPE: PRT
<213> ORGANISM: Homo sapiens

<400> SEQUENCE: 223

Leu Ala Ser Asp Glu Ser Leu Trp Gln Thr Leu Asp Leu Thr Gly Lys
1               5                   10                  15

<210> SEQ ID NO 224
<211> LENGTH: 15
<212> TYPE: PRT
<213> ORGANISM: Homo sapiens

<400> SEQUENCE: 224

Ser Phe Met Asp Gln Pro Leu Ala Glu His Phe Ser Pro Phe Arg
1               5                   10                  15

<210> SEQ ID NO 225
<211> LENGTH: 16
<212> TYPE: PRT
<213> ORGANISM: Homo sapiens

<400> SEQUENCE: 225

Cys Pro Asn Leu Val His Leu Asp Leu Ser Asp Ser Val Met Leu Lys
1               5                   10                  15

<210> SEQ ID NO 226
<211> LENGTH: 17
<212> TYPE: PRT
<213> ORGANISM: Homo sapiens

<400> SEQUENCE: 226

Thr Leu Gln Val Phe Gly Ile Val Pro Asp Gly Thr Leu Gln Leu Leu
1               5                   10                  15

Lys

<210> SEQ ID NO 227
<211> LENGTH: 15
<212> TYPE: PRT
<213> ORGANISM: Homo sapiens

<400> SEQUENCE: 227

Leu Asp Glu Leu Asn Leu Ser Trp Cys Phe Asp Phe Thr Glu Lys
1               5                   10                  15

<210> SEQ ID NO 228
<211> LENGTH: 19
<212> TYPE: PRT
<213> ORGANISM: Homo sapiens

<400> SEQUENCE: 228

Cys Tyr Asp Ile Ile Pro Glu Thr Leu Leu Glu Leu Gly Glu Ile Pro
1               5                   10                  15

Thr Leu Lys

<210> SEQ ID NO 229
<211> LENGTH: 22
<212> TYPE: PRT
<213> ORGANISM: Homo sapiens

<400> SEQUENCE: 229

His Val Gln Val Ala Val Ala His Val Ser Glu Thr Ile Thr Gln Leu
1               5                   10                  15

Asn Leu Ser Gly Tyr Arg
            20

<210> SEQ ID NO 230
<211> LENGTH: 23
<212> TYPE: PRT
<213> ORGANISM: Homo sapiens

<400> SEQUENCE: 230

Leu Asn Leu Ser Gly Cys Ser Gly Phe Ser Glu Phe Ala Leu Gln Thr
1               5                   10                  15

Leu Leu Ser Ser Cys Ser Arg
            20

<210> SEQ ID NO 231
<211> LENGTH: 20
<212> TYPE: PRT
<213> ORGANISM: Homo sapiens

<400> SEQUENCE: 231

Asn Asp Cys Phe Gln Glu Phe Phe Gln Leu Asn Tyr Leu Gln His Leu
1               5                   10                  15

Ser Leu Ser Arg
            20

<210> SEQ ID NO 232
<211> LENGTH: 24
<212> TYPE: PRT
<213> ORGANISM: Homo sapiens

<400> SEQUENCE: 232

Glu Glu Pro Asp Ser Glu Asn Ile Pro Gln Gly Leu Leu Ser Asn Leu
1               5                   10                  15

Gly His Pro Glu Ser Pro Pro Arg
            20

<210> SEQ ID NO 233
<211> LENGTH: 24
<212> TYPE: PRT
<213> ORGANISM: Homo sapiens

<400> SEQUENCE: 233

His Leu Gln Glu Ile Pro Asp Leu Ser Ser Asn Val Ala Thr Ser Phe
1               5                   10                  15

Thr Trp Gly Trp Asp Ser Ser Lys
            20

<210> SEQ ID NO 234
<211> LENGTH: 24
<212> TYPE: PRT
<213> ORGANISM: Homo sapiens

```
<400> SEQUENCE: 234

Glu Ala Leu Pro His Leu Gln Ile Asn Cys Ser His Phe Thr Thr Ile
1               5                   10                  15

Ala Arg Pro Thr Ile Gly Asn Lys
            20

<210> SEQ ID NO 235
<211> LENGTH: 25
<212> TYPE: PRT
<213> ORGANISM: Homo sapiens

<400> SEQUENCE: 235

Val Gln His Met Asp Leu Ser Asn Ser Val Ile Glu Val Ser Thr Leu
1               5                   10                  15

His Gly Ile Leu Ser Gln Cys Ser Lys
            20                  25

<210> SEQ ID NO 236
<211> LENGTH: 30
<212> TYPE: PRT
<213> ORGANISM: Homo sapiens

<400> SEQUENCE: 236

Glu Asn Phe Pro Gly Val Ser Trp Asp Ser Leu Pro Asp Glu Leu Leu
1               5                   10                  15

Leu Gly Ile Phe Ser Cys Leu Cys Leu Pro Glu Leu Leu Lys
            20                  25                  30

<210> SEQ ID NO 237
<211> LENGTH: 6
<212> TYPE: PRT
<213> ORGANISM: Homo sapiens

<400> SEQUENCE: 237

Glu Thr Gly Ser Ser Lys
1               5

<210> SEQ ID NO 238
<211> LENGTH: 5
<212> TYPE: PRT
<213> ORGANISM: Homo sapiens

<400> SEQUENCE: 238

Ile Met Leu Asn Lys
1               5

<210> SEQ ID NO 239
<211> LENGTH: 5
<212> TYPE: PRT
<213> ORGANISM: Homo sapiens

<400> SEQUENCE: 239

Glu Asp Asp Asp Arg
1               5

<210> SEQ ID NO 240
<211> LENGTH: 6
<212> TYPE: PRT
<213> ORGANISM: Homo sapiens

<400> SEQUENCE: 240

Ile Ile Ala Pro Ser Arg
1               5
```

```
<210> SEQ ID NO 241
<211> LENGTH: 5
<212> TYPE: PRT
<213> ORGANISM: Homo sapiens

<400> SEQUENCE: 241

Glu Glu Val Trp Lys
1               5

<210> SEQ ID NO 242
<211> LENGTH: 8
<212> TYPE: PRT
<213> ORGANISM: Homo sapiens

<400> SEQUENCE: 242

Gln Ser Ser Gly Pro Glu Met Ala
1               5

<210> SEQ ID NO 243
<211> LENGTH: 8
<212> TYPE: PRT
<213> ORGANISM: Homo sapiens

<400> SEQUENCE: 243

Asp Ser Leu Asp Leu Leu Asp Lys
1               5

<210> SEQ ID NO 244
<211> LENGTH: 8
<212> TYPE: PRT
<213> ORGANISM: Homo sapiens

<400> SEQUENCE: 244

Ala Met Leu Ser Glu Gln Asn Arg
1               5

<210> SEQ ID NO 245
<211> LENGTH: 8
<212> TYPE: PRT
<213> ORGANISM: Homo sapiens

<400> SEQUENCE: 245

Leu Glu Glu Ile Tyr Pro Pro Lys
1               5

<210> SEQ ID NO 246
<211> LENGTH: 10
<212> TYPE: PRT
<213> ORGANISM: Homo sapiens

<400> SEQUENCE: 246

Glu Asp Gly Gly Ala Glu Phe Ser Ala Arg
1               5                   10

<210> SEQ ID NO 247
<211> LENGTH: 10
<212> TYPE: PRT
<213> ORGANISM: Homo sapiens

<400> SEQUENCE: 247

Tyr Met Ala Thr Gln Glu Asn Val Val Lys
1               5                   10
```

```
<210> SEQ ID NO 248
<211> LENGTH: 10
<212> TYPE: PRT
<213> ORGANISM: Homo sapiens

<400> SEQUENCE: 248

Val Tyr Pro Asn Ser Thr Cys Lys Pro Arg
1               5                   10

<210> SEQ ID NO 249
<211> LENGTH: 10
<212> TYPE: PRT
<213> ORGANISM: Homo sapiens

<400> SEQUENCE: 249

Trp Met Val Pro Phe Ala Met Val Ile Arg
1               5                   10

<210> SEQ ID NO 250
<211> LENGTH: 12
<212> TYPE: PRT
<213> ORGANISM: Homo sapiens

<400> SEQUENCE: 250

Gly Ser Pro Leu Pro Val Leu Ser Trp Ala Asn Arg
1               5                   10

<210> SEQ ID NO 251
<211> LENGTH: 16
<212> TYPE: PRT
<213> ORGANISM: Homo sapiens

<400> SEQUENCE: 251

Ala Ser Pro Leu Pro Ser Gly Leu Leu Thr Pro Pro Gln Ser Gly Lys
1               5                   10                  15

<210> SEQ ID NO 252
<211> LENGTH: 12
<212> TYPE: PRT
<213> ORGANISM: Homo sapiens

<400> SEQUENCE: 252

Glu Thr Phe Tyr Leu Ala Gln Asp Phe Phe Asp Arg
1               5                   10

<210> SEQ ID NO 253
<211> LENGTH: 14
<212> TYPE: PRT
<213> ORGANISM: Homo sapiens

<400> SEQUENCE: 253

Gly Val Ala Asp Glu Asp Ala His Asn Ile Gln Thr His Arg
1               5                   10

<210> SEQ ID NO 254
<211> LENGTH: 16
<212> TYPE: PRT
<213> ORGANISM: Homo sapiens

<400> SEQUENCE: 254

Thr Leu Leu Gln Leu Ile Gly Ile Ser Ser Leu Phe Ile Ala Ala Lys
1               5                   10                  15

<210> SEQ ID NO 255
<211> LENGTH: 14
```

```
<212> TYPE: PRT
<213> ORGANISM: Homo sapiens

<400> SEQUENCE: 255

Asp Gln His Phe Leu Glu Gln His Pro Leu Leu Gln Pro Lys
1               5                   10

<210> SEQ ID NO 256
<211> LENGTH: 14
<212> TYPE: PRT
<213> ORGANISM: Homo sapiens

<400> SEQUENCE: 256

Val Ser Gly Tyr Gln Trp Cys Asp Ile Glu Asn Cys Val Lys
1               5                   10

<210> SEQ ID NO 257
<211> LENGTH: 16
<212> TYPE: PRT
<213> ORGANISM: Homo sapiens

<400> SEQUENCE: 257

Ala Asn Val Thr Val Phe Leu Gln Asp Pro Asp Glu Glu Met Ala Lys
1               5                   10                  15

<210> SEQ ID NO 258
<211> LENGTH: 15
<212> TYPE: PRT
<213> ORGANISM: Homo sapiens

<400> SEQUENCE: 258

Ala Ile Leu Leu Asp Trp Leu Met Glu Val Cys Glu Val Tyr Lys
1               5                   10                  15

<210> SEQ ID NO 259
<211> LENGTH: 26
<212> TYPE: PRT
<213> ORGANISM: Homo sapiens

<400> SEQUENCE: 259

Asp Gln Cys Gly Ser Gln Pro Trp Asp Asn Asn Ala Val Cys Ala Asp
1               5                   10                  15

Pro Cys Ser Leu Ile Pro Thr Pro Asp Lys
            20                  25

<210> SEQ ID NO 260
<211> LENGTH: 26
<212> TYPE: PRT
<213> ORGANISM: Homo sapiens

<400> SEQUENCE: 260

Leu His Gln Phe Ala Tyr Val Thr Asp Gly Ala Cys Ser Gly Asp Glu
1               5                   10                  15

Ile Leu Thr Met Glu Leu Met Ile Met Lys
            20                  25

<210> SEQ ID NO 261
<211> LENGTH: 5
<212> TYPE: PRT
<213> ORGANISM: Homo sapiens

<400> SEQUENCE: 261

Phe Ser Glu Gly Arg
1               5
```

<210> SEQ ID NO 262
<211> LENGTH: 5
<212> TYPE: PRT
<213> ORGANISM: Homo sapiens

<400> SEQUENCE: 262

Ser Asp Gly Tyr Arg
1               5

<210> SEQ ID NO 263
<211> LENGTH: 4
<212> TYPE: PRT
<213> ORGANISM: Homo sapiens

<400> SEQUENCE: 263

Phe Tyr Trp Arg
1

<210> SEQ ID NO 264
<211> LENGTH: 7
<212> TYPE: PRT
<213> ORGANISM: Homo sapiens

<400> SEQUENCE: 264

Gly Val Val Val Pro Thr Arg
1               5

<210> SEQ ID NO 265
<211> LENGTH: 6
<212> TYPE: PRT
<213> ORGANISM: Homo sapiens

<400> SEQUENCE: 265

Trp Pro Ala Leu Pro Arg
1               5

<210> SEQ ID NO 266
<211> LENGTH: 7
<212> TYPE: PRT
<213> ORGANISM: Homo sapiens

<400> SEQUENCE: 266

Ser Ala Ser Glu Val Asp Arg
1               5

<210> SEQ ID NO 267
<211> LENGTH: 7
<212> TYPE: PRT
<213> ORGANISM: Homo sapiens

<400> SEQUENCE: 267

Asp Asp Val Asn Gly Ile Arg
1               5

<210> SEQ ID NO 268
<211> LENGTH: 7
<212> TYPE: PRT
<213> ORGANISM: Homo sapiens

<400> SEQUENCE: 268

Ala Gln Met Val Asp Pro Arg
1               5

```
<210> SEQ ID NO 269
<211> LENGTH: 7
<212> TYPE: PRT
<213> ORGANISM: Homo sapiens

<400> SEQUENCE: 269

Met Leu Leu Phe Ser Gly Arg
1               5

<210> SEQ ID NO 270
<211> LENGTH: 7
<212> TYPE: PRT
<213> ORGANISM: Homo sapiens

<400> SEQUENCE: 270

Leu Phe Phe Phe Ser Gly Arg
1               5

<210> SEQ ID NO 271
<211> LENGTH: 7
<212> TYPE: PRT
<213> ORGANISM: Homo sapiens

<400> SEQUENCE: 271

Ala Tyr Phe Cys Gln Asp Arg
1               5

<210> SEQ ID NO 272
<211> LENGTH: 9
<212> TYPE: PRT
<213> ORGANISM: Homo sapiens

<400> SEQUENCE: 272

Ala Val Ile Asp Asp Ala Phe Ala Arg
1               5

<210> SEQ ID NO 273
<211> LENGTH: 8
<212> TYPE: PRT
<213> ORGANISM: Homo sapiens

<400> SEQUENCE: 273

Leu Asp Ser Val Phe Glu Glu Arg
1               5

<210> SEQ ID NO 274
<211> LENGTH: 8
<212> TYPE: PRT
<213> ORGANISM: Homo sapiens

<400> SEQUENCE: 274

Leu Phe Gly Phe Cys Pro Thr Arg
1               5

<210> SEQ ID NO 275
<211> LENGTH: 8
<212> TYPE: PRT
<213> ORGANISM: Homo sapiens

<400> SEQUENCE: 275

Phe Gly Phe Cys Pro Ser Glu Arg
1               5

<210> SEQ ID NO 276
<211> LENGTH: 9
```

```
<212> TYPE: PRT
<213> ORGANISM: Homo sapiens

<400> SEQUENCE: 276

Phe Thr Glu Gly Pro Pro Leu His Lys
1               5

<210> SEQ ID NO 277
<211> LENGTH: 9
<212> TYPE: PRT
<213> ORGANISM: Homo sapiens

<400> SEQUENCE: 277

Phe Gln Thr Phe Glu Gly Asp Leu Lys
1               5

<210> SEQ ID NO 278
<211> LENGTH: 10
<212> TYPE: PRT
<213> ORGANISM: Homo sapiens

<400> SEQUENCE: 278

Ser Tyr Ser Ala Cys Thr Thr Asp Gly Arg
1               5                   10

<210> SEQ ID NO 279
<211> LENGTH: 10
<212> TYPE: PRT
<213> ORGANISM: Homo sapiens

<400> SEQUENCE: 279

Glu Tyr Ser Thr Cys Thr Ser Glu Gly Arg
1               5                   10

<210> SEQ ID NO 280
<211> LENGTH: 10
<212> TYPE: PRT
<213> ORGANISM: Homo sapiens

<400> SEQUENCE: 280

Trp Cys Ala Thr Thr Ala Asn Tyr Asp Arg
1               5                   10

<210> SEQ ID NO 281
<211> LENGTH: 13
<212> TYPE: PRT
<213> ORGANISM: Homo sapiens

<400> SEQUENCE: 281

Gly Ser Arg Pro Gln Gly Pro Phe Leu Ile Ala Asp Lys
1               5                   10

<210> SEQ ID NO 282
<211> LENGTH: 15
<212> TYPE: PRT
<213> ORGANISM: Homo sapiens

<400> SEQUENCE: 282

Leu Gly Leu Gly Ala Asp Val Ala Gln Val Thr Gly Ala Leu Arg
1               5                   10                  15

<210> SEQ ID NO 283
<211> LENGTH: 14
<212> TYPE: PRT
<213> ORGANISM: Homo sapiens
```

<400> SEQUENCE: 283

Gln Val Trp Val Tyr Thr Gly Ala Ser Val Leu Gly Pro Arg
1               5                   10

<210> SEQ ID NO 284
<211> LENGTH: 13
<212> TYPE: PRT
<213> ORGANISM: Homo sapiens

<400> SEQUENCE: 284

Leu Trp Cys Ala Thr Thr Ser Asn Phe Asp Ser Asp Lys
1               5                   10

<210> SEQ ID NO 285
<211> LENGTH: 15
<212> TYPE: PRT
<213> ORGANISM: Homo sapiens

<400> SEQUENCE: 285

Ala Phe Ala Leu Trp Ser Ala Val Thr Pro Leu Thr Phe Thr Arg
1               5                   10                  15

<210> SEQ ID NO 286
<211> LENGTH: 16
<212> TYPE: PRT
<213> ORGANISM: Homo sapiens

<400> SEQUENCE: 286

Met Phe Pro Gly Val Pro Leu Asp Thr His Asp Val Phe Gln Tyr Arg
1               5                   10                  15

<210> SEQ ID NO 287
<211> LENGTH: 18
<212> TYPE: PRT
<213> ORGANISM: Homo sapiens

<400> SEQUENCE: 287

Phe Gly Asn Ala Asp Gly Ala Ala Cys His Phe Pro Phe Ile Phe Glu
1               5                   10                  15

Gly Arg

<210> SEQ ID NO 288
<211> LENGTH: 18
<212> TYPE: PRT
<213> ORGANISM: Homo sapiens

<400> SEQUENCE: 288

Ser Asp Gly Leu Pro Trp Cys Ser Thr Thr Ala Asn Tyr Asp Thr Asp
1               5                   10                  15

Asp Arg

<210> SEQ ID NO 289
<211> LENGTH: 22
<212> TYPE: PRT
<213> ORGANISM: Homo sapiens

<400> SEQUENCE: 289

Asp Ala Asp Ile Val Ile Gln Phe Gly Val Ala Glu His Gly Asp Gly
1               5                   10                  15

Tyr Pro Phe Asp Gly Lys
            20

<210> SEQ ID NO 290
<211> LENGTH: 24
<212> TYPE: PRT
<213> ORGANISM: Homo sapiens

<400> SEQUENCE: 290

Ala Asp Ser Thr Val Met Gly Gly Asn Ser Ala Gly Glu Leu Cys Val
1               5                   10                  15

Phe Pro Phe Thr Phe Leu Gly Lys
            20

<210> SEQ ID NO 291
<211> LENGTH: 19
<212> TYPE: PRT
<213> ORGANISM: Homo sapiens

<400> SEQUENCE: 291

Trp His His His Asn Ile Thr Tyr Trp Ile Gln Asn Tyr Ser Glu Asp
1               5                   10                  15

Leu Pro Arg

<210> SEQ ID NO 292
<211> LENGTH: 22
<212> TYPE: PRT
<213> ORGANISM: Homo sapiens

<400> SEQUENCE: 292

Ser Glu Leu Asn Gln Val Asp Gln Val Gly Tyr Val Thr Tyr Asp Ile
1               5                   10                  15

Leu Gln Cys Pro Glu Asp
            20

<210> SEQ ID NO 293
<211> LENGTH: 30
<212> TYPE: PRT
<213> ORGANISM: Homo sapiens

<400> SEQUENCE: 293

Asp Gly Leu Leu Ala His Ala Phe Pro Pro Gly Pro Gly Ile Gln Gly
1               5                   10                  15

Asp Ala His Phe Asp Asp Asp Glu Leu Trp Ser Leu Gly Lys
            20                  25                  30

<210> SEQ ID NO 294
<211> LENGTH: 32
<212> TYPE: PRT
<213> ORGANISM: Homo sapiens

<400> SEQUENCE: 294

Leu Tyr Thr Gln Asp Gly Asn Ala Asp Gly Lys Pro Cys Gln Phe Pro
1               5                   10                  15

Phe Ile Phe Gln Gly Gln Ser Tyr Ser Ala Cys Thr Thr Asp Gly Arg
            20                  25                  30

<210> SEQ ID NO 295
<211> LENGTH: 6
<212> TYPE: PRT
<213> ORGANISM: Homo sapiens

<400> SEQUENCE: 295

Ala Gly Ser Gly Ser Arg
1               5

<210> SEQ ID NO 296
<211> LENGTH: 4
<212> TYPE: PRT
<213> ORGANISM: Homo sapiens

<400> SEQUENCE: 296

Leu Phe Phe Lys
1

<210> SEQ ID NO 297
<211> LENGTH: 5
<212> TYPE: PRT
<213> ORGANISM: Homo sapiens

<400> SEQUENCE: 297

Glu Ser Gly Leu Arg
1               5

<210> SEQ ID NO 298
<211> LENGTH: 6
<212> TYPE: PRT
<213> ORGANISM: Homo sapiens

<400> SEQUENCE: 298

Gly Asp Leu Thr Ala Lys
1               5

<210> SEQ ID NO 299
<211> LENGTH: 6
<212> TYPE: PRT
<213> ORGANISM: Homo sapiens

<400> SEQUENCE: 299

Met Asp Glu Ala Asp Arg
1               5

<210> SEQ ID NO 300
<211> LENGTH: 8
<212> TYPE: PRT
<213> ORGANISM: Homo sapiens

<400> SEQUENCE: 300

Val Ala Asn Ala Val Ser Val Lys
1               5

<210> SEQ ID NO 301
<211> LENGTH: 9
<212> TYPE: PRT
<213> ORGANISM: Homo sapiens

<400> SEQUENCE: 301

Thr Gly Ser Asn Ile Asp Cys Glu Lys
1               5

<210> SEQ ID NO 302
<211> LENGTH: 9
<212> TYPE: PRT
<213> ORGANISM: Homo sapiens

<400> SEQUENCE: 302

Gln Leu Ile Ile Asp Leu Glu Thr Arg
1               5

```
<210> SEQ ID NO 303
<211> LENGTH: 10
<212> TYPE: PRT
<213> ORGANISM: Homo sapiens

<400> SEQUENCE: 303

Gln Met Pro Gly Cys Phe Asn Phe Leu Arg
1               5                   10

<210> SEQ ID NO 304
<211> LENGTH: 11
<212> TYPE: PRT
<213> ORGANISM: Homo sapiens

<400> SEQUENCE: 304

Phe Ser Ser Leu His Phe Met Val Glu Val Lys
1               5                   10

<210> SEQ ID NO 305
<211> LENGTH: 12
<212> TYPE: PRT
<213> ORGANISM: Homo sapiens

<400> SEQUENCE: 305

Leu Phe Phe Ile Gln Ala Cys Gly Gly Glu Gln Lys
1               5                   10

<210> SEQ ID NO 306
<211> LENGTH: 13
<212> TYPE: PRT
<213> ORGANISM: Homo sapiens

<400> SEQUENCE: 306

Glu Leu Phe Arg Pro His Met Ile Glu Asp Ile Gln Arg
1               5                   10

<210> SEQ ID NO 307
<211> LENGTH: 18
<212> TYPE: PRT
<213> ORGANISM: Homo sapiens

<400> SEQUENCE: 307

Ile Val Asn Ile Phe Asn Gly Thr Ser Cys Pro Ser Leu Gly Gly Lys
1               5                   10                  15

Pro Lys

<210> SEQ ID NO 308
<211> LENGTH: 17
<212> TYPE: PRT
<213> ORGANISM: Homo sapiens

<400> SEQUENCE: 308

Leu Val Glu Glu Leu Gln Val Asp Gln Leu Trp Asp Ala Leu Leu Ser
1               5                   10                  15

Arg

<210> SEQ ID NO 309
<211> LENGTH: 19
<212> TYPE: PRT
<213> ORGANISM: Homo sapiens

<400> SEQUENCE: 309

Leu Ser Lys Pro Thr Leu Glu Asn Leu Thr Pro Val Val Leu Arg Pro
1               5                   10                  15
```

Glu Ile Arg

<210> SEQ ID NO 310
<211> LENGTH: 25
<212> TYPE: PRT
<213> ORGANISM: Homo sapiens

<400> SEQUENCE: 310

Gly Ser Gln Ala Leu Pro Leu Phe Ile Ser Cys Leu Glu Asp Thr Gly
1               5                   10                  15

Gln Asp Met Leu Ala Ser Phe Leu Arg
            20                  25

<210> SEQ ID NO 311
<211> LENGTH: 30
<212> TYPE: PRT
<213> ORGANISM: Homo sapiens

<400> SEQUENCE: 311

Lys Pro Glu Val Leu Arg Pro Glu Thr Pro Arg Pro Val Asp Ile Gly
1               5                   10                  15

Ser Gly Gly Phe Gly Asp Val Gly Ala Leu Glu Ser Leu Arg
            20                  25                  30

<210> SEQ ID NO 312
<211> LENGTH: 27
<212> TYPE: PRT
<213> ORGANISM: Homo sapiens

<400> SEQUENCE: 312

Gly Asn Ala Asp Leu Ala Tyr Ile Leu Ser Met Glu Pro Cys Gly His
1               5                   10                  15

Cys Leu Ile Ile Asn Asn Val Asn Phe Cys Arg
            20                  25

<210> SEQ ID NO 313
<211> LENGTH: 28
<212> TYPE: PRT
<213> ORGANISM: Homo sapiens

<400> SEQUENCE: 313

Ser Gly Ser Trp Tyr Val Glu Thr Leu Asp Asp Ile Phe Glu Gln Trp
1               5                   10                  15

Ala His Ser Glu Asp Leu Gln Ser Leu Leu Leu Arg
            20                  25

<210> SEQ ID NO 314
<211> LENGTH: 32
<212> TYPE: PRT
<213> ORGANISM: Homo sapiens

<400> SEQUENCE: 314

Asp His Gly Phe Glu Val Ala Ser Thr Ser Pro Glu Asp Glu Ser Pro
1               5                   10                  15

Gly Ser Asn Pro Glu Pro Asp Ala Thr Pro Phe Gln Glu Gly Leu Arg
            20                  25                  30

<210> SEQ ID NO 315
<211> LENGTH: 31
<212> TYPE: PRT
<213> ORGANISM: Homo sapiens

<400> SEQUENCE: 315

Thr Phe Asp Gln Leu Asp Ala Ile Ser Ser Leu Pro Thr Pro Ser Asp
1               5                   10                  15

Ile Phe Val Ser Tyr Ser Thr Phe Pro Gly Phe Val Ser Trp Arg
            20                  25                  30

<210> SEQ ID NO 316
<211> LENGTH: 51
<212> TYPE: PRT
<213> ORGANISM: Homo sapiens

<400> SEQUENCE: 316

Met Val Leu Ala Leu Leu Glu Leu Ala Gln Gln Asp His Gly Ala Leu
1               5                   10                  15

Asp Cys Cys Val Val Ile Leu Ser His Gly Cys Gln Ala Ser His
            20                  25                  30

Leu Gln Phe Pro Gly Ala Val Tyr Gly Thr Asp Gly Cys Pro Val Ser
        35                  40                  45

Val Glu Lys
    50

<210> SEQ ID NO 317
<211> LENGTH: 6
<212> TYPE: PRT
<213> ORGANISM: Homo sapiens

<400> SEQUENCE: 317

Met Ser Gln Ser Asn Arg
1               5

<210> SEQ ID NO 318
<211> LENGTH: 7
<212> TYPE: PRT
<213> ORGANISM: Homo sapiens

<400> SEQUENCE: 318

Asp Gly Val Asn Trp Gly Arg
1               5

<210> SEQ ID NO 319
<211> LENGTH: 9
<212> TYPE: PRT
<213> ORGANISM: Homo sapiens

<400> SEQUENCE: 319

Glu Val Ile Pro Met Ala Ala Val Lys
1               5

<210> SEQ ID NO 320
<211> LENGTH: 8
<212> TYPE: PRT
<213> ORGANISM: Homo sapiens

<400> SEQUENCE: 320

Glu Met Gln Val Leu Val Ser Arg
1               5

<210> SEQ ID NO 321
<211> LENGTH: 9
<212> TYPE: PRT
<213> ORGANISM: Homo sapiens

<400> SEQUENCE: 321

```
Glu Ala Gly Asp Glu Phe Glu Leu Arg
1               5
```

<210> SEQ ID NO 322
<211> LENGTH: 10
<212> TYPE: PRT
<213> ORGANISM: Homo sapiens

<400> SEQUENCE: 322

```
Glu Leu Val Val Asp Phe Leu Ser Tyr Lys
1               5                   10
```

<210> SEQ ID NO 323
<211> LENGTH: 14
<212> TYPE: PRT
<213> ORGANISM: Homo sapiens

<400> SEQUENCE: 323

```
Gly Tyr Ser Trp Ser Gln Phe Ser Asp Val Glu Glu Asn Arg
1               5                   10
```

<210> SEQ ID NO 324
<211> LENGTH: 18
<212> TYPE: PRT
<213> ORGANISM: Homo sapiens

<400> SEQUENCE: 324

```
Ile Val Ala Phe Phe Ser Phe Gly Gly Ala Leu Cys Val Glu Ser Val
1               5                   10                  15

Asp Lys
```

<210> SEQ ID NO 325
<211> LENGTH: 20
<212> TYPE: PRT
<213> ORGANISM: Homo sapiens

<400> SEQUENCE: 325

```
Trp Phe Leu Thr Gly Met Thr Val Ala Gly Val Val Leu Leu Gly Ser
1               5                   10                  15

Leu Phe Ser Arg
            20
```

<210> SEQ ID NO 326
<211> LENGTH: 29
<212> TYPE: PRT
<213> ORGANISM: Homo sapiens

<400> SEQUENCE: 326

```
Ala Phe Ser Asp Leu Thr Ser Gln Leu His Ile Thr Pro Gly Thr Ala
1               5                   10                  15

Tyr Gln Ser Phe Glu Gln Val Val Asn Glu Leu Phe Arg
            20                  25
```

<210> SEQ ID NO 327
<211> LENGTH: 39
<212> TYPE: PRT
<213> ORGANISM: Homo sapiens

<400> SEQUENCE: 327

```
Ile Ala Ala Trp Met Ala Thr Tyr Leu Asn Asp His Leu Glu Pro Trp
1               5                   10                  15

Ile Gln Glu Asn Gly Gly Trp Asp Thr Phe Val Glu Leu Tyr Gly Asn
```

-continued

```
                 20                  25                  30

Asn Ala Ala Ala Glu Ser Arg
        35

<210> SEQ ID NO 328
<211> LENGTH: 44
<212> TYPE: PRT
<213> ORGANISM: Homo sapiens

<400> SEQUENCE: 328

Thr Glu Ala Pro Glu Gly Thr Glu Ser Glu Met Glu Thr Pro Ser Ala
1               5                   10                  15

Ile Asn Gly Asn Pro Ser Trp His Leu Ala Asp Ser Pro Ala Val Asn
            20                  25                  30

Gly Ala Thr Gly His Ser Ser Ser Leu Asp Ala Arg
        35                  40

<210> SEQ ID NO 329
<211> LENGTH: 6
<212> TYPE: PRT
<213> ORGANISM: Homo sapiens

<400> SEQUENCE: 329

Ala Ile Pro Ala Thr Arg
1               5

<210> SEQ ID NO 330
<211> LENGTH: 6
<212> TYPE: PRT
<213> ORGANISM: Homo sapiens

<400> SEQUENCE: 330

Asn Ser Pro Val Thr Lys
1               5

<210> SEQ ID NO 331
<211> LENGTH: 5
<212> TYPE: PRT
<213> ORGANISM: Homo sapiens

<400> SEQUENCE: 331

Ile Ile Tyr Asp Arg
1               5

<210> SEQ ID NO 332
<211> LENGTH: 6
<212> TYPE: PRT
<213> ORGANISM: Homo sapiens

<400> SEQUENCE: 332

Asn Ser Pro Glu Asp Lys
1               5

<210> SEQ ID NO 333
<211> LENGTH: 6
<212> TYPE: PRT
<213> ORGANISM: Homo sapiens

<400> SEQUENCE: 333

Phe Leu Met Glu Cys Arg
1               5

<210> SEQ ID NO 334
```

```
<211> LENGTH: 12
<212> TYPE: PRT
<213> ORGANISM: Homo sapiens

<400> SEQUENCE: 334

Ala Gly Gly Glu Glu Ser Gln Phe Glu Met Asp Ile
1               5                   10

<210> SEQ ID NO 335
<211> LENGTH: 14
<212> TYPE: PRT
<213> ORGANISM: Homo sapiens

<400> SEQUENCE: 335

Ala Cys Ser Gly Gly Ser Ser Cys Ser Gln Thr Pro Ser Arg
1               5                   10

<210> SEQ ID NO 336
<211> LENGTH: 26
<212> TYPE: PRT
<213> ORGANISM: Homo sapiens

<400> SEQUENCE: 336

Asp Leu Pro Thr Ile Pro Gly Val Thr Ser Pro Ser Asp Glu Pro
1               5                   10                  15

Pro Met Glu Ala Ser Gln Ser His Leu Arg
            20                  25

<210> SEQ ID NO 337
<211> LENGTH: 31
<212> TYPE: PRT
<213> ORGANISM: Homo sapiens

<400> SEQUENCE: 337

Val Val Leu Gly Asp Gly Val Gln Leu Pro Pro Gly Asp Tyr Ser Thr
1               5                   10                  15

Thr Pro Gly Gly Thr Leu Phe Ser Thr Thr Pro Gly Gly Thr Arg
            20                  25                  30

<210> SEQ ID NO 338
<211> LENGTH: 5
<212> TYPE: PRT
<213> ORGANISM: Homo sapiens

<400> SEQUENCE: 338

Glu Ile Val Met Lys
1               5

<210> SEQ ID NO 339
<211> LENGTH: 6
<212> TYPE: PRT
<213> ORGANISM: Homo sapiens

<400> SEQUENCE: 339

Met Ala His Ala Gly Arg
1               5

<210> SEQ ID NO 340
<211> LENGTH: 5
<212> TYPE: PRT
<213> ORGANISM: Homo sapiens

<400> SEQUENCE: 340

Tyr Ile His Tyr Lys
```

```
1               5
```

<210> SEQ ID NO 341
<211> LENGTH: 6
<212> TYPE: PRT
<213> ORGANISM: Homo sapiens

<400> SEQUENCE: 341

```
Thr Gly Tyr Asp Asn Arg
1               5
```

<210> SEQ ID NO 342
<211> LENGTH: 7
<212> TYPE: PRT
<213> ORGANISM: Homo sapiens

<400> SEQUENCE: 342

```
Asp Gly Val Asn Trp Gly Arg
1               5
```

<210> SEQ ID NO 343
<211> LENGTH: 8
<212> TYPE: PRT
<213> ORGANISM: Homo sapiens

<400> SEQUENCE: 343

```
Gln Ala Gly Asp Asp Phe Ser Arg
1               5
```

<210> SEQ ID NO 344
<211> LENGTH: 10
<212> TYPE: PRT
<213> ORGANISM: Homo sapiens

<400> SEQUENCE: 344

```
Phe Ala Thr Val Val Glu Glu Leu Phe Arg
1               5                   10
```

<210> SEQ ID NO 345
<211> LENGTH: 17
<212> TYPE: PRT
<213> ORGANISM: Homo sapiens

<400> SEQUENCE: 345

```
Asp Phe Ala Glu Met Ser Ser Gln Leu His Leu Thr Pro Phe Thr Ala
1               5                   10                  15

Arg
```

<210> SEQ ID NO 346
<211> LENGTH: 18
<212> TYPE: PRT
<213> ORGANISM: Homo sapiens

<400> SEQUENCE: 346

```
Ile Val Ala Phe Phe Glu Phe Gly Gly Val Met Cys Val Glu Ser Val
1               5                   10                  15

Asn Arg
```

<210> SEQ ID NO 347
<211> LENGTH: 21
<212> TYPE: PRT
<213> ORGANISM: Homo sapiens

<400> SEQUENCE: 347

```
Thr Leu Leu Ser Leu Ala Leu Val Gly Ala Cys Ile Thr Leu Gly Ala
1               5                   10                  15

Tyr Leu Gly His Lys
            20
```

<210> SEQ ID NO 348
<211> LENGTH: 19
<212> TYPE: PRT
<213> ORGANISM: Homo sapiens

<400> SEQUENCE: 348

```
Glu Met Ser Pro Leu Val Asp Asn Ile Ala Leu Trp Met Thr Glu Tyr
1               5                   10                  15

Leu Asn Arg
```

<210> SEQ ID NO 349
<211> LENGTH: 30
<212> TYPE: PRT
<213> ORGANISM: Homo sapiens

<400> SEQUENCE: 349

```
Thr Ser Pro Leu Gln Thr Pro Ala Ala Pro Gly Ala Ala Gly Pro
1               5                   10                  15

Ala Leu Ser Pro Val Pro Pro Val Val His Leu Thr Leu Arg
            20                  25                  30
```

<210> SEQ ID NO 350
<211> LENGTH: 37
<212> TYPE: PRT
<213> ORGANISM: Homo sapiens

<400> SEQUENCE: 350

```
Gly Tyr Glu Trp Asp Ala Gly Asp Val Gly Ala Ala Pro Pro Gly Ala
1               5                   10                  15

Ala Pro Ala Pro Gly Ile Phe Ser Ser Gln Pro Gly His Thr Pro His
            20                  25                  30

Pro Ala Ala Ser Arg
        35
```

<210> SEQ ID NO 351
<211> LENGTH: 35
<212> TYPE: PRT
<213> ORGANISM: Homo sapiens

<400> SEQUENCE: 351

```
His Leu His Thr Trp Ile Gln Asp Asn Gly Gly Trp Asp Ala Phe Val
1               5                   10                  15

Glu Leu Tyr Gly Pro Ser Met Arg Pro Leu Phe Asp Phe Ser Trp Leu
            20                  25                  30

Ser Leu Lys
        35
```

<210> SEQ ID NO 352
<211> LENGTH: 8
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Selenocysteine

<400> SEQUENCE: 352

```
Gly Pro Ser Ser Gly Gly Xaa Gly
1               5

<210> SEQ ID NO 353
<211> LENGTH: 4
<212> TYPE: PRT
<213> ORGANISM: Homo sapiens

<400> SEQUENCE: 353

Gln Leu Asp Arg
1

<210> SEQ ID NO 354
<211> LENGTH: 6
<212> TYPE: PRT
<213> ORGANISM: Homo sapiens

<400> SEQUENCE: 354

Gln Leu Glu Glu Glu Lys
1               5

<210> SEQ ID NO 355
<211> LENGTH: 8
<212> TYPE: PRT
<213> ORGANISM: Homo sapiens

<400> SEQUENCE: 355

Gln Glu Ala Leu Ala Ala Ala Arg
1               5

<210> SEQ ID NO 356
<211> LENGTH: 12
<212> TYPE: PRT
<213> ORGANISM: Homo sapiens

<400> SEQUENCE: 356

Ala Ala Ala Ala Val Glu Pro Asp Val Val Val Lys
1               5                   10

<210> SEQ ID NO 357
<211> LENGTH: 11
<212> TYPE: PRT
<213> ORGANISM: Homo sapiens

<400> SEQUENCE: 357

Met Gln Glu Glu Leu Asn Ala Gln Val Glu Lys
1               5                   10

<210> SEQ ID NO 358
<211> LENGTH: 11
<212> TYPE: PRT
<213> ORGANISM: Homo sapiens

<400> SEQUENCE: 358

Ile Glu Met Trp Asp Ser Met Gln Glu Gly Lys
1               5                   10

<210> SEQ ID NO 359
<211> LENGTH: 17
<212> TYPE: PRT
<213> ORGANISM: Homo sapiens

<400> SEQUENCE: 359

Lys Pro Gln Glu Glu Asp Ser Pro Gly Pro Ser Thr Ser Ser Val Leu
```

```
                1               5              10              15

Lys

<210> SEQ ID NO 360
<211> LENGTH: 17
<212> TYPE: PRT
<213> ORGANISM: Homo sapiens

<400> SEQUENCE: 360

Gln Glu Glu Ser Leu Ser Ala Arg Pro Ala Leu Glu Thr Glu Gly Leu
1               5                   10                  15

Arg

<210> SEQ ID NO 361
<211> LENGTH: 21
<212> TYPE: PRT
<213> ORGANISM: Homo sapiens

<400> SEQUENCE: 361

Gly Gly Gly Tyr Asn Pro Leu Ser Gly Glu Gly Gly Ala Cys Ser
1               5                   10                  15

Trp Arg Pro Gly Arg
            20

<210> SEQ ID NO 362
<211> LENGTH: 30
<212> TYPE: PRT
<213> ORGANISM: Homo sapiens

<400> SEQUENCE: 362

Phe Leu His Thr Thr Val Gly Ser Leu Leu Ala Thr Tyr Gly Trp Tyr
1               5                   10                  15

Ile Val Phe Ser Cys Ile Leu Leu Tyr Val Val Phe Gln Lys
                20                  25                  30

<210> SEQ ID NO 363
<211> LENGTH: 5
<212> TYPE: PRT
<213> ORGANISM: Homo sapiens

<400> SEQUENCE: 363

Gln Leu Tyr Asn Lys
1               5

<210> SEQ ID NO 364
<211> LENGTH: 7
<212> TYPE: PRT
<213> ORGANISM: Homo sapiens

<400> SEQUENCE: 364

Gln Glu Thr Leu Pro Ser Lys
1               5

<210> SEQ ID NO 365
<211> LENGTH: 9
<212> TYPE: PRT
<213> ORGANISM: Homo sapiens

<400> SEQUENCE: 365

Gly Asp Ser Val Val Tyr Gly Leu Arg
1               5
```

```
<210> SEQ ID NO 366
<211> LENGTH: 10
<212> TYPE: PRT
<213> ORGANISM: Homo sapiens

<400> SEQUENCE: 366

Gln Ala Asp Ser Gly Ser Ser Glu Glu Lys
1               5                   10

<210> SEQ ID NO 367
<211> LENGTH: 13
<212> TYPE: PRT
<213> ORGANISM: Homo sapiens

<400> SEQUENCE: 367

Ile Ser His Glu Leu Asp Ser Ala Ser Ser Glu Val Asn
1               5                   10

<210> SEQ ID NO 368
<211> LENGTH: 16
<212> TYPE: PRT
<213> ORGANISM: Homo sapiens

<400> SEQUENCE: 368

Tyr Pro Asp Ala Val Ala Thr Trp Leu Asn Pro Asp Pro Ser Gln Lys
1               5                   10                  15

<210> SEQ ID NO 369
<211> LENGTH: 17
<212> TYPE: PRT
<213> ORGANISM: Homo sapiens

<400> SEQUENCE: 369

Ala Ile Pro Val Ala Gln Asp Leu Asn Ala Pro Ser Asp Trp Asp Ser
1               5                   10                  15

Arg

<210> SEQ ID NO 370
<211> LENGTH: 19
<212> TYPE: PRT
<213> ORGANISM: Homo sapiens

<400> SEQUENCE: 370

Gln Asn Leu Leu Ala Pro Gln Asn Ala Val Ser Ser Glu Glu Thr Asn
1               5                   10                  15

Asp Phe Lys

<210> SEQ ID NO 371
<211> LENGTH: 19
<212> TYPE: PRT
<213> ORGANISM: Homo sapiens

<400> SEQUENCE: 371

Ala Asn Asp Glu Ser Asn Glu His Ser Asp Val Ile Asp Ser Gln Glu
1               5                   10                  15

Leu Ser Lys

<210> SEQ ID NO 372
<211> LENGTH: 19
<212> TYPE: PRT
<213> ORGANISM: Homo sapiens

<400> SEQUENCE: 372
```

```
Asp Ser Tyr Glu Thr Ser Gln Leu Asp Asp Gln Ser Ala Glu Thr His
1               5                   10                  15

Ser His Lys

<210> SEQ ID NO 373
<211> LENGTH: 19
<212> TYPE: PRT
<213> ORGANISM: Homo sapiens

<400> SEQUENCE: 373

Glu Phe His Ser His Glu Phe His Ser His Glu Asp Met Leu Val Val
1               5                   10                  15

Asp Pro Lys

<210> SEQ ID NO 374
<211> LENGTH: 28
<212> TYPE: PRT
<213> ORGANISM: Homo sapiens

<400> SEQUENCE: 374

Arg Pro Asp Ile Gln Tyr Pro Asp Ala Thr Asp Glu Asp Ile Thr Ser
1               5                   10                  15

His Met Glu Ser Glu Glu Leu Asn Gly Ala Tyr Lys
            20                  25

<210> SEQ ID NO 375
<211> LENGTH: 6
<212> TYPE: PRT
<213> ORGANISM: Homo sapiens

<400> SEQUENCE: 375

Ala Ala Pro Ala Ala Arg
1               5

<210> SEQ ID NO 376
<211> LENGTH: 6
<212> TYPE: PRT
<213> ORGANISM: Homo sapiens

<400> SEQUENCE: 376

Ala Ala Gly Ser Pro Arg
1               5

<210> SEQ ID NO 377
<211> LENGTH: 6
<212> TYPE: PRT
<213> ORGANISM: Homo sapiens

<400> SEQUENCE: 377

Ala Leu Pro Gly Gly Arg
1               5

<210> SEQ ID NO 378
<211> LENGTH: 6
<212> TYPE: PRT
<213> ORGANISM: Homo sapiens

<400> SEQUENCE: 378

Gly Thr Ala Ala Pro Arg
1               5

<210> SEQ ID NO 379
<211> LENGTH: 4
```

```
<212> TYPE: PRT
<213> ORGANISM: Homo sapiens

<400> SEQUENCE: 379

Leu Tyr Cys Lys
1

<210> SEQ ID NO 380
<211> LENGTH: 6
<212> TYPE: PRT
<213> ORGANISM: Homo sapiens

<400> SEQUENCE: 380

Thr Gly Pro Gly Gln Lys
1               5

<210> SEQ ID NO 381
<211> LENGTH: 5
<212> TYPE: PRT
<213> ORGANISM: Homo sapiens

<400> SEQUENCE: 381

Thr Gly Gln Tyr Lys
1               5

<210> SEQ ID NO 382
<211> LENGTH: 6
<212> TYPE: PRT
<213> ORGANISM: Homo sapiens

<400> SEQUENCE: 382

Gly Val Val Ser Ile Lys
1               5

<210> SEQ ID NO 383
<211> LENGTH: 5
<212> TYPE: PRT
<213> ORGANISM: Homo sapiens

<400> SEQUENCE: 383

Tyr Leu Ala Met Lys
1               5

<210> SEQ ID NO 384
<211> LENGTH: 6
<212> TYPE: PRT
<213> ORGANISM: Homo sapiens

<400> SEQUENCE: 384

Gly Val Cys Ala Asn Arg
1               5

<210> SEQ ID NO 385
<211> LENGTH: 6
<212> TYPE: PRT
<213> ORGANISM: Homo sapiens

<400> SEQUENCE: 385

Ile His Pro Asp Gly Arg
1               5

<210> SEQ ID NO 386
<211> LENGTH: 6
<212> TYPE: PRT
<213> ORGANISM: Homo sapiens
```

<400> SEQUENCE: 386

Ser Asp Pro His Ile Lys
1               5

<210> SEQ ID NO 387
<211> LENGTH: 7
<212> TYPE: PRT
<213> ORGANISM: Homo sapiens

<400> SEQUENCE: 387

His Pro Ser Val Asn Pro Arg
1               5

<210> SEQ ID NO 388
<211> LENGTH: 7
<212> TYPE: PRT
<213> ORGANISM: Homo sapiens

<400> SEQUENCE: 388

Asn Gly Gly Phe Phe Leu Arg
1               5

<210> SEQ ID NO 389
<211> LENGTH: 8
<212> TYPE: PRT
<213> ORGANISM: Homo sapiens

<400> SEQUENCE: 389

Leu Gln Leu Gln Ala Glu Glu Arg
1               5

<210> SEQ ID NO 390
<211> LENGTH: 9
<212> TYPE: PRT
<213> ORGANISM: Homo sapiens

<400> SEQUENCE: 390

Thr Glu Glu Arg Pro Ser Gly Ser Arg
1               5

<210> SEQ ID NO 391
<211> LENGTH: 10
<212> TYPE: PRT
<213> ORGANISM: Homo sapiens

<400> SEQUENCE: 391

Ala Ile Leu Phe Leu Pro Met Ser Ala Lys
1               5                   10

<210> SEQ ID NO 392
<211> LENGTH: 9
<212> TYPE: PRT
<213> ORGANISM: Homo sapiens

<400> SEQUENCE: 392

Tyr Thr Ser Trp Tyr Val Ala Leu Lys
1               5

<210> SEQ ID NO 393
<211> LENGTH: 10
<212> TYPE: PRT
<213> ORGANISM: Homo sapiens

<400> SEQUENCE: 393

```
Leu Glu Ser Asn Asn Tyr Asn Thr Tyr Arg
1               5                   10

<210> SEQ ID NO 394
<211> LENGTH: 11
<212> TYPE: PRT
<213> ORGANISM: Homo sapiens

<400> SEQUENCE: 394

Cys Val Thr Asp Glu Cys Phe Phe Phe Glu Arg
1               5                   10

<210> SEQ ID NO 395
<211> LENGTH: 17
<212> TYPE: PRT
<213> ORGANISM: Homo sapiens

<400> SEQUENCE: 395

Gly Cys Asn Gly Ile Pro Gly Ala Ala Ala Trp Glu Ala Ala Leu Pro
1               5                   10                  15

Arg

<210> SEQ ID NO 396
<211> LENGTH: 24
<212> TYPE: PRT
<213> ORGANISM: Homo sapiens

<400> SEQUENCE: 396

Met Val Gly Val Gly Gly Gly Asp Val Glu Asp Val Thr Pro Arg Pro
1               5                   10                  15

Gly Gly Cys Gln Ile Ser Gly Arg
            20

<210> SEQ ID NO 397
<211> LENGTH: 36
<212> TYPE: PRT
<213> ORGANISM: Homo sapiens

<400> SEQUENCE: 397

Gly Ser Arg Pro Gly Pro Ala Gly Thr Met Ala Ala Gly Ser Ile Thr
1               5                   10                  15

Thr Leu Pro Ala Leu Pro Glu Asp Gly Gly Ser Gly Ala Phe Pro Pro
            20                  25                  30

Gly His Phe Lys
            35

<210> SEQ ID NO 398
<211> LENGTH: 6
<212> TYPE: PRT
<213> ORGANISM: Homo sapiens

<400> SEQUENCE: 398

Glu Ala Thr Ser Pro Lys
1               5

<210> SEQ ID NO 399
<211> LENGTH: 6
<212> TYPE: PRT
<213> ORGANISM: Homo sapiens

<400> SEQUENCE: 399

Ile Pro Val Ala Ile Lys
```

```
1               5

<210> SEQ ID NO 400
<211> LENGTH: 5
<212> TYPE: PRT
<213> ORGANISM: Homo sapiens

<400> SEQUENCE: 400

Glu Leu Pro Met Arg
1               5

<210> SEQ ID NO 401
<211> LENGTH: 5
<212> TYPE: PRT
<213> ORGANISM: Homo sapiens

<400> SEQUENCE: 401

Glu Cys Val Asp Lys
1               5

<210> SEQ ID NO 402
<211> LENGTH: 5
<212> TYPE: PRT
<213> ORGANISM: Homo sapiens

<400> SEQUENCE: 402

Glu Thr Glu Phe Lys
1               5

<210> SEQ ID NO 403
<211> LENGTH: 5
<212> TYPE: PRT
<213> ORGANISM: Homo sapiens

<400> SEQUENCE: 403

Leu Leu Gln Glu Arg
1               5

<210> SEQ ID NO 404
<211> LENGTH: 6
<212> TYPE: PRT
<213> ORGANISM: Homo sapiens

<400> SEQUENCE: 404

Gly Glu Asn Ser Cys Lys
1               5

<210> SEQ ID NO 405
<211> LENGTH: 6
<212> TYPE: PRT
<213> ORGANISM: Homo sapiens

<400> SEQUENCE: 405

Thr Pro Gln His Val Lys
1               5

<210> SEQ ID NO 406
<211> LENGTH: 6
<212> TYPE: PRT
<213> ORGANISM: Homo sapiens

<400> SEQUENCE: 406

Asp Glu Ala Thr Cys Lys
1               5
```

```
<210> SEQ ID NO 407
<211> LENGTH: 7
<212> TYPE: PRT
<213> ORGANISM: Homo sapiens

<400> SEQUENCE: 407

Leu Leu Gly Ala Glu Glu Lys
1               5

<210> SEQ ID NO 408
<211> LENGTH: 6
<212> TYPE: PRT
<213> ORGANISM: Homo sapiens

<400> SEQUENCE: 408

Cys Glu Gly Pro Cys Arg
1               5

<210> SEQ ID NO 409
<211> LENGTH: 6
<212> TYPE: PRT
<213> ORGANISM: Homo sapiens

<400> SEQUENCE: 409

Asp Cys Val Ser Cys Arg
1               5

<210> SEQ ID NO 410
<211> LENGTH: 8
<212> TYPE: PRT
<213> ORGANISM: Homo sapiens

<400> SEQUENCE: 410

Leu Phe Gly Thr Ser Gly Gln Lys
1               5

<210> SEQ ID NO 411
<211> LENGTH: 8
<212> TYPE: PRT
<213> ORGANISM: Homo sapiens

<400> SEQUENCE: 411

Ile Thr Asp Phe Gly Leu Ala Lys
1               5

<210> SEQ ID NO 412
<211> LENGTH: 8
<212> TYPE: PRT
<213> ORGANISM: Homo sapiens

<400> SEQUENCE: 412

Glu Tyr His Ala Glu Gly Gly Lys
1               5

<210> SEQ ID NO 413
<211> LENGTH: 8
<212> TYPE: PRT
<213> ORGANISM: Homo sapiens

<400> SEQUENCE: 413

Val Cys Gln Gly Thr Ser Asn Lys
1               5

<210> SEQ ID NO 414
```

```
<211> LENGTH: 7
<212> TYPE: PRT
<213> ORGANISM: Homo sapiens

<400> SEQUENCE: 414

Glu Asp Ser Phe Leu Gln Arg
1               5

<210> SEQ ID NO 415
<211> LENGTH: 8
<212> TYPE: PRT
<213> ORGANISM: Homo sapiens

<400> SEQUENCE: 415

Glu Leu Ile Ile Glu Phe Ser Lys
1               5

<210> SEQ ID NO 416
<211> LENGTH: 8
<212> TYPE: PRT
<213> ORGANISM: Homo sapiens

<400> SEQUENCE: 416

Gly Met Asn Tyr Leu Glu Asp Arg
1               5

<210> SEQ ID NO 417
<211> LENGTH: 8
<212> TYPE: PRT
<213> ORGANISM: Homo sapiens

<400> SEQUENCE: 417

Asn Tyr Asp Leu Ser Phe Leu Lys
1               5

<210> SEQ ID NO 418
<211> LENGTH: 9
<212> TYPE: PRT
<213> ORGANISM: Homo sapiens

<400> SEQUENCE: 418

Glu Ala Lys Pro Asn Gly Ile Phe Lys
1               5

<210> SEQ ID NO 419
<211> LENGTH: 9
<212> TYPE: PRT
<213> ORGANISM: Homo sapiens

<400> SEQUENCE: 419

Asn Gly Leu Gln Ser Cys Pro Ile Lys
1               5

<210> SEQ ID NO 420
<211> LENGTH: 9
<212> TYPE: PRT
<213> ORGANISM: Homo sapiens

<400> SEQUENCE: 420

Gly Leu Trp Ile Pro Glu Gly Glu Lys
1               5

<210> SEQ ID NO 421
<211> LENGTH: 9
<212> TYPE: PRT
```

```
<213> ORGANISM: Homo sapiens

<400> SEQUENCE: 421

Tyr Ser Phe Gly Ala Thr Cys Val Lys
1               5

<210> SEQ ID NO 422
<211> LENGTH: 8
<212> TYPE: PRT
<213> ORGANISM: Homo sapiens

<400> SEQUENCE: 422

Glu Ser Asp Cys Leu Val Cys Arg
1               5

<210> SEQ ID NO 423
<211> LENGTH: 9
<212> TYPE: PRT
<213> ORGANISM: Homo sapiens

<400> SEQUENCE: 423

Cys Asn Leu Leu Glu Gly Glu Pro Arg
1               5

<210> SEQ ID NO 424
<211> LENGTH: 9
<212> TYPE: PRT
<213> ORGANISM: Homo sapiens

<400> SEQUENCE: 424

Tyr Leu Val Ile Gln Gly Asp Glu Arg
1               5

<210> SEQ ID NO 425
<211> LENGTH: 11
<212> TYPE: PRT
<213> ORGANISM: Homo sapiens

<400> SEQUENCE: 425

Val Ala Pro Gln Ser Ser Glu Phe Ile Gly Ala
1               5                   10

<210> SEQ ID NO 426
<211> LENGTH: 11
<212> TYPE: PRT
<213> ORGANISM: Homo sapiens

<400> SEQUENCE: 426

Asp Ser Leu Ser Ile Asn Ala Thr Asn Ile Lys
1               5                   10

<210> SEQ ID NO 427
<211> LENGTH: 10
<212> TYPE: PRT
<213> ORGANISM: Homo sapiens

<400> SEQUENCE: 427

Ile Ile Cys Ala Gln Gln Cys Ser Gly Arg
1               5                   10

<210> SEQ ID NO 428
<211> LENGTH: 11
<212> TYPE: PRT
<213> ORGANISM: Homo sapiens
```

```
<400> SEQUENCE: 428

Val Cys Asn Gly Ile Gly Ile Gly Glu Phe Lys
1               5                   10

<210> SEQ ID NO 429
<211> LENGTH: 12
<212> TYPE: PRT
<213> ORGANISM: Homo sapiens

<400> SEQUENCE: 429

Val Leu Gly Ser Gly Ala Phe Gly Thr Val Tyr Lys
1               5                   10

<210> SEQ ID NO 430
<211> LENGTH: 10
<212> TYPE: PRT
<213> ORGANISM: Homo sapiens

<400> SEQUENCE: 430

Ile Pro Leu Glu Asn Leu Gln Ile Ile Arg
1               5                   10

<210> SEQ ID NO 431
<211> LENGTH: 11
<212> TYPE: PRT
<213> ORGANISM: Homo sapiens

<400> SEQUENCE: 431

Gly Ser Thr Ala Glu Asn Ala Glu Tyr Leu Arg
1               5                   10

<210> SEQ ID NO 432
<211> LENGTH: 11
<212> TYPE: PRT
<213> ORGANISM: Homo sapiens

<400> SEQUENCE: 432

Asn Leu Gln Glu Ile Leu His Gly Ala Val Arg
1               5                   10

<210> SEQ ID NO 433
<211> LENGTH: 10
<212> TYPE: PRT
<213> ORGANISM: Homo sapiens

<400> SEQUENCE: 433

Trp Met Ala Leu Glu Ser Ile Leu His Arg
1               5                   10

<210> SEQ ID NO 434
<211> LENGTH: 13
<212> TYPE: PRT
<213> ORGANISM: Homo sapiens

<400> SEQUENCE: 434

Glu Ile Ser Asp Gly Asp Val Ile Ile Ser Gly Asn Lys
1               5                   10

<210> SEQ ID NO 435
<211> LENGTH: 11
<212> TYPE: PRT
<213> ORGANISM: Homo sapiens

<400> SEQUENCE: 435
```

Cys Trp Met Ile Asp Ala Asp Ser Arg Pro Lys
1               5                   10

<210> SEQ ID NO 436
<211> LENGTH: 11
<212> TYPE: PRT
<213> ORGANISM: Homo sapiens

<400> SEQUENCE: 436

Asn Leu Cys Tyr Ala Asn Thr Ile Asn Trp Lys
1               5                   10

<210> SEQ ID NO 437
<211> LENGTH: 12
<212> TYPE: PRT
<213> ORGANISM: Homo sapiens

<400> SEQUENCE: 437

Asn Tyr Val Val Thr Asp His Gly Ser Cys Val Arg
1               5                   10

<210> SEQ ID NO 438
<211> LENGTH: 13
<212> TYPE: PRT
<213> ORGANISM: Homo sapiens

<400> SEQUENCE: 438

Met His Leu Pro Ser Pro Thr Asp Ser Asn Phe Tyr Arg
1               5                   10

<210> SEQ ID NO 439
<211> LENGTH: 13
<212> TYPE: PRT
<213> ORGANISM: Homo sapiens

<400> SEQUENCE: 439

Thr Asp Leu His Ala Phe Glu Asn Leu Glu Ile Ile Arg
1               5                   10

<210> SEQ ID NO 440
<211> LENGTH: 15
<212> TYPE: PRT
<213> ORGANISM: Homo sapiens

<400> SEQUENCE: 440

Ala Cys Gly Ala Asp Ser Tyr Glu Met Glu Glu Asp Gly Val Arg
1               5                   10                  15

<210> SEQ ID NO 441
<211> LENGTH: 16
<212> TYPE: PRT
<213> ORGANISM: Homo sapiens

<400> SEQUENCE: 441

Thr Cys Pro Ala Gly Val Met Gly Glu Asn Asn Thr Leu Val Trp Lys
1               5                   10                  15

<210> SEQ ID NO 442
<211> LENGTH: 15
<212> TYPE: PRT
<213> ORGANISM: Homo sapiens

<400> SEQUENCE: 442

Glu Ile Thr Gly Phe Leu Leu Ile Gln Ala Trp Pro Glu Asn Arg
1               5                   10                  15

<210> SEQ ID NO 443
<211> LENGTH: 17
<212> TYPE: PRT
<213> ORGANISM: Homo sapiens

<400> SEQUENCE: 443

Asn Cys Thr Ser Ile Ser Gly Asp Leu His Ile Leu Pro Val Ala Phe
1               5                   10                  15
Arg

<210> SEQ ID NO 444
<211> LENGTH: 16
<212> TYPE: PRT
<213> ORGANISM: Homo sapiens

<400> SEQUENCE: 444

Leu Thr Gln Leu Gly Thr Phe Glu Asp His Phe Leu Ser Leu Gln Arg
1               5                   10                  15

<210> SEQ ID NO 445
<211> LENGTH: 16
<212> TYPE: PRT
<213> ORGANISM: Homo sapiens

<400> SEQUENCE: 445

Phe Ser Asn Asn Pro Ala Leu Cys Asn Val Glu Ser Ile Gln Trp Arg
1               5                   10                  15

<210> SEQ ID NO 446
<211> LENGTH: 18
<212> TYPE: PRT
<213> ORGANISM: Homo sapiens

<400> SEQUENCE: 446

Thr Ile Gln Glu Val Ala Gly Tyr Val Leu Ile Ala Leu Asn Thr Val
1               5                   10                  15
Glu Arg

<210> SEQ ID NO 447
<211> LENGTH: 17
<212> TYPE: PRT
<213> ORGANISM: Homo sapiens

<400> SEQUENCE: 447

Leu Pro Gln Pro Pro Ile Cys Thr Ile Asp Val Tyr Met Ile Met Val
1               5                   10                  15
Lys

<210> SEQ ID NO 448
<211> LENGTH: 17
<212> TYPE: PRT
<213> ORGANISM: Homo sapiens

<400> SEQUENCE: 448

Asp Asn Ile Gly Ser Gln Tyr Leu Leu Asn Trp Cys Val Gln Ile Ala
1               5                   10                  15
Lys

<210> SEQ ID NO 449
<211> LENGTH: 19
<212> TYPE: PRT

<213> ORGANISM: Homo sapiens

<400> SEQUENCE: 449

Glu Leu Val Glu Pro Leu Thr Pro Ser Gly Glu Ala Pro Asn Gln Ala
1               5                   10                  15

Leu Leu Arg

<210> SEQ ID NO 450
<211> LENGTH: 18
<212> TYPE: PRT
<213> ORGANISM: Homo sapiens

<400> SEQUENCE: 450

Ser Pro Ser Asp Cys Cys His Asn Gln Cys Ala Ala Gly Cys Thr Gly
1               5                   10                  15

Pro Arg

<210> SEQ ID NO 451
<211> LENGTH: 19
<212> TYPE: PRT
<213> ORGANISM: Homo sapiens

<400> SEQUENCE: 451

Gly Asp Ser Phe Thr His Thr Pro Pro Leu Asp Pro Gln Glu Leu Asp
1               5                   10                  15

Ile Leu Lys

<210> SEQ ID NO 452
<211> LENGTH: 20
<212> TYPE: PRT
<213> ORGANISM: Homo sapiens

<400> SEQUENCE: 452

Gln His Gly Gln Phe Ser Leu Ala Val Val Ser Leu Asn Ile Thr Ser
1               5                   10                  15

Leu Gly Leu Arg
            20

<210> SEQ ID NO 453
<211> LENGTH: 21
<212> TYPE: PRT
<213> ORGANISM: Homo sapiens

<400> SEQUENCE: 453

Thr Pro Leu Leu Ser Ser Leu Ser Ala Thr Ser Asn Asn Ser Thr Val
1               5                   10                  15

Ala Cys Ile Asp Arg
            20

<210> SEQ ID NO 454
<211> LENGTH: 19
<212> TYPE: PRT
<213> ORGANISM: Homo sapiens

<400> SEQUENCE: 454

Glu Ile Leu Asp Glu Ala Tyr Val Met Ala Ser Val Asp Asn Pro His
1               5                   10                  15

Val Cys Arg

<210> SEQ ID NO 455
<211> LENGTH: 19

<212> TYPE: PRT
<213> ORGANISM: Homo sapiens

<400> SEQUENCE: 455

Gly Ser His Gln Ile Ser Leu Asp Asn Pro Asp Tyr Gln Gln Asp Phe
1               5                   10                  15

Phe Pro Lys

<210> SEQ ID NO 456
<211> LENGTH: 19
<212> TYPE: PRT
<213> ORGANISM: Homo sapiens

<400> SEQUENCE: 456

Gly Pro Asp Asn Cys Ile Gln Cys Ala His Tyr Ile Asp Gly Pro His
1               5                   10                  15

Cys Val Lys

<210> SEQ ID NO 457
<211> LENGTH: 19
<212> TYPE: PRT
<213> ORGANISM: Homo sapiens

<400> SEQUENCE: 457

Met Phe Asn Asn Cys Glu Val Val Leu Gly Asn Leu Glu Ile Thr Tyr
1               5                   10                  15

Val Gln Arg

<210> SEQ ID NO 458
<211> LENGTH: 20
<212> TYPE: PRT
<213> ORGANISM: Homo sapiens

<400> SEQUENCE: 458

Cys Asp Pro Ser Cys Pro Asn Gly Ser Cys Trp Gly Ala Gly Glu Glu
1               5                   10                  15

Asn Cys Gln Lys
            20

<210> SEQ ID NO 459
<211> LENGTH: 21
<212> TYPE: PRT
<213> ORGANISM: Homo sapiens

<400> SEQUENCE: 459

Ala Thr Gly Gln Val Cys His Ala Leu Cys Ser Pro Glu Gly Cys Trp
1               5                   10                  15

Gly Pro Glu Pro Arg
            20

<210> SEQ ID NO 460
<211> LENGTH: 22
<212> TYPE: PRT
<213> ORGANISM: Homo sapiens

<400> SEQUENCE: 460

Arg Pro Ala Gly Ser Val Gln Asn Pro Val Tyr His Asn Gln Pro Leu
1               5                   10                  15

Asn Pro Ala Pro Ser Arg
            20

-continued

<210> SEQ ID NO 461
<211> LENGTH: 21
<212> TYPE: PRT
<213> ORGANISM: Homo sapiens

<400> SEQUENCE: 461

Gly Asn Met Tyr Tyr Glu Asn Ser Tyr Ala Leu Ala Val Leu Ser Asn
1               5                   10                  15

Tyr Asp Ala Asn Lys
            20

<210> SEQ ID NO 462
<211> LENGTH: 23
<212> TYPE: PRT
<213> ORGANISM: Homo sapiens

<400> SEQUENCE: 462

Asp Thr Cys Pro Pro Leu Met Leu Tyr Asn Pro Thr Thr Tyr Gln Met
1               5                   10                  15

Asp Val Asn Pro Glu Gly Lys
            20

<210> SEQ ID NO 463
<211> LENGTH: 27
<212> TYPE: PRT
<213> ORGANISM: Homo sapiens

<400> SEQUENCE: 463

Ile Pro Ser Ile Ala Thr Gly Met Val Gly Ala Leu Leu Leu Leu
1               5                   10                  15

Val Val Ala Leu Gly Ile Gly Leu Phe Met Arg
            20                  25

<210> SEQ ID NO 464
<211> LENGTH: 24
<212> TYPE: PRT
<213> ORGANISM: Homo sapiens

<400> SEQUENCE: 464

Asp Ile Val Ser Ser Asp Phe Leu Ser Asn Met Ser Met Asp Phe Gln
1               5                   10                  15

Asn His Leu Gly Ser Cys Gln Lys
            20

<210> SEQ ID NO 465
<211> LENGTH: 27
<212> TYPE: PRT
<213> ORGANISM: Homo sapiens

<400> SEQUENCE: 465

Leu Leu Gly Ile Cys Leu Thr Ser Thr Val Gln Leu Ile Thr Gln Leu
1               5                   10                  15

Met Pro Phe Gly Cys Leu Leu Asp Tyr Val Arg
            20                  25

<210> SEQ ID NO 466
<211> LENGTH: 27
<212> TYPE: PRT
<213> ORGANISM: Homo sapiens

<400> SEQUENCE: 466

Glu Phe Val Glu Asn Ser Glu Cys Ile Gln Cys His Pro Glu Cys Leu
1               5                   10                  15

```
Pro Gln Ala Met Asn Ile Thr Cys Thr Gly Arg
            20                  25
```

<210> SEQ ID NO 467
<211> LENGTH: 31
<212> TYPE: PRT
<213> ORGANISM: Homo sapiens

<400> SEQUENCE: 467

```
Tyr Ser Ser Asp Pro Thr Gly Ala Leu Thr Glu Asp Ser Ile Asp Asp
1               5                   10                  15

Thr Phe Leu Pro Val Pro Glu Tyr Ile Asn Gln Ser Val Pro Lys
            20                  25                  30
```

<210> SEQ ID NO 468
<211> LENGTH: 32
<212> TYPE: PRT
<213> ORGANISM: Homo sapiens

<400> SEQUENCE: 468

```
Ala Leu Met Asp Glu Glu Asp Met Asp Asp Val Val Asp Ala Asp Glu
1               5                   10                  15

Tyr Leu Ile Pro Gln Gln Gly Phe Phe Ser Ser Pro Ser Thr Ser Arg
            20                  25                  30
```

<210> SEQ ID NO 469
<211> LENGTH: 33
<212> TYPE: PRT
<213> ORGANISM: Homo sapiens

<400> SEQUENCE: 469

```
Tyr Ala Asp Ala Gly His Val Cys His Leu Cys His Pro Asn Cys Thr
1               5                   10                  15

Tyr Gly Cys Thr Gly Pro Gly Leu Glu Gly Cys Pro Thr Asn Gly Pro
            20                  25                  30

Lys
```

<210> SEQ ID NO 470
<211> LENGTH: 39
<212> TYPE: PRT
<213> ORGANISM: Homo sapiens

<400> SEQUENCE: 470

```
Asp Pro His Tyr Gln Asp Pro His Ser Thr Ala Val Gly Asn Pro Glu
1               5                   10                  15

Tyr Leu Asn Thr Val Gln Pro Thr Cys Val Asn Ser Thr Phe Asp Ser
            20                  25                  30

Pro Ala His Trp Ala Gln Lys
            35
```

<210> SEQ ID NO 471
<211> LENGTH: 40
<212> TYPE: PRT
<213> ORGANISM: Homo sapiens

<400> SEQUENCE: 471

```
Ile Tyr Thr His Gln Ser Asp Val Trp Ser Tyr Gly Val Thr Val Trp
1               5                   10                  15

Glu Leu Met Thr Phe Gly Ser Lys Pro Tyr Asp Gly Ile Pro Ala Ser
            20                  25                  30
```

Glu Ile Ser Ser Ile Leu Glu Lys
            35                  40

<210> SEQ ID NO 472
<211> LENGTH: 6
<212> TYPE: PRT
<213> ORGANISM: Homo sapiens

<400> SEQUENCE: 472

Thr Leu Ser Pro Gly Lys
1               5

<210> SEQ ID NO 473
<211> LENGTH: 6
<212> TYPE: PRT
<213> ORGANISM: Homo sapiens

<400> SEQUENCE: 473

Ile Pro Val Ala Ile Lys
1               5

<210> SEQ ID NO 474
<211> LENGTH: 5
<212> TYPE: PRT
<213> ORGANISM: Homo sapiens

<400> SEQUENCE: 474

Glu Thr Glu Leu Arg
1               5

<210> SEQ ID NO 475
<211> LENGTH: 5
<212> TYPE: PRT
<213> ORGANISM: Homo sapiens

<400> SEQUENCE: 475

Glu Leu Gln Leu Arg
1               5

<210> SEQ ID NO 476
<211> LENGTH: 5
<212> TYPE: PRT
<213> ORGANISM: Homo sapiens

<400> SEQUENCE: 476

Asp Ile Phe His Lys
1               5

<210> SEQ ID NO 477
<211> LENGTH: 6
<212> TYPE: PRT
<213> ORGANISM: Homo sapiens

<400> SEQUENCE: 477

Glu Asn Thr Ser Pro Lys
1               5

<210> SEQ ID NO 478
<211> LENGTH: 6
<212> TYPE: PRT
<213> ORGANISM: Homo sapiens

<400> SEQUENCE: 478

Ser Pro Asn His Val Lys
1               5

```
<210> SEQ ID NO 479
<211> LENGTH: 6
<212> TYPE: PRT
<213> ORGANISM: Homo sapiens

<400> SEQUENCE: 479

Gln Val Pro Leu Gln Arg
1               5

<210> SEQ ID NO 480
<211> LENGTH: 7
<212> TYPE: PRT
<213> ORGANISM: Homo sapiens

<400> SEQUENCE: 480

Gly Gly Val Leu Ile Gln Arg
1               5

<210> SEQ ID NO 481
<211> LENGTH: 6
<212> TYPE: PRT
<213> ORGANISM: Homo sapiens

<400> SEQUENCE: 481

Glu Tyr Val Asn Ala Arg
1               5

<210> SEQ ID NO 482
<211> LENGTH: 7
<212> TYPE: PRT
<213> ORGANISM: Homo sapiens

<400> SEQUENCE: 482

Val Leu Gln Gly Leu Pro Arg
1               5

<210> SEQ ID NO 483
<211> LENGTH: 7
<212> TYPE: PRT
<213> ORGANISM: Homo sapiens

<400> SEQUENCE: 483

Ser Leu Thr Glu Ile Leu Lys
1               5

<210> SEQ ID NO 484
<211> LENGTH: 8
<212> TYPE: PRT
<213> ORGANISM: Homo sapiens

<400> SEQUENCE: 484

Gly Ala Pro Pro Ser Thr Phe Lys
1               5

<210> SEQ ID NO 485
<211> LENGTH: 7
<212> TYPE: PRT
<213> ORGANISM: Homo sapiens

<400> SEQUENCE: 485

Gly Cys Pro Ala Glu Gln Arg
1               5
```

```
<210> SEQ ID NO 486
<211> LENGTH: 7
<212> TYPE: PRT
<213> ORGANISM: Homo sapiens

<400> SEQUENCE: 486

Cys Ser Lys Pro Cys Ala Arg
1               5

<210> SEQ ID NO 487
<211> LENGTH: 8
<212> TYPE: PRT
<213> ORGANISM: Homo sapiens

<400> SEQUENCE: 487

Ile Thr Asp Phe Gly Leu Ala Arg
1               5

<210> SEQ ID NO 488
<211> LENGTH: 9
<212> TYPE: PRT
<213> ORGANISM: Homo sapiens

<400> SEQUENCE: 488

Thr Val Cys Ala Gly Gly Cys Ala Arg
1               5

<210> SEQ ID NO 489
<211> LENGTH: 8
<212> TYPE: PRT
<213> ORGANISM: Homo sapiens

<400> SEQUENCE: 489

Glu Ile Pro Asp Leu Leu Glu Lys
1               5

<210> SEQ ID NO 490
<211> LENGTH: 8
<212> TYPE: PRT
<213> ORGANISM: Homo sapiens

<400> SEQUENCE: 490

Asp Pro Pro Phe Cys Val Ala Arg
1               5

<210> SEQ ID NO 491
<211> LENGTH: 8
<212> TYPE: PRT
<213> ORGANISM: Homo sapiens

<400> SEQUENCE: 491

Glu Leu Val Ser Glu Phe Ser Arg
1               5

<210> SEQ ID NO 492
<211> LENGTH: 9
<212> TYPE: PRT
<213> ORGANISM: Homo sapiens

<400> SEQUENCE: 492

Gly Met Ser Tyr Leu Glu Asp Val Arg
1               5

<210> SEQ ID NO 493
<211> LENGTH: 9
```

<212> TYPE: PRT
<213> ORGANISM: Homo sapiens

<400> SEQUENCE: 493

Trp Met Ala Leu Glu Ser Ile Leu Arg
1               5

<210> SEQ ID NO 494
<211> LENGTH: 10
<212> TYPE: PRT
<213> ORGANISM: Homo sapiens

<400> SEQUENCE: 494

Thr Gln Val Cys Thr Gly Thr Asp Met Lys
1               5                   10

<210> SEQ ID NO 495
<211> LENGTH: 9
<212> TYPE: PRT
<213> ORGANISM: Homo sapiens

<400> SEQUENCE: 495

Gly Gln Glu Cys Val Glu Glu Cys Arg
1               5

<210> SEQ ID NO 496
<211> LENGTH: 12
<212> TYPE: PRT
<213> ORGANISM: Homo sapiens

<400> SEQUENCE: 496

Val Leu Gly Ser Gly Ala Phe Gly Thr Val Tyr Lys
1               5                   10

<210> SEQ ID NO 497
<211> LENGTH: 11
<212> TYPE: PRT
<213> ORGANISM: Homo sapiens

<400> SEQUENCE: 497

Gly Ile Trp Ile Pro Asp Gly Glu Asn Val Lys
1               5                   10

<210> SEQ ID NO 498
<211> LENGTH: 10
<212> TYPE: PRT
<213> ORGANISM: Homo sapiens

<400> SEQUENCE: 498

Ala Cys His Pro Cys Ser Pro Met Cys Lys
1               5                   10

<210> SEQ ID NO 499
<211> LENGTH: 11
<212> TYPE: PRT
<213> ORGANISM: Homo sapiens

<400> SEQUENCE: 499

Val Cys Tyr Gly Leu Gly Met Glu His Leu Arg
1               5                   10

<210> SEQ ID NO 500
<211> LENGTH: 13
<212> TYPE: PRT
<213> ORGANISM: Homo sapiens

<400> SEQUENCE: 500

Leu Pro Ala Ser Pro Glu Thr His Leu Asp Met Leu Arg
1               5                   10

<210> SEQ ID NO 501
<211> LENGTH: 13
<212> TYPE: PRT
<213> ORGANISM: Homo sapiens

<400> SEQUENCE: 501

Asn Asn Gln Leu Ala Leu Thr Leu Ile Asp Thr Asn Arg
1               5                   10

<210> SEQ ID NO 502
<211> LENGTH: 14
<212> TYPE: PRT
<213> ORGANISM: Homo sapiens

<400> SEQUENCE: 502

Ala Val Thr Ser Ala Asn Ile Gln Glu Phe Ala Gly Cys Lys
1               5                   10

<210> SEQ ID NO 503
<211> LENGTH: 11
<212> TYPE: PRT
<213> ORGANISM: Homo sapiens

<400> SEQUENCE: 503

Cys Trp Met Ile Asp Ser Glu Cys Arg Pro Arg
1               5                   10

<210> SEQ ID NO 504
<211> LENGTH: 15
<212> TYPE: PRT
<213> ORGANISM: Homo sapiens

<400> SEQUENCE: 504

Gly Leu Gln Ser Leu Pro Thr His Asp Pro Ser Pro Leu Gln Arg
1               5                   10                  15

<210> SEQ ID NO 505
<211> LENGTH: 15
<212> TYPE: PRT
<213> ORGANISM: Homo sapiens

<400> SEQUENCE: 505

Leu Leu Asp Ile Asp Glu Thr Glu Tyr His Ala Asp Gly Gly Lys
1               5                   10                  15

<210> SEQ ID NO 506
<211> LENGTH: 13
<212> TYPE: PRT
<213> ORGANISM: Homo sapiens

<400> SEQUENCE: 506

Asn Pro Gln Leu Cys Tyr Gln Asp Thr Ile Leu Trp Lys
1               5                   10

<210> SEQ ID NO 507
<211> LENGTH: 14
<212> TYPE: PRT
<213> ORGANISM: Homo sapiens

<400> SEQUENCE: 507

```
Cys Trp Gly Glu Ser Ser Glu Asp Cys Gln Ser Leu Thr Arg
1               5                   10
```

<210> SEQ ID NO 508
<211> LENGTH: 17
<212> TYPE: PRT
<213> ORGANISM: Homo sapiens

<400> SEQUENCE: 508

```
Gly Thr Pro Thr Ala Glu Asn Pro Glu Tyr Leu Gly Leu Asp Val Pro
1               5                   10                  15

Val
```

<210> SEQ ID NO 509
<211> LENGTH: 15
<212> TYPE: PRT
<213> ORGANISM: Homo sapiens

<400> SEQUENCE: 509

```
Leu Gly Ser Gln Asp Leu Leu Asn Trp Cys Met Gln Ile Ala Lys
1               5                   10                  15
```

<210> SEQ ID NO 510
<211> LENGTH: 18
<212> TYPE: PRT
<213> ORGANISM: Homo sapiens

<400> SEQUENCE: 510

```
Glu Gly Pro Leu Pro Ala Ala Arg Pro Ala Gly Ala Thr Leu Glu Arg
1               5                   10                  15

Pro Lys
```

<210> SEQ ID NO 511
<211> LENGTH: 16
<212> TYPE: PRT
<213> ORGANISM: Homo sapiens

<400> SEQUENCE: 511

```
Cys Pro Ser Gly Val Lys Pro Asp Leu Ser Tyr Met Pro Ile Trp Lys
1               5                   10                  15
```

<210> SEQ ID NO 512
<211> LENGTH: 19
<212> TYPE: PRT
<213> ORGANISM: Homo sapiens

<400> SEQUENCE: 512

```
Ser Gly Gly Gly Asp Leu Thr Leu Gly Leu Glu Pro Ser Glu Glu Glu
1               5                   10                  15

Ala Pro Arg
```

<210> SEQ ID NO 513
<211> LENGTH: 17
<212> TYPE: PRT
<213> ORGANISM: Homo sapiens

<400> SEQUENCE: 513

```
Leu Pro Gln Pro Pro Ile Cys Thr Ile Asp Val Tyr Met Ile Met Val
1               5                   10                  15

Lys
```

```
<210> SEQ ID NO 514
<211> LENGTH: 19
<212> TYPE: PRT
<213> ORGANISM: Homo sapiens

<400> SEQUENCE: 514

Glu Ile Leu Asp Glu Ala Tyr Val Met Ala Gly Val Gly Ser Pro Tyr
1               5                   10                  15

Val Ser Arg

<210> SEQ ID NO 515
<211> LENGTH: 20
<212> TYPE: PRT
<213> ORGANISM: Homo sapiens

<400> SEQUENCE: 515

Gly Pro Leu Pro Thr Asp Cys Cys His Glu Gln Cys Ala Ala Gly Cys
1               5                   10                  15

Thr Gly Pro Lys
            20

<210> SEQ ID NO 516
<211> LENGTH: 24
<212> TYPE: PRT
<213> ORGANISM: Homo sapiens

<400> SEQUENCE: 516

Ser Pro Leu Ala Pro Ser Glu Gly Ala Gly Ser Asp Val Phe Asp Gly
1               5                   10                  15

Asp Leu Gly Met Gly Ala Ala Lys
            20

<210> SEQ ID NO 517
<211> LENGTH: 19
<212> TYPE: PRT
<213> ORGANISM: Homo sapiens

<400> SEQUENCE: 517

Gly His Cys Trp Gly Pro Gly Pro Thr Gln Cys Val Asn Cys Ser Gln
1               5                   10                  15

Phe Leu Arg

<210> SEQ ID NO 518
<211> LENGTH: 21
<212> TYPE: PRT
<213> ORGANISM: Homo sapiens

<400> SEQUENCE: 518

Phe Val Val Ile Gln Asn Glu Asp Leu Gly Pro Ala Ser Pro Leu Asp
1               5                   10                  15

Ser Thr Phe Tyr Arg
            20

<210> SEQ ID NO 519
<211> LENGTH: 22
<212> TYPE: PRT
<213> ORGANISM: Homo sapiens

<400> SEQUENCE: 519

Ile Leu His Asn Gly Ala Tyr Ser Leu Thr Leu Gln Gly Leu Gly Ile
1               5                   10                  15

Ser Trp Leu Gly Leu Arg
```

<210> SEQ ID NO 520
<211> LENGTH: 24
<212> TYPE: PRT
<213> ORGANISM: Homo sapiens

<400> SEQUENCE: 520

Leu Leu Gln Glu Thr Glu Leu Val Glu Pro Leu Thr Pro Ser Gly Ala
1               5                   10                  15

Met Pro Asn Gln Ala Gln Met Arg
            20

<210> SEQ ID NO 521
<211> LENGTH: 29
<212> TYPE: PRT
<213> ORGANISM: Homo sapiens

<400> SEQUENCE: 521

Ala Ser Pro Leu Thr Ser Ile Ile Ser Ala Val Val Gly Ile Leu Leu
1               5                   10                  15

Val Val Val Leu Gly Val Val Phe Gly Ile Leu Ile Lys
            20                  25

<210> SEQ ID NO 522
<211> LENGTH: 25
<212> TYPE: PRT
<213> ORGANISM: Homo sapiens

<400> SEQUENCE: 522

Phe Pro Asp Glu Glu Gly Ala Cys Gln Pro Cys Pro Ile Asn Cys Thr
1               5                   10                  15

His Ser Cys Val Asp Leu Asp Asp Lys
            20                  25

<210> SEQ ID NO 523
<211> LENGTH: 27
<212> TYPE: PRT
<213> ORGANISM: Homo sapiens

<400> SEQUENCE: 523

Leu Leu Gly Ile Cys Leu Thr Ser Thr Val Gln Leu Val Thr Gln Leu
1               5                   10                  15

Met Pro Tyr Gly Cys Leu Leu Asp His Val Arg
            20                  25

<210> SEQ ID NO 524
<211> LENGTH: 28
<212> TYPE: PRT
<213> ORGANISM: Homo sapiens

<400> SEQUENCE: 524

Glu Leu Gly Ser Gly Leu Ala Leu Ile His His Asn Thr His Leu Cys
1               5                   10                  15

Phe Val His Thr Val Pro Trp Asp Gln Leu Phe Arg
            20                  25

<210> SEQ ID NO 525
<211> LENGTH: 30
<212> TYPE: PRT
<213> ORGANISM: Homo sapiens

<400> SEQUENCE: 525

```
Asn Pro His Gln Ala Leu Leu His Thr Ala Asn Arg Pro Glu Asp Glu
1               5                  10                  15

Cys Val Gly Glu Gly Leu Ala Cys His Gln Leu Cys Ala Arg
            20                  25                  30

<210> SEQ ID NO 526
<211> LENGTH: 31
<212> TYPE: PRT
<213> ORGANISM: Homo sapiens

<400> SEQUENCE: 526

Phe Thr His Gln Ser Asp Val Trp Ser Tyr Gly Val Thr Val Trp Glu
1               5                  10                  15

Leu Met Thr Phe Gly Ala Lys Pro Tyr Asp Gly Ile Pro Ala Arg
            20                  25                  30

<210> SEQ ID NO 527
<211> LENGTH: 35
<212> TYPE: PRT
<213> ORGANISM: Homo sapiens

<400> SEQUENCE: 527

Gly Thr Gln Leu Phe Glu Asp Asn Tyr Ala Leu Ala Val Leu Asp Asn
1               5                  10                  15

Gly Asp Pro Leu Asn Asn Thr Thr Pro Val Thr Gly Ala Ser Pro Gly
            20                  25                  30

Gly Leu Arg
        35

<210> SEQ ID NO 528
<211> LENGTH: 33
<212> TYPE: PRT
<213> ORGANISM: Homo sapiens

<400> SEQUENCE: 528

His Cys Leu Pro Cys His Pro Glu Cys Gln Pro Gln Asn Gly Ser Val
1               5                  10                  15

Thr Cys Phe Gly Pro Glu Ala Asp Gln Cys Val Ala Cys Ala His Tyr
            20                  25                  30

Lys

<210> SEQ ID NO 529
<211> LENGTH: 40
<212> TYPE: PRT
<213> ORGANISM: Homo sapiens

<400> SEQUENCE: 529

Ser Leu Leu Glu Asp Asp Asp Met Gly Asp Leu Val Asp Ala Glu Glu
1               5                  10                  15

Tyr Leu Val Pro Gln Gln Gly Phe Phe Cys Pro Asp Pro Ala Pro Gly
            20                  25                  30

Ala Gly Gly Met Val His His Arg
        35                  40

<210> SEQ ID NO 530
<211> LENGTH: 15
<212> TYPE: PRT
<213> ORGANISM: Homo sapiens

<400> SEQUENCE: 530
```

```
Glu Glu Trp Thr Thr Ala Ile Gln Thr Val Ala Asp Gly Leu Lys
1               5                   10                  15
```

<210> SEQ ID NO 531
<211> LENGTH: 13
<212> TYPE: PRT
<213> ORGANISM: Homo sapiens

<400> SEQUENCE: 531

```
Phe Phe Ala Gly Ile Val Trp Gln His Val Tyr Glu Lys
1               5                   10
```

<210> SEQ ID NO 532
<211> LENGTH: 10
<212> TYPE: PRT
<213> ORGANISM: Homo sapiens

<400> SEQUENCE: 532

```
Phe Ala Thr Val Val Glu Glu Leu Phe Arg
1               5                   10
```

<210> SEQ ID NO 533
<211> LENGTH: 10
<212> TYPE: PRT
<213> ORGANISM: Homo sapiens

<400> SEQUENCE: 533

```
Glu Leu Val Val Asp Phe Leu Ser Tyr Lys
1               5                   10
```

<210> SEQ ID NO 534
<211> LENGTH: 9
<212> TYPE: PRT
<213> ORGANISM: Homo sapiens

<400> SEQUENCE: 534

```
Glu Val Ile Pro Met Ala Ala Val Lys
1               5
```

<210> SEQ ID NO 535
<211> LENGTH: 32
<212> TYPE: PRT
<213> ORGANISM: Homo sapiens

<400> SEQUENCE: 535

```
Asp His Gly Phe Glu Val Ala Ser Thr Ser Pro Glu Asp Glu Ser Pro
1               5                   10                  15

Gly Ser Asn Pro Glu Pro Asp Ala Thr Pro Phe Gln Glu Gly Leu Arg
            20                  25                  30
```

<210> SEQ ID NO 536
<211> LENGTH: 9
<212> TYPE: PRT
<213> ORGANISM: Homo sapiens

<400> SEQUENCE: 536

```
Gln Leu Ile Ile Asp Leu Glu Thr Arg
1               5
```

<210> SEQ ID NO 537
<211> LENGTH: 15
<212> TYPE: PRT
<213> ORGANISM: Homo sapiens

<400> SEQUENCE: 537

Ala Cys Gln Glu Gln Ile Glu Ala Leu Leu Glu Ser Ser Leu Arg
1               5                   10                  15

<210> SEQ ID NO 538
<211> LENGTH: 13
<212> TYPE: PRT
<213> ORGANISM: Homo sapiens

<400> SEQUENCE: 538

Ala Glu Glu Thr Cys Ala Pro Ser Val Ser Tyr Phe Lys
1               5                   10

<210> SEQ ID NO 539
<211> LENGTH: 19
<212> TYPE: PRT
<213> ORGANISM: Homo sapiens

<400> SEQUENCE: 539

Gly Asp Ser Phe Thr His Thr Pro Pro Leu Asp Pro Gln Glu Leu Asp
1               5                   10                  15

Ile Leu Lys

<210> SEQ ID NO 540
<211> LENGTH: 10
<212> TYPE: PRT
<213> ORGANISM: Homo sapiens

<400> SEQUENCE: 540

Ile Pro Leu Glu Asn Leu Gln Ile Ile Arg
1               5                   10

<210> SEQ ID NO 541
<211> LENGTH: 14
<212> TYPE: PRT
<213> ORGANISM: Homo sapiens

<400> SEQUENCE: 541

Ile Val Ile Gly Tyr Gln Ser His Ala Asp Thr Ala Thr Lys
1               5                   10

<210> SEQ ID NO 542
<211> LENGTH: 7
<212> TYPE: PRT
<213> ORGANISM: Homo sapiens

<400> SEQUENCE: 542

Trp Ala Leu Trp Phe Phe Lys
1               5

<210> SEQ ID NO 543
<211> LENGTH: 11
<212> TYPE: PRT
<213> ORGANISM: Homo sapiens

<400> SEQUENCE: 543

Asp Ala Asn Leu Tyr Ile Ser Gly Leu Pro Arg
1               5                   10

<210> SEQ ID NO 544
<211> LENGTH: 11
<212> TYPE: PRT
<213> ORGANISM: Homo sapiens

<400> SEQUENCE: 544

Val Leu Val Asp Gln Thr Thr Gly Leu Ser Arg
1               5                   10

<210> SEQ ID NO 545
<211> LENGTH: 10
<212> TYPE: PRT
<213> ORGANISM: Homo sapiens

<400> SEQUENCE: 545

Ala Ile Leu Phe Leu Pro Met Ser Ala Lys
1               5                   10

<210> SEQ ID NO 546
<211> LENGTH: 11
<212> TYPE: PRT
<213> ORGANISM: Homo sapiens

<400> SEQUENCE: 546

Cys Val Thr Asp Glu Cys Phe Phe Phe Glu Arg
1               5                   10

<210> SEQ ID NO 547
<211> LENGTH: 11
<212> TYPE: PRT
<213> ORGANISM: Homo sapiens

<400> SEQUENCE: 547

Gly Ile Trp Ile Pro Asp Gly Glu Asn Val Lys
1               5                   10

<210> SEQ ID NO 548
<211> LENGTH: 12
<212> TYPE: PRT
<213> ORGANISM: Homo sapiens

<400> SEQUENCE: 548

Val Leu Gly Ser Gly Ala Phe Gly Thr Val Tyr Lys
1               5                   10

<210> SEQ ID NO 549
<211> LENGTH: 14
<212> TYPE: PRT
<213> ORGANISM: Homo sapiens

<400> SEQUENCE: 549

Phe Glu Glu Ile Thr Gly Val Ile Asn Pro Ala Leu Asp Lys
1               5                   10

<210> SEQ ID NO 550
<211> LENGTH: 15
<212> TYPE: PRT
<213> ORGANISM: Homo sapiens

<400> SEQUENCE: 550

Leu Leu Asp Ile Gly Gly Gly Phe Pro Gly Ser Glu Asp Val Lys
1               5                   10                  15

<210> SEQ ID NO 551
<211> LENGTH: 11
<212> TYPE: PRT
<213> ORGANISM: Homo sapiens

<400> SEQUENCE: 551

Asp Thr Val Tyr Thr Asp Phe Asp Gly Thr Arg

```
1               5                   10

<210> SEQ ID NO 552
<211> LENGTH: 12
<212> TYPE: PRT
<213> ORGANISM: Homo sapiens

<400> SEQUENCE: 552

Ile Ser Asp Trp Gly Glu Leu Pro Asn Gly Thr Arg
1               5                   10

<210> SEQ ID NO 553
<211> LENGTH: 12
<212> TYPE: PRT
<213> ORGANISM: Homo sapiens

<400> SEQUENCE: 553

Ala Ala Ala Ala Val Glu Pro Asp Val Val Val Lys
1               5                   10

<210> SEQ ID NO 554
<211> LENGTH: 11
<212> TYPE: PRT
<213> ORGANISM: Homo sapiens

<400> SEQUENCE: 554

Met Gln Glu Glu Leu Asn Ala Gln Val Glu Lys
1               5                   10

<210> SEQ ID NO 555
<211> LENGTH: 11
<212> TYPE: PRT
<213> ORGANISM: Homo sapiens

<400> SEQUENCE: 555

Leu Ser Asp Pro Ile Val Asn Thr Leu Ala Lys
1               5                   10

<210> SEQ ID NO 556
<211> LENGTH: 17
<212> TYPE: PRT
<213> ORGANISM: Homo sapiens

<400> SEQUENCE: 556

Thr Leu Gln Val Phe Gly Ile Val Pro Asp Gly Thr Leu Gln Leu Leu
1               5                   10                  15

Lys

<210> SEQ ID NO 557
<211> LENGTH: 17
<212> TYPE: PRT
<213> ORGANISM: Homo sapiens

<400> SEQUENCE: 557

Ala Ile Pro Val Ala Gln Asp Leu Asn Ala Pro Ser Asp Trp Asp Ser
1               5                   10                  15

Arg

<210> SEQ ID NO 558
<211> LENGTH: 9
<212> TYPE: PRT
<213> ORGANISM: Homo sapiens

<400> SEQUENCE: 558
```

Gly Asp Ser Val Val Tyr Gly Leu Arg
1               5

<210> SEQ ID NO 559
<211> LENGTH: 117
<212> TYPE: PRT
<213> ORGANISM: Homo sapiens
<220> FEATURE:
<223> OTHER INFORMATION: N-term Ac

<400> SEQUENCE: 559

Ser Gly Gly Ser Ser Cys Ser Gln Thr Pro Ser Arg Ala Ile Pro Ala
1               5                   10                  15

Thr Arg Arg Val Val Leu Gly Asp Gly Val Gln Leu Pro Pro Gly Asp
                20                  25                  30

Tyr Ser Thr Thr Pro Gly Gly Thr Leu Phe Ser Thr Thr Pro Gly Gly
            35                  40                  45

Thr Arg Ile Ile Tyr Asp Arg Lys Phe Leu Met Glu Cys Arg Asn Ser
        50                  55                  60

Pro Val Thr Lys Thr Pro Arg Asp Leu Pro Thr Ile Pro Gly Val
65                  70                  75                  80

Thr Ser Pro Ser Ser Asp Glu Pro Pro Met Glu Ala Ser Gln Ser His
                85                  90                  95

Leu Arg Asn Ser Pro Glu Asp Lys Arg Ala Gly Gly Glu Glu Ser Gln
            100                 105                 110

Phe Glu Met Asp Ile
        115

<210> SEQ ID NO 560
<211> LENGTH: 480
<212> TYPE: PRT
<213> ORGANISM: Homo sapiens

<400> SEQUENCE: 560

Met Ser Asp Val Ala Ile Val Lys Glu Gly Trp Leu His Lys Arg Gly
1               5                   10                  15

Glu Tyr Ile Lys Thr Trp Arg Pro Arg Tyr Phe Leu Leu Lys Asn Asp
                20                  25                  30

Gly Thr Phe Ile Gly Tyr Lys Glu Arg Pro Gln Asp Val Asp Gln Arg
            35                  40                  45

Glu Ala Pro Leu Asn Asn Phe Ser Val Ala Gln Cys Gln Leu Met Lys
        50                  55                  60

Thr Glu Arg Pro Arg Pro Asn Thr Phe Ile Ile Arg Cys Leu Gln Trp
65                  70                  75                  80

Thr Thr Val Ile Glu Arg Thr Phe His Val Glu Thr Pro Glu Glu Arg
                85                  90                  95

Glu Glu Trp Thr Thr Ala Ile Gln Thr Val Ala Asp Gly Leu Lys Lys
            100                 105                 110

Gln Glu Glu Glu Met Asp Phe Arg Ser Gly Ser Pro Ser Asp Asn
        115                 120                 125

Ser Gly Ala Glu Glu Met Glu Val Ser Leu Ala Lys Pro Lys His Arg
130                 135                 140

Val Thr Met Asn Glu Phe Glu Tyr Leu Lys Leu Leu Gly Lys Gly Thr
145                 150                 155                 160

Phe Gly Lys Val Ile Leu Val Lys Glu Lys Ala Thr Gly Arg Tyr Tyr
                165                 170                 175

```
Ala Met Lys Ile Leu Lys Lys Glu Val Ile Val Ala Lys Asp Glu Val
            180                 185                 190

Ala His Thr Leu Thr Glu Asn Arg Val Leu Gln Asn Ser Arg His Pro
            195                 200                 205

Phe Leu Thr Ala Leu Lys Tyr Ser Phe Gln Thr His Asp Arg Leu Cys
            210                 215                 220

Phe Val Met Glu Tyr Ala Asn Gly Gly Glu Leu Phe Phe His Leu Ser
225                 230                 235                 240

Arg Glu Arg Val Phe Ser Glu Asp Arg Ala Arg Phe Tyr Gly Ala Glu
                245                 250                 255

Ile Val Ser Ala Leu Asp Tyr Leu His Ser Glu Lys Asn Val Val Tyr
            260                 265                 270

Arg Asp Leu Lys Leu Glu Asn Leu Met Leu Asp Lys Asp Gly His Ile
            275                 280                 285

Lys Ile Thr Asp Phe Gly Leu Cys Lys Glu Gly Ile Lys Asp Gly Ala
            290                 295                 300

Thr Met Lys Thr Phe Cys Gly Thr Pro Glu Tyr Leu Ala Pro Glu Val
305                 310                 315                 320

Leu Glu Asp Asn Asp Tyr Gly Arg Ala Val Asp Trp Trp Gly Leu Gly
                325                 330                 335

Val Val Met Tyr Glu Met Met Cys Gly Arg Leu Pro Phe Tyr Asn Gln
            340                 345                 350

Asp His Glu Lys Leu Phe Glu Leu Ile Leu Met Glu Glu Ile Arg Phe
            355                 360                 365

Pro Arg Thr Leu Gly Pro Glu Ala Lys Ser Leu Leu Ser Gly Leu Leu
            370                 375                 380

Lys Lys Asp Pro Lys Gln Arg Leu Gly Gly Gly Ser Glu Asp Ala Lys
385                 390                 395                 400

Glu Ile Met Gln His Arg Phe Phe Ala Gly Ile Val Trp Gln His Val
                405                 410                 415

Tyr Glu Lys Lys Leu Ser Pro Pro Phe Lys Pro Gln Val Thr Ser Glu
            420                 425                 430

Thr Asp Thr Arg Tyr Phe Asp Glu Glu Phe Thr Ala Gln Met Ile Thr
            435                 440                 445

Ile Thr Pro Pro Asp Gln Asp Asp Ser Met Glu Cys Val Asp Ser Glu
            450                 455                 460

Arg Arg Pro His Phe Pro Gln Phe Ser Tyr Ser Ala Ser Gly Thr Ala
465                 470                 475                 480
```